US011782059B2

(12) United States Patent
Fan et al.

(10) Patent No.: US 11,782,059 B2
(45) Date of Patent: *Oct. 10, 2023

(54) MEASUREMENT OF PROTEIN EXPRESSION USING REAGENTS WITH BARCODED OLIGONUCLEOTIDE SEQUENCES

(71) Applicant: CELLULAR RESEARCH, INC., San Jose, CA (US)

(72) Inventors: Christina Fan, San Jose, CA (US); Olaf Zoellner, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 867 days.

This patent is subject to a terminal disclaimer.

(21) Appl. No.: 16/459,444

(22) Filed: Jul. 1, 2019

(65) Prior Publication Data

US 2020/0124601 A1 Apr. 23, 2020

Related U.S. Application Data

(63) Continuation of application No. 15/993,468, filed on May 30, 2018, now Pat. No. 10,338,066, which is a continuation of application No. 15/715,028, filed on Sep. 25, 2017.

(60) Provisional application No. 62/515,952, filed on Jun. 6, 2017, provisional application No. 62/464,279, filed on Feb. 27, 2017, provisional application No. 62/399,795, filed on Sep. 26, 2016.

(51) Int. Cl.
| | |
|---|---|
| G01N 33/566 | (2006.01) |
| G16B 99/00 | (2019.01) |
| G01N 33/50 | (2006.01) |
| G01N 33/543 | (2006.01) |
| G01N 33/68 | (2006.01) |
| C12Q 1/6804 | (2018.01) |
| G16Z 99/00 | (2019.01) |
| C12N 15/10 | (2006.01) |
| C12Q 1/6806 | (2018.01) |
| C12Q 1/6823 | (2018.01) |
| C12Q 1/6869 | (2018.01) |
| C12Q 1/68 | (2018.01) |
| G16B 25/10 | (2019.01) |
| G16H 20/13 | (2018.01) |
| G16H 10/20 | (2018.01) |

(52) U.S. Cl.
CPC ....... *G01N 33/566* (2013.01); *C12N 15/1006* (2013.01); *C12N 15/1096* (2013.01); *C12Q 1/68* (2013.01); *C12Q 1/6804* (2013.01); *C12Q 1/6806* (2013.01); *C12Q 1/6823* (2013.01); *C12Q 1/6869* (2013.01); *G01N 33/505* (2013.01); *G01N 33/54306* (2013.01); *G01N 33/54313* (2013.01); *G01N 33/6842* (2013.01); *G01N 33/6857* (2013.01); *G16B 99/00* (2019.02); *G16Z 99/00* (2019.02); *B01J 2219/00646* (2013.01); *B01J 2219/00722* (2013.01); *B01J 2219/00725* (2013.01); *C07K 2319/01* (2013.01); *G16B 25/10* (2019.02); *G16H 10/20* (2018.01); *G16H 20/13* (2018.01)

(58) Field of Classification Search
CPC .................................. C12Q 1/68; C01N 33/53
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |

(Continued)

FOREIGN PATENT DOCUMENTS

| | | |
|---|---|---|
| CA | 2474509 | 2/2003 |
| DE | 102008025656 | 12/2009 |

(Continued)

OTHER PUBLICATIONS

Lustig et al., J of Molecular Biology 180 :753-759 (Year: 1984).*
Winter et al. The EMBO Journal 8(6) 1867-1889 (Year: 1989).*
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.

(Continued)

*Primary Examiner* — Ethan C Whisenant
(74) *Attorney, Agent, or Firm* — Sheppard, Mullin, Richter & Hampton LLP

(57) ABSTRACT

Some embodiments disclosed herein provide a plurality of compositions each comprising a protein binding reagent conjugated with an oligonucleotide. The oligonucleotide comprises a unique identifier for the protein binding reagent it is conjugated with, and the protein binding reagent is capable of specifically binding to a protein target. Further disclosed are methods and kits for quantitative analysis of a plurality of protein targets in a sample and for simultaneous quantitative analysis of protein and nucleic acid targets in a sample. Also disclosed herein are systems and methods for preparing a labeled biomolecule reagent, including a labeled biomolecule agent comprising a protein binding reagent conjugated with an oligonucleotide.

27 Claims, 56 Drawing Sheets

Specification includes a Sequence Listing.

(56) References Cited

U.S. PATENT DOCUMENTS

| | | |
|---|---|---|
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,309,306 B2 * | 11/2012 | Nolan .............. C07K 1/13 435/7.1 |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,290,808 B2 | 3/2016 | Fodor et al. |
| 9,290,809 B2 | 3/2016 | Fodor et al. |
| 9,297,047 B2 | 3/2016 | Furchak et al. |
| 9,315,857 B2 | 4/2016 | Fu et al. |
| 9,371,598 B2 | 6/2016 | Chee |
| 9,567,645 B2 * | 2/2017 | Fan .............. C12Q 1/6888 |
| 9,567,646 B2 * | 2/2017 | Fan .............. C12Q 1/6876 |
| 9,582,877 B2 | 2/2017 | Fu et al. |
| 9,593,365 B2 | 3/2017 | Frisen et al. |
| 9,598,736 B2 * | 3/2017 | Fan .............. C12Q 1/6874 |
| 9,637,799 B2 * | 5/2017 | Fan .............. C12Q 1/6881 |
| 9,644,204 B2 | 5/2017 | Hindson et al. |
| 9,677,131 B2 | 6/2017 | Fredriksson et al. |
| 9,689,024 B2 | 6/2017 | Hindson et al. |
| 9,695,468 B2 | 7/2017 | Hindson et al. |
| 9,708,659 B2 | 7/2017 | Fodor et al. |
| 9,727,810 B2 * | 8/2017 | Fodor .............. C12Q 1/6853 |
| 9,787,810 B1 | 10/2017 | Chiang |
| 9,816,137 B2 | 11/2017 | Fodor et al. |
| 9,845,502 B2 | 12/2017 | Fodor et al. |

(56) References Cited

U.S. PATENT DOCUMENTS

| | | | |
|---|---|---|---|
| 9,850,515 B2 | 12/2017 | McCoy et al. | |
| 9,856,530 B2 | 1/2018 | Hindson et al. | |
| 9,868,979 B2 | 1/2018 | Chee et al. | |
| 9,879,313 B2 | 1/2018 | Chee et al. | |
| 9,905,005 B2 | 2/2018 | Fu et al. | |
| 9,938,523 B2 | 4/2018 | LaBaer | |
| 9,951,386 B2 | 4/2018 | Hindson et al. | |
| 9,988,660 B2 | 6/2018 | Rashtchian et al. | |
| 10,002,316 B2 * | 6/2018 | Fodor | C12Q 1/6813 |
| 10,011,872 B1 | 7/2018 | Belgrader et al. | |
| 10,017,761 B2 | 7/2018 | Weissman et al. | |
| 10,023,910 B2 | 7/2018 | Drmanac et al. | |
| 10,030,267 B2 | 7/2018 | Hindson et al. | |
| 10,041,116 B2 | 8/2018 | Hindson et al. | |
| 10,047,394 B2 | 8/2018 | Fodor et al. | |
| 10,059,991 B2 | 8/2018 | Fodor et al. | |
| 10,131,958 B1 | 11/2018 | Fan et al. | |
| 10,138,518 B2 | 11/2018 | Chun | |
| 10,151,003 B2 * | 12/2018 | Fan | C12N 15/1075 |
| 10,202,641 B2 | 2/2019 | Shum | |
| 10,202,646 B2 | 2/2019 | Fodor et al. | |
| 10,208,343 B2 | 2/2019 | Hindson et al. | |
| 10,208,356 B1 * | 2/2019 | Fan | C12N 15/1075 |
| 10,227,648 B2 | 3/2019 | Hindson et al. | |
| 10,246,703 B2 | 4/2019 | Church et al. | |
| 10,253,364 B2 | 4/2019 | Hindson et al. | |
| 10,253,375 B1 * | 4/2019 | Fan | C12Q 1/6876 |
| 10,266,874 B2 | 4/2019 | Weissleder et al. | |
| 10,273,541 B2 | 4/2019 | Hindson et al. | |
| 10,288,608 B2 | 5/2019 | Kozlov et al. | |
| 10,294,511 B2 | 5/2019 | Sanches-Kuiper et al. | |
| 10,301,677 B2 | 5/2019 | Shum et al. | |
| 10,308,982 B2 | 6/2019 | Chee | |
| 10,323,278 B2 | 6/2019 | Belgrader et al. | |
| 10,337,061 B2 | 7/2019 | Hindson et al. | |
| 10,338,066 B2 * | 7/2019 | Fan | G01N 33/54313 |
| 10,344,329 B2 | 7/2019 | Hindson et al. | |
| 10,392,661 B2 | 8/2019 | Fodor et al. | |
| 10,450,607 B2 | 10/2019 | Hindson et al. | |
| 10,550,429 B2 | 2/2020 | Harada et al. | |
| 10,619,186 B2 | 4/2020 | Betts et al. | |
| 10,619,203 B2 | 4/2020 | Fodor et al. | |
| RE47,983 E | 5/2020 | Gao et al. | |
| 10,669,570 B2 * | 6/2020 | Chang | C12Q 1/6816 |
| 10,676,779 B2 * | 6/2020 | Chang | C12Q 1/6804 |
| 10,927,419 B2 * | 2/2021 | Fan | C12Q 1/6874 |
| 10,954,570 B2 * | 3/2021 | Fan | C12Q 1/6876 |
| 11,092,607 B2 | 8/2021 | Gaublomme et al. | |
| 11,390,914 B2 * | 7/2022 | Fu | C12Q 1/6837 |
| 11,460,468 B2 * | 10/2022 | Fan | C12Q 1/6806 |
| 11,467,157 B2 * | 10/2022 | Fan | C12Q 1/6806 |
| 11,535,882 B2 | 12/2022 | Fu et al. | |
| 2001/0024784 A1 | 9/2001 | Wagner | |
| 2001/0036632 A1 | 11/2001 | Yu et al. | |
| 2002/0019005 A1 | 2/2002 | Kamb | |
| 2002/0051986 A1 | 5/2002 | Baez et al. | |
| 2002/0065609 A1 | 5/2002 | Ashby | |
| 2002/0072058 A1 | 6/2002 | Voelker et al. | |
| 2002/0094116 A1 | 7/2002 | Forst et al. | |
| 2002/0106666 A1 | 8/2002 | Hayashizaki | |
| 2002/0132241 A1 | 9/2002 | Fan et al. | |
| 2002/0168665 A1 | 11/2002 | Okawa | |
| 2002/0172953 A1 | 11/2002 | Mirkin et al. | |
| 2002/0187480 A1 | 12/2002 | Brandon | |
| 2002/0192687 A1 | 12/2002 | Mirkin et al. | |
| 2003/0003490 A1 | 1/2003 | Fan et al. | |
| 2003/0013091 A1 | 1/2003 | Dimitrov | |
| 2003/0032049 A1 | 2/2003 | Wagner | |
| 2003/0049616 A1 | 3/2003 | Brenner et al. | |
| 2003/0077611 A1 | 4/2003 | Slepnev | |
| 2003/0082818 A1 | 5/2003 | Bahnson et al. | |
| 2003/0087242 A1 | 5/2003 | Mirkin et al. | |
| 2003/0104436 A1 | 6/2003 | Morris et al. | |
| 2003/0165935 A1 | 9/2003 | Vann et al. | |
| 2003/0175908 A1 | 9/2003 | Linnarsson | |
| 2003/0186251 A1 | 10/2003 | Dunn et al. | |
| 2003/0207296 A1 | 11/2003 | Park et al. | |
| 2003/0207300 A1 | 11/2003 | Matray et al. | |
| 2004/0047769 A1 | 3/2004 | Tanaami | |
| 2004/0091864 A1 | 5/2004 | French et al. | |
| 2004/0096368 A1 | 5/2004 | Davis et al. | |
| 2004/0096892 A1 | 5/2004 | Wang et al. | |
| 2004/0121342 A1 | 6/2004 | McKeown | |
| 2004/0146901 A1 | 7/2004 | Morris et al. | |
| 2004/0147435 A1 | 7/2004 | Hawiger et al. | |
| 2004/0157243 A1 | 8/2004 | Huang et al. | |
| 2004/0209298 A1 | 10/2004 | Kamberov et al. | |
| 2004/0224325 A1 | 11/2004 | Knapp et al. | |
| 2004/0259118 A1 | 12/2004 | Macevicz | |
| 2005/0019776 A1 | 1/2005 | Callow et al. | |
| 2005/0032110 A1 | 2/2005 | Shen et al. | |
| 2005/0048500 A1 | 3/2005 | Lawton | |
| 2005/0053952 A1 | 3/2005 | Hong et al. | |
| 2005/0105077 A1 | 5/2005 | Padmanabhan et al. | |
| 2005/0170373 A1 | 8/2005 | Monforte | |
| 2005/0175993 A1 | 8/2005 | Wei | |
| 2005/0196760 A1 | 9/2005 | Pemov et al. | |
| 2005/0214825 A1 | 9/2005 | Stuelpnagel | |
| 2005/0250146 A1 | 11/2005 | McMillan | |
| 2005/0250147 A1 | 11/2005 | Macevicz | |
| 2006/0002824 A1 | 1/2006 | Chang et al. | |
| 2006/0035258 A1 | 2/2006 | Tadakamalla et al. | |
| 2006/0040297 A1 | 2/2006 | Leamon et al. | |
| 2006/0041385 A1 | 2/2006 | Bauer | |
| 2006/0057634 A1 | 3/2006 | Rye | |
| 2006/0073506 A1 | 4/2006 | Christians et al. | |
| 2006/0211030 A1 | 9/2006 | Brenner | |
| 2006/0257902 A1 | 11/2006 | Mendoza et al. | |
| 2006/0263709 A1 | 11/2006 | Matsumura et al. | |
| 2006/0263789 A1 | 11/2006 | Kincaid | |
| 2006/0280352 A1 | 12/2006 | Muschler et al. | |
| 2006/0281092 A1 | 12/2006 | Wille et al. | |
| 2006/0286570 A1 | 12/2006 | Rowlen et al. | |
| 2007/0020640 A1 | 1/2007 | Mccloskey et al. | |
| 2007/0031829 A1 | 2/2007 | Yasuno et al. | |
| 2007/0042400 A1 | 2/2007 | Choi et al. | |
| 2007/0042419 A1 | 2/2007 | Barany et al. | |
| 2007/0065823 A1 | 3/2007 | Dressman et al. | |
| 2007/0065844 A1 | 3/2007 | Golub et al. | |
| 2007/0105090 A1 | 5/2007 | Cassidy et al. | |
| 2007/0117121 A1 | 5/2007 | Hutchison et al. | |
| 2007/0117134 A1 | 5/2007 | Kou | |
| 2007/0117177 A1 | 5/2007 | Luo et al. | |
| 2007/0133856 A1 | 6/2007 | Dutta-Choudhury | |
| 2007/0172873 A1 | 7/2007 | Brenner et al. | |
| 2007/0178478 A1 | 8/2007 | Dhallan et al. | |
| 2007/0202523 A1 | 8/2007 | Becker et al. | |
| 2007/0281317 A1 | 12/2007 | Becker et al. | |
| 2008/0038727 A1 | 2/2008 | Spier | |
| 2008/0070303 A1 | 3/2008 | West et al. | |
| 2008/0119736 A1 | 5/2008 | Dentinger | |
| 2008/0194414 A1 | 8/2008 | Albert et al. | |
| 2008/0261204 A1 | 10/2008 | Lexow | |
| 2008/0268508 A1 | 10/2008 | Sowlay | |
| 2008/0269068 A1 | 10/2008 | Church et al. | |
| 2008/0274458 A1 | 11/2008 | Latham et al. | |
| 2008/0299609 A1 | 12/2008 | Kwon et al. | |
| 2008/0318802 A1 | 12/2008 | Brenner | |
| 2009/0053669 A1 | 2/2009 | Liu et al. | |
| 2009/0061513 A1 | 3/2009 | Andersson Svahn et al. | |
| 2009/0105959 A1 | 4/2009 | Braverman et al. | |
| 2009/0131269 A1 | 5/2009 | Martin et al. | |
| 2009/0137407 A1 | 5/2009 | Church et al. | |
| 2009/0220385 A1 | 9/2009 | Brown et al. | |
| 2009/0226891 A2 | 9/2009 | Nova et al. | |
| 2009/0252414 A1 | 10/2009 | Suzuki | |
| 2009/0253586 A1 | 10/2009 | Nelson et al. | |
| 2009/0283676 A1 | 11/2009 | Skoglund | |
| 2009/0290151 A1 | 11/2009 | Agrawal et al. | |
| 2009/0298709 A1 | 12/2009 | Ma | |
| 2009/0311694 A1 | 12/2009 | Gallagher et al. | |
| 2010/0069250 A1 | 3/2010 | White, III | |
| 2010/0105049 A1 | 4/2010 | Ehrich et al. | |
| 2010/0105112 A1 | 4/2010 | Holtze et al. | |

(56) References Cited

U.S. PATENT DOCUMENTS

| | | |
|---|---|---|
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0010151 A1 | 1/2016 | Fan et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0253584 A1 | 9/2016 | Fodor et al. |

(56) References Cited

U.S. PATENT DOCUMENTS

| | | |
|---|---|---|
| 2016/0257993 A1 | 9/2016 | Fu et al. |
| 2016/0258012 A2 | 9/2016 | Fodor et al. |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0289740 A1 | 10/2016 | Fu et al. |
| 2016/0298180 A1 | 10/2016 | Chee |
| 2016/0312276 A1* | 10/2016 | Fu ................. C12Q 1/6855 |
| 2016/0320720 A1 | 11/2016 | Murata et al. |
| 2016/0326584 A1 | 11/2016 | Fodor et al. |
| 2016/0355879 A1 | 12/2016 | Kamberov et al. |
| 2016/0362730 A1 | 12/2016 | Alexander et al. |
| 2016/0376583 A1 | 12/2016 | Fodor et al. |
| 2016/0376648 A1 | 12/2016 | Fodor et al. |
| 2017/0044525 A1 | 2/2017 | Kaper et al. |
| 2017/0073730 A1 | 3/2017 | Betts et al. |
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0337459 A1 | 11/2017 | Fodor et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0002764 A1 | 1/2018 | Fan et al. |
| 2018/0016634 A1 | 1/2018 | Hindson et al. |
| 2018/0024139 A1* | 1/2018 | Peikon ............ C12Q 1/6804 506/4 |
| 2018/0030504 A1* | 2/2018 | Nolan ............. C12Q 1/6804 |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0258500 A1 | 9/2018 | Fan et al. |
| 2018/0267036 A1 | 9/2018 | Fan et al. |
| 2018/0276332 A1 | 9/2018 | Fan et al. |
| 2018/0282803 A1 | 10/2018 | Belgrader et al. |
| 2018/0291470 A1 | 10/2018 | Fan et al. |
| 2018/0002738 A1 | 11/2018 | Wang et al. |
| 2018/0320241 A1 | 11/2018 | Nolan et al. |
| 2018/0327835 A1 | 11/2018 | Fodor et al. |
| 2018/0327836 A1 | 11/2018 | Fodor et al. |
| 2018/0327866 A1 | 11/2018 | Fan et al. |
| 2018/0327867 A1 | 11/2018 | Fan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0040474 A1 | 2/2019 | Fan et al. |
| 2019/0085412 A1 | 3/2019 | Fan et al. |
| 2019/0095578 A1 | 3/2019 | Shum et al. |
| 2019/0100798 A1 | 4/2019 | Fodor et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0145982 A1* | 5/2019 | Chee ............... G01N 33/6824 435/6.11 |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338278 A1 | 11/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0124601 A1 | 4/2020 | Fan et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |
| 2023/0083422 A1 | 3/2023 | Fu et al. |
| 2023/0109336 A1 | 4/2023 | Shum et al. |

FOREIGN PATENT DOCUMENTS

| | | |
|---|---|---|
| EP | 1473080 | 11/2004 |
| EP | 1647600 | 4/2006 |
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 1745155 | 10/2014 |
| EP | 2805769 | 11/2014 |
| EP | 2556171 | 9/2015 |

(56) References Cited

FOREIGN PATENT DOCUMENTS

| | | |
|---|---|---|
| EP | 2970958 | 12/2017 |
| EP | 3263715 | 1/2018 |
| EP | 2670863 B1 | 6/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 A | 3/2001 |
| JP | 2005233974 | 9/2005 |
| JP | 2007504831 | 3/2007 |
| JP | 2008256428 | 10/2008 |
| JP | 2013039275 | 2/2013 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2010131645 | 11/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |

(56) References Cited

FOREIGN PATENT DOCUMENTS

| | | |
|---|---|---|
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020219721 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO20210178199 | 9/2021 |
| WO | WO2021247593 | 12/2021 |
| WO | WO2022015667 | 1/2022 |
| WO | WO2022026909 | 2/2022 |
| WO | WO2022040453 | 2/2022 |
| WO | WO2022143221 | 7/2022 |
| WO | WO2022256324 | 12/2022 |
| WO | WO2023/034739 | 3/2023 |
| WO | WO2023/034789 | 3/2023 |
| WO | WO2023/034790 | 3/2023 |
| WO | WO2023/034794 | 3/2023 |
| WO | WO2023/034872 | 3/2023 |
| WO | WO2023/039433 | 3/2023 |

OTHER PUBLICATIONS

Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, "Useful fundamental numbers in molecular biology," http://bionumbers.hms.harvard.edu/KeyNumbers/aspx, 1-4.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.

(56) References Cited

OTHER PUBLICATIONS

Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster. AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition." EpiBio 2009. 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chern Int Ed Engl. 2011, 50(10), 2289-2293.
Chee et al., "Accessing genetic information with high-density DNA arrays," Science 1996, 274, 610-614.

Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "Smart™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 21, 2016 in European Patent Application No. EP 10762102.1.
Complaint filed in *Becton, Dickinson and Company and Cellular Research Inc.* v. *10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomic's Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.

(56) References Cited

OTHER PUBLICATIONS

Defendant 10X Genomic's Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to *Becton, Dickinson, and Company and Cellular Research, Inc.*, dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomic's Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomic's Request for Oral Argument Under D. Del. LR 7.1.4, dated Apr. 18, 2019 in the USDC for the District of Delaware, C.A. 18-1800-RGA 2 pp.
Defendant 10X Genomic's Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.

(56) References Cited

OTHER PUBLICATIONS

Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.

Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 15, 2019 in PCT Application No. PCT/US2018/014385.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.

(56) References Cited

OTHER PUBLICATIONS

International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated Jun. 30, 2020 in PCT Application No. PCT/US2020/017890.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA). 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., iCLIP reveals the function of hnRNAP particles in splicing at individual nucleotide resolution, Nature Structural & Molecular Biology 2010, 17(7), 909-916.

(56) References Cited

OTHER PUBLICATIONS

Kotake et al., "A simple nested RT-PCR method for quantitation of the relative amounts of multiple cytokine mRNAs in small tissue samples," Journal of Immunological Methods 1996, 199, 193-203.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chern. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in Bacillus subtilis," Science 2007, 317, 526-529.
Macaulay et al., "Single Cell Genomics: Advances and Future Perspectives," PLoS Genetics 2014, 10(1), 1-9.
Macaulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
Mccloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chern. 2001, 73, 1043-1047.
Navin et al., "The first five years of single-cell cancer genomics and beyond," Genome Research 2015, 25, 1499-1507.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.

(56) References Cited

OTHER PUBLICATIONS

Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.

(56) References Cited

OTHER PUBLICATIONS

Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and—Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Roche Diagnostics GmbH, "Genome Sequencer 20 System: First to the Finish," 2006, 1 -40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody—DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.

(56) References Cited

OTHER PUBLICATIONS

Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10). 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for *Mycobacterium tuberculosis* DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.

(56) References Cited

OTHER PUBLICATIONS

Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91 (5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21 (9), 1529-1542.
Ye et al., Fluorescent microsphere-based readout technology for multiplexed human single nucleotide polymorphism analysis and bacterial identification. Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
Advisory Action dated Aug. 25, 2020 in U.S. Appl. No. 15/084,307.
Biosciences Product Catalogue, Dynal® Catalog 1999, Oslo, Norway, 49-51.
Examination Report dated Jul. 6, 2020 in European Patent Application No. 17781265.8.
Examination Report dated Sep. 21, 2020 in European Patent Application No. 18703156.2.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
International Search Report and Written Opinion dated May 18, 2020 in PCT Application No. PCT/US2020/014339.
Kooiker & Xue, "cDNA Library Preparation," Cereal Genomics 2013, 1099, 29-40.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Notice of Allowance dated Sep. 23, 2020 in Korean Patent Application No. 10-2016-7008144.
Notice of Allowance dated Oct. 29, 2020 in U.S. Appl. No. 15/987,851.
Office Action dated Jul. 20, 2020 in Japanese Patent Application No. 2018-512152.
Rhee et al., "Simultaneous detection of mRNA and protein stem cell markers in live cells," BMC Biotechnology 2009, 9(30), 1-10.
Search Report and Written Opinion dated Aug. 26, 2020 in Singapore Patent Application No. 10201806890V.
S.H.KO, "An 'equalized cDNA library' by the reassociation of short double-stranded cDNAs," Nucleic Acids Res. 1990, 18(19), 5705-5711.
Adey et al., "Rapid, low-input, low-bias construction of shotgun fragment libraries by high-density in vitro transposition," Genome Biology 2010, 11 (R19), in 17 pages.
Ahern, "Biochemical, Reagent Kits Offer Scientists Good Return on Investment," The Scientist 1995, 9(15), in 5 pages.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
Chang et al., "Single-cell protein and gene expression profiling of stem memory T cells by BD Ab-seq," Annual Joint Meeting of the American Society for Cell Biology and the European Molecular Biology Organization 2017, 28(26), P1896.
Chen et al., "High-throughput sequencing of the transcriptome and chromatin accessibility in the same cell," Nature Biotechnology 2019, 37, 1452-1457.
Dengl et al., "Engineered hapten-binding antibody derivatives for modulation of pharmacokinetic properties of small molecules and targeted payload delivery," Immunol Rev. 2016, 270, 165-177.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Extended European Search Report dated May 6, 2021 in European Patent Application No. 20207621.2.
Extended European Search Report dated May 28, 2021 in European Patent Application No. 20209777.0.

(56) References Cited

OTHER PUBLICATIONS

Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Fitzgerald and Grivel, "A Universal Nanoparticle Cell Secretion Capture Assay," Cytometry Part A 2012, 83A(2), 205-211.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Minnoye et al., "Chromatin accessibility profiling methods," Nature Reviews Method Primers 2021, 1-24.
Monneron, "One-step Isolation and Characterization of Nuclear Membranes, 1974 Electron Microscopy and Composition of Biological Membranes and Envelops," The Royal Publishing Society 1974, 268, 101-108.
New COVID-19 Variants, Centers for Disease Control and Prevention 2021, accessed Jan. 21, 2021, 3 pp.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.

(56) References Cited

OTHER PUBLICATIONS

Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 2017800587991.
Office Action dated Feb. 9, 2022 in Japanese Patent Application No. 2019-540515.
Office Action dated Mar. 7, 2022 in Korean Patent Application No. 10-2022-7004715.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
O'shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated May 5, 2021 in U.S. Appl. No. 16/400,886.
Restriction Requirement dated May 28, 2021 in U.S. Appl. No. 16/781,814.
Restriction Requirement dated Jun. 4, 2021 in U.S. Appl. No. 16/551,620.
Restriction Requirement dated Sep. 20, 2021 in U.S. Appl. No. 16/525,054.
Restriction Requirement dated Oct. 1, 2021 in U.S. Appl. No. 16/525,054.
Restriction Requirement dated Dec. 27, 2021 in U.S. Appl. No. 16/747,737.
Restriction Requirement dated Aug. 8, 2022 in U.S. Appl. No. 17/163,177.
Restriction Requirement dated Aug. 11, 2022 in U.S. Appl. No. 17/091,639.

(56) References Cited

OTHER PUBLICATIONS

Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Stoeckius et al., "Cell Hashing with barcoded antibodies enables multiplexing and doublet detection for single cell genomics," Genome Biology 2018, 19(224), 1-12.
Summons to Attend Oral Proceedings dated Nov. 16, 2020 in European Patent Application No. 17202409.3.
Takara Bio, "SMARTer Human BCR IgG IgM H/K/L Profiling Kit User Manual," Takara Bio USA Inc. 2019, 1-22.
TotalSeq™-A0251 anti-human Hashtag 1 Antibody, BioLegend®, Jul. 2018, 1-10.
Trzupek et al., "Discovery of CD80 and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Yang & Zhao, "Quantitative Analysis of Nonoxynol-9 in Blood," Contraception 1991, 43(2), 161-166.
Zeberg et al., "The major genetic risk factor for severe COVID-19 is inherited from Neanderthals," Nature 2020, 587(7835), 1-13.
Zhang et al., "Immunoaffinity Purification of Plasma Membrane with Secondary Antibody Superparamagnetic Beads," Journal of Proteome 2006, 6, 34-43.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
De Simone et al., "Single Cell T Cell Receptor Sequencing: Techniques and Future Challenges," Frontiers in Immunology 2018, 9(1638), 1-7.
Dovgan et al., "Antibody—Oligonucleotide Conjugates as Therapeutic, Imaging, and Detection Agents," Bioconjugate Chem. 2019, 30, 2483-2501.
Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
Lee et al., "Comparison of Surface Markers between Human and Rabbit Mesenchymal Stem Cells," PLoS ONE 2014, 9(11), in 10 pages.
Mayer et al., "Obtaining deeper insights into microbiome diversity using a simple method to block host and nontargets in amplicon sequencing," Molecular Ecology Resources 2021, 21(6), 1952-1965.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Notice of Allowance dated Apr. 26, 2022 in Chinese Patent Application No. 201780058799.1.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Office Action dated May 5, 2022 in European Patent Application No. 19787547.9.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.

(56) References Cited

OTHER PUBLICATIONS

Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 4, 2023 in U.S. Appl. No. 17/161,558.
Uellendahl-Werth et al., "A benchmark of hemoglobin blocking during library preparation for mRNA Sequencing of human blood samples," Scientific Reports 2020, 10(1), 5630.
Wangsanuwat et al., "Efficient and cost-effective bacterial mRNA sequencing from low input samples through ribosomal RNA depletion," BMC Genomics 2020, 21(1), 1-12.

* cited by examiner

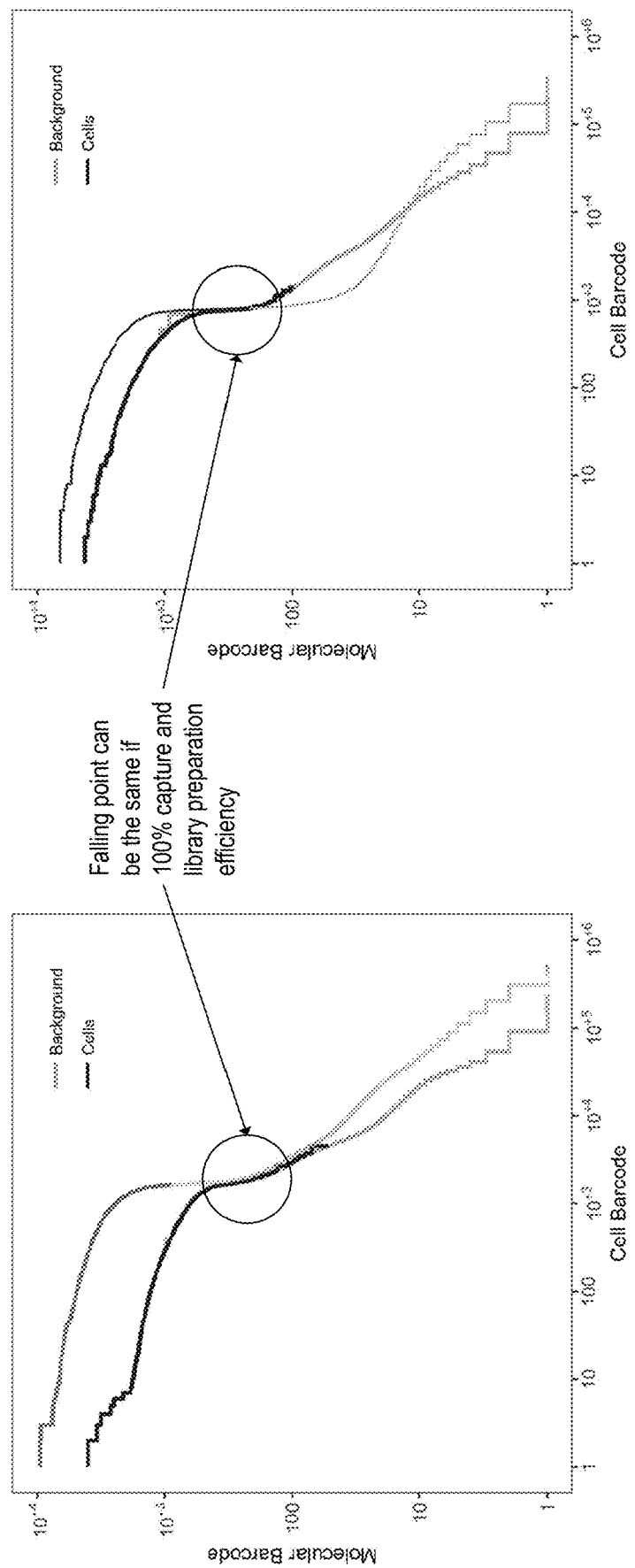

ON DEMAND CONJUGATES REQUEST FORM

FORMAT: [BV421 ▼] (1501a)

CLONE: [CD4 – RPA-T4 ▼] (1501b)

QUANTITY (MINIMUM 50 ug): [50] (1502)

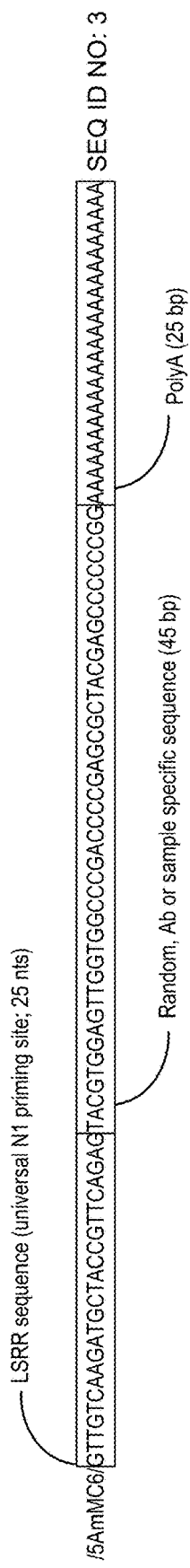
FIG. 18

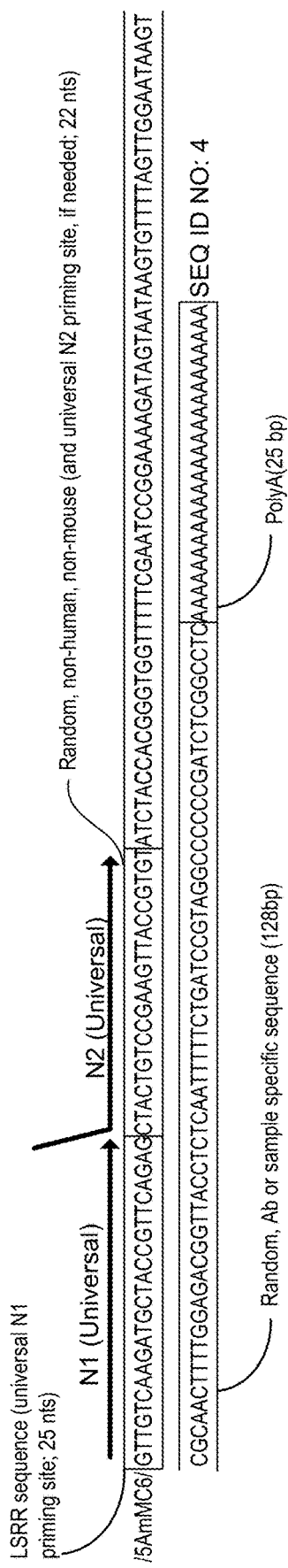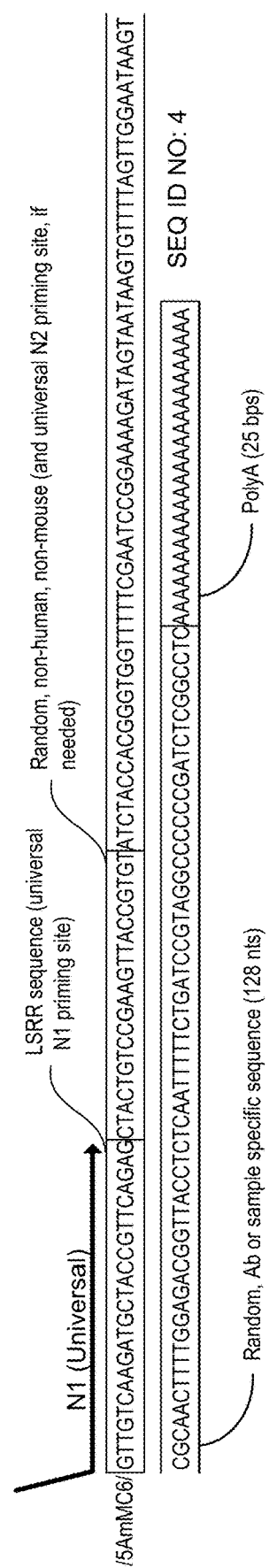
FIG. 18 (Continued)

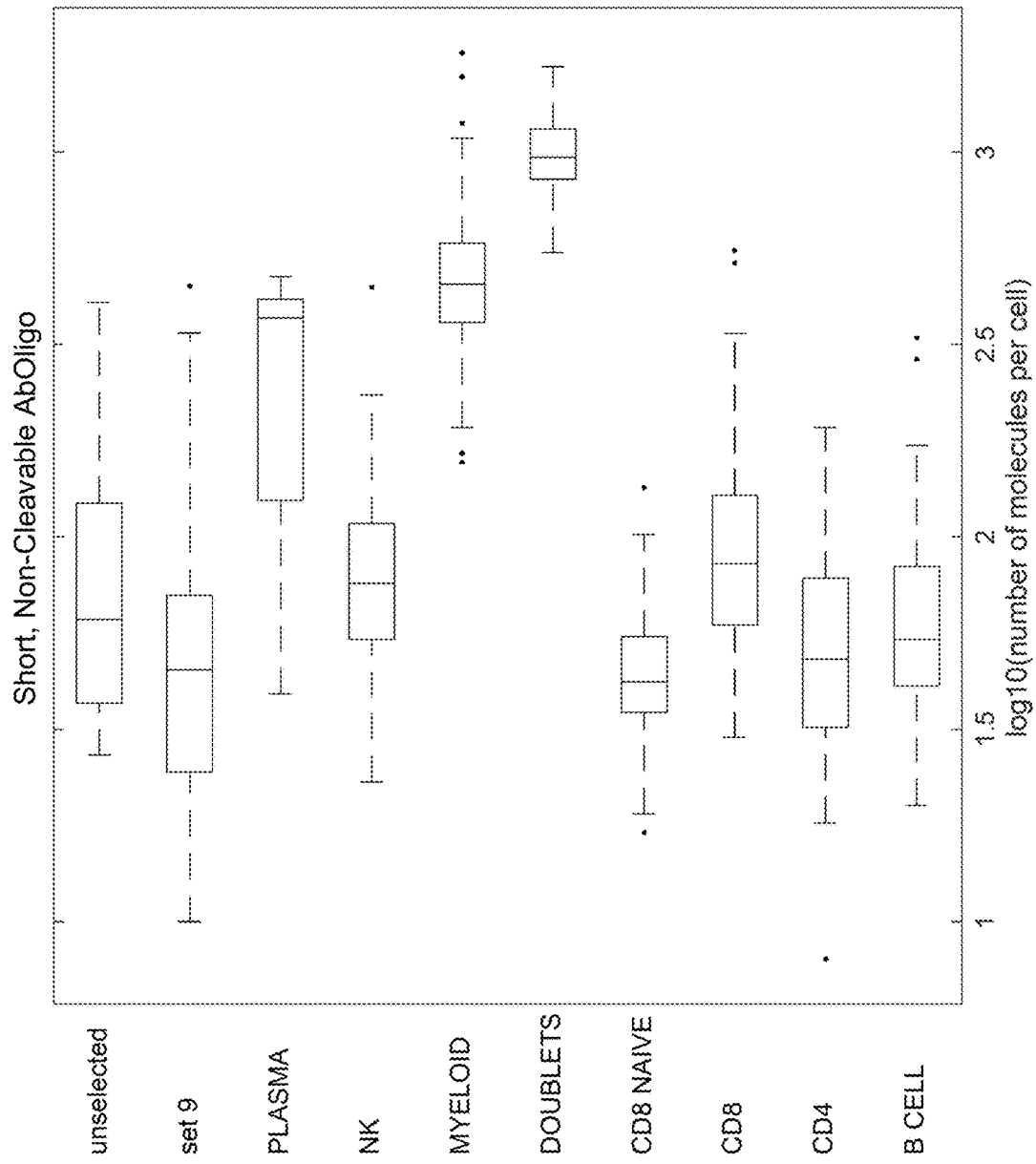

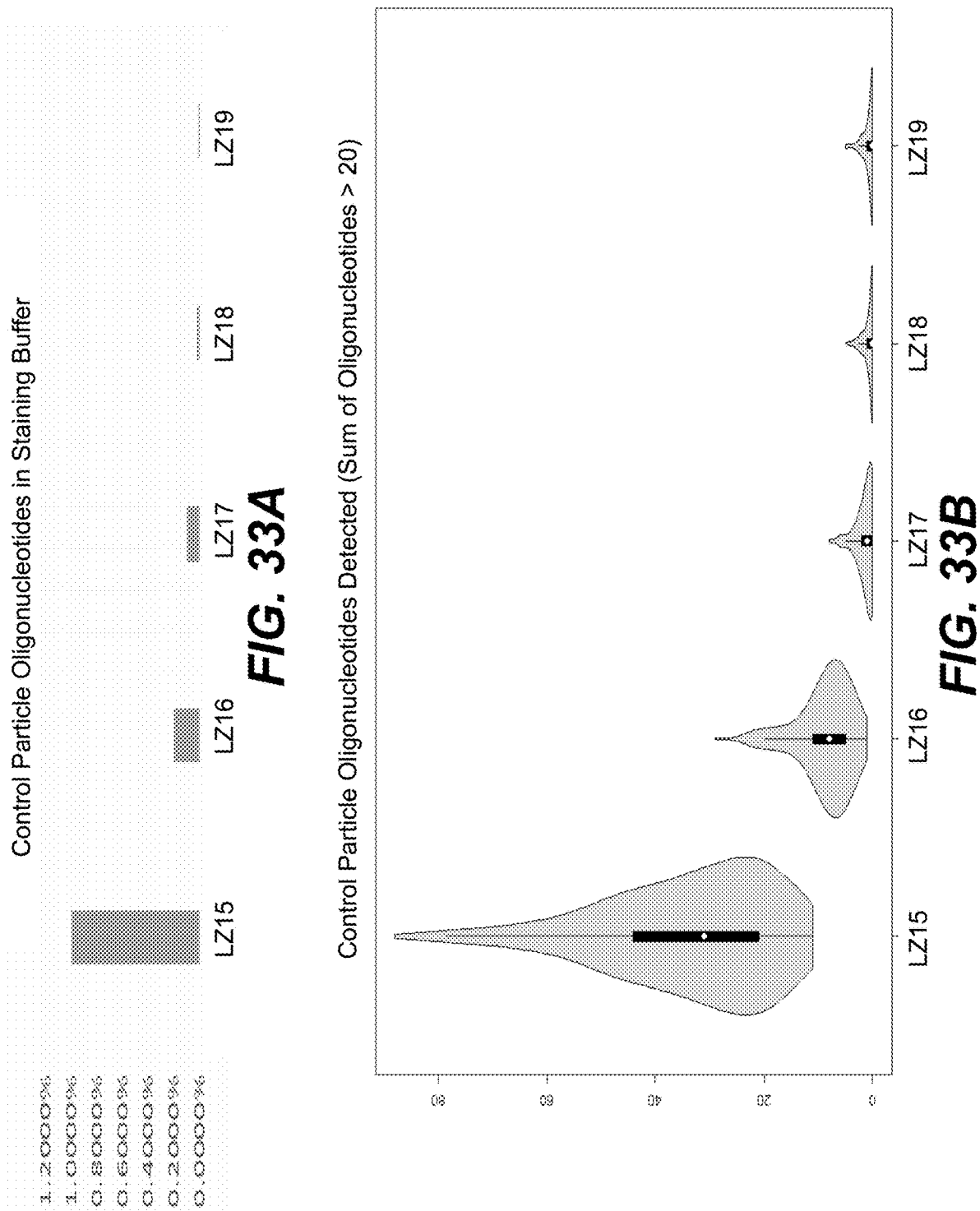

MEASUREMENT OF PROTEIN EXPRESSION USING REAGENTS WITH BARCODED OLIGONUCLEOTIDE SEQUENCES

RELATED APPLICATIONS

The present application is a continuation of U.S. patent application Ser. No. 15/993,468, filed on May 30, 2018, which is a continuation of U.S. patent application Ser. No. 15/715,028, filed on Sep. 25, 2017, which claims priority under 35 U.S.C. § 119(e) to U.S. Provisional Application No. 62/399,795, filed on Sep. 26, 2016; U.S. Provisional Application No. 62/464,279, filed on Feb. 27, 2017; and U.S. Provisional Application No. 62/515,952, filed on Jun. 6, 2017. The content of each of these related applications is herein expressly incorporated by reference in its entirety.

REFERENCE TO SEQUENCE LISTING

The present application is being filed along with a Sequence Listing in electronic format. The Sequence Listing is provided as a file entitled Sequence_Listing.txt, created Jul. 1, 2019 which is 2,779 bytes in size. The information in the electronic format of the Sequence Listing is incorporated herein by reference in its entirety.

BACKGROUND

Field

The present disclosure relates generally to molecular biology, and more particular to simultaneous measurements of protein expressions and gene expressions.

Description of the Related Art

Current technology allows measurement of gene expression of single cells in a massively parallel manner (e.g., >10,000 cells) by attaching cell specific oligonucleotide barcodes to poly(A) mRNA molecules from individual cells as each of the cells is co-localized with a barcoded reagent bead in a picoliter microwell. Other available technologies allow measurement of gene expression of 96 to 384 single cells at a time. Indexed sorting can be achieved by first labeling cells with fluorescent antibodies and sorting by a flow sorter, e.g. BD FACSseq machine. FACSseq is an affordable flow sorter that allows one parameter sorting. For researchers who would like to examine expression of multiple proteins, they would require a more complex multi-color flow sorter.

There is a need for methods and systems that can quantitatively analyze protein expression as well as methods and systems that allow simultaneous measurement of protein expression and gene expression in cells.

SUMMARY

Some embodiments disclosed herein provide a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to a protein target. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, oligonucleotide is conjugated to the protein binding reagent through a linker. In some embodiments, the linker comprises a chemical group. In some embodiments, the oligonucleotide comprises the linker. In some embodiments, the chemical group is reversibly attached to the protein binding reagent. In some embodiments, the chemical group is selected from the group consisting of a UV photocleavable group, a streptavidin, a biotin, an amine, and any combination thereof. In some embodiments, the unique identifier is not homologous to genomic sequences of a sample. In some embodiments, the sample is a single cell, a plurality of cells, a tissue, a tumor sample, or any combination thereof. In some embodiments, the sample is a mammalian sample, a bacterial sample, a viral sample, a yeast sample, a fungal sample, or any combination thereof. In some embodiments, the oligonucleotide comprises a barcode sequence (e.g., a molecular label sequence), a poly(A) tail, or a combination thereof. In some embodiments, the plurality of compositions comprises at least 100 different protein binding reagents. In some embodiments, the plurality of compositions comprises at least 100 different protein binding reagents. In some embodiments, the plurality of compositions comprises at least 1,000 different protein binding reagents. In some embodiments, the plurality of compositions comprises at least 10,000 different protein binding reagents. In some embodiments, each protein binding reagent is conjugated with one or more oligonucleotides comprising at least one barcode sequence selected from a set of at least 10 different barcode sequences. In some embodiments, each protein binding reagent is conjugated with one or more oligonucleotides comprising at least one barcode sequence selected from a set of at least 100 different barcode sequences. In some embodiments, each protein binding reagent is conjugated with one or more oligonucleotides comprising at least one barcode sequence selected from a set of at least 1,000 different barcode sequences. The plurality of compositions can further comprise a second protein binding reagent not conjugated with the oligonucleotide. The protein binding reagent and the second protein binding reagent can be the same. In some embodiments, the plurality of compositions is capable of specifically binding to a plurality of protein targets. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets comprises 10-400 different protein targets.

Some embodiments disclosed herein provide methods of quantitative analysis of a plurality of protein targets in a sample comprising: providing a sample comprising a plurality of protein targets; providing a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to at least one of the plurality of protein targets; contacting the plurality of compositions with the sample for specific binding with the plurality of protein targets; removing unbound compositions; providing a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences; contacting the plurality of oligonucleotide probes with the oligonucleotides of the plurality of compositions; extending the oligonucleotide probes hybridized to the oligonucleotides to produce a plurality of labeled nucleic acids, wherein each of the labeled nucleic acid comprises a unique identifier and a barcode sequence; and determining the number of unique barcode sequences for each unique identifier, whereby the quantity of each protein target in the sample is determined. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, oligonucleotide is conjugated to the protein binding reagent through a linker. In some embodiments, the linker comprises a chemical group. In some embodiments, the oligonucleotide comprises the linker. In some embodiments, the chemical group is reversibly attached to the protein binding reagent. In some embodiments, the chemical group is selected from the group consisting of a UV photocleavable group, a streptavidin, a biotin, an amine, and any combination thereof. In some embodiments, the sample comprises a single cell. In some embodiments, the plurality of protein targets is expressed on the surface of the single cell. In some embodiments, the removing unbound compositions comprises washing the single cell with a washing buffer. In some embodiments, the methods comprise lysing the single cell. In some embodiments, the methods comprise detaching the oligonucleotides from the protein binding reagents. In some embodiments, the oligonucleotides are detached from the protein binding reagent by UV photocleaving, chemical treatment (dithiothreitol), heating, enzyme treatment, or any combination thereof. In some embodiments, each of the oligonucleotide probes comprises a cell label, a binding site for a universal primer, or any combination thereof. In some embodiments, the target binding region comprises poly(dT). In some embodiments, the plurality of oligonucleotide probes is immobilized on a solid support. In some embodiments, the solid support is a bead. In some embodiments, the methods further comprise amplifying the plurality of labeled nucleic acids to produce a plurality of amplicons. In some embodiments, the amplifying comprises PCR amplification of at least a portion of the barcode sequence, and at least a portion of the unique identifier. In some embodiments, the diverse set of unique barcode sequences comprises at least 100 unique barcode sequences. In some embodiments, the diverse set of unique barcode sequences comprises at least 1,000 unique barcode sequences. In some embodiments, the diverse set of unique barcode sequences comprises at least 10,000 unique barcode sequences. The plurality of compositions can further comprise a second protein binding reagent not conjugated with the oligonucleotide. The protein binding reagent and the second protein binding reagent can be the same. In some embodiments, the methods further comprise sequencing the plurality of amplicons. In some embodiments, the sequencing comprises sequencing at least a portion of the barcode sequence, and at least a portion of the unique identifier.

Some embodiments disclosed herein provide methods of simultaneous quantitative analysis of a plurality of protein targets and a plurality of nucleic acid target molecules in a sample comprising: providing a sample comprising a plurality of protein targets and a plurality of nucleic acid target molecules; providing a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to at least one of the plurality of protein targets; contacting the plurality of compositions with the sample for specific binding with the plurality of protein targets; removing unbound compositions; providing a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences; contacting the plurality of oligonucleotide probes with the oligonucleotides of the compositions and the plurality of nucleic acid target molecules for hybridization; extending the oligonucleotide probes hybridized to the oligonucleotides and nucleic acid target molecules to produce a plurality of labeled nucleic acids, wherein each of the labeled nucleic acid comprises a unique identifier or a nucleic acid target molecule, and a barcode sequence; and determining the number of unique barcode sequences for each unique identifier and each nucleic acid target molecule, whereby the quantity of each protein target and each nucleic acid target molecule in the sample is determined. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, oligonucleotide is conjugated to the protein binding reagent through a linker. In some embodiments, the linker comprises a chemical group. In some embodiments, the oligonucleotide comprises the linker. In some embodiments, the chemical group is reversibly attached to the protein binding reagent. In some embodiments, the chemical group is selected from the group consisting of a UV photocleavable group, a streptavidin, a biotin, an amine, and any combination thereof. In some embodiments, the sample comprises a single cell. In some embodiments, the plurality of protein targets is expressed on the surface of the single cell. In some embodiments, the removing unbound compositions comprises washing the single cell with a washing buffer. In some embodiments, the methods comprise lysing the single cell. In some embodiments, the methods comprise detaching the oligonucleotides from the protein binding reagents. In some embodiments, the oligonucleotides are detached from the protein binding reagent by UV photocleaving, chemical treatment (dithiothreitol), heating, enzyme treatment, or any combination thereof. In some embodiments, each of the oligonucleotide probes comprises a cell label, a binding site for a universal primer, or any combination thereof. In some embodiments, the target binding region comprises poly(dT). In some embodiments, the plurality of oligonucleotide probes is immobilized on a solid support. In some embodiments, the solid support is a bead. In some embodiments, the methods further comprise amplifying the plurality of labeled nucleic acids to produce a plurality of amplicons. In some embodiments, the amplifying comprises PCR amplification of at least a portion of the barcode sequence, at least a portion of the unique identifier, and at least a portion of the nucleic acid target molecule. In some embodiments, the diverse set of unique barcode sequences comprises at least 100 unique barcode sequences. In some embodiments, the diverse set of unique barcode sequences comprises at least 1,000 unique barcode sequences. In some embodiments, the diverse set of unique barcode sequences comprises at least 10,000 unique barcode sequences. The plurality of compositions can further comprise a second protein binding reagent not conjugated with the oligonucleotide. The protein binding reagent and the second protein binding reagent can be the same. In some embodiments, the methods further comprise sequencing the plurality of amplicons. In some embodiments, the sequencing comprises sequencing at least a portion of the barcode sequence, at least a portion of the unique identifier, and at least a portion of the nucleic acid target molecule.

Some embodiments disclosed herein provide kits for simultaneous quantitative analysis of a plurality of protein targets and a plurality of nucleic acid target molecules in a sample comprising a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to a protein target, and a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences. Disclosed herein include kits for simultaneous quantitative analysis of a plurality of protein targets and a plurality of nucleic acid target molecules in a sample comprising a plurality of compositions each comprising two or more protein binding reagents each conjugated with an oligonucleotide, wherein the oligonucleotide comprises a unique identifier for one of the two or more protein binding reagents that it is conjugated therewith, and the protein binding reagents are capable of specifically binding to a protein target, and a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences. Disclosed herein include kits for simultaneous quantitative analysis of a plurality of protein targets and a plurality of nucleic acid target molecules in a sample comprising a plurality of compositions each comprising two or more protein binding reagents each conjugated with an oligonucleotide, wherein the oligonucleotide comprises a unique identifier for the protein binding reagent that it is conjugated therewith, and the protein binding reagents are capable of specifically binding to a protein target, and a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences.

In some embodiments, each of the oligonucleotide probes comprises a cell label, a binding site for a universal primer, or any combination thereof. In some embodiments, the target binding region comprises poly(dT). In some embodiments, the plurality of oligonucleotide probes is immobilized on a solid support. In some embodiments, the solid support is a bead. In some embodiments, the diverse set of unique barcode sequences comprises at least 100 unique barcode sequences. In some embodiments, the diverse set of unique barcode sequences comprises at least 1,000 unique barcode sequences. In some embodiments, the diverse set of unique barcode sequences comprises at least 10,000 unique barcode sequences. In some embodiments, the kits comprise at least 1,000 oligonucleotide probes. In some embodiments, the kits comprise at least 10,000 oligonucleotide probes. In some embodiments, the kits comprise at least 100,000 oligonucleotide probes. In some embodiments, the kits comprise at least 1,000,000 oligonucleotide probes. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. The plurality of compositions can further comprise a second protein binding reagent not conjugated with the oligonucleotide. The protein binding reagent and the second protein binding reagent can be the same. In some embodiments, the plurality of compositions comprises a plurality of antibodies, a plurality of aptamers, or a combination thereof. In some embodiments, oligonucleotide is conjugated to the protein binding reagent through a linker. In some embodiments, the linker comprises a chemical group. In some embodiments, the oligonucleotide comprises the linker. In some embodiments, the chemical group is reversibly attached to the protein binding reagent. In some embodiments, the chemical group is selected from the group consisting of a UV photocleavable group, a streptavidin, a biotin, an amine, and any combination thereof. In some embodiments, the unique identifier is not homologous to genomic sequences of a sample. In some embodiments, the sample is a single cell, a plurality of cells, a tissue, a tumor sample, or any combination thereof. In some embodiments, the sample is a mammalian sample, a bacterial sample, a viral sample, a yeast sample, a fungal sample, or any combination thereof. In some embodiments, the oligonucleotide comprises a barcode sequence (e.g., a molecular label sequence), a poly(A) tail, or a combination thereof. In some embodiments, the plurality of compositions comprises at least 100 different protein binding reagents. In some embodiments, the plurality of compositions comprises at least 100 different protein binding reagents. In some embodiments, the plurality of compositions comprises at least 1,000 different protein binding reagents. In some embodiments, the plurality of compositions comprises at least 10,000 different protein binding reagents. In some embodiments, the plurality of compositions comprises at least 10,000 different protein binding reagents. In some embodiments, each protein binding reagent is conjugated with one or more oligonucleotides comprising at least one barcode sequence selected from a set of at least 10 different barcode sequences. In some embodiments, each protein binding reagent is conjugated with one or more oligonucleotides comprising at least one barcode sequence selected from a set of at least 100 different barcode sequences. In some embodiments, each protein binding reagent is conjugated with one or more oligonucleotides comprising at least one barcode sequence selected from a set of at least 1,000 different barcode sequences. In some embodiments, the plurality of compositions is capable of specifically binding to a plurality of protein targets. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets comprises 10-400 different protein targets.

Some embodiments disclosed herein provide methods of identifying a biomarker in a sample comprising: providing a sample comprising a plurality of protein targets and a plurality of nucleic acid target molecules; providing a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to at least one of the plurality of protein targets; contacting the plurality of compositions with the sample for specific binding with the plurality of protein targets; removing unbound compositions; providing a plurality of oligonucleotide probes, wherein each of the plurality of oligonucleotide probes comprises a target binding region and a barcode sequence (e.g., a molecular label sequence), wherein the barcode sequence is from a diverse set of unique barcode sequences; contacting the plurality of oligonucleotide probes with the oligonucleotides of the compositions and the plurality of nucleic acid target molecules for hybridization; extending the oligonucleotide probes hybridized to the oligonucleotides and nucleic acid target molecules to produce a plurality of labeled nucleic acids, wherein each of the labeled nucleic acid comprises a unique identifier or a nucleic acid target molecule, and a barcode sequence (e.g., a molecular label sequence); determining the number of unique barcode sequences for each unique identifier and each nucleic acid target molecule; and identifying a biomarker using the quantity of a protein target or the quantity of a nucleic acid target molecule. In some embodiments, the methods comprise determining the quantity of at least one protein target and at least one nucleic acid target molecule. In some embodiments, the methods comprise comparing the quantity of at least one protein target and its corresponding nucleic acid target molecule. In some embodiments, the methods comprise identifying a biomarker if the quantity of a protein target is greater than its corresponding nucleic acid target molecule. In some embodiments, the methods comprise identifying a biomarker if the quantity of a protein target is at least 10× greater than its corresponding nucleic acid target molecule. In some embodiments, the methods comprise identifying a biomarker if the quantity of a protein target's corresponding nucleic acid target molecule is less than 10. In some embodiments, the methods comprise identifying a biomarker if the quantity of a protein target's corresponding nucleic acid target molecule is 0.

Disclosed herein include control particle compositions. In some embodiments, the control particle composition comprises a plurality of control particle oligonucleotides associated with a control particle, wherein each of the plurality of control particle oligonucleotides comprises a control barcode sequence and a poly(dA) region. At least two of the plurality of control particle oligonucleotides can comprise different control barcode sequences. The control particle oligonucleotide can comprise a barcode sequence (e.g., a molecular label sequence). The control particle oligonucleotide can comprise a binding site for a universal primer.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 5, 10, 100, 1000, or more of the plurality of control particle oligonucleotides can be identical. The control barcode sequences of about 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence, and wherein the first control barcode sequence and the second control barcode sequence have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, the control barcode sequence is not homologous to genomic sequences of a species. The control barcode sequence can be homologous to genomic sequences of a species. The species can be a non-mammalian species. The non-mammalian species can be a phage species. The phage species can be T7 phage, a PhiX phage, or a combination thereof.

In some embodiments, at least one of the plurality of control particle oligonucleotides is associated with the control particle through a linker. The at least one of the plurality of control particle oligonucleotides can comprise the linker. The linker can comprise a chemical group. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, 7.5 micrometer, or a combination thereof.

In some embodiments, the plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle. The control particle can be disruptable. The control particle can be a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The control particle can comprise a disruptable hydrogel particle.

In some embodiments, the control particle is associated with a detectable moiety. The control particle oligonucleotide can be associated with a detectable moiety.

In some embodiments, the control particle is associated with a plurality of first protein binding reagents, and at least one of the plurality of first protein binding reagents is associated with one of the plurality of control particle oligonucleotides. The first protein binding reagent can comprise a first antibody. The control particle oligonucleotide can be conjugated to the first protein binding reagent through a linker. The first control particle oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the first protein binding reagent is associated with two or more of the plurality of control particle oligonucleotides with an identical control barcode sequence. The first protein binding reagent can be associated with two or more of the plurality of control particle oligonucleotides with different control barcode sequences. In some embodiments, at least one of the plurality of first protein binding reagents is not associated with any of the plurality of control particle oligonucleotides. The first protein binding reagent associated with the control particle oligonucleotide and the first protein binding reagent not associated with any control particle oligonucleotide can be identical protein binding reagents.

In some embodiments, the control particle is associated with a plurality of second protein binding reagents. At least one of the plurality of second protein binding reagents can be associated with one of the plurality of control particle oligonucleotides. The control particle oligonucleotide associated with the first protein binding reagent and the control particle oligonucleotide associated with the second protein binding reagent can comprise different control barcode sequences. The first protein binding reagent and the second protein binding reagent can be identical protein binding reagents.

In some embodiments, the first protein binding reagent can be associated with a partner binding reagent, and wherein the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent can be associated with a detectable moiety. The second protein binding reagent can be associated with a detectable moiety.

Disclosed herein are methods for determining the numbers of targets. In some embodiments, the method comprises: barcoding (e.g., stochastically barcoding) a plurality of targets of a cell of a plurality of cells and a plurality of control particle oligonucleotides using a plurality of barcodes (e.g., stochastic barcodes) to create a plurality of barcoded targets (e.g., stochastically barcoded targets) and a plurality of barcoded control particle oligonucleotides (e.g., stochastically barcoded control particle oligonucleotides). In some embodiments, each of the plurality of stochastic barcodes comprises one or more of: a cell label sequence, a barcode sequence (e.g., a molecular label sequence), and a target-binding region. The barcode sequences of at least two barcodes of the plurality of barcodes can comprise different sequences. At least two barcodes of the plurality of barcodes can comprise an identical cell label sequence. In some embodiments, a control particle composition comprises a control particle associated with the plurality of control particle oligonucleotides, wherein each of the plurality of control particle oligonucleotides comprises a control barcode sequence and a pseudo-target region comprising a sequence substantially complementary to the target-binding region of at least one of the plurality of barcodes. The method can comprise: obtaining sequencing data of the plurality of barcoded targets and the plurality of barcoded control particle oligonucleotides; counting the number of barcode sequences with distinct sequences associated with the plurality of control particle oligonucleotides with the control barcode sequence in the sequencing data. The method can comprise: for at least one target of the plurality of targets: counting the number of barcode sequences with distinct sequences associated with the target in the sequencing data; and estimating the number of the target, wherein the number of the target estimated correlates with the number of barcode sequences with distinct sequences associated with the target counted and the number of barcode sequences with distinct sequences associated with the control barcode sequence.

In some embodiments, the pseudo-target region comprises a poly(dA) region. The pseudo-target region can comprise a subsequence of the target. In some embodiments, the control barcode sequence can be at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or any combination thereof. The control barcode sequences of at least 5, 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence. The first control barcode sequence and the second control barcode sequence can have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, counting the number of barcode sequences with distinct sequences associated with the plurality of control particle oligonucleotides with the control barcode sequence in the sequencing data comprises: counting the number of barcode sequences with distinct sequences associated with the first control barcode sequence in the sequencing data; and counting the number of barcode sequences with distinct sequences associated with the second control barcode sequence in the sequencing data. The number of the target estimated can correlate with the number of barcode sequences with distinct sequences associated with the target counted, the number of barcode sequences with distinct sequences associated with the first control barcode sequence, and the number of barcode sequences with distinct sequences associated with the second control barcode sequence. The number of the target estimated can correlate with the number of barcode sequences with distinct sequences associated with the target counted, the number of barcode sequences with distinct sequences associated with the control barcode sequence, and the number of the plurality of control particle oligonucleotides comprising the control barcode sequence. The number of the target estimated can correlate with the number of barcode sequences with distinct sequences associated with the target counted, and a ratio of the number of the plurality of control particle oligonucleotides comprising the control barcode sequence and the number of barcode sequences with distinct sequences associated with the control barcode sequence.

In some embodiments, the control particle oligonucleotide is not homologous to genomic sequences of the cell. The control particle oligonucleotide can be not homologous to genomic sequences of the species. The control particle oligonucleotide can be homologous to genomic sequences of a species. The species can be a non-mammalian species. The non-mammalian species can be a phage species. The phage species can be T7 phage, a PhiX phage, or a combination thereof.

In some embodiments, the control particle oligonucleotide can be conjugated to the control particle through a linker. At least one of the plurality of control particle oligonucleotides can be associated with the control particle through a linker. The at least one of the plurality of control particle oligonucleotides can comprise the linker. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, about 7.5 micrometer, or a combination thereof. The plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle.

In some embodiments, the method comprises releasing the at least one of the plurality of control particle oligonucleotides from the control particle prior to barcoding the plurality of targets and the control particle and the plurality of control particle oligonucleotides.

In some embodiments, the control particle is disruptable. The control particle can be a control particle bead. The control particle bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The control particle can comprise a disruptable hydrogel particle.

In some embodiments, the control particle is associated with a detectable moiety. The control particle oligonucleotide can be associated with a detectable moiety.

In some embodiments, the control particle can be associated with a plurality of first protein binding reagents, and at least one of the plurality of first protein binding reagents can be associated with one of the plurality of control particle oligonucleotides. The first protein binding reagent can comprise a first antibody. The control particle oligonucleotide can be conjugated to the first protein binding reagent through a linker. The first control particle oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the first protein binding reagent can be associated with two or more of the plurality of control particle oligonucleotides with an identical control barcode sequence. The first protein binding reagent can be associated with two or more of the plurality of control particle oligonucleotides with different control barcode sequences. At least one of the plurality of first protein binding reagents can be not associated with any of the plurality of control particle oligonucleotides. The first protein binding reagent associated with the control particle oligonucleotide and the first protein binding reagent not associated with any control particle oligonucleotide can be identical protein binding reagents. The control particle can associated with a plurality of second protein binding reagents At least one of the plurality of second protein binding reagents can be associated with one of the plurality of control particle oligonucleotides. The control particle oligonucleotide associated with the first protein binding reagent and the control particle oligonucleotide associated with the second protein binding reagent can comprise different control barcode sequences. The first protein binding reagent and the second protein binding reagent can be identical protein binding reagents.

In some embodiments, the first protein binding reagent is associated with a partner binding reagent, and wherein the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent can be associated with a detectable moiety. The second protein binding reagent can be associated with a detectable moiety.

In some embodiments, the barcode comprises a binding site for a universal primer. The target-binding region can comprise a poly(dT) region.

In some embodiments, the plurality of barcodes is associated with a barcoding particle. For example, at least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle.

In some embodiments, the barcoding particle is disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The barcoding particle can comprise a disruptable hydrogel particle.

In some embodiments, the barcodes of the barcoding particle comprise barcode sequences selected from at least 1000, 10000, or more different barcode sequences. In some embodiments, the barcode sequences of the barcodes comprise random sequences. In some embodiments, the barcoding particle comprises at least 10000 barcodes.

In some embodiments, barcoding the plurality of targets and the plurality of control particle oligonucleotides using the plurality of barcodes comprises: contacting the plurality of barcodes with targets of the plurality of targets and control particle oligonucleotides of the plurality of control particle oligonucleotides to generate barcodes hybridized to the targets and the control particle oligonucleotides; and extending the barcodes hybridized to the targets and the control particle oligonucleotides to generate the plurality of barcoded targets and the plurality of barcoded control particle oligonucleotides. Extending the barcodes can comprise extending the barcodes using a DNA polymerase, a reverse transcriptase, or a combination thereof.

In some embodiments, the method comprises amplifying the plurality of barcoded targets and the plurality of barcoded control particle oligonucleotides to produce a plurality of amplicons. Amplifying the plurality of barcoded targets and the plurality of barcoded control particle oligonucleotides can comprise amplifying, using polymerase chain reaction (PCR), at least a portion of the barcode sequence and at least a portion of the control particle oligonucleotide or at least a portion of the barcode sequence and at least a portion of the control particle oligonucleotide. Obtaining the sequencing data can comprise obtaining sequencing data of the plurality of amplicons. Obtaining the sequencing data can comprise sequencing the at least a portion of the barcode sequence and the at least a portion of the control particle oligonucleotide, or the at least a portion of the barcode sequence and the at least a portion of the control particle oligonucleotide.

Disclosed herein are kits. In some embodiments, the kit comprises: a control particle composition comprising a plurality of control particle oligonucleotides associated with a control particle, wherein each of the plurality of control particle oligonucleotides comprises a control barcode sequence and a poly(dA) region.

In some embodiments, at least two of the plurality of control particle oligonucleotides comprises different control barcode sequences. In some embodiments, the control barcode sequence can be at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or any combination thereof. The control barcode sequences of at least 5, 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence. The first control barcode sequence and the second control barcode sequence can have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, the control particle oligonucleotide is not homologous to genomic sequences of the cell. The control particle oligonucleotide can be not homologous to genomic sequences of the species. The control particle oligonucleotide can be homologous to genomic sequences of a species. The species can be a non-mammalian species. The non-mammalian species can be a phage species. The phage species can be T7 phage, a PhiX phage, or a combination thereof.

In some embodiments, the control particle oligonucleotide can be conjugated to the control particle through a linker. At least one of the plurality of control particle oligonucleotides can be associated with the control particle through a linker. The at least one of the plurality of control particle oligonucleotides can comprise the linker. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, about 7.5 micrometer, or a combination thereof. The plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle.

In some embodiments, the control particle is disruptable. The control particle can be a control particle bead. The control particle bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The control particle can comprise a disruptable hydrogel particle.

In some embodiments, the control particle is associated with a detectable moiety. The control particle oligonucleotide can be associated with a detectable moiety.

In some embodiments, the control particle can be associated with a plurality of first protein binding reagents, and at least one of the plurality of first protein binding reagents can be associated with one of the plurality of control particle oligonucleotides. The first protein binding reagent can comprise a first antibody. The control particle oligonucleotide can be conjugated to the first protein binding reagent through a linker. The first control particle oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the first protein binding reagent can be associated with two or more of the plurality of control particle oligonucleotides with an identical control barcode sequence. The first protein binding reagent can be associated with two or more of the plurality of control particle oligonucleotides with different control barcode sequences. At least one of the plurality of first protein binding reagents can be not associated with any of the plurality of control particle oligonucleotides. The first protein binding reagent associated with the control particle oligonucleotide and the first protein binding reagent not associated with any control particle oligonucleotide can be identical protein binding reagents. The control particle can associated with a plurality of second protein binding reagents At least one of the plurality of second protein binding reagents can be associated with one of the plurality of control particle oligonucleotides. The control particle oligonucleotide associated with the first protein binding reagent and the control particle oligonucleotide associated with the second protein binding reagent can comprise different control barcode sequences. The first protein binding reagent and the second protein binding reagent can be identical protein binding reagents.

In some embodiments, the first protein binding reagent is associated with a partner binding reagent, and wherein the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody. can comprise an immunoglobulin G (IgG), a F(ab') fragment, a F(ab')2 fragment, a combination thereof, or a fragment thereof.

In some embodiments, the first protein binding reagent can be associated with a detectable moiety. The second protein binding reagent can be associated with a detectable moiety.

In some embodiments, the kit comprises a plurality of barcodes. A barcode of the plurality of barcodes can comprise a target-binding region and a barcode sequence (e.g., a molecular label sequence), and barcode sequences of at least two barcodes of the plurality of barcodes can comprise different molecule label sequences. The barcode can comprise a cell label sequence, a binding site for a universal primer, or any combination thereof. The target-binding region comprises a poly(dT) region.

In some embodiments, the plurality of barcodes can be associated with a barcoding particle. At least one barcode of the plurality of barcodes can be immobilized on the barcoding particle. At least one barcode of the plurality of barcodes is partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can be a second bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The barcoding particle can comprise a disruptable hydrogel particle.

In some embodiments, the barcodes of the barcoding particle comprise barcode sequences selected from at least 1000, 10000, or more different barcode sequences. The barcode sequences of the barcodes can comprise random sequences. The barcoding particle can comprise at least 10000 barcodes. The kit can comprise a DNA polymerase. The kit can comprise reagents for polymerase chain reaction (PCR).

Disclosed herein are methods and compositions that can be used for sequencing control. In some embodiments, the method comprises: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic of the one or more cells using at least one characteristic of the plurality of barcoded control oligonucleotides in the sequencing data. In some embodiments, the pseudo-target region comprises a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of barcode sequences with distinct sequences associated with the cell label and the control barcode sequence; and determining the number of the one or more cells using the number of barcode sequences with distinct sequences associated with the cell label and the control barcode sequence. Determining the number of barcode sequences with distinct sequences associated with the cell label and the control barcode sequence can comprise: for each cell label in the sequencing data, determining the number of barcode sequences with the highest number of distinct sequences associated with the cell label and the control barcode sequence. Determining the number of the one or more cells using the number of barcode sequences with distinct sequences associated with the cell label and the control barcode sequence can comprise: generating a plot of the number of barcode sequences with the highest number of distinct sequences with the number of cell labels in the sequencing data associated with the number of barcode sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises releasing the control oligonucleotide from the protein binding reagent prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound cell identification compositions can comprise selecting cells bound to at least one protein binding reagent of the control composition using flow cytometry.

In some embodiments, at least one of the plurality of protein targets is on a cell surface. At least one of the plurality of protein targets can comprise a cell-surface protein, a cell marker, a B-cell receptor, a T-cell receptor, a major histocompatibility complex, a tumor antigen, a receptor, an integrin, or any combination thereof. The protein binding reagent can comprise an antibody. The control oligonucleotide can be conjugated to the protein binding reagent through a linker. The control oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the protein binding reagent is associated with two or more control oligonucleotides with an identical control barcode sequence. The protein binding reagent can be associated with two or more control oligonucleotides with different identical control barcode sequences. In some embodiments, a second protein binding reagent of the plurality of control compositions is not associated with the control oligonucleotide. The protein binding reagent and the second protein binding reagent can be identical.

In some embodiments, the barcode comprises a binding site for a universal primer. The target-binding region can comprise a poly(dT) region. In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes is enclosed in the barcoding particle. At least one barcode of the plurality of barcodes is partially enclosed in the barcoding particle. The barcoding particle can be disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The barcoding particle can comprise a disruptable hydrogel particle.

In some embodiments, the barcoding particle is associated with an optical moiety. The control oligonucleotide can be associated with an optical moiety.

In some embodiments, the barcodes of the barcoding particle comprise barcode sequences selected from at least 1000, 10000, or more different barcode sequences. In some embodiments, the barcode sequences of the barcodes comprise random sequences. In some embodiments, the barcoding particle comprises at least 10000 barcodes.

In some embodiments, barcoding the control oligonucleotides comprises: barcoding the control oligonucleotides using a plurality of barcodes to create a plurality of barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the barcode sequence and at least a portion of the control oligonucleotide. In some embodiments, obtaining the sequencing data comprises obtaining sequencing data of the plurality of amplicons. Obtaining the sequencing data can comprise sequencing the at least a portion of the barcode sequence and the at least a portion of the control oligonucleotide.

Disclosed herein include methods for sequencing control. In some embodiments, the method comprises: contacting one or more cells of a plurality of cells with a control composition of a plurality of control compositions, wherein a cell of the plurality of cells comprises a plurality of targets and a plurality of binding targets, wherein each of the plurality of control compositions comprises a cellular component binding reagent associated with a control oligonucleotide, wherein the cellular component binding reagent is capable of specifically binding to at least one of the plurality of binding targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic of the one or more cells using at least one characteristic of the plurality of barcoded control oligonucleotides in the sequencing data. In some embodiments, the pseudo-target region comprises a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. In some embodiments, the method comprises: determining single cell capture efficiency based the number of the one or more cells determined. In some embodiments, the method comprises: determining single cell capture efficiency based on the ratio of the number of the one or more cells determined and the number of the plurality of cells.

In some embodiments, determining the at least one characteristic of the one or more cells can comprise: for each cell label in the sequencing data, determining the number of barcode sequences with distinct sequences associated with the cell label and the control barcode sequence; and determining the number of the one or more cells using the number of barcode sequences with distinct sequences associated with the cell label and the control barcode sequence. Determining the number of barcode sequences with distinct sequences associated with the cell label and the control barcode sequence comprises: for each cell label in the sequencing data, determining the number of barcode sequences with the highest number of distinct sequences associated with the cell label and the control barcode sequence. Determining the number of the one or more cells using the number of barcode sequences with distinct sequences associated with the cell label and the control barcode sequence can comprise: generating a plot of the number of barcode sequences with the highest number of distinct sequences with the number of cell labels in the sequencing data associated with the number of barcode sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises: releasing the control oligonucleotide from the cellular component binding reagent prior to barcoding the control oligonucleotides. At least one of the plurality of binding targets can be expressed on a cell surface. At least one of the plurality of binding targets can comprise a cell-surface protein, a cell marker, a B-cell receptor, a T-cell receptor, a major histocompatibility complex, a tumor antigen, a receptor, an integrin, or any combination thereof. The cellular component binding reagent can comprise a cell surface binding reagent, an antibody, a tetramer, an aptamers, a protein scaffold, an invasion, or a combination thereof.

In some embodiments, binding target of the cellular component binding reagent is selected from a group comprising 10-100 different binding targets. A binding target of the cellular component binding reagent can comprise a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. The control oligonucleotide can be conjugated to the cellular component binding reagent through a linker. The control oligonucleotide can comprise the linker. The linker can comprise a chemical group. The chemical group can be reversibly attached to the first cellular component binding reagent. The chemical group can comprise a UV photocleavable group, a streptavidin, a biotin, an amine, a disulfide linkage, or any combination thereof.

In some embodiments, the cellular component binding reagent can be associated with two or more control oligonucleotides with an identical control barcode sequence. The cellular component binding reagent can be associated with two or more control oligonucleotides with different identical control barcode sequences. In some embodiments, a second cellular component binding reagent of the plurality of control compositions is not associated with the control oligonucleotide. The cellular component binding reagent and the second cellular component binding reagent can be identical.

In some embodiments, the barcode comprises a binding site for a universal primer. In some embodiments, the target-binding region comprises a poly(dT) region.

In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can be a barcoding bead. In some embodiments, the barcoding bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The barcoding particle can comprise a disruptable hydrogel particle. The barcoding particle can be associated with an optical moiety.

In some embodiments, the control oligonucleotide can be associated with an optical moiety. In some embodiments, the barcodes of the barcoding particle comprise barcode sequences selected from at least 1000, 10000, or more different barcode sequences. In some embodiments, the barcode sequences of the barcodes comprise random sequences. The barcoding particle can comprise at least 10000 barcodes.

In some embodiments, barcoding the control oligonucleotides comprises: barcoding the control oligonucleotides using a plurality of barcodes to create a plurality of barcoded control oligonucleotides Barcoding the plurality of control oligonucleotides using the plurality of barcodes can comprise: contacting the plurality of barcodes with control oligonucleotides of the plurality of control compositions to generate barcodes hybridized to the control oligonucleotides; and extending the barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiment, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the barcode sequence and at least a portion of the control oligonucleotide. Obtaining the sequencing data can comprise obtaining sequencing data of the plurality of amplicons. Obtaining the sequencing data can comprise sequencing the at least a portion of the barcode sequence and the at least a portion of the control oligonucleotide.

Disclosed herein are methods for sequencing control. In some embodiments, the method comprises: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; and determining at least one characteristic of the one or more cells using at least one characteristic of the plurality of control oligonucleotides. The pseudo-target region can comprise a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of barcode sequences with distinct sequences associated with the cell label and the control barcode sequence; and determining the number of the one or more cells using the number of barcode sequences with distinct sequences associated with the cell label and the control barcode sequence. Determining the number of barcode sequences with distinct sequences associated with the cell label and the control barcode sequence can comprise: for each cell label in the sequencing data, determining the number of barcode sequences with the highest number of distinct sequences associated with the cell label and the control barcode sequence. Determining the number of the one or more cells using the number of barcode sequences with distinct sequences associated with the cell label and the control barcode sequence can comprise: generating a plot of the number of barcode sequences with the highest number of distinct sequences with the number of cell labels in the sequencing data associated with the number of barcode sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises releasing the control oligonucleotide from the protein binding reagent prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound cell identification compositions can comprise selecting cells bound to at least one protein binding reagent of the control composition using flow cytometry.

In some embodiments, at least one of the plurality of protein targets is on a cell surface. At least one of the plurality of protein targets can comprise a cell-surface protein, a cell marker, a B-cell receptor, a T-cell receptor, a major histocompatibility complex, a tumor antigen, a receptor, an integrin, or any combination thereof. The protein binding reagent can comprise an antibody. The control oligonucleotide can be conjugated to the protein binding reagent through a linker. The control oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the protein binding reagent is associated with two or more control oligonucleotides with an identical control barcode sequence. The protein binding reagent can be associated with two or more control oligonucleotides with different identical control barcode sequences. In some embodiments, a second protein binding reagent of the plurality of control compositions is not associated with the control oligonucleotide. The protein binding reagent and the second protein binding reagent can be identical.

In some embodiments, the barcode comprises a binding site for a universal primer. The target-binding region can comprise a poly(dT) region. In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes is enclosed in the barcoding particle. At least one barcode of the plurality of barcodes is partially enclosed in the barcoding particle. The barcoding particle can be disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The barcoding particle can comprise a disruptable hydrogel particle.

In some embodiments, the barcoding particle is associated with an optical moiety. The control oligonucleotide can be associated with an optical moiety.

In some embodiments, the method comprises: barcoding the control oligonucleotides using a plurality of barcodes to create a plurality of barcoded control oligonucleotides, wherein each of the plurality of barcodes comprises a cell label sequence, a barcode sequence, and/or a target-binding region, wherein the barcode sequences of at least two barcodes of the plurality of barcodes comprise different sequences, and wherein at least two barcodes of the plurality of barcodes comprise an identical cell label sequence; and obtaining sequencing data of the plurality of barcoded control oligonucleotides;

In some embodiments, the barcodes of the barcoding particle comprise barcode sequences selected from at least 1000, 10000, or more different barcode sequences. In some embodiments, the barcode sequences of the barcodes comprise random sequences. In some embodiments, the barcoding particle comprises at least 10000 barcodes.

In some embodiments, barcoding the control oligonucleotides comprises: barcoding the control oligonucleotides using a plurality of barcodes to create a plurality of barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the barcode sequence and at least a portion of the control oligonucleotide. In some embodiments, obtaining the sequencing data comprises obtaining sequencing data of the plurality of amplicons. Obtaining the sequencing data can comprise sequencing the at least a portion of the barcode sequence and the at least a portion of the control oligonucleotide.

Disclosed herein includes methods for cell identification. In some embodiments, the method comprises: contacting a first plurality of cells and a second plurality of cells with two cell identification compositions respectively, wherein each of the first plurality of cells and each of the second plurality of cells comprise one or more antigen targets, wherein each of the two cell identification compositions comprises an antigen binding reagent associated with a cell identification oligonucleotide, wherein the antigen binding reagent is capable of specifically binding to at least one of the one or more antigen targets, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying a cell label sequence associated with two or more cell identification sequences in the sequencing data obtained; and removing sequencing data associated with the cell label sequence from the sequencing data obtained and/or excluding the sequencing data associated with the cell label sequence from subsequent analysis. In some embodiments, the cell identification oligonucleotide comprises a barcode sequence, a binding site for a universal primer, or a combination thereof.

Disclosed herein includes methods for multiplet identification. In some embodiments, the method comprises: contacting a first plurality of cells and a second plurality of cells with two cell identification compositions respectively, wherein each of the first plurality of cells and each of the second plurality of cells comprise one or more antigen targets, wherein each of the two cell identification compositions comprises an antigen binding reagent associated with a cell identification oligonucleotide, wherein the antigen binding reagent is capable of specifically binding to at least one of the one or more antigen targets, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained. In some embodiments, the method comprises: removing the sequencing data associated with the one or more multiplet cell label sequences from the sequencing data obtained and/or excluding the sequencing data associated with the one or more multiplet cell label sequences from subsequent analysis. In some embodiments, the cell identification oligonucleotide comprises a barcode sequence (e.g., a molecular label sequence), a binding site for a universal primer, or a combination thereof.

In some embodiments, contacting the first plurality of cells and the second plurality of cells with the two cell identification compositions respectively comprises: contacting the first plurality of cells with a first cell identification compositions of the two cell identification compositions; and contacting the first plurality of cells with a second cell identification compositions of the two cell identification compositions.

In some embodiments, the cell identification sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The cell identification oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, cell identification sequences of at least 10, 100, 1000, or more cell identification compositions of the plurality of cell identification compositions comprise different sequences.

In some embodiments, the antigen binding reagent comprises an antibody, a tetramer, an aptamers, a protein scaffold, or a combination thereof. The cell identification oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises single cells. The at least one of the one or more antigen targets can be on a cell surface.

In some embodiments, the method comprises: removing unbound cell identification compositions of the two cell identification compositions. Removing the unbound cell identification compositions can comprise washing cells of the first plurality of cells and the second plurality of cells with a washing buffer. Removing the unbound cell identification compositions can comprise selecting cells bound to at least one antigen binding reagent of the two cell identification compositions using flow cytometry. In some embodiments, the method comprises: lysing one or more cells of the first plurality of cells and the second plurality of cells.

In some embodiments, the cell identification oligonucleotide is configured to be detachable or non-detachable from the antigen binding reagent. The method can comprise detaching the cell identification oligonucleotide from the antigen binding reagent. Detaching the cell identification oligonucleotide can comprise detaching the cell identification oligonucleotide from the antigen binding reagent by UV photocleaving, chemical treatment (e.g., using reducing reagent, such as dithiothreitol), heating, enzyme treatment, or any combination thereof.

In some embodiments, the cell identification oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cells, a mammalian cell, a bacterial cell, a viral cell, a yeast cell, a fungal cell, or any combination thereof. The cell identification oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the cell identification oligonucleotide complementary to the capture sequence of the barcode can comprise a poly(dA) region.

In some embodiments, the antigen target comprises an extracellular protein, an intracellular protein, or any combination thereof. The antigen target can comprise a cell-surface protein, a cell marker, a B-cell receptor, a T-cell receptor, a major histocompatibility complex, a tumor antigen, a receptor, an integrin, or any combination thereof. The antigen target can comprise a lipid, a carbohydrate, or any combination thereof. The antigen target can be selected from a group comprising 10-100 different antigen targets.

In some embodiments, the antigen binding reagent is associated with two or more cell identification oligonucleotides with an identical sequence. The antigen binding reagent can be associated with two or more cell identification oligonucleotides with different cell identification sequences. The cell identification composition of the plurality of cell identification compositions can comprise a second antigen binding reagent not conjugated with the cell identification oligonucleotide. The antigen binding reagent and the second antigen binding reagent can be identical.

In some embodiments, a barcode of the plurality of barcodes comprises a target-binding region and a barcode sequence (e.g., a molecular label sequence), and barcode sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane/(PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle.

In some embodiments, the antigen binding reagent is associated with a detectable moiety. In some embodiments, the particle is associated with a detectable moiety. The cell identification oligonucleotide is associated with an optical moiety. In some embodiments, the barcodes of the particle can comprise barcode sequences selected from at least 1000, 10000, or more different barcode sequences. The barcode sequences of the barcodes can comprise random sequences. The particle can comprise at least 10000 barcodes.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of the barcode sequence and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Disclosed herein includes methods for cell identification. In some embodiments, the method comprises: contacting a first plurality of cells and a second plurality of cells with two cell identification compositions respectively, wherein each of the first plurality of cells and each of the second plurality of cells comprise one or more cellular component targets, wherein each of the two cell identification compositions comprises a cellular component binding reagent associated with a cell identification oligonucleotide, wherein the cellular component binding reagent is capable of specifically binding to at least one of the one or more cellular component targets, wherein the cell identification oligonucleotide comprises a cell identification sequence, and wherein cell identification sequences of the two cell identification compositions of the plurality of cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis. In some embodiments, the cell identification oligonucleotide comprises a barcode sequence (e.g., a molecular label sequence), a binding site for a universal primer, or a combination thereof.

Disclosed herein includes methods for multiplet identification. In some embodiments, the method comprises: contacting a first plurality of cells and a second plurality of cells with two cell identification compositions respectively, wherein each of the first plurality of cells and each of the second plurality of cells comprise one or more cellular component targets, wherein each of the two cell identification compositions comprises a cellular component binding reagent associated with a cell identification oligonucleotide, wherein the cellular component binding reagent is capable of specifically binding to at least one of the one or more cellular component targets, wherein the cell identification oligonucleotide comprises a cell identification sequence, and wherein cell identification sequences of the two cell identification compositions of the plurality of cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; identifying one or more multiplet cell label sequences that is each associated with two or more cell identification sequences in the sequencing data obtained. In some embodiments, the method comprises: removing the sequencing data associated with the one or more multiplet cell label sequences from the sequencing data obtained and/or excluding the sequencing data associated with the one or more multiplet cell label sequences from subsequent analysis. In some embodiments, the cell identification oligonucleotide comprises a barcode sequence (e.g., a molecular label sequence), a binding site for a universal primer, or a combination thereof.

In some embodiments, contacting the first plurality of cells and the second plurality of cells with the two cell identification compositions respectively comprises: contacting the first plurality of cells with a first cell identification compositions of the two cell identification compositions; and contacting the first plurality of cells with a second cell identification compositions of the two cell identification compositions.

In some embodiments, the cell identification sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The cell identification oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, cell identification sequences of at least 10, 100, 1000, or more cell identification compositions of the plurality of cell identification compositions comprise different sequences.

In some embodiments, the cellular component binding reagent comprises an antibody, a tetramer, an aptamers, a protein scaffold, or a combination thereof. The cell identification oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises a single cell. The at least one of the one or more cellular component targets can be on a cell surface.

In some embodiments, the method comprises: removing unbound cell identification compositions of the two cell identification compositions. Removing the unbound cell identification compositions can comprise washing cells of the first plurality of cells and the second plurality of cells with a washing buffer. Removing the unbound cell identification compositions can comprise selecting cells bound to at least one cellular component binding reagent of the two cell identification compositions using flow cytometry. In some embodiments, the method comprises: lysing one or more cells of the first plurality of cells and the second plurality of cells.

In some embodiments, the cell identification oligonucleotide is configured to be detachable or non-detachable from the cellular component binding reagent. The method can comprise detaching the cell identification oligonucleotide from the cellular component binding reagent. Detaching the cell identification oligonucleotide can comprise detaching the cell identification oligonucleotide from the cellular component binding reagent by UV photocleaving, chemical treatment (e.g., using reducing reagent, such as dithiothreitol), heating, enzyme treatment, or any combination thereof.

In some embodiments, the cell identification oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cell, a mammalian cell, a bacterial cell, a viral cell, a yeast cell, a fungal cell, or any combination thereof. The cell identification oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the cell identification oligonucleotide complementary to the capture sequence of the barcode can comprise a poly(dA) region.

In some embodiments, the antigen target comprises an extracellular protein, an intracellular protein, or any combination thereof. The antigen target can comprise a cell-surface protein, a cell marker, a B-cell receptor, a T-cell receptor, a major histocompatibility complex, a tumor antigen, a receptor, an integrin, or any combination thereof. The antigen target can comprise a lipid, a carbohydrate, or any combination thereof. The antigen target can be selected from a group comprising 10-100 different antigen targets.

In some embodiments, the cellular component binding reagent is associated with two or more cell identification oligonucleotides with an identical sequence. The cellular component binding reagent can be associated with two or more cell identification oligonucleotides with different cell identification sequences. The cell identification composition of the plurality of cell identification compositions can comprise a second cellular component binding reagent not conjugated with the cell identification oligonucleotide. The cellular component binding reagent and the second cellular component binding reagent can be identical.

In some embodiments, a barcode of the plurality of barcodes comprises a target-binding region and a barcode sequence (e.g., a molecular label sequence), and barcode sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle.

In some embodiments, the cellular component binding reagent is associated with a detectable moiety. In some embodiments, the particle is associated with a detectable moiety. The cell identification oligonucleotide is associated with an optical moiety.

In some embodiments, the barcodes of the particle can comprise barcode sequences selected from at least 1000, 10000, or more different barcode sequences. The barcode sequences of the barcodes can comprise random sequences. The particle can comprise at least 10000 barcodes.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of the barcode sequence and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Disclosed herein includes methods for cell identification. In some embodiments, the method comprises: contacting one or more cells from each of a first plurality of cells and a second plurality of cells with a cell identification composition of a plurality of two cell identification compositions respectively, wherein each of the first plurality of cells and each of the second plurality of cells comprises one or more antigen targets, wherein each of the two cell identification compositions comprises an antigen binding reagent associated with a cell identification oligonucleotide, wherein the antigen binding reagent is capable of specifically binding to at least one of the one or more antigen targets, wherein the cell identification oligonucleotide comprises a cell identification sequence, and wherein cell identification sequences of the two cell identification compositions comprise different sequences; and identifying one or more cells that is each associated with two or more cell identification sequences. In some embodiments, the cell identification oligonucleotide comprises a barcode sequence, a binding site for a universal primer, or a combination thereof.

Disclosed herein are methods for multiplet identification. In some embodiments, the method comprises: contacting one or more cells from each of a first plurality of cells and a second plurality of cells with a cell identification composition of a plurality of two cell identification compositions respectively, wherein each of the first plurality of cells and each of the second plurality of cells comprises one or more antigen targets, wherein each of the two cell identification compositions comprises an antigen binding reagent associated with a cell identification oligonucleotide, wherein the antigen binding reagent is capable of specifically binding to at least one of the one or more antigen targets, wherein the cell identification oligonucleotide comprises a cell identification sequence, and wherein cell identification sequences of the two cell identification compositions comprise different sequences; and identifying one or more cells that is each associated with two or more cell identification sequences as multiplet cells.

In some embodiments, identifying the cells that is each associated with two or more cell identification sequences comprises: barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and/or a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained. The method can comprise removing the sequencing data associated with the one or more cell label sequences that is each associated with two or more cell identification sequences from the sequencing data obtained and/or excluding the sequencing data associated with the one or more cell label sequences that is each associated with the two or more cell identification sequences from subsequent analysis.

In some embodiments, contacting the first plurality of cells and the second plurality of cells with the two cell identification compositions respectively comprises: contacting the first plurality of cells with a first cell identification compositions of the two cell identification compositions; and contacting the first plurality of cells with a second cell identification compositions of the two cell identification compositions.

In some embodiments, the cell identification sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The cell identification oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, cell identification sequences of at least 10, 100, 1000, or more cell identification compositions of the plurality of cell identification compositions comprise different sequences.

In some embodiments, the antigen binding reagent comprises an antibody, a tetramer, an aptamers, a protein scaffold, or a combination thereof. The cell identification oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises single cells. The at least one of the one or more antigen targets can be on a cell surface. In some embodiments, the method comprises: removing unbound cell identification compositions of the two cell identification compositions. Removing the unbound cell identification compositions can comprise washing cells of the first plurality of cells and the second plurality of cells with a washing buffer. Removing the unbound cell identification compositions can comprise selecting cells bound to at least one antigen binding reagent of the two cell identification compositions using flow cytometry. In some embodiments, the method comprises: lysing one or more cells of the first plurality of cells and the second plurality of cells.

In some embodiments, the cell identification oligonucleotide is configured to be detachable or non-detachable from the antigen binding reagent. The method can comprise detaching the cell identification oligonucleotide from the antigen binding reagent. Detaching the cell identification oligonucleotide can comprise detaching the cell identification oligonucleotide from the antigen binding reagent by UV photocleaving, chemical treatment (e.g., using reducing reagent, such as dithiothreitol), heating, enzyme treatment, or any combination thereof.

In some embodiments, the cell identification oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cells, a mammalian cell, a bacterial cell, a viral cell, a yeast cell, a fungal cell, or any combination thereof. The cell identification oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the cell identification oligonucleotide complementary to the capture sequence of the barcode can comprise a poly(dA) region.

In some embodiments, the antigen target comprises an extracellular protein, an intracellular protein, or any combination thereof. The antigen target can comprise a cell-surface protein, a cell marker, a B-cell receptor, a T-cell receptor, a major histocompatibility complex, a tumor antigen, a receptor, an integrin, or any combination thereof. The antigen target can comprise a lipid, a carbohydrate, or any combination thereof. The antigen target can be selected from a group comprising 10-100 different antigen targets.

In some embodiments, the antigen binding reagent is associated with two or more cell identification oligonucleotides with an identical sequence. The antigen binding reagent can be associated with two or more cell identification oligonucleotides with different cell identification sequences. The cell identification composition of the plurality of cell identification compositions can comprise a second antigen binding reagent not conjugated with the cell identification oligonucleotide. The antigen binding reagent and the second antigen binding reagent can be identical.

In some embodiments, a barcode of the plurality of barcodes comprises a target-binding region and a barcode sequence (e.g., a molecular label sequence), and barcode sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle.

In some embodiments, the antigen binding reagent is associated with a detectable moiety. In some embodiments, the particle is associated with a detectable moiety. The cell identification oligonucleotide is associated with an optical moiety.

In some embodiments, the barcodes of the particle can comprise barcode sequences selected from at least 1000, 10000, or more different barcode sequences. The barcode sequences of the barcodes can comprise random sequences. The particle can comprise at least 10000 barcodes.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of the barcode sequence and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Disclosed herein are methods for determining protein-protein interactions. In some embodiments, the method comprises: contacting a cell with a first pair of interaction determination compositions, wherein the cell comprises a first protein target and a second protein target, wherein each of the first pair of interaction determination compositions comprises a protein binding reagent associated with an interaction determination oligonucleotide, wherein the protein binding reagent of one of the first pair of interaction determination compositions is capable of specifically binding to the first protein target and the protein binding reagent of the other of the first pair of interaction determination compositions is capable of specifically binding to the second protein target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second protein targets based on the association of the interaction determination sequences of the first pair of interaction determination compositions in the obtained sequencing data.

In some embodiments, the method comprises: contacting a cell with a first pair of interaction determination compositions, wherein the cell comprises a first cellular component target and a second cellular component target, wherein each of the first pair of interaction determination compositions comprises a cellular component binding reagent associated with an interaction determination oligonucleotide, wherein the cellular component binding reagent of one of the first pair of interaction determination compositions is capable of specifically binding to the first cellular component target and the cellular component binding reagent of the other of the first pair of interaction determination compositions is capable of specifically binding to the second cellular component target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second cellular component targets based on the association of the interaction determination sequences of the first pair of interaction determination compositions in the obtained sequencing data. In some embodiments, at least one of the two cellular component binding reagent comprises a protein binding reagent, wherein the protein binding reagent is associated with one of the two interaction determination oligonucleotides, and wherein the one or more cellular component targets comprises at least one protein target.

In some embodiments, contacting the cell with the first pair of interaction determination compositions comprises: contacting the cell with each of the first pair of interaction determination compositions sequentially or simultaneously. The first protein target can be the same as the second protein target. The first protein target can be different from the second protein target.

In some embodiments, the interaction determination sequence is at least 6 nucleotides in length, 25-60 nucleotides in length, about 45 nucleotides in length, about 50 nucleotides in length, about 100 nucleotides in length, about 128 nucleotides in length, at least 128 nucleotides in length, about 200 nucleotides in length, at least 200 nucleotides in length, less than about 200-300 nucleotides in length, about 200-500 nucleotides in length, about 500 nucleotides in length, or any combination thereof.

In some embodiments, the method comprises contacting the cell with a second pair of interaction determination compositions, wherein the cell comprises a third protein target and a fourth protein target, wherein each of the second pair of interaction determination compositions comprises a protein binding reagent associated with an interaction determination oligonucleotide, wherein the protein binding reagent of one of the second pair of interaction determination compositions is capable of specifically binding to the third protein target and the protein binding reagent of the other of the second pair of interaction determination compositions is capable of specifically binding to the fourth protein target. At least one of the third and fourth protein targets can be different from one of the first and second protein targets. At least one of the third and fourth protein targets and at least one of the first and second protein targets can be identical.

In some embodiments, the method comprises contacting the cell with three or more pairs of interaction determination compositions. The interaction determination sequences of at least 10, 100, 1000, or any combination thereof, interaction determination compositions of the plurality of pairs of interaction determination compositions can comprise different sequences.

In some embodiments, the bridge oligonucleotide hybridization regions of the first pair of interaction determination compositions comprise different sequences. At least one of the bridge oligonucleotide hybridization regions can be complementary to at least one of the two hybridization regions of the bridge oligonucleotide.

In some embodiments, ligating the interaction determination oligonucleotides of the first pair of interaction determination compositions using the bridge oligonucleotide comprises: hybridizing a first hybridization regions of the bridge oligonucleotide with a first bridge oligonucleotide hybridization region of the bridge oligonucleotide hybridization regions of the interaction determination oligonucleotides; hybridizing a second hybridization regions of the bridge oligonucleotide with a second bridge oligonucleotide hybridization region of the bridge oligonucleotide hybridization regions of the interaction determination oligonucleotides; and ligating the interaction determination oligonucleotides hybridized to the bridge oligonucleotide to generate a ligated interaction determination oligonucleotide.

In some embodiments, the protein binding reagent comprises an antibody, a tetramer, an aptamers, a protein scaffold, an integrin, or a combination thereof.

In some embodiments, the interaction determination oligonucleotide is conjugated to the protein binding reagent through a linker. The oligonucleotide can comprise the linker. The linker can comprise a chemical group. The chemical group can be reversibly or irreversibly attached to the protein binding reagent. The chemical group can comprise a UV photocleavable group, a disulfide bond, a streptavidin, a biotin, an amine, a disulfide linkage or any combination thereof. The at least one of the one or more protein targets can be on a cell surface.

In some embodiments, the method comprises: fixating the cell prior to contacting the cell with the first pair of interaction determination compositions. The method can comprise: removing unbound interaction determination compositions of the first pair of interaction determination compositions. Removing the unbound interaction determination compositions can comprise washing the cell with a washing buffer. Removing the unbound interaction determination compositions can comprise selecting the cell using flow cytometry. The method can comprise lysing the cell.

In some embodiments, the interaction determination oligonucleotide is configured to be detachable or non-detachable from the protein binding reagent. The method can comprise detaching the interaction determination oligonucleotide from the protein binding reagent. Detaching the interaction determination oligonucleotide can comprise detaching the interaction determination oligonucleotide from the protein binding reagent by UV photocleaving, chemical treatment, heating, enzyme treatment, or any combination thereof.

In some embodiments, the interaction determination oligonucleotide is not homologous to genomic sequences of the cell. The interaction determination oligonucleotide can be homologous to genomic sequences of a species. The species can be a non-mammalian species. The non-mammalian species can be a phage species. The phage species can T7 phage, a PhiX phage, or a combination thereof.

In some embodiment, the cell comprises a tumor cell or non-tumor cell. The cell can comprise a mammalian cell, a bacterial cell, a viral cell, a yeast cell, a fungal cell, or any combination thereof.

In some embodiments, the method comprises: contacting two or more cells with the first pair of interaction determination compositions, and wherein each of the two or more cells comprises the first and the second protein targets. At least one of the two or more cells can comprise a single cell.

In some embodiments, the barcode comprises a cell label sequence, a binding site for a universal primer, or any combination thereof. At least two barcodes of the plurality of barcodes can comprise an identical cell label sequence.

The interaction determination oligonucleotide of the one of the first pair of interaction determination compositions can comprise a sequence complementary to the capture sequence. The capture sequence can comprise a poly(dT) region. The sequence of the interaction determination oligonucleotide complementary to the capture sequence can comprise a poly(dA) region. The interaction determination oligonucleotide can comprise a second barcode sequence. The interaction determination oligonucleotide of the other of the first pair of interaction identification compositions can comprise a binding site for a universal primer.

In some embodiments, the protein target comprises an extracellular protein, an intracellular protein, or any combination thereof. The protein target can comprise a cell-surface protein, a cell marker, a B-cell receptor, a T-cell receptor, a major histocompatibility complex, a tumor antigen, a receptor, an integrin, or any combination thereof.

In some embodiments, the protein target comprises a lipid, a carbohydrate, or any combination thereof. The protein target can be selected from a group comprising 10-100 different protein targets.

In some embodiments, the protein binding reagent is associated with two or more interaction determination oligonucleotides with an identical sequence. The protein binding reagent can be associated with two or more interaction determination oligonucleotides with different interaction determination sequences.

In some embodiments, the one of the plurality of interaction determination compositions comprises a second protein binding reagent not associated with the interaction determination oligonucleotide. The protein binding reagent and the second protein binding reagent can be identical. The protein binding reagent can be associated with a detectable moiety.

In some embodiments, the plurality of barcodes is associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can comprise a bead. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle. The particle can be associated with a detectable moiety. The interaction determination oligonucleotide can be associated with a detectable moiety. The barcodes of the particle comprise barcode sequences can be selected from, about, at least, at most, 1000, 10000, or more, or less, or any combination thereof different barcode sequences. The barcodes sequences of the barcodes can comprise random sequences. The particle can comprise at least 10000 barcodes.

In some embodiments barcoding the interaction determination oligonucleotides using the plurality of barcodes comprises: contacting the plurality of barcodes with the interaction determination oligonucleotides to generate barcodes hybridized to the interaction determination oligonucleotides; and extending the barcodes hybridized to the interaction determination oligonucleotides to generate the plurality of barcoded interaction determination oligonucleotides. Extending the barcodes can comprise extending the barcodes using a DNA polymerase to generate the plurality of barcoded interaction determination oligonucleotides. Extending the barcodes can comprise extending the barcodes using a reverse transcriptase to generate the plurality of barcoded interaction determination oligonucleotides. Extending the barcodes can comprise extending the barcodes using a Moloney Murine Leukemia Virus (M-MLV) reverse transcriptase or a Taq DNA polymerase to generate the plurality of barcoded interaction determination oligonucleotides. Extending the barcodes can comprise displacing the bridge oligonucleotide from the ligated interaction determination oligonucleotide. The method can comprise: amplifying the plurality of barcoded interaction determination oligonucleotides to produce a plurality of amplicons. Amplifying the plurality of barcoded interaction determination oligonucleotides can comprise amplifying, using polymerase chain reaction (PCR), at least a portion of the barcode sequence and at least a portion of the interaction determination oligonucleotide.

In some embodiments, obtaining the sequencing data of the plurality of barcoded interaction determination oligonucleotides can comprise obtaining sequencing data of the plurality of amplicons. Obtaining the sequencing data can comprise sequencing at least a portion of the barcode sequence and at least a portion of the interaction determination oligonucleotide. Obtaining sequencing data of the plurality of barcoded interaction determination oligonucleotides can comprise obtaining partial and/or complete sequences of the plurality of barcoded interaction determination oligonucleotides.

In some embodiments, wherein the plurality of barcodes comprises a plurality of stochastic barcodes, wherein the barcode sequence of each of the plurality of stochastic barcodes comprises a molecular label sequence, wherein the molecular label sequences of at least two stochastic barcodes of the plurality of stochastic barcodes comprise different sequences, and wherein barcoding the interaction determination oligonucleotides using the plurality of barcodes to create the plurality of barcoded interaction determination oligonucleotides comprises stochastically barcoding the interaction determination oligonucleotides using the plurality of stochastic barcodes to create a plurality of stochastically barcoded interaction determination oligonucleotides.

In some embodiments, barcoding a plurality of targets of the cell using the plurality of barcodes to create a plurality of barcoded targets; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using the plurality of stochastic barcodes to create a plurality of stochastically barcoded targets.

Embodiments disclosed herein include kits for identifying protein-protein interactions. In some embodiments, the kit comprises: a first pair of interaction determination compositions, wherein each of the first pair of interaction determination compositions comprises a protein binding reagent associated with an interaction determination oligonucleotide, wherein the protein binding reagent of one of the first pair of interaction determination compositions is capable of specifically binding to a first protein target and a protein binding reagent of the other of the first pair of interaction determination compositions is capable of specifically binding to the second protein target, wherein the interaction determination oligonucleotide comprises an interaction determination sequence and a bridge oligonucleotide hybridization region, and wherein the interaction determination sequences of the first pair of interaction determination compositions comprise different sequences; and a plurality of bridge oligonucleotides each comprising two hybridization regions capable of specifically binding to the bridge oligonucleotide hybridization regions of the first pair of interaction determination compositions.

Ins some embodiments, the interaction determination sequence is at least 6 nucleotides in length, 25-60 nucleotides in length, about 45 nucleotides in length, about 50 nucleotides in length, about 100 nucleotides in length, about 128 nucleotides in length, at least 128 nucleotides in length, about 200-500 nucleotides in length, about 200 nucleotides in length, at least 200 nucleotides in length, about 200-300 nucleotides in length, about 500 nucleotides in length, or any combination thereof.

In some embodiments, the kit comprises: a second pair of interaction determination compositions, wherein each of the second pair of interaction determination compositions comprises a protein binding reagent associated with an interaction determination oligonucleotide, wherein the protein binding reagent of one of the second pair of interaction determination compositions is capable of specifically binding to a third protein target and the protein binding reagent of the other of the second pair of interaction determination compositions is capable of specifically binding to a fourth protein target. At least one of the third and fourth protein targets can be different from one of the first and second protein targets. At least one of the third and fourth protein targets and at least one of the first and second protein targets can be identical.

In some embodiments, the kit comprises: three or more pairs of interaction determination compositions. The interaction determination sequences of at least 10 interaction determination compositions of the three or more pairs of interaction determination compositions can comprise different sequences. The interaction determination sequences of at least 100 interaction determination compositions of the three or more pairs of interaction determination compositions can comprise different sequences. The interaction determination sequences of at least 1000 interaction determination compositions of the three or more pairs of interaction determination compositions can comprise different sequences.

In some embodiments, the bridge oligonucleotide hybridization regions of two interaction determination compositions of the plurality of interaction determination compositions comprise different sequences. At least one of the bridge oligonucleotide hybridization regions can be complementary to at least one of the two hybridization regions of the bridge oligonucleotide.

In some embodiments, the protein binding reagent can comprise an antibody, a tetramer, an aptamers, a protein scaffold, or a combination thereof. The interaction determination oligonucleotide can be conjugated to the protein binding reagent through a linker. The at least one interaction determination oligonucleotide can comprise the linker. The linker can comprise a chemical group. The chemical group can be reversibly or irreversibly attached to the protein binding reagent. The chemical group can comprise a UV photocleavable group, a disulfide bond, a streptavidin, a biotin, an amine, a disulfide linkage, or any combination thereof.

In some embodiments, the interaction determination oligonucleotide is not homologous to genomic sequences of any cell of interest. The cell of interest can comprise a tumor cell or non-tumor cell. The cell of interest can comprise a single cell, a mammalian cell, a bacterial cell, a viral cell, a yeast cell, a fungal cell, or any combination thereof.

In some embodiments, the kit comprises: a plurality of barcodes, wherein each of the plurality of barcodes comprises a barcode sequence and a capture sequence. The interaction determination oligonucleotide of the one of the first pair of interaction determination compositions can comprise a sequence complementary to the capture sequence of at least one barcode of a plurality of barcodes. The capture sequence can comprise a poly(dT) region. The sequence of the interaction determination oligonucleotide complementary to the capture sequence of the barcode can comprise a poly(dA) region. The interaction determination oligonucleotide of the other of the first pair of interaction identification compositions can comprise a cell label sequence, a binding site for a universal primer, or any combination thereof. The plurality of barcodes can comprise a plurality of stochastic barcodes, wherein the barcode sequence of each of the plurality of stochastic barcodes comprises a molecular label sequence, wherein the molecular label sequences of at least two stochastic barcodes of the plurality of stochastic barcodes comprise different sequences.

In some embodiments, the protein target comprises an extracellular protein, an intracellular protein, or any combination thereof. The protein target can comprise a cell-surface protein, a cell marker, a B-cell receptor, a T-cell receptor, a major histocompatibility complex, a tumor antigen, a receptor, or any combination thereof. The protein target can be selected from a group comprising 10-100 different protein targets.

In some embodiments, the protein binding reagent can be associated with two or more interaction determination oligonucleotides with an identical sequence. The protein binding reagent can be associated with two or more interaction determination oligonucleotides with different interaction determination sequences.

In some embodiments, the one of the first pair of interaction determination compositions comprises a second protein binding reagent not associated with the interaction determination oligonucleotide. The first protein binding reagent and the second protein binding reagent can be identical or different. The protein binding reagent can be associated with a detectable moiety. In some embodiments, the interaction determination oligonucleotide is associated with a detectable moiety.

In some embodiments, the plurality of barcodes is associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can comprise a bead. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle. The particle can be associated with a detectable moiety.

The barcodes of the particle can comprise barcode sequences selected from at least 1000 different barcode sequences. The barcodes of the particle can comprise barcode sequences selected from least 10000 different barcode sequences. The barcodes sequences of the barcodes can comprise random sequences. The particle can comprise at least 10000 barcodes.

In some embodiments, the kit comprises: a DNA polymerase. The kit can comprise a reverse transcriptase. The kit can comprise: a Moloney Murine Leukemia Virus (M-MLV) reverse transcriptase or a Taq DNA polymerase. In some embodiments, the method comprises a fixation agent (e.g., formalin, paraformaldehyde, glutaraldehyde/osmium tetroxide, Alcoholic fixatives, Hepes-glutamic acid buffer-mediated organic solvent protection effect (HOPE), Bouin solution, or any combination thereof).

Disclosed herein are systems and methods for delivering high quality and performance specific products across a wide range of biomolecule and detectable label portfolios in a fast, efficient and highly scalable manner. In embodiments of the invention, a request for a labeled biomolecule is made and in response to the request the labeled biomolecule is prepared from a pre-existing collection of activated biomolecules and activated labels.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules. The one or more labeled biomolecule reagents can further comprise a second biomolecule not covalently coupled to the label. The biomolecule and the second biomolecule can be the same.

In some embodiments, the label comprises a fluorophore, a chromophore, a polypeptide, a protein, an enzyme, an enzyme substrate, a catalyst, a redox label, a radiolabels, an acoustic label, a Raman (SERS) tag, a mass tag, an isotope tag, a magnetic particle, a microparticle, a nanoparticle, an oligonucleotide, or any combination thereof. In some embodiments, the label comprises an enzyme, an enzyme substrate, or a combination thereof, and wherein the enzyme is capable of modifying the enzyme substrate into a corresponding modified enzyme substrate.

In some embodiments, the enzyme substrate differs from the corresponding modified enzyme substrate by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate, or any combination thereof.

In some embodiments, the enzyme comprises a methyltransferase, a glycoside hydrolase, a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, a xylosidase, or a combination thereof.

In some embodiments, the enzyme substrate comprises 6-mercaptopurine, cellobiose, cellotetraose, xylotetraose, isoprimeverose, β-D-gentiobiose, xyloglucan and mannotriose, agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences.

In some embodiments, the label is conjugated to the biomolecule through a linker. The label can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

Aspects of the present disclosure also include systems for use in preparing a labeled biomolecule reagent. Systems according to some embodiments include an input manager for receiving a request for a labeled biomolecule reagent, a memory for storing a dataset having a plurality of labeled biomolecule reagent storage identifiers, a processing module communicatively coupled to the memory and configured to identify one or more labeled biomolecule reagent storage identifiers from the dataset that corresponds to the labeled biomolecule reagent request and an output manager for providing the one or more identified labeled biomolecule reagent storage identifiers. In some embodiments, the request for a labeled biomolecule reagent includes a biomolecule request and a label request. In other embodiments, the request for a labeled biomolecule reagent is a labeled biomolecule request. In some embodiments, the label request comprises an enzyme request and a substrate request.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the label comprises a fluorophore, a chromophore, a polypeptide, a protein, an enzyme, an enzyme substrate, a catalyst, a redox label, a radiolabels, an acoustic label, a Raman (SERS) tag, a mass tag, an isotope tag, a magnetic particle, a microparticle, a nanoparticle, an oligonucleotide, or any combination thereof. In some embodiments, the label comprises an enzyme, an enzyme substrate, or a combination thereof, and wherein the enzyme is capable of modifying the enzyme substrate into a corresponding modified enzyme substrate.

In some embodiments, the enzyme substrate differs from the corresponding modified enzyme substrate by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate, or any combination thereof.

In some embodiments, the enzyme comprises a methyltransferase, a glycoside hydrolase, a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, a xylosidase, or a combination thereof.

In some embodiments, the enzyme substrate comprises 6-mercaptopurine, cellobiose, cellotetraose, xylotetraose, isoprimeverose, β-D-gentiobiose, xyloglucan and mannotriose, agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences.

In some embodiments, the label is conjugated to the biomolecule through a linker. The label can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

The input manager may be operatively coupled to a graphical user interface, such as a website menu interface where the request for a labeled biomolecule reagent is entered into an internet website. In some embodiments, the input manager is configured to receive a labeled biomolecule request. In other embodiments, the input manager is configured to receive a biomolecule request and a label request. In some embodiments, the label request comprises an enzyme request and a substrate request. The input manager may receive a plurality of labeled biomolecule reagent requests, such as from a single user or from a plurality of users.

The subject systems include memory for storing one or more datasets that include storage identifiers for labeled biomolecules, biomolecules, activated biomolecules, labels, activated labels and reactive linkers. Systems also include a processing module communicatively coupled to the memory that identifies a storage identifier from the one or more datasets that corresponds to the components (e.g., biomolecule request, label request, labeled biomolecule request, etc.) of the labeled biomolecule reagent request. In some embodiments, an output manager is operatively coupled to a communication component to display the identified storage identifiers, such as on an electronic display or by printing the storage identifiers with a printer.

In some embodiments, systems of interest further include a reagent preparatory apparatus in operative communication with the output manager for preparing a labeled biomolecule reagent. The reagent preparatory manager is configured to receive the identified storage identifiers from the output manager and produce a labeled biomolecule reagent that corresponds to the labeled biomolecule reagent request.

In embodiments, the reagent preparatory apparatus includes a plurality of activated biomolecules, a plurality of activated labels and sampling device to provide an activated biomolecule and an activated label to a contacting apparatus. In some embodiments, the reagent preparatory apparatus includes a reagent analyzer which may be used to characterize, formulate or purify the produced labeled biomolecule reagent, such as by solid phase liquid chromatography.

The biomolecule may be a polypeptide, a nucleic acid or a polysaccharide. In some embodiments, the biomolecule is a nucleic acid, such as an oligonucleotide, DNA or RNA. In other embodiments, the biomolecule is a polypeptide, such as a protein, an enzyme or an antibody. Labels may include fluorophores, chromophores, enzymes, enzyme substrates, catalysts, chemiluminescent substrates, electro-chemiluminescent substrates, redox labels, radio labels, acoustic labels, Raman (SERS) tags, mass tags, isotope tags (e.g., isotopically pure rare earth elements), magnetic particles, microparticles, nanoparticles, oligonucleotides, or any combination thereof.

The labeled biomolecule reagents are prepared by coupling an activated biomolecule with an activated label. The activated biomolecule and activated label each include a reactive linker. In embodiments, the reactive linkers react to form a chemical linkage between the activated biomolecule and the activated linker.

Aspects of the present disclosure also include methods for preparing a labeled biomolecule reagent. Methods according to some embodiments include receiving a request for a labeled biomolecule reagent, identifying a storage identifier that corresponds with the components of the labeled biomolecule reagent request (e.g., storage identifiers corresponding to a biomolecule request and a label request) and outputting one or more identified storage identifiers. In some embodiments, the identified biomolecule storage identifier and label storage identifier is outputted onto an electronic display or is printed with a printer. In some embodiments, a plurality of requests for labeled biomolecule reagents are received, such as from a single user or a plurality of users. In some instances, the request for the labeled biomolecule reagent may include a plurality of biomolecule requests and a plurality of label requests. In some embodiments, the request for the labeled biomolecule reagent may include a plurality of biomolecule requests and a single label request.

In still some embodiments, the request for the labeled biomolecule reagent may include a single biomolecule request and a plurality of label requests. In some embodiments, the label request comprises an enzyme request and a substrate request.

In some embodiments, methods further include contacting an activated biomolecule with an activated label to produce a labeled biomolecule reagent. In some embodiments, the activated biomolecule and activated label are contacted in a reagent preparatory apparatus. In some instances, the labeled biomolecule reagent is further purified. After preparation, the labeled biomolecule reagent may be packaged and transported to a remote location.

Aspects of the present disclosure also include methods for requesting and receiving a labeled biomolecule reagent. Methods according to some embodiments include communicating a request for a labeled biomolecule reagent (e.g., to one of the subject systems described herein) and receiving a labeled biomolecule reagent that includes a biomolecule covalently bonded to a label. In some embodiments, communicating a request for a labeled biomolecule reagent includes inputting the biomolecule request and the label request into a graphical user interface, such as a website menu interface on an internet website. In some embodiments, communicating a request for a labeled biomolecule reagent includes inputting a plurality of biomolecule requests and a plurality of label requests. In some embodiments, the label request comprises an enzyme request and a substrate request. In other embodiments, communicating a request for a labeled biomolecule reagent includes inputting a single biomolecule request and a plurality of label requests. In yet other embodiments, communicating a request for a labeled biomolecule reagent includes inputting a plurality of biomolecule requests and inputting a single label request. In still other embodiments, communicating a request for a labeled biomolecule reagent includes inputting a labeled biomolecule request.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules. Receiving the labeled biomolecule reagent can comprise receiving the labeled biomolecule covalently coupled to the label and a second biomolecule not covalently coupled to the label. The labeled biomolecule and the second biomolecule can be the same.

In some embodiments, the label comprises a fluorophore, a chromophore, a polypeptide, a protein, an enzyme, an enzyme substrate, a catalyst, a redox label, a radiolabels, an acoustic label, a Raman (SERS) tag, a mass tag, an isotope tag, a magnetic particle, a microparticle, a nanoparticle, an oligonucleotide, or any combination thereof. In some embodiments, the label comprises an enzyme, an enzyme substrate, or a combination thereof, and wherein the enzyme is capable of modifying the enzyme substrate into a corresponding modified enzyme substrate.

In some embodiments, the enzyme substrate differs from the corresponding modified enzyme substrate by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate, or any combination thereof.

In some embodiments, the enzyme comprises a methyltransferase, a glycoside hydrolase, a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, a xylosidase, or a combination thereof.

In some embodiments, the enzyme substrate comprises 6-mercaptopurine, cellobiose, cellotetraose, xylotetraose, isoprimeverose, β-D-gentiobiose, xyloglucan and mannotriose, agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences. In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

BRIEF DESCRIPTION OF THE DRAWINGS

FIGS. 11A-11C are plots showing that control oligonucleotides can be used for cell counting.

FIG. 15 depicts a graphical user interface for communicating a request for a labeled biomolecule reagent according to some embodiments of the invention.

FIG. 18 panels (a)-(d) show non-limiting exemplary designs of oligonucleotides for determining protein expression and gene expression simultaneously.

FIGS. 30A-30C are non-limiting exemplary plots showing that oligonucleotide-conjugated anti-CD147 antibody molecules can be used to label various cell types. The cell types were determined using the expression profiles of 488 genes in a blood panel (FIG. 30A). The cells were stained with a mixture of 10% hot antibody:90% cold antibody prepared using a 1:100 diluted stock, resulting in a clear signal in a histogram showing the numbers of molecules of antibody oligonucleotides detected (FIG. 30B). The labeling of the various cell types by the antibody oligonucleotide is shown in FIG. 30C.

FIGS. 33A-33B are plots showing the composition of control particle oligonucleotides in a staining buffer and control particle oligonucleotides associated with control particles detected using the workflow illustrated in FIG. 7.

DETAILED DESCRIPTION

Figure 1:
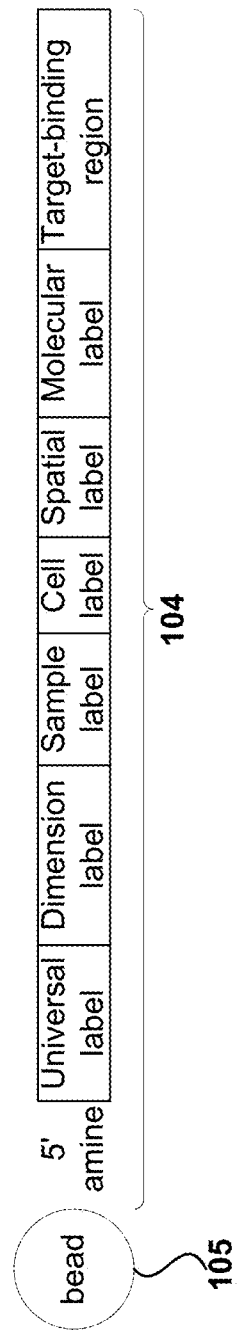
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, CA)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular labels, and the numbers of mRNA molecules.

Methods for determining mRNA expression profiles of single cells can be performed in a massively parallel manner. For example, the Precise™ assay can be used to determine the mRNA expression profiles of more than 10,000 cells simultaneously. The number of single cells (e.g., 100s or 1,000s of singles) for analysis per sample can be lower than the capacity of the current single cell technology. Pooling of cells from different samples enables improved utilization of the capacity of the current single technology, thus lowering reagents wasted and the cost of single cell analysis. Pooling of cells from different samples can minimize the variations in cDNA library preparation of cells of different samples, thus enabling more accurate comparisons of different samples.

Some embodiments disclosed herein provide a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to a protein target. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, the plurality of compositions comprises at least 100 different protein binding reagents. In some embodiments, the plurality of compositions comprises at least 100 different protein binding reagents. In some embodiments, the plurality of compositions comprises at least 1,000 different protein binding reagents. In some embodiments, the plurality of compositions comprises at least 10,000 different protein binding reagents. In some embodiments, the plurality of compositions comprises at least 10,000 different protein binding reagents. In some embodiments, each protein binding reagent is conjugated with one or more oligonucleotides comprising at least one barcode sequence (e.g., one molecular label sequence) selected from a set of at least 10 different barcode sequences. In some embodiments, each protein binding reagent is conjugated with one or more oligonucleotides comprising at least one barcode sequence selected from a set of at least 100 different barcode sequences. In some embodiments, each protein binding reagent is conjugated with one or more oligonucleotides comprising at least one barcode sequence selected from a set of at least 1,000 different barcode sequences. In some embodiments, the plurality of compositions is capable of specifically binding to a plurality of protein targets. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets comprises 10-400 different protein targets.

Definitions

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, an antibody can be a full-length (e.g., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "attached", or "immobilized" to one another or to a common solid or semisolid surface. An association may refer to covalent or non-covalent means for attaching labels to solid or semi-solid supports such as beads. An association may comprise hybridization between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequenceable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" refers to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" refers to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins, polypeptides or peptides. In some embodiments targets are lipids. As used herein, "target" can be used interchangeably with "species."

The term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Some embodiments disclosed herein provide a plurality of compositions each comprising a protein binding reagent conjugated with an oligonucleotide, wherein the oligonucleotide comprises a unique identifier for the protein binding reagent that it is conjugated therewith, and the protein binding reagent is capable of specifically binding to a protein target. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, the plurality of compositions comprises at least 100 different protein binding reagents. In some embodiments, the plurality of compositions comprises at least 100 different protein binding reagents. In some embodiments, the plurality of compositions comprises at least 1,000 different protein binding reagents. In some embodiments, the plurality of compositions comprises at least 10,000 different protein binding reagents. In some embodiments, the plurality of compositions comprises at least 10,000 different protein binding reagents. In some embodiments, each protein binding reagent is conjugated with one or more oligonucleotides comprising at least one barcode sequence (e.g., molecular label sequence) selected from a set of at least 10 different barcode sequences. In some embodiments, each protein binding reagent is conjugated with one or more oligonucleotides comprising at least one barcode sequence selected from a set of at least 100 different barcode sequences. In some embodiments, each protein binding reagent is conjugated with one or more oligonucleotides comprising at least one barcode sequence selected from a set of at least 1,000 different barcode sequences. In some embodiments, the plurality of compositions is capable of specifically binding to a plurality of protein targets. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets comprises 10-400 different protein targets.

Barcodes

Barcoding, such as stochastic barcoding, has been described in, for example, US20150299784, WO2015031691, and Fu et al, Proc Natl Acad Sci U.S.A. 2011 May 31; 108(22):9026-31, the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., bead), but different for different solid supports (e.g., beads). In some embodiments, at least 60%, 70%, 80%, 85%, 90%, 95%, 97%, 99% or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all barcodes attached to a given solid support (e.g., bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., beads), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., bead).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., bead).

For stochastic barcoding using a plurality of stochastic barcodes, the ratio of the number of different molecular label sequences and the number of occurrence of any of the targets can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length.

A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Error Correction

The cell label and/or any label of the disclosure can further comprise a unique set of nucleic acid sub-sequences of defined length, e.g. 7 nucleotides each (equivalent to the number of bits used in some Hamming error correction codes), which are designed to provide error correction capability. Hamming codes, like other error-correcting codes, are based on the principle of redundancy and can be constructed by adding redundant parity bits to data that is to be transmitted over a noisy medium. Such error-correcting codes can encode sample identifiers with redundant parity bits, and "transmit" these sample identifiers as code words. A Hamming code can refer an arithmetic process that identifies unique binary codes based upon inherent redundancy that are capable of correcting single bit errors. For example, a Hamming code can be matched with a nucleic acid barcode in order to screen for single nucleotide errors occurring during nucleic acid amplification. The identification of a single nucleotide error by using a Hamming code, thereby can allow for the correction of the nucleic acid barcode.

Hamming codes can be represented by a subset of the possible code words that are chosen from the center of multidimensional spheres (i.e., for example, hyperspheres) in a binary subspace. Single bit errors may fall within hyperspheres associated with a specific code word and can thus be corrected. On the other hand, double bit errors that do not associate with a specific code word can be detected, but not corrected. Consider a first hypersphere centered at coordinates (0, 0, 0) (i.e., for example, using an x-y-z coordinate system), wherein any single-bit error can be corrected by falling within a radius of 1 from the center coordinates; i.e., for example, single bit errors having the coordinates of (0, 0, 0); (0, 1, 0); (0, 0, 1); (1, 0, 0), or (1, 1, 0). Likewise, a second hypersphere may be constructed wherein single-bit errors can be corrected by falling within a radius of 1 of its center coordinates (1, 1, 1) (i.e., for example, (1, 1, 1); (1, 0, 1); (0, 1, 0); or (0, 1, 1)).

In some embodiments, the length of the nucleic acid sub-sequences used for creating error correction codes can vary, for example, they can be at least 3 nucleotides, at least 7 nucleotides, at least 15 nucleotides, or at least 31 nucleotides in length. In some embodiments, nucleic acid sub-sequences of other lengths can be used for creating error correction codes.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
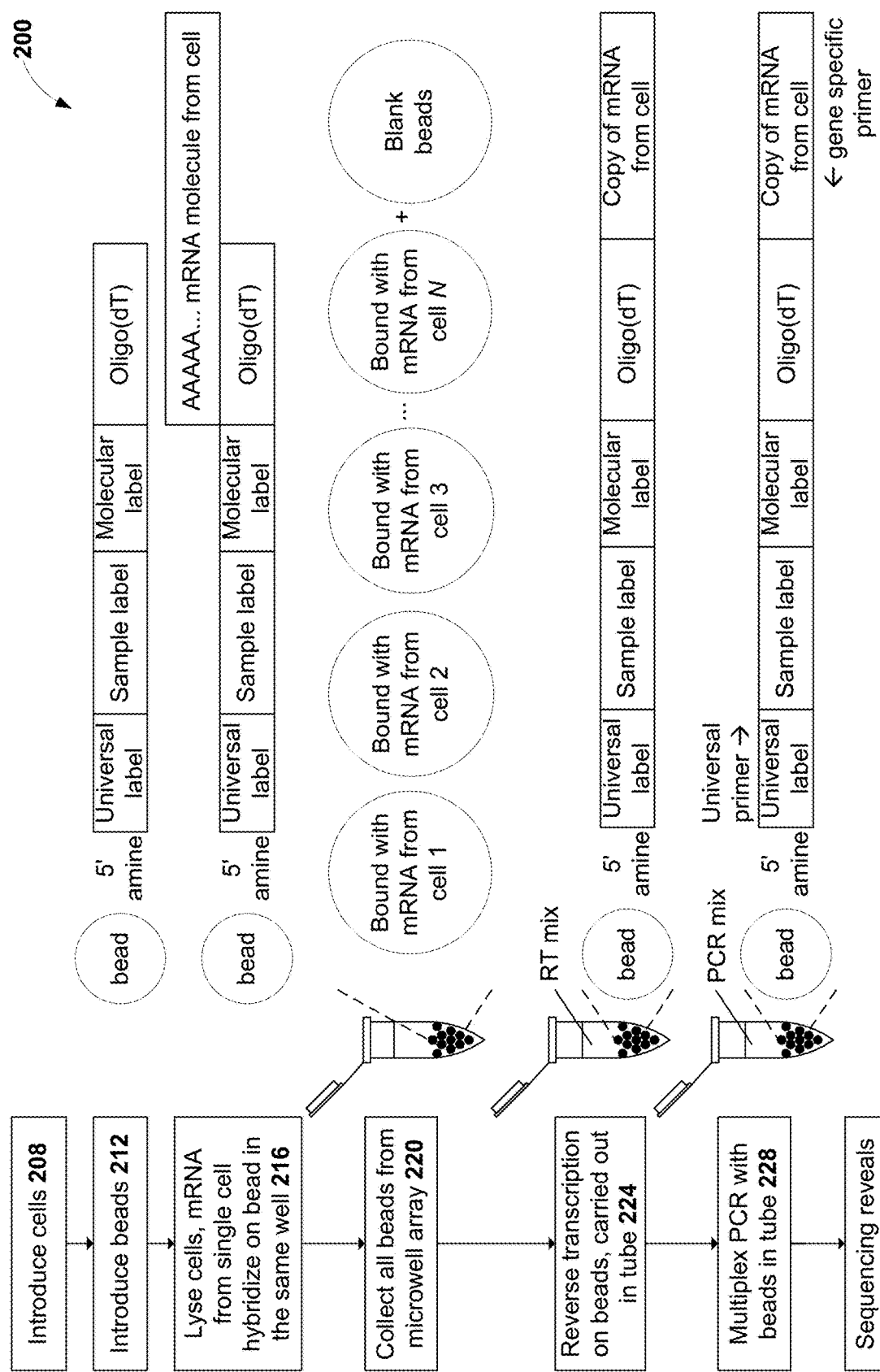
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof. In some embodiments, the bead (e.g., the bead to which the labels are attached) is a hydrogel bead. In some embodiments, the bead comprises hydrogel.

Some embodiments disclosed herein include one or more particles (for example beads). Each of the particles can comprise a plurality of oligonucleotides (e.g., barcodes). Each of the plurality of oligonucleotides can comprise a barcode sequence (e.g., a molecular label), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different barcode sequences (e.g., molecular labels). In some embodiments, the number of barcode sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameters of the bead can be at least, or at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameters of the beads can be at least, or at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose barcodes (e.g., stochastic barcodes) of the disclosure to targets. For example, a biological molecule can comprise barcodes that are inaccessible due to folding of the biological molecule. Upon modification of the biological molecule (e.g., acetylation), the biological molecule can change conformation to expose the barcodes. The timing of the modification can provide another time dimension to the method of barcoding of the disclosure.

In some embodiments, the biological molecule comprising barcode reagents of the disclosure can be located in the cytoplasm of a cell. Upon activation, the biological molecule can move to the nucleus, whereupon barcoding can take place. In this way, modification of the biological molecule can encode additional space-time information for the targets identified by the barcodes.

Substrates and Microwell Array

As used herein, a substrate can refer to a type of solid support. A substrate can refer to a solid support that can comprise barcodes and stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). A microwell can comprise combinatorial barcode reagents of the disclosure.

The microwells of the array can be fabricated in a variety of shapes and sizes. Well geometries can include, but are not limited to, cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The opening of the microwell can be at the upper surface of the substrate. The opening of the microwell can be at the lower surface of the substrate. The closed end (or bottom) of the microwell can be flat. The closed end (or bottom) of the microwell can have a curved surface (e.g., convex or concave). The shape and/or size of the microwell can be determined based on the types of cells or solid supports to be trapped within the microwells.

The portion of the substrate between the wells can have a topology. For example, the portion of the substrate between the wells can be rounded. The portion of the substrate between the wells can be pointed. The spacing portion of the substrate between the wells can be flat. The portion of the substrate between the wells may not be flat. In some instances, the portion of the substrate between wells is rounded. In other words, the portion of the substrate that does not comprise a well can have a curved surface. The curved surface can be fabricated such that the highest point (e.g., apex) of the curved surface may be at the furthest point between the edges of two or more wells (e.g., equidistant from the wells). The curved surface can be fabricated such that the start of the curved surface is at the edge of a first microwell and creates a parabola that ends at the end of a second microwell. This parabola can be extended in 2 dimensions to capture microwells nearby on the hexagonal grid of wells. The curved surface can be fabricated such that the surface between the wells is higher and/or curved than the plane of the opening of the well. The height of the curved surface can be, or be at least, 0.1, 0.5, 1, 1.5, 2, 2.5, 3, 3.5, 4, 4.5, 5, 5.5, 6, 6.5, or 7 or more micrometers. In some embodiments, the height of the curved surface can be at most 0.1, 0.5, 1, 1.5, 2, 2.5, 3, 3.5, 4, 4.5, 5, 5.5, 6, 6.5, or 7 or more micrometers.

Microwell dimensions can be characterized in terms of the diameter and depth of the well. As used herein, the diameter of the microwell refers to the largest circle that can be inscribed within the planar cross-section of the microwell geometry. The diameter of the microwells can range from about 1-fold to about 10-fold the diameter of the cells or solid supports to be trapped within the microwells. The microwell diameter can be, or be at least, 1-fold, at least 1.5-fold, at least 2-fold, at least 3-fold, at least 4-fold, at least 5-fold, or at least 10-fold the diameter of the cells or solid supports to be trapped within the microwells. In some embodiments, the microwell diameter can be at most 10-fold, at most 5-fold, at most 4-fold, at most 3-fold, at most 2-fold, at most 1.5-fold, or at most 1-fold the diameter of the cells or solid supports to be trapped within the microwells. The microwell diameter can be about 2.5-fold the diameter of the cells or solid supports to be trapped within the microwells.

The diameter of the microwells can be specified in terms of absolute dimensions. The diameter of the microwells can range from about 5 to about 60 micrometers. The microwell diameter can be, or be at least, 5 micrometers, at least 10 micrometers, at least 15 micrometers, at least 20 micrometers, at least 25 micrometers, at least 30 micrometers, at least 35 micrometers, at least 40 micrometers, at least 45 micrometers, at least 50 micrometers, or at least 60 micrometers. The microwell diameter can be at most 60 micrometers, at most 50 micrometers, at most 45 micrometers, at most 40 micrometers, at most 35 micrometers, at most 30 micrometers, at most 25 micrometers, at most 20 micrometers, at most 15 micrometers, at most 10 micrometers, or at most 5 micrometers. The microwell diameter can be about 30 micrometers.

The microwell depth may be chosen to provide efficient trapping of cells and solid supports. The microwell depth may be chosen to provide efficient exchange of assay buffers and other reagents contained within the wells. The ratio of diameter to height (i.e. aspect ratio) may be chosen such that once a cell and solid support settle inside a microwell, they will not be displaced by fluid motion above the microwell. The dimensions of the microwell may be chosen such that the microwell has sufficient space to accommodate a solid support and a cell of various sizes without being dislodged by fluid motion above the microwell. The depth of the microwells can range from about 1-fold to about 10-fold the diameter of the cells or solid supports to be trapped within the microwells. The microwell depth can be, or be at least, 1-fold, at least 1.5-fold, at least 2-fold, at least 3-fold, at least 4-fold, at least 5-fold, or at least 10-fold the diameter of the cells or solid supports to be trapped within the microwells. The microwell depth can be at most 10-fold, at most 5-fold, at most 4-fold, at most 3-fold, at most 2-fold, at most 1.5-fold, or at most 1-fold the diameter of the cells or solid supports to be trapped within the microwells. The microwell depth can be about 2.5-fold the diameter of the cells or solid supports to be trapped within the microwells.

The depth of the microwells can be specified in terms of absolute dimensions. The depth of the microwells may range from about 10 to about 60 micrometers. The microwell depth can be, or be at least, 10 micrometers, at least 20 micrometers, at least 25 micrometers, at least 30 micrometers, at least 35 micrometers, at least 40 micrometers, at least 50 micrometers, or at least 60 micrometers. The microwell depth can be at most 60 micrometers, at most 50 micrometers, at most 40 micrometers, at most 35 micrometers, at most 30 micrometers, at most 25 micrometers, at most 20 micrometers, or at most 10 micrometers. The microwell depth can be about 30 micrometers.

The volume of the microwells used in the methods, devices, and systems of the present disclosure can range from about 200 micrometers$^3$ to about 120,000 micrometers$^3$. The microwell volume can be at least 200 micrometers$^3$, at least 500 micrometers$^3$, at least 1,000 micrometers$^3$, at least 10,000 micrometers$^3$, at least 25,000 micrometers$^3$, at least 50,000 micrometers$^3$, at least 100,000 micrometers$^3$, or at least 120,000 micrometers$^3$. The microwell volume can be at most 120,000 micrometers$^3$, at most 100,000 micrometers$^3$, at most 50,000 micrometers$^3$, at most 25,000 micrometers$^3$, at most 10,000 micrometers$^3$, at most 1,000 micrometers$^3$, at most 500 micrometers$^3$, or at most 200 micrometers$^3$. The microwell volume can be about 25,000 micrometers$^3$. The microwell volume may fall within any range bounded by any of these values (e.g. from about 18,000 micrometers$^3$ to about 30,000 micrometers$^3$).

The volume of the microwell can be, or be at least, 5, 10, 15, 20, 25, 30, 35 40, 45 or 50 or more nanoliters$^3$. The volume of the microwell can be at most 5, 10, 15, 20, 25, 30, 35 40, 45 or 50 or more nanoliters$^3$. The volume of liquid that can fit in the microwell can be at least 5, 10, 15, 20, 25, 30, 35 40, 45 or 50 or more nanoliters$^3$. The volume of liquid that can fit in the microwell can be at most 5, 10, 15, 20, 25, 30, 35 40, 45 or 50 or more nanoliters$^3$. The volume of the microwell can be, or be at least, 5, 10, 15, 20, 25, 30, 35 40, 45 or 50 or more picoliters$^3$. The volume of the microwell can be at most 5, 10, 15, 20, 25, 30, 35 40, 45 or 50 or more picoliters$^3$. The volume of liquid that can fit in the microwell can be at least 5, 10, 15, 20, 25, 30, 35 40, 45 or 50 or more picoliters$^3$. The volume of liquid that can fit in the microwell can be at most 5, 10, 15, 20, 25, 30, 35 40, 45 or 50 or more picoliters$^3$.

The volumes of the microwells used in the methods, devices, and systems of the present disclosure may be further characterized in terms of the variation in volume from one microwell to another. The coefficient of variation (expressed as a percentage) for microwell volume may range from about 1% to about 10%. The coefficient of variation for microwell volume may be at least 1%, at least 2%, at least 3%, at least 4%, at least 5%, at least 6%, at least 7%, at least 8%, at least 9%, or at least 10%. The coefficient of variation for microwell volume may be at most 10%, at most 9%, at most 8%, at most 7%, at most 6%, at most 5%, at most 4%, at most 3%, at most 2%, or at most 1%. The coefficient of variation for microwell volume may have any value within a range encompassed by these values, for example between about 1.5% and about 6.5%. In some embodiments, the coefficient of variation of microwell volume may be about 2.5%.

The ratio of the volume of the microwells to the surface area of the beads (or to the surface area of a solid support to which barcode oligonucleotides may be attached) used in the methods, devices, and systems of the present disclosure can range from about 2.5 to about 1,520 micrometers. The ratio can be at least 2.5, at least 5, at least 10, at least 100, at least 500, at least 750, at least 1,000, or at least 1,520. The ratio can be at most 1,520, at most 1,000, at most 750, at most 500, at most 100, at most 10, at most 5, or at most 2.5. The ratio can be about 67.5. The ratio of microwell volume to the surface area of the bead (or solid support used for immobilization) may fall within any range bounded by any of these values (e.g. from about 30 to about 120).

The wells of the microwell array can be arranged in a one dimensional, two dimensional, or three-dimensional array. In some embodiments, a three dimensional array can be achieved, for example, by stacking a series of two or more two dimensional arrays (that is, by stacking two or more substrates comprising microwell arrays).

The pattern and spacing between microwells can be chosen to optimize the efficiency of trapping a single cell and single solid support (e.g., bead) in each well, as well as to maximize the number of wells per unit area of the array. The microwells may be distributed according to a variety of random or non-random patterns. For example, they may be distributed entirely randomly across the surface of the array substrate, or they may be arranged in a square grid, rectangular grid, hexagonal grid, or the like. In some instances, the microwells are arranged hexagonally. The center-to-center distance (or spacing) between wells may vary from about 5 micrometers to about 75 micrometers. In some instances, the spacing between microwells is about 10 micrometers. In other embodiments, the spacing between wells is at least 5 micrometers, at least 10 micrometers, at least 15 micrometers, at least 20 micrometers, at least 25 micrometers, at least 30 micrometers, at least 35 micrometers, at least 40 micrometers, at least 45 micrometers, at least 50 micrometers, at least 55 micrometers, at least 60 micrometers, at least 65 micrometers, at least 70 micrometers, or at least 75 micrometers. The microwell spacing can be at most 75 micrometers, at most 70 micrometers, at most 65 micrometers, at most 60 micrometers, at most 55 micrometers, at most 50 micrometers, at most 45 micrometers, at most 40 micrometers, at most 35 micrometers, at most 30 micrometers, at most 25 micrometers, at most 20 micrometers, at most 15 micrometers, at most 10 micrometers, at most 5 micrometers. The microwell spacing can be about 55 micrometers. The microwell spacing may fall within any range bounded by any of these values (e.g. from about 18 micrometers to about 72 micrometers).

The microwell array may comprise surface features between the microwells that are designed to help guide cells and solid supports into the wells and/or prevent them from settling on the surfaces between wells. Examples of suitable surface features can include, but are not limited to, domed, ridged, or peaked surface features that encircle the wells or straddle the surface between wells.

The total number of wells in the microwell array can be determined by the pattern and spacing of the wells and the overall dimensions of the array. The number of microwells in the array can range from about 96 to about 5,000,000 or more. The number of microwells in the array can be at least 96, at least 384, at least 1,536, at least 5,000, at least 10,000, at least 25,000, at least 50,000, at least 75,000, at least 100,000, at least 500,000, at least 1,000,000, or at least 5,000,000. The number of microwells in the array can be at most 5,000,000, at most 1,000,000, at most 75,000, at most 50,000, at most 25,000, at most 10,000, at most 5,000, at most 1,536, at most 384, or at most 96 wells. The number of microwells in the array can be about 96, 384, and/or 1536. The number of microwells can be about 150,000. The number of microwells in the array may fall within any range bounded by any of these values (e.g. from about 100 to 325,000).

Microwell arrays may be fabricated using any of a number of fabrication techniques. Examples of fabrication methods that may be used include, but are not limited to, bulk micromachining techniques such as photolithography and wet chemical etching, plasma etching, or deep reactive ion etching; micro-molding and micro-embossing; laser micromachining; 3D printing or other direct write fabrication processes using curable materials; and similar techniques.

Microwell arrays can be fabricated from any of a number of substrate materials. The choice of material can depend on the choice of fabrication technique, and vice versa. Examples of suitable materials can include, but are not limited to, silicon, fused-silica, glass, polymers (e.g. agarose, gelatin, hydrogels, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. In some instances, the microwell comprises optical adhesive. In some instances, the microwell is made out of optical adhesive. In some instances, the microwell array comprises and/or is made out of PDMS. In some instances, the microwell is made of plastic. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can also be used. The use of porous, hydrophilic materials for the fabrication of the microwell array may be desirable in order to facilitate capillary wicking/venting of entrapped air bubbles in the device. The microwell array can be fabricated from a single material. The microwell array may comprise two or more different materials that have been bonded together or mechanically joined.

Microwell arrays can be fabricated using substrates of any of a variety of sizes and shapes. For example, the shape (or footprint) of the substrate within which microwells are fabricated may be square, rectangular, circular, or irregular in shape. The footprint of the microwell array substrate can be similar to that of a microtiter plate. The footprint of the microwell array substrate can be similar to that of standard microscope slides, e.g. about 75 mm long×25 mm wide (about 3" long×1" wide), or about 75 mm long×50 mm wide (about 3" long×2" wide). The thickness of the substrate within which the microwells are fabricated may range from about 0.1 mm thick to about 10 mm thick, or more. The thickness of the microwell array substrate may be at least 0.1 mm thick, at least 0.5 mm thick, at least 1 mm thick, at least 2 mm thick, at least 3 mm thick, at least 4 mm thick, at least 5 mm thick, at least 6 mm thick, at least 7 mm thick, at least 8 mm thick, at least 9 mm thick, or at least 10 mm thick. The thickness of the microwell array substrate may be at most 10 mm thick, at most 9 mm thick, at most 8 mm thick, at most 7 mm thick, at most 6 mm thick, at most 5 mm thick, at most 4 mm thick, at most 3 mm thick, at most 2 mm thick, at most 1 mm thick, at most 0.5 mm thick, or at most 0.1 mm thick. The thickness of the microwell array substrate can be about 1 mm thick. The thickness of the microwell array substrate may be any value within these ranges, for example, the thickness of the microwell array substrate may be between about 0.2 mm and about 9.5 mm. The thickness of the microwell array substrate may be uniform.

A variety of surface treatments and surface modification techniques may be used to alter the properties of microwell array surfaces. Examples can include, but are not limited to, oxygen plasma treatments to render hydrophobic material surfaces more hydrophilic, the use of wet or dry etching techniques to smooth (or roughen) glass and silicon surfaces, adsorption or grafting of polyethylene oxide or other polymer layers (such as pluronic), or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells may be used to covalently couple oligonucleotide probes, peptides, proteins, or other biomolecules to the walls of the microwells. The choice of surface treatment or surface modification utilized can depend both or either on the type of surface property that is desired and on the type of material from which the microwell array is made.

The openings of microwells can be sealed, for example, during cell lysis steps to prevent cross hybridization of target nucleic acid between adjacent microwells. A microwell (or array of microwells) may be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells may comprise any of the solid supports (e.g., beads) of the disclosure. In some instances, the solid supports are cross-linked dextran beads (e.g., Sephadex). Cross-linked dextran can range from about 10 micrometers to about 80 micrometers. The cross-linked dextran beads used for capping can be from 20 micrometers to about 50 micrometers. In some embodiments, the beads may be at least about 10, 20, 30, 40, 50, 60, 70, 80 or 90% larger than the diameter of the microwells. The beads used for capping may be at most about 10, 20, 30, 40, 50, 60, 70, 80 or 90% larger than the diameter of the microwells.

The seal or cap may allow buffer to pass into and out of the microwell, while preventing macromolecules (e.g., nucleic acids) from migrating out of the well. A macromolecule of at least about 1, 2, 3, 4, 5, 6, 7, 8, 9, 10, 12, 13, 14, 15, 16, 17, 18, 19, or 20 or more nucleotides may be blocked from migrating into or out of the microwell by the seal or cap. A macromolecule of at most about 1, 2, 3, 4, 5, 6, 7, 8, 9, 10, 12, 13, 14, 15, 16, 17, 18, 19, or 20 or more nucleotides may be blocked from migrating into or out of the microwell by the seal or cap.

Solid supports (e.g., beads) may be distributed among a substrate. Solid supports (e.g., beads) can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold at least 1, 2, 3, 4, or 5, or more solid supports. A microwell of a substrate can hold at most 1, 2, 3, 4, or 5 or more solid supports. In some instances, a microwell of a substrate can hold one solid support.

Individual cells and beads may be compartmentalized using alternatives to microwells, for example, a single solid support and single cell could be confined within a single droplet in an emulsion (e.g. in a droplet digital microfluidic system).

Cells could potentially be confined within porous beads that themselves comprise the plurality of tethered barcodes. Individual cells and solid supports may be compartmentalized in any type of container, microcontainer, reaction chamber, reaction vessel, or the like.

Single cell combinatorial barcoding or may be performed without the use of microwells. Single cell, combinatorial barcoding assays may be performed without the use of any physical container. For example, combinatorial barcoding without a physical container can be performed by embedding cells and beads in close proximity to each other within a polymer layer or gel layer to create a diffusional barrier between different cell/bead pairs. In another example, combinatorial barcoding without a physical container can be performed in situ, in vivo, on an intact solid tissue, on an intact cell, and/or subcellularly.

Microwell arrays can be a consumable component of the assay system. Microwell arrays may be reusable. Microwell arrays can be configured for use as a standalone device for performing assays manually, or they may be configured to comprise a fixed or removable component of an instrument system that provides for full or partial automation of the assay procedure. In some embodiments of the disclosed methods, the bead-based libraries of barcodes (e.g., stochastic barcodes) can be deposited in the wells of the microwell array as part of the assay procedure. In some embodiments, the beads may be pre-loaded into the wells of the microwell array and provided to the user as part of, for example, a kit for performing barcoding (e.g., stochastic barcoding) and digital counting of nucleic acid targets.

In some embodiments, two mated microwell arrays are provided, one pre-loaded with beads which are held in place by a first magnet, and the other for use by the user in loading individual cells. Following distribution of cells into the second microwell array, the two arrays may be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the barcodes on the bead.

Microwell arrays of the disclosure can be pre-loaded with solid supports (e.g., beads). Each well of a microwell array can comprise a single solid support. At least 10, 20, 30, 40, 50, 60, 70, 80, 90, or 100% of the wells in a microwell array can be pre-loaded with a single solid support. At most 10, 20, 30, 40, 50, 60, 70, 80, 90, or 100% of the wells in a microwell array can be pre-loaded with a single solid support. The solid support can comprise barcodes (e.g., stochastic barcodes) of the disclosure. Cell labels of barcodes on different solid supports can be different. Cell labels of barcodes on the same solid support can be the same.

Methods of Barcoding

The disclosure provides for methods for estimating the number of distinct targets at distinct locations in a physical sample (e.g., tissue, organ, tumor, cell). The methods can comprise placing the barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be crosslinked to the barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e. a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cell label and/or barcode sequence (e.g., molecular label). The amplification reactions can comprise amplifying at least a portion of a sample tag, a cell label, a spatial label, a barcode (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled-amplicon (e.g., a stochastically labeled-amplicon). The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded fragments. The barcodes sequences of different barcodes (e.g., the molecular labels of different stochastic barcodes) can be different from one another. Generating an indexed library of the barcoded targets (e.g., stochastically barcoded targets) includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, barcode sequences (e.g., molecular labels), and sequences of nucleotide fragments of the one or more copies of the targets, for example at block 232 of FIG. 2.

Figure 3:
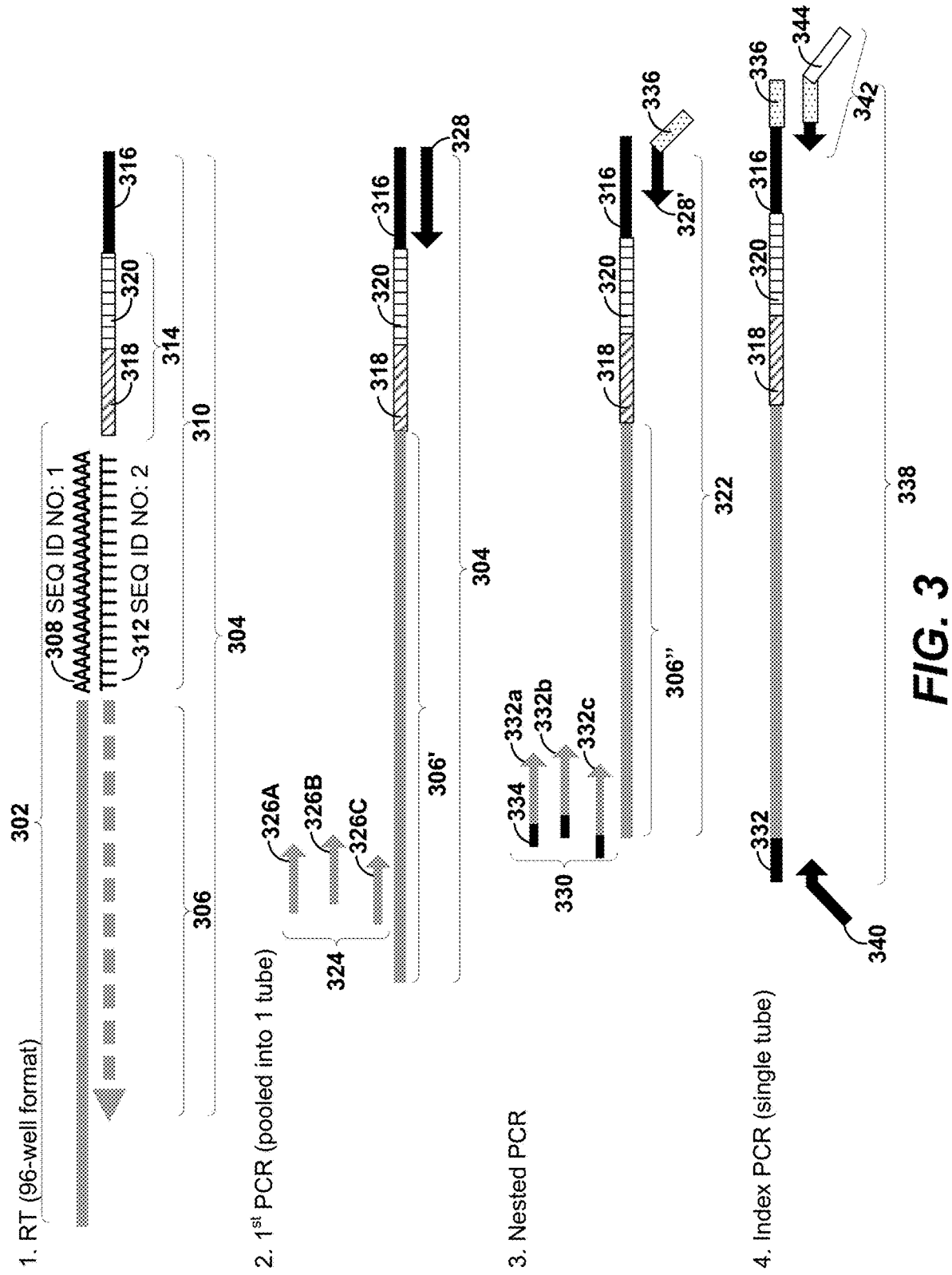
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the barcoded targets (e.g., stochastically barcoded targets), for example mRNAs. As shown in step 1, the reverse transcription process can encode each mRNA molecule with a unique barcode sequence (e.g., molecular label), a cell label, and a universal PCR site. In particular, RNA molecules 302 can be reverse transcribed to produce labeled cDNA molecules 304, including a cDNA region 306, by the hybridization (e.g., stochastic hybridization) of a set of barcodes (e.g., stochastic barcodes) 310) to the poly(A) tail region 308 of the RNA molecules 302. Each of the barcodes 310 can comprise a target-binding region, for example a poly(dT) region 312, a barcode sequence or a molecular label 314, and a universal PCR region 316.

In some embodiments, the cell label can include 3 to 20 nucleotides. In some embodiments, the barcode sequence (e.g., molecular label) can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a 1$^{st}$ PCR primer pool and a 1$^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise 1$^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a 2$^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a 2$^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the 2$^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Compositions Comprising Cellular Component Binding Reagents Conjugated with Oligonucleotides Some embodiments disclosed herein provide a plurality of compositions each comprising a cellular component binding regent (e.g., a protein binding reagent) conjugated with an oligonucleotide, wherein the oligonucleotide comprises a unique identifier for the cellular component binding reagent that it is conjugated with. A binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., the protein binding reagent) is capable of specifically binding to a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length. In some embodiments, the poly(A) tail can be 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides. In some embodiments, the unique identifier is a nucleotide sequence of 25 nucleotides to about 45 nucleotides in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 2,000, at least 5,000, or more different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, or more. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable protein binding reagents are contemplated in this disclosure, such as antibodies or fragments thereof, aptamers, small molecules, ligands, peptides, oligonucleotides, etc., or any combination thereof. In some embodiments, the protein binding reagents can be polyclonal antibodies, monoclonal antibodies, recombinant antibodies, single chain antibody (sc-Ab), or fragments thereof, such as Fab, Fv, etc. In some embodiments, the plurality of protein binding reagents can comprise at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 2,000, at least 5,000, or more different protein binding reagents.

The oligonucleotide can be conjugated with the protein binding reagent through various mechanism. In some embodiments, the oligonucleotide can be conjugated with the protein binding reagent covalently. In some embodiment, the oligonucleotide can be conjugated with the protein binding reagent non-covalently. In some embodiments, the oligonucleotide is conjugated with the protein binding reagent through a linker. The linker can be, for example, cleavable or detachable from the protein binding reagent and/or the oligonucleotide. In some embodiments, the linker can comprise a chemical group that reversibly attaches the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, streptavidin, biotin, amine, etc. In some embodiments, the chemical group can be conjugated to the protein binding reagent through a primary amine on an amino acid, such as lysine, or the N-terminus. Commercially available conjugation kits, such as the Protein-Oligo Conjugation Kit (Solulink, Inc., San Diego, California), the Thunder-Link® oligo conjugation system (Innova Biosciences, Cambridge, United Kingdom), etc., can be used to conjugate the oligonucleotide to the protein binding reagent.

The oligonucleotide can be conjugated to any suitable site of the cellular component binding reagent (e.g., the protein binding reagent), as long as it does not interfere with the specific binding between the cellular component binding reagent and its cellular component target. In some embodiments, the cellular component binding regent is a protein. In some embodiments, the cellular component binding reagent is not an antibody. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the CL domain, etc. Methods of conjugating oligonucleotides to antibodies have been previously disclosed, for example, in U.S. Pat. No. 6,531,283, the content of which is hereby expressly incorporated by reference in its entirety. Stoichiometry of oligonucleotide to protein binding reagent can be varied. To increase the sensitivity of detecting the protein binding reagent specific oligonucleotide in sequencing, it may be advantageous to increase the ratio of oligonucleotide to protein binding reagent during conjugation. In some embodiments, each protein binding reagent can be conjugated with a single oligonucleotide molecule. In some embodiments, each protein binding reagent can be conjugated with more than one oligonucleotide molecule, for example, at least 2, at least 3, at least 4, at least 5, at least 10, at least 20, at least 30, at least 40, at least 50, at least 100, at least 1,000, or more oligonucleotide molecules, wherein each of the oligonucleotide molecule comprises the same unique identifier.

Figure 4:
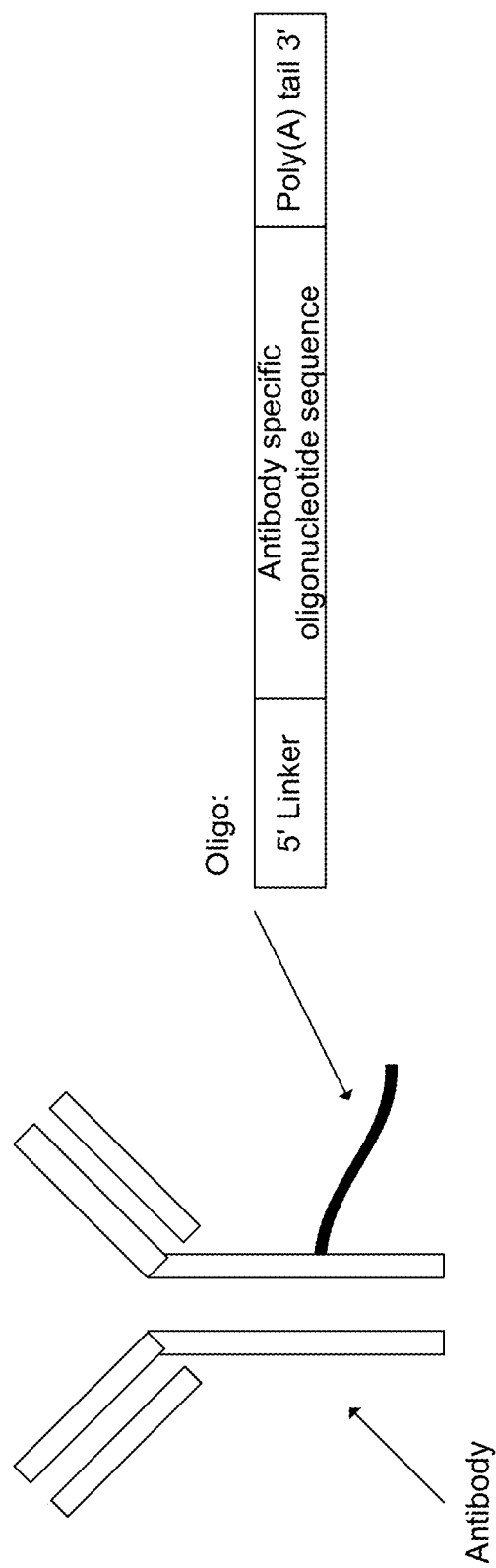
FIG. 4 shows a schematic illustration of an exemplary protein binding reagent (antibody illustrated here) conjugated with an oligonucleotide comprising a unique identifier for the protein binding reagent.

FIG. 4 shows a schematic illustration of an exemplary protein binding reagent, e.g., an antibody, that is conjugated with an oligonucleotide comprising a unique identifier sequence for the antibody. An oligonucleotide-conjugated with an antibody, an oligonucleotide for conjugation with an antibody, or an oligonucleotide previously conjugated with an antibody can be referred to herein as an antibody oligonucleotide (abbreviated as "AbOligo" or "AbO"). The oligonucleotide can also comprise additional components, including but not limited to, one or more linker, one or more unique identifier for the antibody, optionally one or more barcode sequences (e.g., molecular labels), and a poly(A) tail. In some embodiments, the oligonucleotide can comprise, from 5' to 3', a linker, a unique identifier, a barcode sequence (e.g., a molecular label), and a poly(A) tail.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the cellular component binding reagents are protein binding reagents, and the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets can comprise intracellular proteins. In some embodiments, the plurality of protein targets can comprise intracellular proteins. In some embodiments, the plurality of proteins can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded proteins in an organism. In some embodiments, the plurality of protein targets can comprise at least 2, at least 3, at least 4, at least 5, at least 10, at least 20, at least 30, at least 40, at least 50, at least 100, at least 1,000, at least 10,000, or more different protein targets.

The antibody oligonucleotide disclosed herein can, for example, comprise a barcode sequence (e.g., a molecular label), a poly(A) tail, or a combination thereof. In some embodiments, the antibody oligonucleotide comprises a sequence complementary to a capture sequence of at least one barcode of the plurality of barcodes. A target binding region of the barcode can comprise the capture sequence. The target binding region can, for example, comprise a poly(dT) region. In some embodiments, the sequence of the antibody oligonucleotide complementary to the capture sequence of the barcode can comprise a poly(A) tail. The antibody oligonucleotide can comprise a barcode sequence (e.g., a molecular label).

In some embodiments, the antibody oligonucleotide sequence comprises a nucleotide sequence of, or about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the antibody oligonucleotide sequence comprises a nucleotide sequence of at least, or at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the protein binding reagent comprises an antibody, a tetramer, an aptamers, a protein scaffold, or a combination thereof. The antibody oligonucleotide can be conjugated to the protein binding reagent, for example, through a linker. The one antibody oligonucleotide can comprise the linker. The linker can comprise a chemical group. The chemical group can be reversibly attached to the molecule of the protein binding reagent. The chemical group can be selected from the group consisting of a UV photocleavable group, a streptavidin, a biotin, an amine, and any combination thereof.

In some embodiments, the protein binding reagent can bind to ADAM10, CD156c, ANO6, ATP1B2, ATP1B3, BSG, CD147, CD109, CD230, CD29, CD298, ATP1B3, CD44, CD45, CD47, CD51, CD59, CD63, CD97, CD98, SLC3A2, CLDND1, HLA-ABC, ICAM1, ITFG3, MPZL1, NA K ATPase alpha1, ATP1A1, NPTN, PMCA ATPase, ATP2B1, SLC1A5, SLC29A1, SLC2A1, SLC44A2, or any combination thereof.

In some embodiments, the protein target comprises an extracellular protein, an intracellular protein, or any combination thereof. In some embodiments, the protein target comprises a cell-surface protein, a cell marker, a B-cell receptor, a T-cell receptor, a major histocompatibility complex, a tumor antigen, a receptor, an integrin, or any combination thereof. The protein target can comprise a lipid, a carbohydrate, or any combination thereof. The protein target can be selected from a group comprising a number of protein targets. The number of protein targets can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. The number of protein targets can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The protein binding reagent can be associated with two or more antibody oligonucleotides with the same sequence. The protein binding reagent can be associated with two or more antibody oligonucleotides with different antibody oligonucleotide sequences. The number of antibody oligonucleotides associated with the protein binding reagent can be different in different implementations. In some embodiments, the number of antibody oligonucleotides, whether having the same or different sequences, can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibody oligonucleotides can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The plurality of compositions can comprise one or more additional protein binding reagents not conjugated with the antibody oligonucleotide (also referred to herein as the antibody oligonucleotide-free protein binding reagent). The number of additional protein binding reagents in the plurality of composition can be different in different implementations. In some embodiments, the number of additional protein binding reagents can be, or about, 1, 2, 3, 4, 5, 6, 7, 8, 9, 10, 20, 30, 40, 50, 60, 70, 80, 90, 100, or a number or a range between any two of these values. In some embodiments, the number of additional protein binding reagents can be at least, or at most, 1, 2, 3, 4, 5, 6, 7, 8, 9, 10, 20, 30, 40, 50, 60, 70, 80, 90, or 100. The protein binding reagent and any of the additional protein binding reagents can be, in some embodiments, the same.

In some embodiments, a mixture comprising protein binding reagent(s) that is conjugated with one or more antibody oligonucleotides and protein binding reagent(s) that is not conjugated with antibody oligonucleotides is provided. The mixture can be used in some embodiments of the methods disclosed herein, for example, to contact the sample(s) or cell(s). The ratio of (1) the number of a protein binding reagent conjugated with an antibody oligonucleotide and (2) the number of another protein binding reagent (e.g., the same protein binding reagent) not conjugated with the antibody oligonucleotide or other antibody oligonucleotide(s) in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A protein binding reagent can be conjugated with an antibody oligonucleotide or not. In some embodiments, the percentage of the protein binding reagent conjugated with an antibody oligonucleotide in a mixture comprising the protein binding reagent that is conjugated with the antibody oligonucleotide and the protein binding reagent(s) that is not conjugated with the antibody oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the protein binding reagent conjugated with an antibody oligonucleotide in a mixture can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, or 100%.

In some embodiments, the percentage of the protein binding reagent not conjugated with an antibody oligonucleotide in a mixture comprising a protein binding reagent conjugated with an antibody oligonucleotide and the protein binding reagent that is not conjugated with the antibody oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the protein binding reagent not conjugated with an antibody oligonucleotide in a mixture can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Methods of Quantitative Analysis of Cellular Component Targets

Some embodiments disclosed herein provide methods of quantitative analysis of a plurality of cellular component targets (e.g., protein targets) in a sample using the compositions disclosed herein and oligonucleotide probes that can associate a barcode sequence (e.g., a molecular label sequence) to the oligonucleotides of the cellular component binding regents (e.g., protein binding reagents). In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

The binding target of the cellular component binding reagent (i.e., cellular component target) for example, can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component target is a protein target. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets can comprise intracellular proteins. In some embodiments, the plurality of proteins can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded proteins in an organism. In some embodiments, the plurality of protein targets can comprise at least 2, at least 3, at least 4, at least 5, at least 10, at least 20, at least 30, at least 40, at least 50, at least 100, at least 1,000, at least 10,000, or more different protein targets.

In some embodiments, the plurality of protein binding reagents is contacted with the sample for specific binding with the plurality of protein targets. Unbound protein binding reagents can be removed, for example, by washing. In embodiments where the sample comprises cells, any protein binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that at most 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that the number of cells in the diluted population is, or is at least, 1, 5, 10, 15, 20, 25, 30, 35, 40, 45, 50, 55, 60, 65, 70, 75, 80, 85, 90, 95 or 100% of the number of wells on the substrate. The population of cells can be diluted such that the number of cells in the diluted population is, or is at least, 1, 5, 10, 15, 20, 25, 30, 35, 40, 45, 50, 55, 60, 65, 70, 75, 80, 85, 90, 95 or 100% of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1, 0.5, 1, 2, 3, 4, 5, 6, 7, 8, 9 or 10% or more probability that a well of the substrate has more than one cell. There can be at least a 0.1, 0.5, 1, 2, 3, 4, 5, 6, 7, 8, 9 or 10% or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the protein binding reagents can be additionally conjugated with fluorescent molecules to enable flow sorting of cells into individual compartments.

In some embodiments, the methods disclosed herein provide contacting a plurality of compositions with the sample for specific binding with the plurality of protein targets. It would be appreciated that the conditions used may allow specific binding of the protein binding reagents, e.g., antibodies, to the protein targets. Following the contacting step, unbound compositions can be removed. For example, in embodiments where the sample comprises cells, and the compositions specifically bind to protein targets are cell-surface proteins, unbound compositions can be removed by washing the cells with buffer such that only compositions that specifically bind to the protein targets remain with the cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of oligonucleotides of the protein binding reagents. For example, a plurality of oligonucleotide probes comprising a barcode can be used to hybridize to the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of oligonucleotides of the protein binding reagents, the plurality of oligonucleotides of the protein binding reagents can hybridize to the oligonucleotide probes. The oligonucleotide probes can be contacted at a non-depletable ratio such that each distinct oligonucleotide of the protein binding reagents can associate with oligonucleotide probes having different barcode sequences (e.g., molecular labels) of the disclosure.

In some embodiments, the methods disclosed herein provide detaching the oligonucleotides from the protein binding reagents that are specifically bound to the protein targets. Detachment can be performed in a variety of ways to separate the chemical group from the protein binding reagent, such as UV photocleaving, chemical treatment (e.g., dithiothreitol), heating, enzyme treatment, or any combination thereof. Detaching the oligonucleotide from the protein binding reagent can be performed either before, after, or during the step of hybridizing the plurality of oligonucleotide probes to the plurality of oligonucleotides of the compositions.

Methods of Simultaneous Quantitative Analysis of Protein and Nucleic Acid Targets Some embodiments disclosed herein provide methods of simultaneous quantitative analysis of a plurality of protein targets and a plurality of nucleic acid target molecules in a sample using the compositions disclosed herein and oligonucleotide probes that can associate a barcode sequence (e.g., a molecular label sequence) to both the oligonucleotides of the protein binding reagents and nucleic acid target molecules. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets can comprise intracellular proteins. In some embodiments, the plurality of proteins can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded proteins in an organism. In some embodiments, the plurality of protein targets can comprise at least 2, at least 3, at least 4, at least 5, at least 10, at least 20, at least 30, at least 40, at least 50, at least 100, at least 1,000, at least 10,000, or more different protein targets.

In some embodiments, the plurality of protein binding reagents is contacted with the sample for specific binding with the plurality of protein targets. Unbound protein binding reagents can be removed, for example, by washing. In embodiments where the sample comprises cells, any protein binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that at most 1, 5, 10, 15, 20, 25, 30, 35, 40, 45, 50, 55, 60, 65, 70, 75, 80, 85, 90, 95 or 100% of wells of the substrate receive a single cell. The population of cells can be diluted such that the number of cells in the diluted population is, or is at least, 1, 5, 10, 15, 20, 25, 30, 35, 40, 45, 50, 55, 60, 65, 70, 75, 80, 85, 90, 95 or 100% of the number of wells on the substrate. The population of cells can be diluted such that the number of cells in the diluted population is, or is at least, 1, 5, 10, 15, 20, 25, 30, 35, 40, 45, 50, 55, 60, 65, 70, 75, 80, 85, 90, 95 or 100% of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1, 0.5, 1, 2, 3, 4, 5, 6, 7, 8, 9 or 10% or more probability that a well of the substrate has more than one cell. There can be at least a 0.1, 0.5, 1, 2, 3, 4, 5, 6, 7, 8, 9 or 10% or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the protein binding reagents can be additionally conjugated with fluorescent molecules to enable flow sorting of cells into individual compartments.

In some embodiments, the methods disclosed herein provide contacting a plurality of compositions with the sample for specific binding with the plurality of protein targets. It would be appreciated that the conditions used may allow specific binding of the protein binding reagents, e.g., antibodies, to the protein targets. Following the contacting step, unbound compositions can be removed. For example, in embodiments where the sample comprises cells, and the compositions specifically bind to protein targets are cell-surface proteins, unbound compositions can be removed by washing the cells with buffer such that only compositions that specifically bind to the protein targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprise at least 100, at least 1,000, at least 10,000, at least 20,000, at least 30,000, at least 40,000, at least 50,000, at least 100,000, at least 1,000,000, or more species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the protein binding reagents. For example, a plurality of oligonucleotide probes comprising a barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of nucleic acid target molecules and the plurality of oligonucleotides of the protein binding reagents, the plurality of nucleic acid target molecules and the plurality of oligonucleotides of the protein binding reagents can hybridize to the oligonucleotide probes. The oligonucleotide probes can be contacted at a non-depletable ratio such that each distinct nucleic acid target molecules and oligonucleotides of the protein binding reagents can associate with oligonucleotide probes having different barcode sequences (e.g., molecular labels) of the disclosure.

In some embodiments, the methods disclosed herein provide detaching the oligonucleotides from the protein binding reagents that are specifically bound to the protein targets. Detachment can be performed in a variety of ways to separate the chemical group from the protein binding reagent, such as UV photocleaving, chemical treatment (e.g., dithiothreitol), heating, enzyme treatment, or any combination thereof. Detaching the oligonucleotide from the protein binding reagent can be performed either before, after, or during the step of hybridizing the plurality of oligonucleotide probes to the plurality of nucleic acid target molecules and the plurality of oligonucleotides of the compositions.

Association of Barcodes

The oligonucleotides of the protein binding reagents and/or the nucleic acid molecules may randomly associate with the oligonucleotide probes. Association can, for example, comprise hybridization of an oligonucleotide probe's target binding region to a complementary portion of the target nucleic acid molecule and/or the oligonucleotides of the protein binding reagents (e.g., oligo(dT) of the barcode can interact with a poly(A) tail of a target nucleic acid molecule and/or a poly(A) tail of an oligonucleotide of a protein binding reagent). The assay conditions used for hybridization (e.g. buffer pH, ionic strength, temperature, etc.) can be chosen to promote formation of specific, stable hybrids.

The disclosure provides for methods of associating a barcode sequence (e.g., a molecular label) with a target nucleic acid and/or an oligonucleotide of a protein binding reagent using reverse transcription. As a reverse transcriptase can use both RNA and DNA as template, the oligonucleotide originally conjugated on the protein binding reagent can compose of either RNA or DNA bases, or both. The protein binding reagent specific oligonucleotides can be copied and covalently linked to the cell label and barcode sequence (e.g., molecular label) in addition to cellular mRNA molecules.

In some embodiments, barcode sequences (e.g., molecular labels) can be added by ligation of an oligonucleotide probe target binding region and a portion of the target nucleic acid molecule and/or the oligonucleotides of the protein binding reagents. For example, the target binding region may comprise a nucleic acid sequence that can be capable of specific hybridization to a restriction site overhang (e.g. an EcoRI sticky-end overhang). The methods can further comprise treating the target nucleic acids and/or the oligonucleotides of the protein binding reagents with a restriction enzyme (e.g. EcoRI) to create a restriction site overhang. A ligase (e.g., T4 DNA ligase) may be used to join the two fragments.

Simultaneous Quantitative Analysis of Protein and Nucleic Acid Targets

Figure 5:
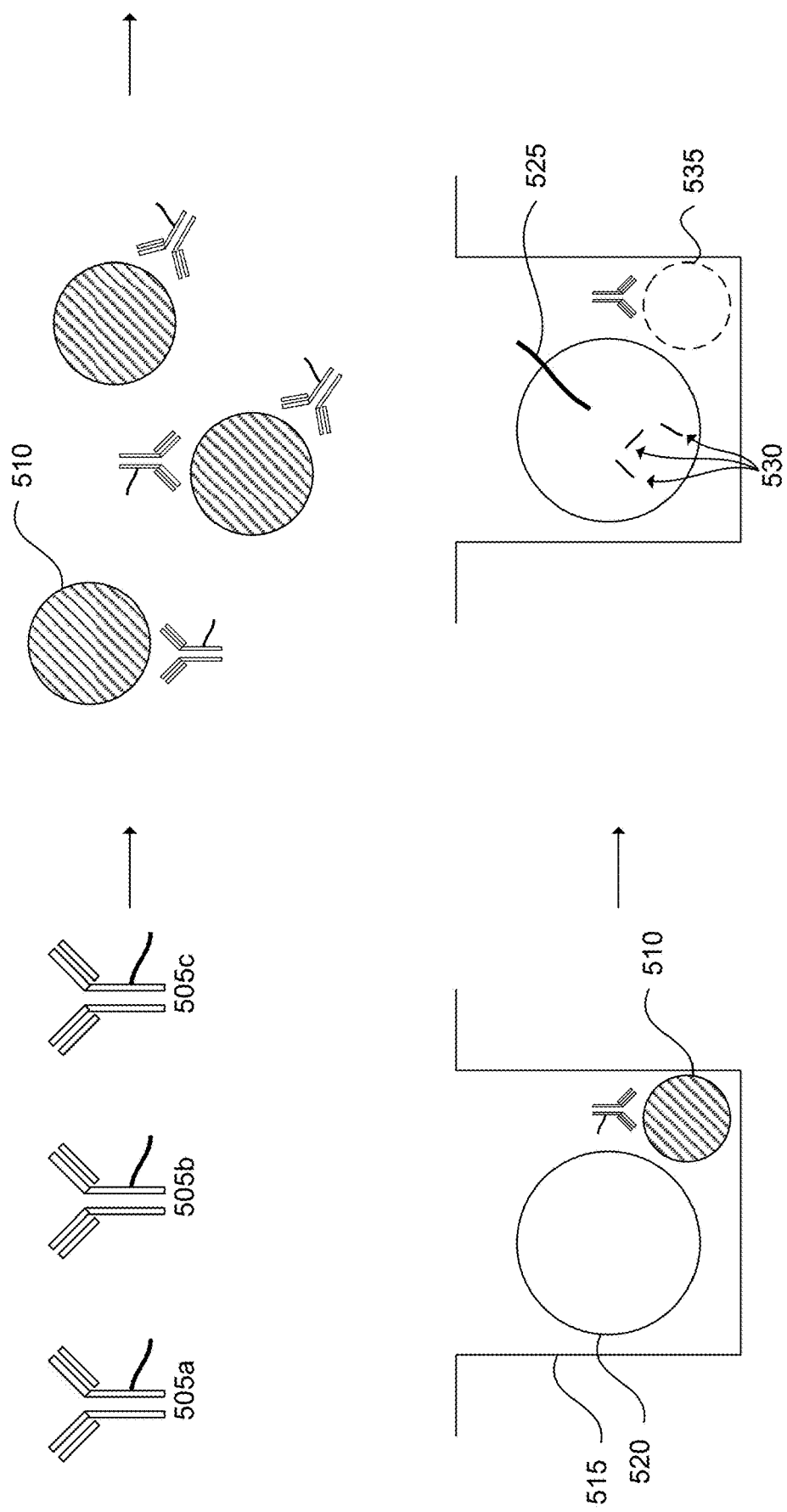
FIG. 5 shows a schematic illustration of an exemplary workflow using oligonucleotide conjugated antibodies to measure protein expression and gene expression simultaneously in a high throughput manner.

FIG. 5 shows a schematic illustration of an exemplary method of simultaneous quantitative analysis of both protein and nucleic acid targets in single cells. In some embodiments, a plurality of compositions 505, 505b, 505c, etc., each comprising a protein binding reagent, such as an antibody, is provided. Different protein binding reagents, such as antibodies, which bind to different protein targets are conjugated with different unique identifiers. Next, the protein binding reagents can be incubates with a sample containing a plurality of cells 510. The different protein binding reagents can specifically bind to proteins on the cell surface, such as a cell marker, a B-cell receptor, a T-cell receptor, an antibody, a major histocompatibility complex, a tumor antigen, a receptor, or any combination thereof. Unbound protein binding reagents can be removed, e.g., by washing the cells with a buffer. The cells with the protein binding reagents can be then separated into a plurality of compartments, such as a microwell array, wherein a single compartment 515 is sized to fit a single cell and a single bead 520. Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 525 conjugated to the antibody can be detached from the antibody using chemical, optical or other means. The cell can be lysed 535 to release nucleic acids within the cell, such as genomic DNA or cellular mRNA 530. Cellular mRNA 530, oligonucleotides 525 or both can be captured by the oligonucleotide probes on bead 520, for example, by hybridizing to the poly(dT) sequence. A reverse transcriptase can be used to extend the oligonucleotide probes hybridized to the cellular mRNA 530 and the oligonucleotides 525 using the cellular mRNA 530 and the oligonucleotides 525 as templates. The extension products produced by the reverse transcriptase can be subject to amplification and sequencing. Sequencing reads can be subject to demultiplexing of a cell label, a barcode sequence (e.g., a molecular label), gene identity, antibody specific oligo identity, etc., which can give rise to a digital representation of protein and gene expression of each single cell in the sample.

Determining the Number of Unique Barcode Sequences (e.g., Molecular Label Sequences)

In some embodiments, the methods disclosed herein comprise determining the number of unique barcode sequences (e.g., molecular label sequences) for each unique identifier and/or each nucleic acid target molecule. For example, the sequencing reads can be used to determine the number of unique barcode sequences for each unique identifier and/or each nucleic acid target molecule.

In some embodiments, the number of unique barcode sequences for each unique identifier and/or each nucleic acid target molecule indicates the quantity of each protein target and/or each nucleic acid target molecule in the sample. In some embodiments, the quantity of a protein target and the quantity of its corresponding nucleic acid target molecules, e.g., mRNA molecules, can be compared to each other. In some embodiments, the ratio of the quantity of a protein target and the quantity of its corresponding nucleic acid target molecules, e.g., mRNA molecules, can be calculated. The protein targets can be, for example, cell surface protein markers. In some embodiments, the ratio between the protein level of a cell surface protein marker and the level of the mRNA of the cell surface protein marker is low.

The methods disclosed herein can be used for a variety of applications. For example, the methods disclosed herein can be used for proteome and/or transcriptome analysis of a sample. In some embodiments, the methods disclosed herein can be used to identify a protein target and/or a nucleic acid target, i.e., a biomarker, in a sample. In some embodiments, the protein target and the nucleic acid target correspond to each other, i.e., the nucleic acid target encodes the protein target. In some embodiments, the methods disclosed herein can be used to identify protein targets that have a desired ratio between the quantity of the protein target and the quantity of its corresponding nucleic acid target molecule in a sample, e.g., mRNA molecule. In some embodiments, the ratio is at least 0.001, at least 0.01, at least 0.1, at least 1, at least 10, at least 100, at least 1000, or more, or a range between any two of the above values. In some embodiments, the ratio is at most 0.001, at most 0.01, at most 0.1, at most 1, at most 10, at most 100, at most 1000, or less, or a range between any two of the above values. In some embodiments, the methods disclosed herein can be used to identify protein targets in a sample that the quantity of its corresponding nucleic acid target molecule in the sample is less than 1000, less than 100, less than 10, less than 5, less than 2, less than 1, or is 0.

Kits

Some embodiments disclosed herein provide kits for simultaneous quantitative analysis of a plurality of proteins and a plurality of nucleic acid target molecules in a sample comprising a plurality of protein binding reagents each conjugated with an oligonucleotide, wherein the oligonucleotide comprises a unique identifier for the protein binding reagent, and a plurality of oligonucleotide probes, wherein each of the plurality of oligonucleotide probes comprises a target binding region, a barcode sequence (e.g., a molecular label sequence), wherein the barcode sequence is selected from a diverse set of unique barcode sequences (e.g., molecular label sequences). Disclosed herein include kits for simultaneous quantitative analysis of a plurality of protein targets and a plurality of nucleic acid target molecules in a sample comprising a plurality of compositions each comprising a plurality of protein binding reagents each conjugated with an oligonucleotide, wherein the oligonucleotide comprises a unique identifier for one of the plurality of protein binding reagents that it is conjugated therewith, and the protein binding reagents are capable of specifically binding to a protein target (e.g., different parts of the protein target, different fragments of the protein target, or different isoforms of the protein target), and a plurality of oligonucleotide probes. Disclosed herein include kits for simultaneous quantitative analysis of a plurality of protein targets and a plurality of nucleic acid target molecules in a sample comprising a plurality of compositions each comprising a plurality of protein binding reagents each conjugated with an oligonucleotide, wherein the oligonucleotide comprises a unique identifier for the protein binding reagent that it is conjugated therewith, and the protein binding reagents are capable of specifically binding to a protein target, and a plurality of oligonucleotide probes.

The number of protein binding reagents of the plurality of protein binding reagents that are capable of specifically binding to the protein target can be different in different implementations. In some embodiments, the number of protein binding reagents capable of specifically binding to the protein target can be, or about, 2, 3, 4, 5, 6, 7, 8, 9, 10, 11, 12, 13, 14, 15, 16, 17, 18, 19, 20, 30, 40, 50, 60, 70, 80, 90, 100, or a number or a range between any two of these values. In some embodiments, the number of protein binding reagents capable of specifically binding to the protein target can be at least, or at most, 2, 3, 4, 5, 6, 7, 8, 9, 10, 11, 12, 13, 14, 15, 16, 17, 18, 19, 20, 30, 40, 50, 60, 70, 80, 90, or 100.

In some embodiments, each of the oligonucleotides can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., oligodA$_{18}$ (unanchored to a solid support) or oligoA$_{18}$V (anchored to a solid support). The oligonucleotides can comprise DNA residues, RNA residues, or both.

The unique identifiers can have any suitable length, for example, from about 25 nucleotides to about 45 nucleotides long. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 2,000, at least 5,000, or more different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable protein binding reagents are contemplated in this disclosure, such as antibodies or fragments thereof, aptamers, small molecules, ligands, peptides, oligonucleotides, etc., or any combination thereof. In some embodiments, the protein binding reagents can be polyclonal antibodies, monoclonal antibodies, recombinant antibodies, single-chain antibody (scAb), or fragments thereof, such as Fab, Fv, etc. In some embodiments, the plurality of protein binding reagents can comprise at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 2,000, at least 5,000, or more different protein binding reagents.

In some embodiments, the oligonucleotide is conjugated with the protein binding reagent through a linker. In some embodiments, the oligonucleotide can be conjugated with the protein binding reagent covalently. In some embodiment, the oligonucleotide can be conjugated with the protein binding reagent non-covalently. In some embodiments, the linker can comprise a chemical group that reversibly attaches the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, streptavidin, biotin, amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the CL domain, etc. In some embodiments, each protein binding reagent can be conjugated with a single oligonucleotide molecule. In some embodiments, each protein binding reagent can be conjugated with more than one oligonucleotide molecule, for example, at least 2, at least 3, at least 4, at least 5, at least 10, at least 20, at least 30, at least 40, at least 50, at least 100, at least 1,000, or more oligonucleotide molecules, wherein each of the oligonucleotide molecule comprises the same unique identifier.

In some embodiments, the plurality of protein binding reagents are capable of specifically binding to a plurality of protein targets in a sample, such as a single cell, a plurality of cells, a tissue sample, a tumor sample, a blood sample, or the like. In some embodiments, the plurality of protein targets comprises a cell-surface protein, a cell marker, a B-cell receptor, a T-cell receptor, an antibody, a major histocompatibility complex, a tumor antigen, a receptor, or any combination thereof. In some embodiments, the plurality of protein targets can comprise intracellular proteins. In some embodiments, the plurality of protein targets can comprise intracellular proteins. In some embodiments, the plurality of proteins can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded proteins in an organism. In some embodiments, the plurality of protein targets can comprise at least 2, at least 3, at least 4, at least 5, at least 10, at least 20, at least 30, at least 40, at least 50, at least 100, at least 1,000, at least 10,000, or more different protein targets.

Single Cell Sequencing Control Particles

Figure 6A:
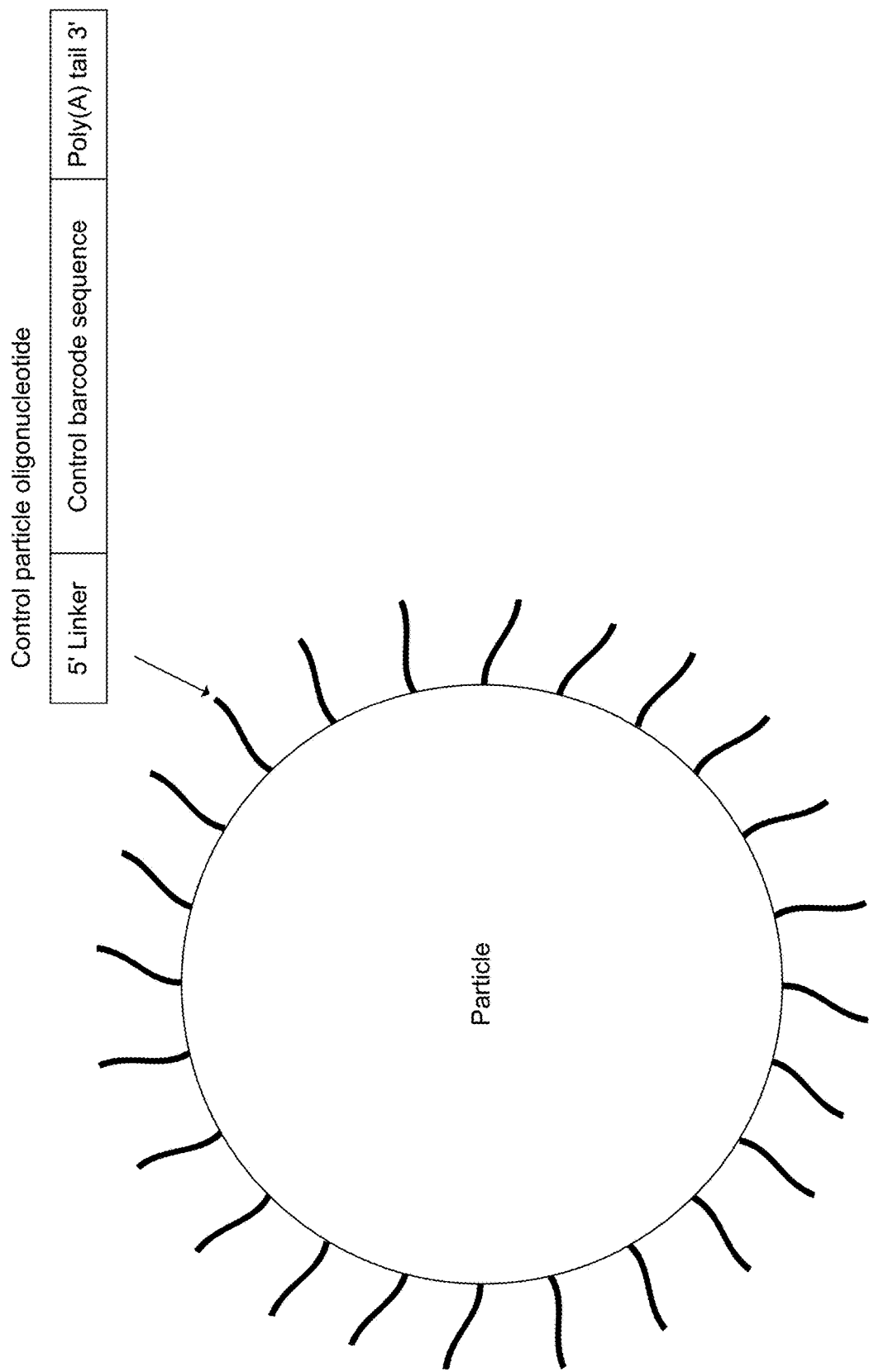
FIGS. 6A-6E show non-limiting exemplary schematic illustrations of particles functionalized with oligonucleotides.

Disclosed herein includes control particle compositions that can be used for, for example, single cell sequencing control. The control particle compositions can be used in any suitable methods, kits and systems disclosed herein, for example the methods, kits and systems for measuring cellular component expression level (for example protein expression level) using cellular component binding reagents associated with oligonucleotides. In some embodiments, the control particle composition comprises a plurality of control particle oligonucleotides associated with a control particle. The control particle associated with the plurality of control particle oligonucleotides is referred to herein also as a functionalized control particle. FIG. 6A is a non-limiting exemplary schematic illustration of a particle functionalized with a plurality of oligonucleotides. FIG. 6A shows that the control particle oligonucleotide associated with the control particle can comprise a control barcode sequence and a poly(dA) region, mimicking a mRNA poly(A) tail. The control particle oligonucleotide can comprise a barcode sequence (e.g., a molecular label sequence), a binding site for a universal primer, or a combination thereof. The control particle oligonucleotides associated with the control particles can be the same or different from one another. In some embodiments, at least two of the control particle oligonucleotides associated with the control particle have different control barcode sequence. In some embodiments, a plurality of a first control particle oligonucleotides and a plurality of a second control oligonucleotides are associated with the control particle, wherein the first and the second particle oligonucleotides have different control barcode sequence.

A bead, such as the CompBead™ Plus (BD (Franklin Lake, New Jersey)) can be functionalized with antibodies conjugated with oligonucleotides. CompBeads Plus are about 7.5 microns in size, which is similar to the size of an immune cell. When functionalized with antibodies conjugated with oligonucleotides, CompBead Plus can be used as control cells or control particles for single cell workflows. The AbO functionalized bead can be used with any single cell workflow as a single cell sequencing control.

Control Particle Oligonucleotide

The length of the control barcode sequence can be different in different implementations. In some embodiments, the control barcode sequence is, or about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the In some embodiments, the control barcode sequence is at least, or at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

The length of the control particle oligonucleotide can be different in different implementations. In some embodiments, the control particle oligonucleotide is, or about, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the In some embodiments, the control particle oligonucleotide is at least, or at most, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the number of the plurality of control particle oligonucleotides can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 100000, 1000000, 10000000, 100000000, 1000000000, or a number or a range between any two of these values. In some embodiments, the number of the plurality of control particle oligonucleotides can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 100000, 1000000, 10000000, 100000000, or 1000000000.

The plurality of control particle oligonucleotides can comprise the same or different control barcode sequences. For example, at least two of the plurality of control particle oligonucleotides can comprise different control barcode sequences. In some embodiments, the control barcode sequences of at least or at most 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 100000, 1000000, 10000000, 100000000, or 1000000000 of the plurality of control particle oligonucleotides can be identical. In some embodiments, the control barcode sequences of, or about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000 100000, 1000000, 10000000, 100000000, 1000000000, or a number or a range between any two of these values, of the plurality of control particle oligonucleotides can be identical.

The control barcode sequences of at least or at most 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values of the plurality of control particle oligonucleotides can be identical. The control barcode sequences of, or about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the plurality of control particle oligonucleotides can be identical.

In some embodiments, the control barcode sequence is not homologous to genomic sequences of a species. The control barcode sequence can be homologous to genomic sequences of a species. The species can be a non-mammalian species. The non-mammalian species can be a phage species. The phage species can be T7 phage, a PhiX phage, or a combination thereof.

Control Particle

In some embodiments, at least one of the plurality of control particle oligonucleotides is associated with the control particle through a linker. The at least one of the plurality of control particle oligonucleotides can comprise the linker. The linker can comprise a chemical group. The chemical group can be reversibly or irreversibly attached to the at least one of the plurality of control particle oligonucleotides. The chemical group can comprise a UV photocleavable group, a disulfide bond, a streptavidin, a biotin, an amine, a disulfide linkage, or any combination thereof.

The diameter of the control particle can be, or about, 1-1000 micrometers, such as 10-100 micrometer or 7.5 micrometer. In some embodiments, the diameter of the control particle can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the diameter of the control particle can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers.

In some embodiments, the plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle. The control particle can be disruptable.

In some embodiments, the control particle can be a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The control particle can comprise a disruptable hydrogel particle.

Protein Binding Reagent

Figure 6B:
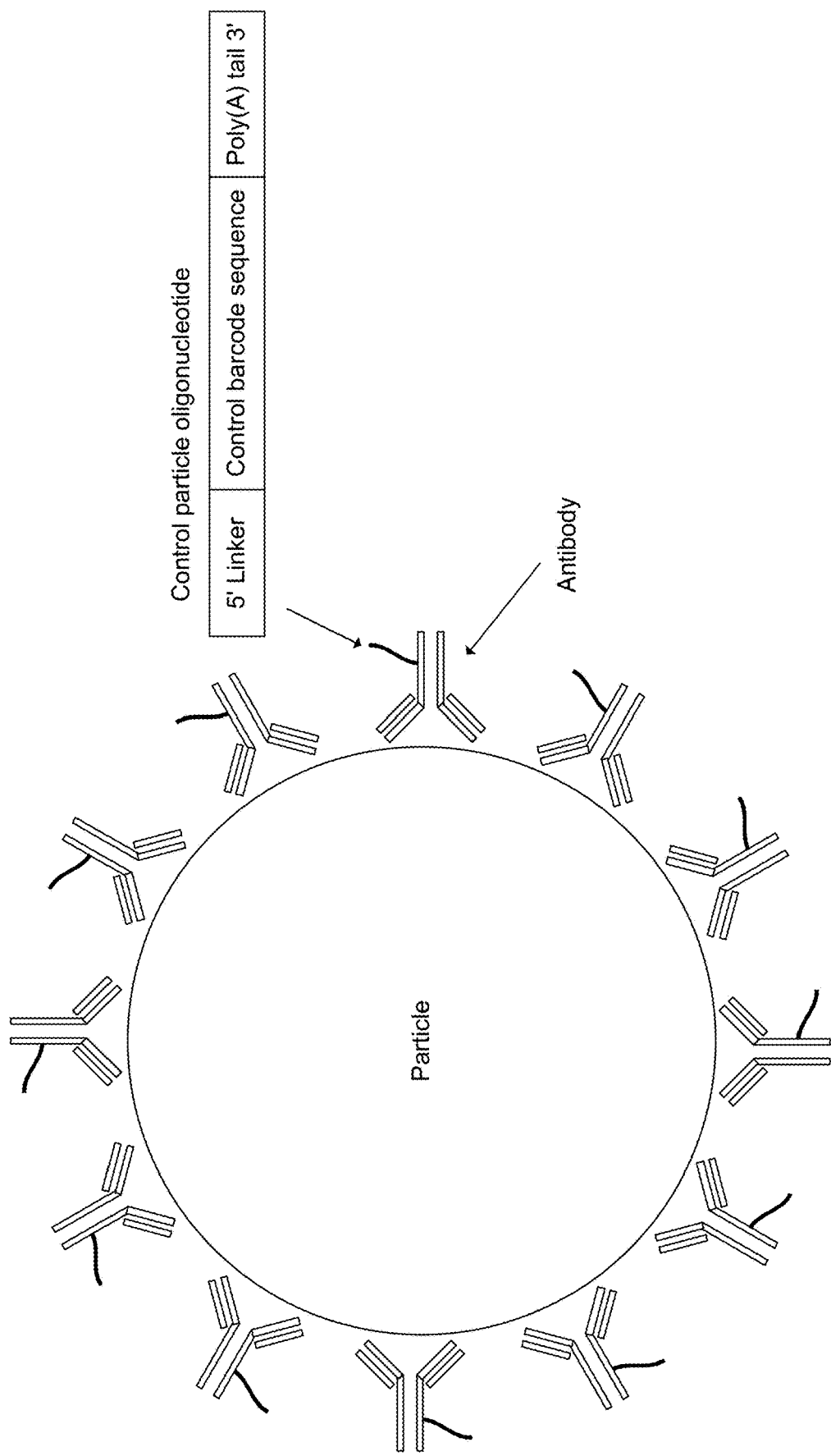

In some embodiments, the control particle is associated with a plurality of first protein binding reagents, and at least one of the plurality of first protein binding reagents is associated with one of the plurality of control particle oligonucleotides. FIG. 6B shows a non-limiting exemplary particle coated with a number of antibodies functionalized with oligonucleotides. The first protein binding reagent can comprise a first antibody (e.g., a primary antibody, or a secondary antibody). The control particle oligonucleotide can be conjugated to the first protein binding reagent through a linker. The first control particle oligonucleotide can comprise the linker. The linker can comprise a chemical group. The chemical group can be reversibly or irreversibly attached to the first protein binding reagent. The chemical group can comprise a UV photocleavable group, a disulfide bond, a streptavidin, a biotin, an amine, a disulfide linkage, or any combination thereof.

Figure 6C:
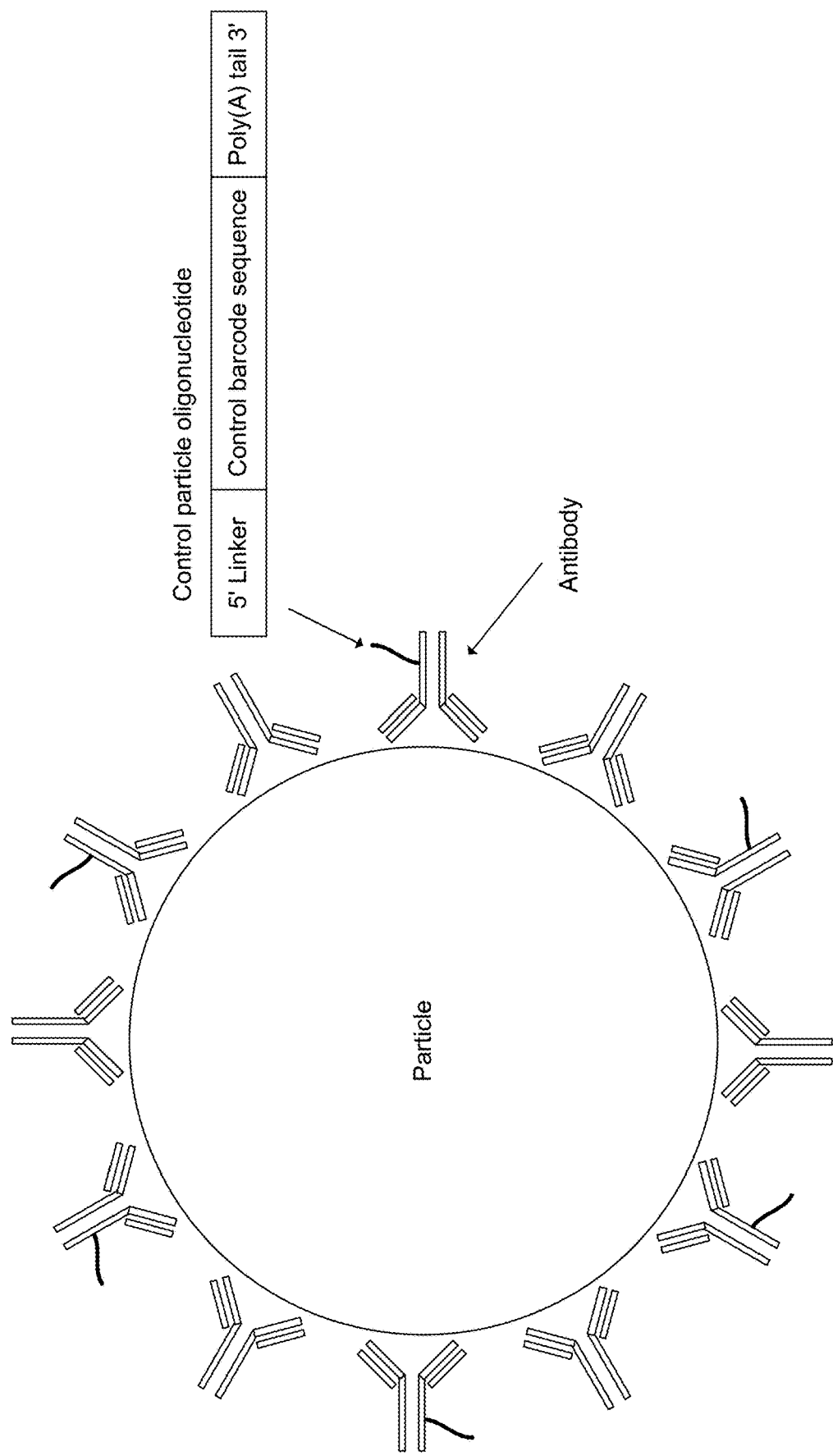

In some embodiments, the control particle is associated with a plurality of second protein binding reagents. At least one of the plurality of second protein binding reagents can be associated with one of the plurality of control particle oligonucleotides. FIG. 6C shows a non-limiting exemplary particle coated with a plurality of first antibodies functionalized with oligonucleotides and a plurality of second antibodies not functionalized with oligonucleotides. The antibodies on the control particle can be titrated with ratios of hot antibodies (e.g., associated with control particle oligonucleotide) and cold antibodies (e.g., not associated with control particle oligonucleotides) to alter the amount of sequencing reads obtained from a control particle. The first antibodies and the second antibodies can be the same or different.

Figure 6D:
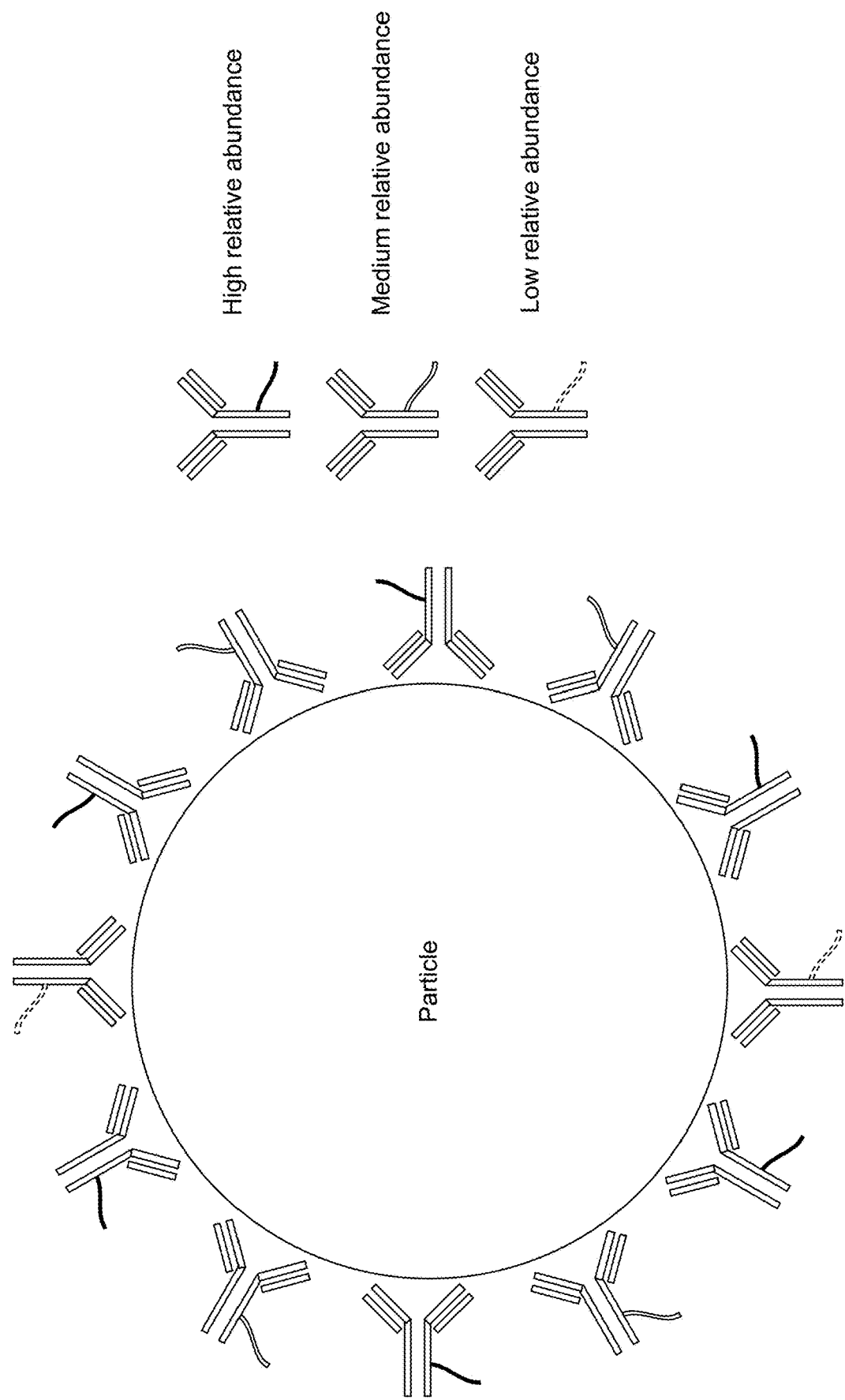

FIG. 6D is a non-limiting exemplary schematic illustration of a particle functionalized with a plurality of first control particle oligonucleotides, a plurality of second control particle oligonucleotides conjugated to a plurality of second antibodies and a plurality of third control particle oligonucleotides with relative high, medium, and low abundance. The plurality of first control particle oligonucleotides can be conjugated to a plurality of first protein binding reagents. The plurality of second control particle oligonucleotides can be conjugated to a plurality of second protein binding reagents. The plurality of third control particle oligonucleotides can be conjugated to a plurality of third protein binding reagents.

The relative abundance of the first, second, and third control particle oligonucleotides can mimic mRNAs with different expression levels. The control particle oligonucleotide associated with the first protein binding reagent and the control particle oligonucleotide associated with the second protein binding reagent can comprise different control barcode sequences. Different protein binding reagents, such as antibodies, and the different control particle oligonucleotides on the control particle can be titrated to generate a standard curve. The first protein binding reagents, the second protein binding reagents, or the third protein binding reagents can be identical or different protein binding reagents.

In some embodiments, the ratio of the number of the plurality of first control particle oligonucleotides and the number of the plurality of second (or third) control particle oligonucleotides can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these numbers. In some embodiments, the ratio of the number of the plurality of first control particle oligonucleotides and the number of the plurality of second (or third) control particle oligonucleotides can be at least, or at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, or 1:100.

In some embodiments, the first protein binding reagent can be associated with a partner binding reagent (e.g., a secondary antibody), and the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent is associated with two or more of the plurality of control particle oligonucleotides with an identical control barcode sequence. The first protein binding reagent can be associated with two or more of the plurality of control particle oligonucleotides with different control barcode sequences. In some embodiments, at least one of the plurality of first protein binding reagents is not associated with any of the plurality of control particle oligonucleotides. The first protein binding reagent associated with the control particle oligonucleotide and the first protein binding reagent not associated with any control particle oligonucleotide can be identical protein binding reagents.

Control Barcode Diversity

The plurality of control particle oligonucleotides associated with one control particle can comprise a number of control particle oligonucleotides with different control barcode sequences. The number of control barcode sequences that control particle oligonucleotides have can be different in different implementation. In some embodiments, the number of control barcode sequences that the control particle oligonucleotides have can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of control barcode sequences that the control particle oligonucleotides have can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the number of control particle oligonucleotides with the same control particle oligonucleotide sequence can be, or about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of control particle oligonucleotides with the same control particle oligonucleotide sequence can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the plurality of control particle oligonucleotides comprises a plurality of first control particle oligonucleotides each comprising a first control barcode sequence, and a plurality of second control particle oligonucleotides each comprising a second control barcode sequence, and the first control barcode sequence and the second control barcode sequence have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides. In some embodiments, the ratio of the number of the plurality of first control particle oligonucleotides and the number of the plurality of second control particle oligonucleotides can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of the number of the plurality of first control particle oligonucleotides and the number of the plurality of second control particle oligonucleotides can be at least, or at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

Detectable Moiety

Figure 6E:
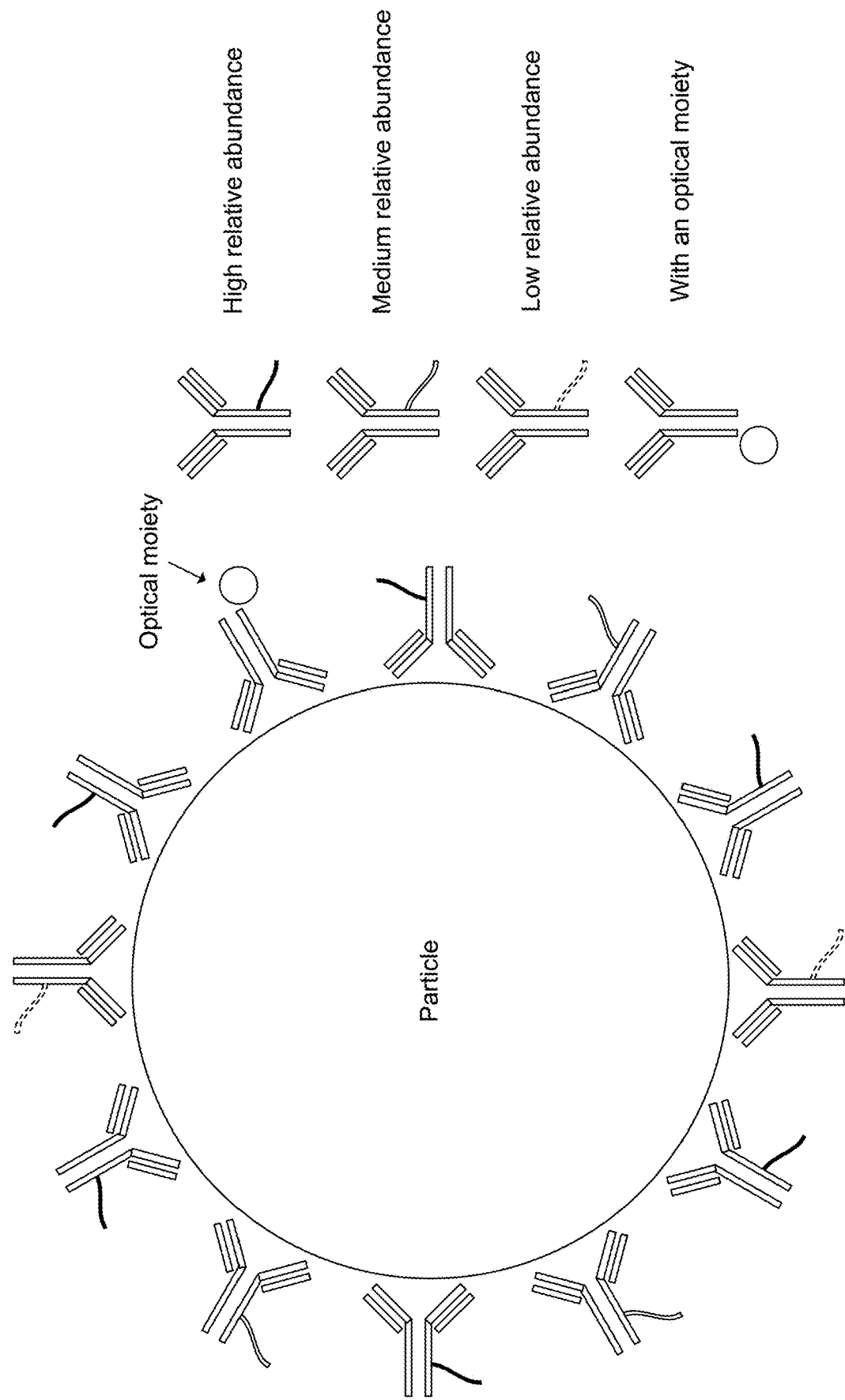

In some embodiments, the control particle is associated with a detectable moiety, for example an optical moiety, such as a fluorophore or a chromophore. The control particle oligonucleotide can be associated with a detectable moiety, for example an optical moiety. In some embodiments, the first protein binding reagent can be associated with an optical moiety (FIG. 6E). The second protein binding reagent can be associated with an optical moiety. A control particle associated with an optical moiety (e.g., a bead fluorescently tagged) can also be used for imaging and flow cytometry.

The detectable moiety can be selected from a group of spectrally-distinct detectable moieties. Spectrally-distinct detectable moieties include detectable moieties with distinguishable emission spectra even if their emission spectral may overlap. Non-limiting examples of detectable moieties include Xanthene derivatives: fluorescein, rhodamine, Oregon green, eosin, and Texas red; Cyanine derivatives: cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives: pyridyloxazole, nitrobenzoxadiazole and benzoxadiazole; Anthracene derivatives: anthraquinones, including DRAQ5, DRAQ7 and CyTRAK Orange; Pyrene derivatives: cascade blue; Oxazine derivatives: Nile red, Nile blue, cresyl violet, oxazine 170; Acridine derivatives: proflavin, acridine orange, acridine yellow; Arylmethine derivatives: auramine, crystal violet, malachite green; and Tetrapyrrole derivatives: porphin, phthalocyanine, bilirubin. Other non-limiting examples of detectable moieties include Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQ5, DRAQ7, Indo-1, Fluo-3, Fluo-4, DCFH, DHR, and SNARF.

The excitation wavelength of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values. The emission wavelength of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values.

The molecular weights of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 Daltons (Da), or a number or a range between any two of these values. The molecular weights of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 kilo Daltons (kDa), or a number or a range between any two of these values.

The group of spectrally distinct detectable moieties can, for example, include five different fluorophores, five different chromophores, a combination of five fluorophores and chromophores, a combination of four different fluorophores and a non-fluorophore, a combination of four chromophores and a non-chromophore, or a combination of four fluorophores and chromophores and a non-fluorophore non-chromophore. In some embodiments, the detectable moieties can be one of 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of spectrally-distinct moieties.

Control Particle Workflow

The AbO functionalized bead can be used with any single cell workflow as a single cell sequencing control. Single cell workflows can utilize microwell arrays or microwell cartridges (e.g., BD Resolve™) or microfluidics devices (e.g., 10× Genomics (San Francisco, CA), Drop-seq (McCarroll Lab, Harvard Medical School (Cambridge, Massachusetts); Macosko et al., Cell, 2015 May 21 16; 5:1202, the content of which is incorporated herein by reference in its entirety), or Abseq (Mission Bio (San Francisco, CA); Shahi et al., Sci Rep. 2017 Mar. 14; 7:44447, the content of which is hereby incorporated by reference in its entirety) in combination with solid or semisolid particles associated with stochastic barcodes (e.g., BD Resolve, or Drop-seq) or disruptable hydrogel particles enclosing releasable stochastic barcodes (e.g., 10× Genomics, or Abseq). The functionalized bead can be a control for determining efficiency of single cell workflows, analogous to external RNA control consortiums (ER-CCs) being used for bulk RNAseq or microarray studies.

Disclosed herein are methods for determining the numbers of targets using a plurality of control particle oligonucleotides. The methods for determining the number of targets (e.g., gene expression) can be used with other methods disclosed herein. For example, a workflow can be used for determining protein expression and gene expression using a plurality of control particle oligonucleotides. [0495] In some embodiments, the method comprises: barcoding (e.g., stochastically barcoding) a plurality of targets of a cell of a plurality of cells and a plurality of control particle oligonucleotides using a plurality of barcodes (e.g., stochastic barcodes) to create a plurality of barcoded targets (e.g., stochastically barcoded targets) and a plurality of barcoded control particle oligonucleotide (e.g., stochastically barcoded control particle oligonucleotides), wherein each of the plurality of barcodes comprises a cell label sequence, a barcode sequence (e.g., a molecular label), and a target-binding region, wherein the barcode sequences of at least two barcodes of the plurality of barcodes comprise different sequences, and wherein at least two barcodes of the plurality of barcodes comprise an identical cell label sequence, wherein a control particle composition comprises a control particle associated with the plurality of control particle oligonucleotides, wherein each of the plurality of control particle oligonucleotides comprises a control barcode sequence and a pseudo-target region comprising a sequence substantially complementary to the target-binding region of at least one of the plurality of barcodes. The method can comprise: obtaining sequencing data of the plurality of stochastically barcoded targets and the plurality of stochastically barcoded control particle oligonucleotides; counting the number of barcode sequences with distinct sequences associated with the plurality of control particle oligonucleotides with the control barcode sequence in the sequencing data. The method can comprise: for at least one target of the plurality of targets: counting the number of barcode sequences with distinct sequences associated with the target in the sequencing data; and estimating the number of the target, wherein the number of the target estimated correlates with the number of barcode sequences with distinct sequences associated with the target counted and the number of barcode sequences with distinct sequences associated with the control barcode sequence. In some embodiments, the pseudo-target region comprises a poly(dA) region. The pseudo-target region can comprise a subsequence of the target.

In some embodiments, the number of the target estimated can correlate with the number of barcode sequences with distinct sequences associated with the target counted, the number of barcode sequences with distinct sequences associated with the control barcode sequence, and the number of the plurality of control particle oligonucleotides comprising the control barcode sequence. The number of the target estimated can correlate with the number of barcode sequences with distinct sequences associated with the target counted, and a ratio of the number of the plurality of control particle oligonucleotides comprising the control barcode sequence and the number of barcode sequences with distinct sequences associated with the control barcode sequence.

For example, if the control particle has 100 control particle oligonucleotides with a particular control barcode sequence and the number of barcode sequences with distinct sequences associated with the control barcode sequence (e.g., the number of control particle oligonucleotides with the control barcode sequence that survive the library preparation process) is 80, then the efficiency of the library preparation (e.g., reverse transcription, amplification, etc.) is 80%. Thus, data from different library preparations can be compared by normalizing using the library preparation efficiency.

As another example, the control particle can comprise five control particle oligonucleotides with a particular control barcode sequencing mimicking a low expression gene. If the number of barcode sequences with distinct sequences associated with the control barcode sequence is five, and a low expression gene is not detected, then a conclusion that the low expression gene is not expressed (or the cell has fewer than five mRNAs of the gene) can be made. However, if the number of barcode sequences with distinct sequences associated with the control barcode sequence is zero, and a low expression gene is not detected, then a conclusion that the low expression gene is not expressed cannot be made.

Capture efficiency can be determined for control particle oligonucleotides with different abundance. Normalization can be performed based on the capture efficiency of control particle oligonucleotides with two or more control barcode sequences. In some embodiments, counting the number of barcode sequences with distinct sequences associated with the plurality of control particle oligonucleotides with the control barcode sequence in the sequencing data comprises: counting the number of barcode sequences with distinct sequences associated with the first control barcode sequence in the sequencing data; and counting the number of barcode sequences with distinct sequences associated with the second control barcode sequence in the sequencing data. The number of the target estimated can correlate with the number of barcode sequences with distinct sequences associated with the target counted, the number of barcode sequences with distinct sequences associated with the first control barcode sequence, and the number of barcode sequences with distinct sequences associated with the second control barcode sequence.

In some embodiments, the method comprises releasing the at least one of the plurality of control particle oligonucleotides from the control particle prior to stochastically barcoding the plurality of targets and the control particle and the plurality of control particle oligonucleotides.

In some embodiments, barcoding (e.g., stochastically barcoding) the plurality of targets and the plurality of control particle oligonucleotides using the plurality of barcodes comprises: contacting the plurality of barcodes with targets of the plurality of targets and control particle oligonucleotides of the plurality of control particle oligonucleotides to generate barcodes (e.g., stochastic barcodes) hybridized to the targets and the control particle oligonucleotides; and extending the barcodes (e.g., stochastic barcodes) hybridized to the targets and the control particle oligonucleotides to generate the plurality of stochastically barcoded targets and the plurality of stochastically barcoded control particle oligonucleotides. Extending the barcodes can comprise extending the barcodes using a DNA polymerase, a reverse transcriptase, or a combination thereof.

In some embodiments, the method comprises amplifying the plurality of stochastically barcoded targets and the plurality of stochastically barcoded control particle oligonucleotides to produce a plurality of amplicons. Amplifying the plurality of stochastically barcoded targets and the plurality of stochastically barcoded control particle oligonucleotides can comprise amplifying, using polymerase chain reaction (PCR), at least a portion of the barcode sequence and at least a portion of the control particle oligonucleotide or at least a portion of the barcode sequence and at least a portion of the control particle oligonucleotide. Obtaining the sequencing data can comprise obtaining sequencing data of the plurality of amplicons. Obtaining the sequencing data can comprise sequencing the at least a portion of the barcode sequence and the at least a portion of the control particle oligonucleotide, or the at least a portion of the barcode sequence and the at least a portion of the control particle oligonucleotide.

Microwell Cartridge or Array Workflow

Figure 7:
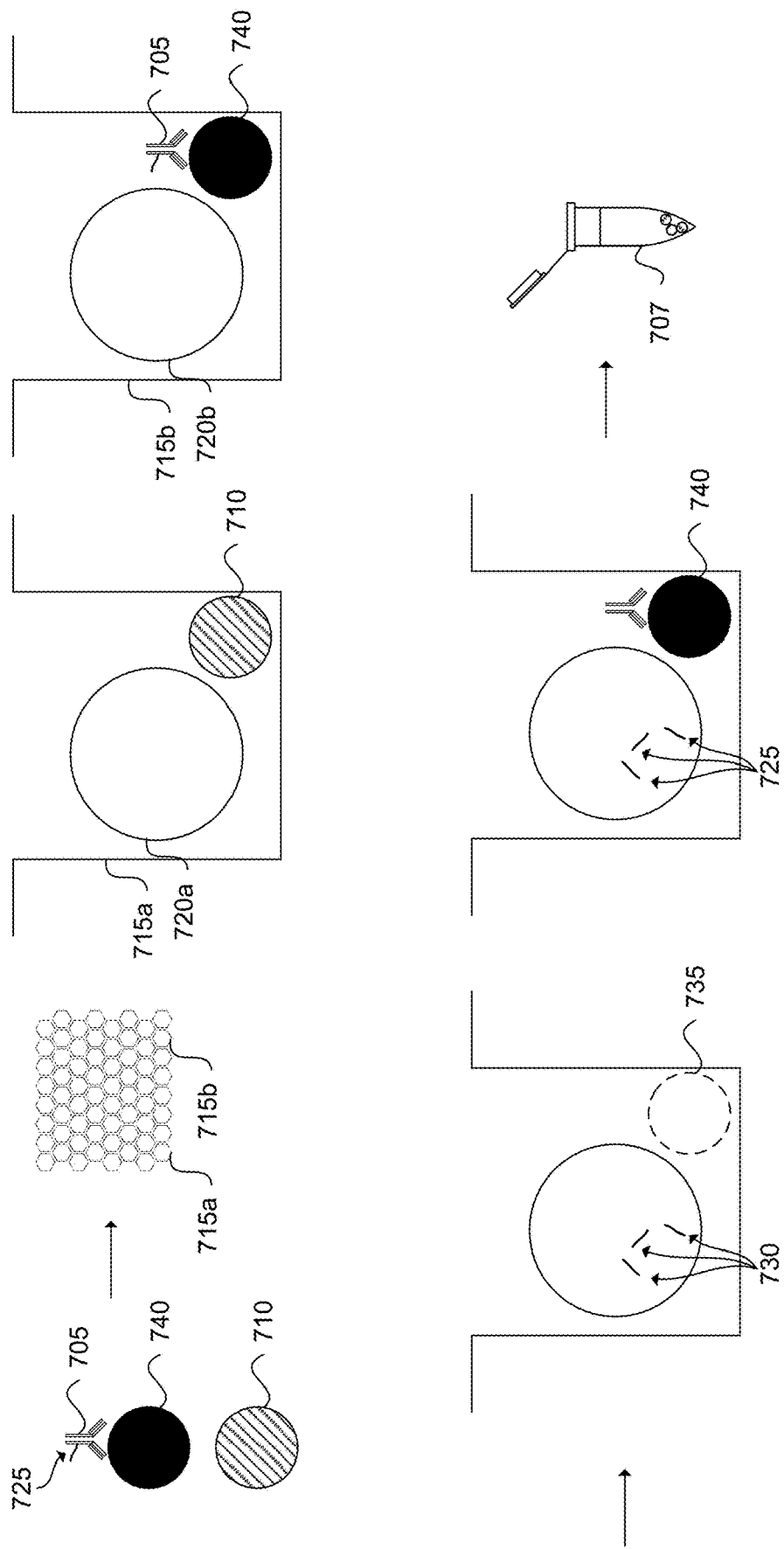
FIG. 7 is a schematic illustration of an exemplary workflow of using particles functionalized with oligonucleotides for single cell sequencing control.

FIG. 7 is a schematic illustration of an exemplary workflow of using particles functionalized with oligonucleotides for single cell sequencing control. In some embodiments, a control particle composition comprises a plurality of control particle oligonucleotides associated with a control particle 704. For example, a control particle 740 can be associated with a control particle oligonucleotide 725 conjugated to an antibody 705 bound to the control particle 740. A plurality of control particles 740 functionalized with control particle oligonucleotides 725 can be spiked into a plurality of cells at, for example, 5%. Control particles 740 can be treated as "cells" in the subsequent workflow. The control particles 740 can also be referred to as control cells or control cell particles. Cells 710 and the control particles 740 can be then separated into a plurality of compartments, such as wells of a microwell array, wherein a single compartment 715a, 715b is sized to fit a single cell or control particle and a single bead 720a, 720b. Beads 720a, 720b can be loaded into the compartments 715a, 715b Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 725 conjugated to the antibody 705 can be detached from the antibody 705 using chemical, optical or other means. The cell 710 can be lysed 735 to release nucleic acids within the cell, such as genomic DNA or cellular mRNA 730. Cellular mRNAs 530 and control particle oligonucleotides 725 can be captured by the oligonucleotide probes on beads 720a, 720b respectively, for example, by hybridizing to the poly(dT) sequence. Beads can be retrieved and the captured cellular mRNAs 730 and control particle oligonucleotides 725 (e.g., corresponding to around 5000 cells in total) can be pooled.

A reverse transcriptase can be used to extend the oligonucleotide probes hybridized to the cellular mRNA 730 and the oligonucleotides 725 using the cellular mRNA 730 and the oligonucleotides 725 as templates. The extension products produced by the reverse transcriptase can be subject to amplification and sequencing. Sequencing reads can be subject to demultiplexing of a cell label, a barcode sequence (e.g., a molecular label), gene identity, control particle oligonucleotide sequence, etc., which can be used to determine single cell gene expression profiles and quantity efficiency of the entire or part of the workflow (e.g., cell capture efficiency). For example, the number of control particles captured can be determined based on the number of cell labels associated with the control barcode sequence in the data. The efficiency of the workflow can be a ratio of the number of control particles captured and the number of control particles spiked in.

Microfluidics Workflow

Figure 8:
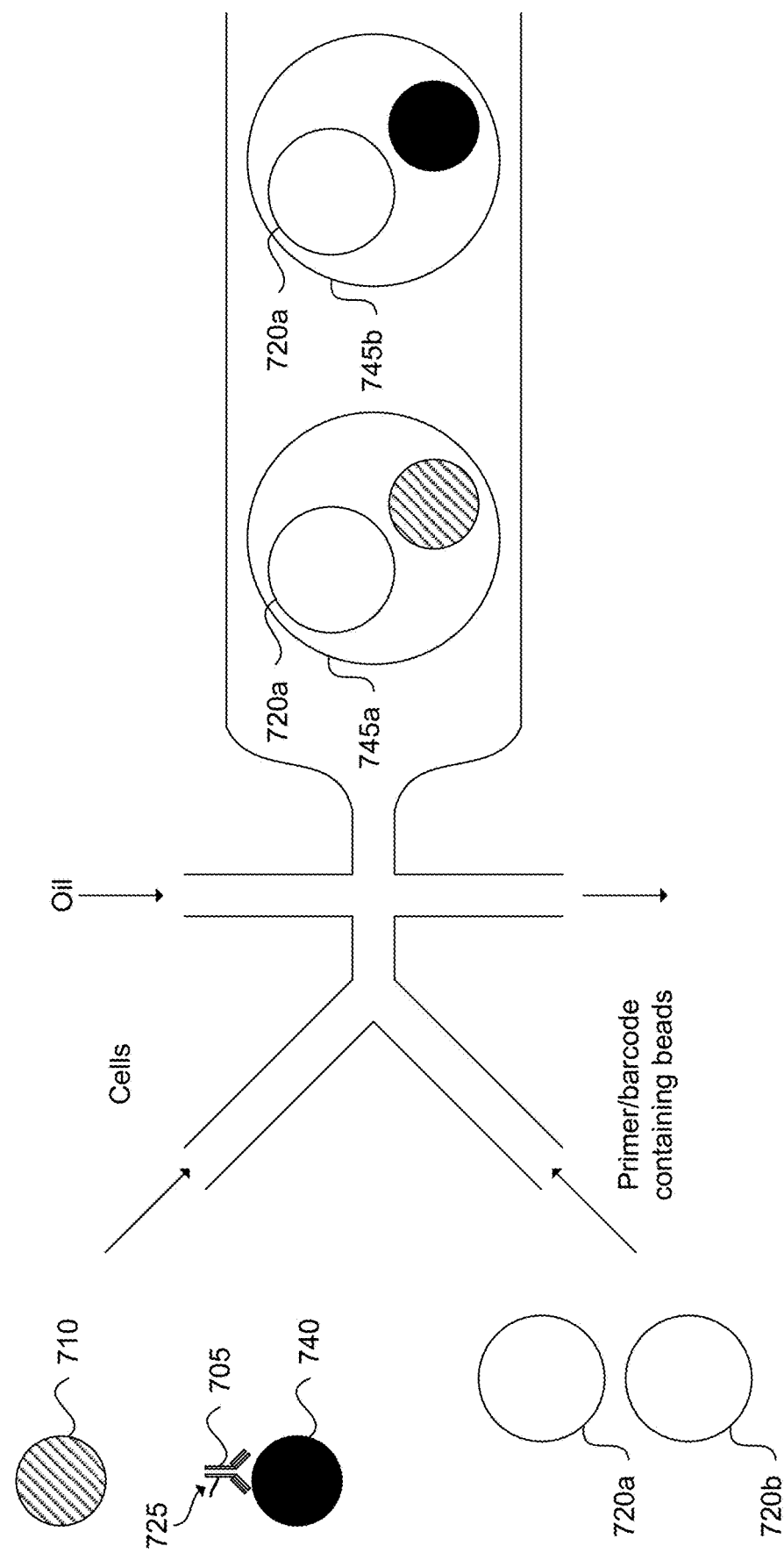
FIG. 8 is a schematic illustration of another exemplary workflow of using particles functionalized with oligonucleotides for single cell sequencing control.

FIG. 8 is a schematic illustration of another exemplary workflow of using particles functionalized with oligonucleotides for single cell sequencing control. A plurality of control particles 740 functionalized with control particle oligonucleotides 725 can be spiked into a plurality of cells at, for example, 5%. Control particles 740 can be treated as "cells" in the subsequent workflow. The control particles 740 can also be referred to as control cells or control cell particles. Cells 710 and the control particles 740 can be then separated using a microfluidics device into a plurality of compartments, such as droplets 745a, 745. Each droplet 745a, 745b can include one cell 710 or one control particle 740 and a hydrogel bead 720a, 720b.

Each bead 720a, 720b can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The bead 720a, 720b can include reagents for the subsequent workflow (e.g., reverse transcription). The oligonucleotides 725 conjugated to the antibody 705 can be detached from the antibody 705 using chemical, optical or other means. The cell 710 can be lysed 735 to release nucleic acids within the cell, such as genomic DNA or cellular mRNA 730. Cellular mRNAs 530 and control particle oligonucleotides 725 can be captured by the oligonucleotide probes released from beads 720a, 720b respectively, for example, by hybridizing to the poly(dT) sequence. A reverse transcriptase can be used to extend the oligonucleotide probes hybridized to the cellular mRNA 730 and the oligonucleotides 725 using the cellular mRNA 730 and the oligonucleotides 725 as templates.

After breaking up the droplets 745a, 745b, the extension products produced by the reverse transcriptase can be pooled and subject to amplification and sequencing. Sequencing reads can be subject to demultiplexing of cell label, molecular label, gene identity, control particle oligonucleotide sequence, etc. to determine single cell gene expression profiles and quantity efficiency of the entire or part of the workflow.

Control Oligonucleotides for Determining Single Cell Sequencing Efficiency

In some embodiments, by labeling single cells with antibodies conjugated with oligonucleotides (e.g., with a universal antibody or biomarker antibody) and generating next generation sequencing libraries with them, the signals from the oligonucleotides in NGS reads can be used to determine single cell NGS efficiency. This can then be used as a QC step or an evaluation tool for efficacy for different single cell sequencing platforms. For example, the control oligonucleotides can be used in any suitable methods, kits and systems disclosed herein, for example the methods, kits and systems for measuring cellular component expression level (for example protein expression level) using cellular component binding reagents associated with oligonucleotides.

Antibodies conjugated with oligonucleotides (referred to herein as "AbOs" can be used with any single cell workflow as a single cell sequencing control. Single cell workflows can utilize microwell arrays or microwell cartridges (e.g., BD Resolve™) or microfluidics devices (e.g., 10× Genomics (San Francisco, CA), Drop-seq (McCarroll Lab, Harvard Medical School (Cambridge, Massachusetts); Macosko et al., Cell, 2015 May 21 16; 5:1202, the content of which is incorporated herein by reference in its entirety), or Abseq (Mission Bio (San Francisco, CA); Shahi et al., Sci Rep. 2017 Mar. 14; 7:44447, the content of which is hereby incorporated by reference in its entirety) in combination with solid or semisolid particles associated with barcodes, such as stochastic barcodes (e.g., BD Resolve, or Drop-seq) or disruptable hydrogel particles enclosing releasable barcodes, such as stochastic barcodes (e.g., 10× Genomics, or Abseq). AbOs can be a control for determining efficiency of single cell workflows. For example, the single cell sequencing platform from 10× Genomics performs single cell capture using emulsions to encapsulate single cells in droplets. Because these droplets cannot be easily visualized, capture efficiency of single cells cannot be easily determined. The use of AbOs upstream of such single cell sequencing workflow allows users to evaluate the single cell capture efficiency after sequencing and rate of doublet formation.

Figure 9:
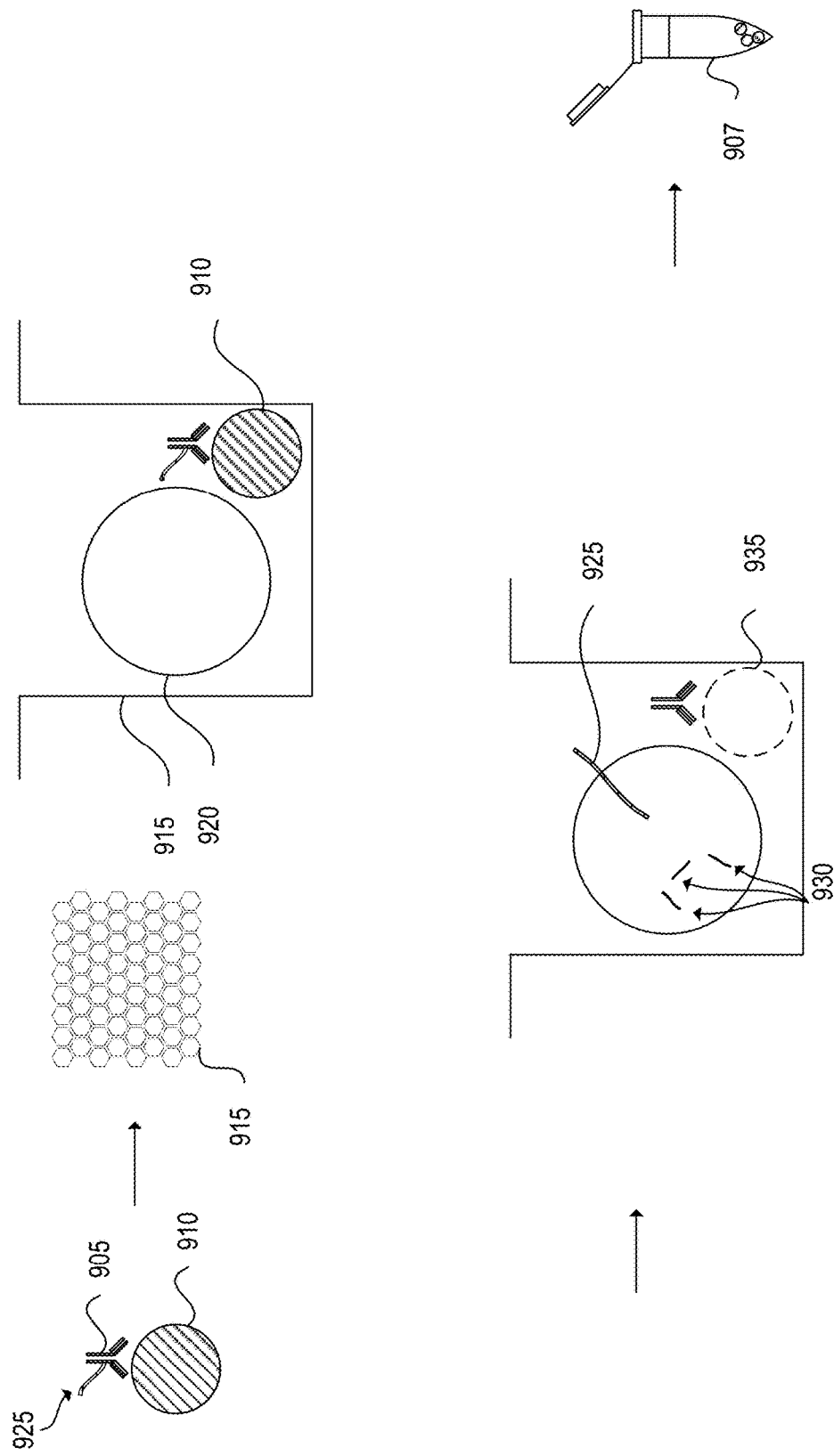
FIG. 9 shows a schematic illustration of an exemplary workflow of using control oligonucleotide-conjugated antibodies for determining single cell sequencing efficiency.

FIG. 9 shows a schematic illustration of an exemplary workflow of using control oligonucleotide-conjugated antibodies for determining single cell sequencing efficiency. In some embodiments, one or more cells (e.g., 5000) 900 can be stained with an antibody 905 conjugated with a control oligonucleotide 925 prior to being loading onto a microwell 915 of a microwell cartridge or array. Cells 910 can be then separated into a plurality of compartments, such as wells of a microwell array, wherein a single compartment 915 is sized to fit a single cell and a single bead 920.

The bead can, for example, comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 925 conjugated to the antibody 905 can be detached from the antibody 905 using chemical, optical or other means. The cell 910 can be lysed 935 to release nucleic acids within the cell, such as genomic DNA or cellular mRNA 930. Cellular mRNAs 930 and control oligonucleotides 925 can be captured by the oligonucleotide probes on a bead 920, for example, by hybridizing to the poly(dT) sequence. Beads can be retrieved and the captured cellular mRNAs 930 (e.g., corresponding to around 5000 cells in total) can be pooled.

A reverse transcriptase can be used to extend the oligonucleotide probes hybridized to the cellular mRNA 930 and the oligonucleotides 925 using the cellular mRNA 930 and the oligonucleotides 925 as templates. The extension products produced by the reverse transcriptase can be subject to amplification and sequencing. Sequencing reads can be subject to demultiplexing of a cell label, a barcode sequence (e.g., a molecular label), gene identity, control oligonucleotide sequence, etc. to determine single cell gene expression profiles and quantity efficiency of the entire or part of the workflow (e.g., cell capture efficiency). The number of cells that are captured and go through the library preparation successfully (e.g., fewer than 5000 cells) can be determined.

Figure 10:
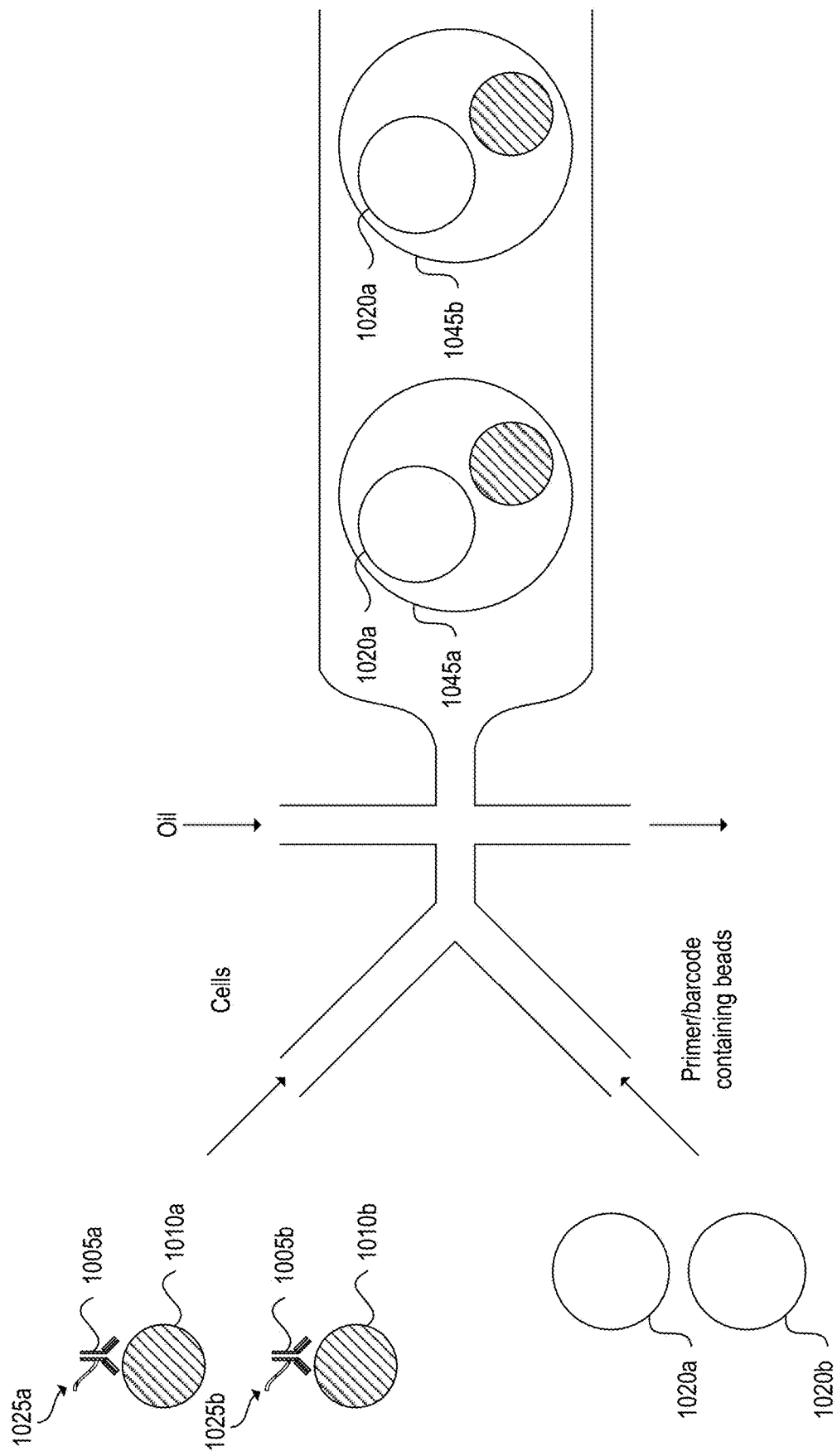
FIG. 10 shows another schematic illustration of an exemplary workflow of using control oligonucleotide-conjugated antibodies for determining single cell sequencing efficiency.

FIG. 10 shows another schematic illustration of an exemplary workflow of using control oligonucleotide-conjugated antibodies for determining single cell sequencing efficiency. In FIG. 10, droplets 1045a, 1045b containing a single cell 1010a, 1010b and a single particle 1020a, 1020b can be formed using a microfluidic device. The single cells 1010a, 1010b can be bound to antibodies 1005a, 1005b conjugated with control oligonucleotides 1025a, 1025b. After cell lysis and reverse transcription in droplets 1045a, 1045b, droplets can be broken up and the content pooled for library preparation. The number of cells that are captured and go through the library preparation successfully can be determined.

Figure 11C:
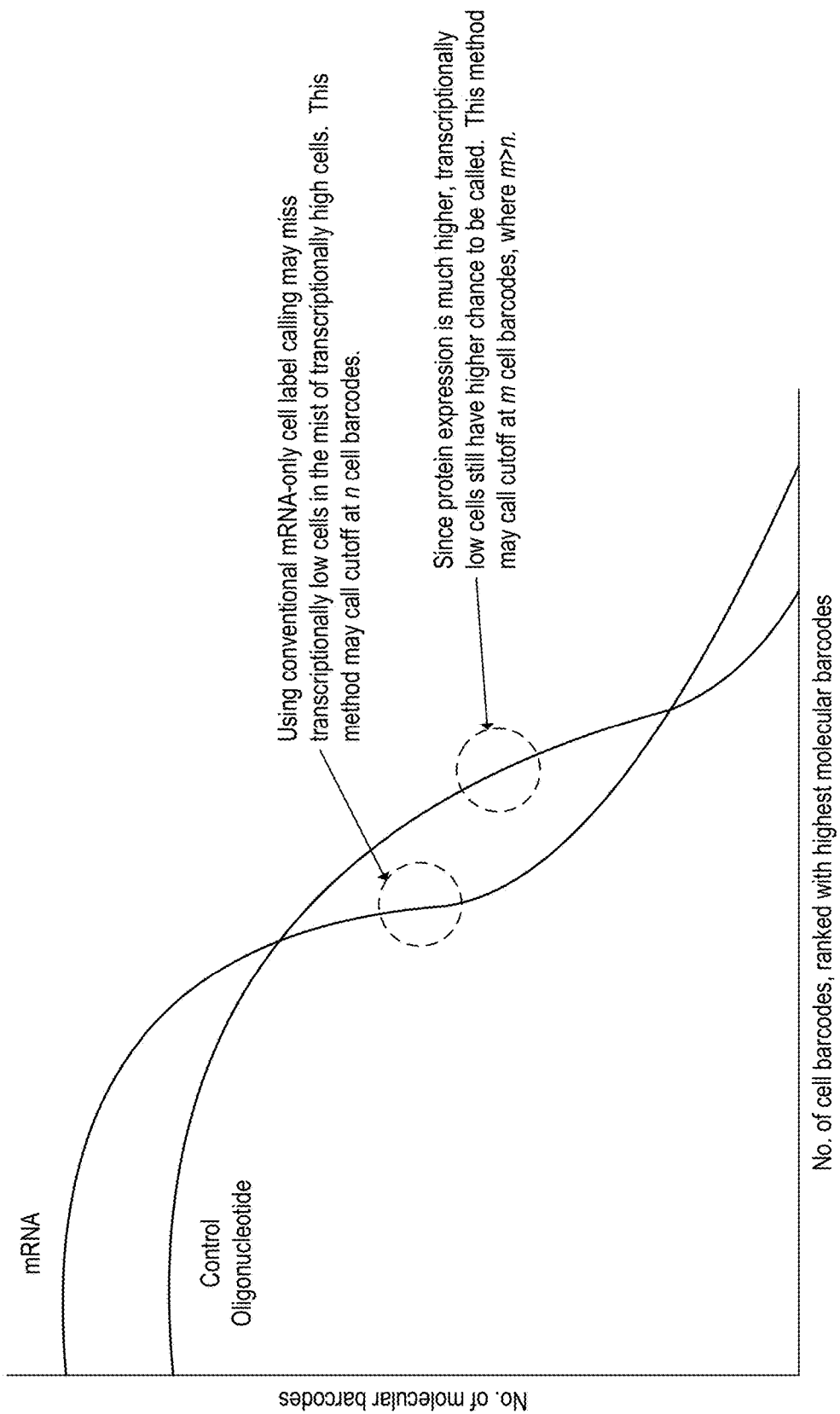

FIGS. 11A-11C are plots showing that control oligonucleotides can be used for cell counting. FIGS. 11A-11B show that control oligonucleotides of AbOs can be used as a control for cell counting. The falling points of the mRNA counts plot and the control oligonucleotide counts plot can coincide if 100% capture and library preparation efficiency is achieved. FIG. 11C shows that using conventional mRNA-only cell label calling may miss transcriptionally low cells in the mist of transcriptionally high cells. This method may call cutoff at n cell barcodes. This may occur when quiescent T cells within a large population of activated T cells, where activated T cells can have several fold higher in RNA transcription. This may also occur when in a targeted panel (e.g., cancer panel), non-targeted cells (non-cancer cells) with low expression of targeted genes are going to be dropped off. However, since protein expression is much higher, transcriptionally low cells still have higher chance to be called. This method may call cutoff at m cell barcodes, where m>n.

Disclosed herein are methods for sequencing control (e.g., determining single cell sequencing efficiency). The methods for determining single cell sequencing efficiency can be used with other methods disclosed herein. For example, the method for used for single cell sequencing efficiency can be used with the method for determining protein expression. As another example, a workflow can be used for determining single cell sequencing efficiency, protein expression, and/or gene expression.

In some embodiments, the method comprises: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic (e.g., the number of cells that are captured and go through the library preparation successfully) of the one or more cells using at least one characteristic of the plurality of barcoded control oligonucleotides in the sequencing data. In some embodiments, the pseudo-target region comprises a poly(dA) region.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of barcode sequences (e.g., molecular label sequences) with distinct sequences associated with the cell label and the control barcode sequence; and determining the number of the one or more cells using the number of barcode sequences with distinct sequences associated with the cell label and the control barcode sequence. Determining the number of barcode sequences with distinct sequences associated with the cell label and the control barcode sequence can comprise: for each cell label in the sequencing data, determining the number of barcode sequences with the highest number of distinct sequences associated with the cell label and the control barcode sequence. Determining the number of the one or more cells using the number of barcode sequences with distinct sequences associated with the cell label and the control barcode sequence can comprise: generating a plot of the number of barcode sequences with the highest number of distinct sequences with the number of cell labels in the sequencing data associated with the number of barcode sequences with the highest number of distinct sequences; and determining a cutoff in the plot as the number of the one or more cells.

In some embodiments, the method comprises releasing the control oligonucleotide from the protein binding reagent prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound cell identification compositions can comprise selecting cells bound to at least one protein binding reagent of the control composition using flow cytometry.

In some embodiments, barcoding the control oligonucleotides comprises: barcoding the control oligonucleotides using a plurality of barcodes (e.g., stochastic barcodes) to create a plurality of stochastically barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the barcode sequence (e.g., molecular label sequence) and at least a portion of the control oligonucleotide. In some embodiments, obtaining the sequencing data comprises obtaining sequencing data of the plurality of amplicons. Obtaining the sequencing data can comprise sequencing the at least a portion of the molecular label sequence and the at least a portion of the control oligonucleotide.

Cell Overloading and Multiplet Identification

Also disclosed herein are methods, kits and systems for identifying cell overloading and multiplet. Such methods, kits and systems can be used in combination with any suitable methods, kits and systems disclosed herein, for example the methods, kits and systems for measuring cellular component expression level (for example protein expression level) using cellular component binding reagents associated with oligonucleotides. Using current cell-loading technology, when about 20000 cells are loaded into a microwell cartridge or array with ~60000 microwells, the number of microwells or droplets with two or more cells (referred to as doublets or multiplets) can be minimal. However, when the number of cells loaded increases, the number of microwells or droplets with multiple cells can increase significantly. For example, when about 50000 cells are loaded into about 60000 microwells of a microwell cartridge or array, the percentage of microwells with multiple cells can be quite high, such as 11-14%. Such loading of high number of cells into microwells can be referred to as cell overloading. However, if the cells are divided into a number of groups (e.g., 5) can labeled with cell identification oligonucleotides with distinct cell identification sequences, a cell label associated with two or more cell identification sequences can be identified in sequencing data and removed from subsequent processing. Such higher number of cells can be loaded into microwells relative to the number of microwells in a microwell cartridge or array.

Disclosed herein includes methods for cell or doublet identification. The methods for cell identification or doublet identification can be used with other methods disclosed herein. For example, the method for doublet identification can be used with the method for determining protein expression. As another example, a workflow can be used for determining doublets, protein expression, and/or gene expression of single cells.

In some embodiments, the method for cell or doublet identification comprises: contacting a first plurality of cells and a second plurality of cells with two cell identification compositions respectively, wherein each of the first plurality of cells and each of the second plurality of cells comprise one or more antigen targets or protein targets, wherein each of the two cell identification compositions comprises a protein binding reagent associated with a cell identification oligonucleotide, wherein the protein binding reagent is capable of specifically binding to at least one of the one or more antigen targets or protein targets, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis (e.g., single cell mRNA profiling, or whole transcriptome analysis). In some embodiments, the cell identification oligonucleotide comprises a barcode sequence (e.g. a molecular label sequence), a binding site for a universal primer, or a combination thereof.

For example, the method can be used to load 50,000 or more cells (compared to 10,000-20,000 cells) using cell identification. Cell identification can use oligonucleotide-conjugated protein binding reagents (e.g., antibodies) or cellular component binding reagents against a universal protein marker to label cells from different samples with unique cellular component binding reagents. When two or more cells from different samples or two or more cells from different populations of cells of a sample are captured in the same microwell or droplet, the combined "cell" (or contents of the two or more cells) can be associated with cell identification oligonucleotides with different cell identification sequences. The number of different populations of cells can be different in different implementations. In some embodiments, the number of different populations can be, or about, 2, 3, 4, 5, 6, 7, 8, 9, 10, 20, 30, 40, 50, 60, 70, 80, 90, 100, or a number or a range between any two of these values. In some embodiments, the number of different populations can be at least, or at most, 2, 3, 4, 5, 6, 7, 8, 9, 10, 20, 30, 40, 50, 60, 70, 80, 90, or 100. Cells of a sample can be divided into multiple populations by aliquoting the cells of the sample into the multiple populations. A cell associated with more than one cell identification sequence can be identified as a "multiplet" based on two or more cell identification sequences associated with one cell label sequence in the sequencing data. The sequencing data of a combined "cell" is also referred to herein as a multiplet. A multiplet can be a doublet, a triplet, a quartet, a quintet, a sextet, a septet, an octet, a nonet, or any combination thereof.

A doublet can refer to a combined "cell" associated with two cell identification oligonucleotides with different cell identification sequences. A doublet can also refer to a combined "cell" associated with cell identification oligonucleotides with two cell identification sequences. A doublet can occur when two cells associated with two cell identification oligonucleotides of different sequences (or two or more cells associated with cell identification oligonucleotides with two different cell identification sequences) are captured in the same microwell or droplet, the combined "cell" can be associated with two cell identification oligonucleotides with different cell identification sequences. A triplet can refer to a combined "cell" associated with three cell identification oligonucleotides all with different cell identification sequences, or a combined "cell" associated with cell identification oligonucleotides with three different cell identification sequences. A quartet can refer to a combined "cell" associated with four cell identification oligonucleotides all with different cell identification sequences, or a combined "cell" associated with cell identification oligonucleotides with four different cell identification sequences. A quintet can refer to a combined "cell" associated with five cell identification oligonucleotides all with different cell identification sequences, or a combined "cell" associated with cell identification oligonucleotides with five different cell identification sequences. A sextet can refer to a combined "cell" associated with six cell identification oligonucleotides all with different cell identification sequences, or a combined "cell" associated with cell identification oligonucleotides with six different cell identification sequences. A septet can refer to a combined "cell" associated with seven cell identification oligonucleotides all with different cell identification sequences, or a combined "cell" associated with cell identification oligonucleotides with seven different cell identification sequences. A octet can refer to a combined "cell" associated with eight cell identification oligonucleotides all with different cell identification sequences, or a combined "cell" associated with cell identification oligonucleotides with eight different cell identification sequences. A nonet can refer to a combined "cell" associated with nine cell identification oligonucleotides all with different cell identification sequences, or a combined "cell" associated with cell identification oligonucleotides with nine different cell identification sequences.

As another example, the method can be used for multiplet identification, whether in the context of sample overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using cell identification, one can recognize some of these multiplets by looking for cell barcodes that are each associated with or assigned to two or more cell identification oligonucleotides with different cell identification sequences (or cell identification oligonucleotides with two or more cell identification sequences). With cell identification sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of cells and a second plurality of cells with two cell identification compositions respectively, wherein each of the first plurality of cells and each of the second plurality of cells comprise one or more protein targets, wherein each of the two cell identification compositions comprises a protein binding reagent associated with a cell identification oligonucleotide, wherein the protein binding reagent is capable of specifically binding to at least one of the one or more protein targets, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With cell identification, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of cells and the second plurality of cells with the two cell identification compositions respectively comprises: contacting the first plurality of cells with a first cell identification compositions of the two cell identification compositions; and contacting the first plurality of cells with a second cell identification compositions of the two cell identification compositions. The number of pluralities of cells and the number of pluralities of cell identification compositions can be different in different implementations. In some embodiments, the number of pluralities of cells and/or cell identification compositions can be, or about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of pluralities of cells and/or cell identification compositions can be at least, or at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound cell identification compositions of the two cell identification compositions. Removing the unbound cell identification compositions can comprise washing cells of the first plurality of cells and the second plurality of cells with a washing buffer. Removing the unbound cell identification compositions can comprise selecting cells bound to at least one protein binding reagent of the two cell identification compositions using flow cytometry. In some embodiments, the method comprises: lysing the one or more cells from each of the plurality of samples.

In some embodiments, the cell identification oligonucleotide is configured to be detachable or non-detachable from the protein binding reagent. The method can comprise detaching the cell identification oligonucleotide from the protein binding reagent. Detaching the cell identification oligonucleotide can comprise detaching the cell identification oligonucleotide from the protein binding reagent by UV photocleaving, chemical treatment (e.g., using reducing reagent, such as dithiothreitol), heating, enzyme treatment, or any combination thereof.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of the barcode sequence and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises barcoding (e.g., stochastically barcoding the cell identification oligonucleotides using a plurality of barcodes (e.g., a plurality of stochastic barcodes) to create a plurality of barcoded cell identification oligonucleotides (e.g., a plurality of stochastically barcoded cell identification oligonucleotides).

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise barcoding (e.g., stochastically barcoding) the plurality of targets of the cell using a plurality of barcodes (e.g., a plurality of stochastic barcodes) to create a plurality of barcoded targets (e.g., a plurality of stochastically barcoded targets).

Determining Cellular Component-Cellular Component Interactions

Disclosed herein are methods for determining protein-protein interactions. The methods for determining protein-protein interactions can be used with other methods disclosed herein. For example, the method for determining protein-protein interactions can be used with the method for determining protein expression. As another example, a workflow can be used for determining protein-protein interactions, protein expression, and/or gene expression of single cells. Such methods can be used in combination with any suitable methods, kits and systems disclosed herein, for example the methods, kits and systems for measuring cellular component expression level (for example protein expression level) using cellular component binding reagents associated with oligonucleotides.

In some embodiments, the method for determining protein-protein interactions comprises: contacting a cell with a first pair of interaction determination compositions, wherein the cell comprises a first cellular component target and a second cellular component target, wherein each of the first pair of interaction determination compositions comprises a cellular component binding reagent associated with an interaction determination oligonucleotide, wherein the cellular component binding reagent of one of the first pair of interaction determination compositions is capable of specifically binding to the first cellular component target and the cellular component binding reagent of the other of the first pair of interaction determination compositions is capable of specifically binding to the second cellular component target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second cellular component targets based on the association of the interaction determination sequences of the first pair of interaction determination compositions in the obtained sequencing data. In some embodiments, at least one of the two cellular component binding reagent comprises a protein binding reagent, wherein the protein binding reagent is associated with one of the two interaction determination oligonucleotides, and wherein the one or more cellular component targets comprises at least one protein target.

In some embodiments, the method comprises: contacting a cell with a first pair of interaction determination compositions, wherein the cell comprises a first protein target and a second protein target, wherein each of the first pair of interaction determination compositions comprises a protein binding reagent associated with an interaction determination oligonucleotide, wherein the protein binding reagent of one of the first pair of interaction determination compositions is capable of specifically binding to the first protein target and the protein binding reagent of the other of the first pair of interaction determination compositions is capable of specifically binding to the second protein target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second protein targets based on the association of the interaction determination sequences of the first pair of interaction determination compositions in the obtained sequencing data.

In some embodiments, contacting the cell with the first pair of interaction determination compositions comprises: contacting the cell with each of the first pair of interaction determination compositions sequentially or simultaneously. The first cellular component target can be the same as the second cellular component target. The first cellular component target can be different from the second cellular component target.

In some embodiments, the interaction determination sequence is at least 6 nucleotides in length, 25-60 nucleotides in length, about 45 nucleotides in length, about 50 nucleotides in length, about 100 nucleotides in length, about 128 nucleotides in length, at least 128 nucleotides in length, about 200 nucleotides in length, at least 200 nucleotides in length, less than about 200-300 nucleotides in length, about 200-500 nucleotides in length, about 500 nucleotides in length, or any combination thereof.

In some embodiments, the method comprises contacting the cell with a second pair of interaction determination compositions, wherein the cell comprises a third cellular component target and a fourth cellular component target, wherein each of the second pair of interaction determination compositions comprises a cellular component binding reagent associated with an interaction determination oligonucleotide, wherein the cellular component binding reagent of one of the second pair of interaction determination compositions is capable of specifically binding to the third cellular component target and the cellular component binding reagent of the other of the second pair of interaction determination compositions is capable of specifically binding to the fourth cellular component target. At least one of the third and fourth cellular component targets can be different from one of the first and second cellular component targets. At least one of the third and fourth cellular component targets and at least one of the first and second cellular component targets can be identical.

In some embodiments, the method comprises contacting the cell with three or more pairs of interaction determination compositions. The interaction determination sequences of at least 10, 100, 1000, or any combination thereof, interaction determination compositions of the plurality of pairs of interaction determination compositions can comprise different sequences.

In some embodiments, the bridge oligonucleotide hybridization regions of the first pair of interaction determination compositions comprise different sequences. At least one of the bridge oligonucleotide hybridization regions can be complementary to at least one of the two hybridization regions of the bridge oligonucleotide.

In some embodiments, ligating the interaction determination oligonucleotides of the first pair of interaction determination compositions using the bridge oligonucleotide comprises: hybridizing a first hybridization regions of the bridge oligonucleotide with a first bridge oligonucleotide hybridization region of the bridge oligonucleotide hybridization regions of the interaction determination oligonucleotides; hybridizing a second hybridization regions of the bridge oligonucleotide with a second bridge oligonucleotide hybridization region of the bridge oligonucleotide hybridization regions of the interaction determination oligonucleotides; and ligating the interaction determination oligonucleotides hybridized to the bridge oligonucleotide to generate a ligated interaction determination oligonucleotide.

In some embodiments, the cellular component binding reagent comprises an antibody, a tetramer, an aptamers, a protein scaffold, an integrin, or a combination thereof.

In some embodiments, the interaction determination oligonucleotide is conjugated to the cellular component binding reagent through a linker. The oligonucleotide can comprise the linker. The linker can comprise a chemical group. The chemical group can be reversibly or irreversibly attached to the cellular component binding reagent. The chemical group can comprise a UV photocleavable group, a disulfide bond, a streptavidin, a biotin, an amine, a disulfide linkage or any combination thereof. The at least one of the one or more cellular component targets can be on a cell surface.

In some embodiments, the method comprises: fixating the cell prior to contacting the cell with the first pair of interaction determination compositions. The method can comprise: removing unbound interaction determination compositions of the first pair of interaction determination compositions. Removing the unbound interaction determination compositions can comprise washing the cell with a washing buffer. Removing the unbound interaction determination compositions can comprise selecting the cell using flow cytometry. The method can comprise lysing the cell.

In some embodiments, the interaction determination oligonucleotide is configured to be detachable or non-detachable from the cellular component binding reagent. The method can comprise detaching the interaction determination oligonucleotide from the cellular component binding reagent. Detaching the interaction determination oligonucleotide can comprise detaching the interaction determination oligonucleotide from the cellular component binding reagent by UV photocleaving, chemical treatment, heating, enzyme treatment, or any combination thereof.

In some embodiments, the interaction determination oligonucleotide is not homologous to genomic sequences of the cell. The interaction determination oligonucleotide can be homologous to genomic sequences of a species. The species can be a non-mammalian species. The non-mammalian species can be a phage species. The phage species can T7 phage, a PhiX phage, or a combination thereof.

In some embodiment, the cell comprises a tumor cell or non-tumor cell. The cell can comprise a mammalian cell, a bacterial cell, a viral cell, a yeast cell, a fungal cell, or any combination thereof.

In some embodiments, the method comprises: contacting two or more cells with the first pair of interaction determination compositions, and wherein each of the two or more cells comprises the first and the second cellular component targets. At least one of the two or more cells can comprise a single cell.

In some embodiments, the barcode comprises a cell label sequence, a binding site for a universal primer, or any combination thereof. At least two barcodes of the plurality of barcodes can comprise an identical cell label sequence. The interaction determination oligonucleotide of the one of the first pair of interaction determination compositions can comprise a sequence complementary to the capture sequence. The capture sequence can comprise a poly(dT) region. The sequence of the interaction determination oligonucleotide complementary to the capture sequence can comprise a poly(dA) region. The interaction determination oligonucleotide can comprise a second barcode sequence. The interaction determination oligonucleotide of the other of the first pair of interaction identification compositions can comprise a binding site for a universal primer.

In some embodiments, the cellular component target comprises an extracellular protein, an intracellular protein, or any combination thereof. The cellular component target can comprise a cell-surface protein, a cell marker, a B-cell receptor, a T-cell receptor, a major histocompatibility complex, a tumor antigen, a receptor, an integrin, or any combination thereof.

In some embodiments, the cellular component target comprises a lipid, a carbohydrate, or any combination thereof. The cellular component target can be selected from a group comprising 10-100 different cellular component targets.

In some embodiments, the cellular component binding reagent is associated with two or more interaction determination oligonucleotides with an identical sequence. The cellular component binding reagent can be associated with two or more interaction determination oligonucleotides with different interaction determination sequences.

In some embodiments, the one of the plurality of interaction determination compositions comprises a second cellular component binding reagent not associated with the interaction determination oligonucleotide. The cellular component binding reagent and the second cellular component binding reagent can be identical. The cellular component binding reagent can be associated with a detectable moiety.

In some embodiments, the plurality of barcodes is associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can comprise a bead. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle. The particle can be associated with a detectable moiety. The interaction determination oligonucleotide can be associated with a detectable moiety. The barcodes of the particle comprise barcode sequences can be selected from, about, at least, at most, 1000, 10000, or more, or less, or any combination thereof different barcode sequences. The barcodes sequences of the barcodes can comprise random sequences. The particle can comprise at least 10000 barcodes.

In some embodiments barcoding the interaction determination oligonucleotides using the plurality of barcodes comprises: contacting the plurality of barcodes with the interaction determination oligonucleotides to generate barcodes hybridized to the interaction determination oligonucleotides; and extending the barcodes hybridized to the interaction determination oligonucleotides to generate the plurality of barcoded interaction determination oligonucleotides. Extending the barcodes can comprise extending the barcodes using a DNA polymerase to generate the plurality of barcoded interaction determination oligonucleotides. Extending the barcodes can comprise extending the barcodes using a reverse transcriptase to generate the plurality of barcoded interaction determination oligonucleotides. Extending the barcodes can comprise extending the barcodes using a Moloney Murine Leukemia Virus (M-MLV)

reverse transcriptase or a Taq DNA polymerase to generate the plurality of barcoded interaction determination oligonucleotides. Extending the barcodes can comprise displacing the bridge oligonucleotide from the ligated interaction determination oligonucleotide. The method can comprise: amplifying the plurality of barcoded interaction determination oligonucleotides to produce a plurality of amplicons. Amplifying the plurality of barcoded interaction determination oligonucleotides can comprise amplifying, using polymerase chain reaction (PCR), at least a portion of the barcode sequence and at least a portion of the interaction determination oligonucleotide.

In some embodiments, obtaining the sequencing data of the plurality of barcoded interaction determination oligonucleotides can comprise obtaining sequencing data of the plurality of amplicons. Obtaining the sequencing data can comprise sequencing at least a portion of the barcode sequence and at least a portion of the interaction determination oligonucleotide. Obtaining sequencing data of the plurality of barcoded interaction determination oligonucleotides can comprise obtaining partial and/or complete sequences of the plurality of barcoded interaction determination oligonucleotides.

In some embodiments, the plurality of barcodes comprises a plurality of stochastic barcodes, the barcode sequence of each of the plurality of stochastic barcodes comprises a barcode sequence (e.g., a molecular label sequence), the barcode sequences of at least two stochastic barcodes of the plurality of stochastic barcodes comprise different sequences, and barcoding the interaction determination oligonucleotides using the plurality of barcodes to create the plurality of barcoded interaction determination oligonucleotides comprises stochastically barcoding the interaction determination oligonucleotides using the plurality of stochastic barcodes to create a plurality of stochastically barcoded interaction determination oligonucleotides.

In some embodiments, barcoding a plurality of targets of the cell using the plurality of barcodes to create a plurality of barcoded targets; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using the plurality of stochastic barcodes to create a plurality of stochastically barcoded targets.

Embodiments disclosed herein include kits for identifying cellular component-cellular component interactions (e.g., protein-protein interactions). In some embodiments, the kit comprises: a first pair of interaction determination compositions, wherein each of the first pair of interaction determination compositions comprises a cellular component binding reagent associated with an interaction determination oligonucleotide, wherein the cellular component binding reagent of one of the first pair of interaction determination compositions is capable of specifically binding to a first cellular component target and a cellular component binding reagent of the other of the first pair of interaction determination compositions is capable of specifically binding to the second cellular component target, wherein the interaction determination oligonucleotide comprises an interaction determination sequence and a bridge oligonucleotide hybridization region, and wherein the interaction determination sequences of the first pair of interaction determination compositions comprise different sequences; and a plurality of bridge oligonucleotides each comprising two hybridization regions capable of specifically binding to the bridge oligonucleotide hybridization regions of the first pair of interaction determination compositions.

In some embodiments, the kit comprises: a second pair of interaction determination compositions, wherein each of the second pair of interaction determination compositions comprises a cellular component binding reagent associated with an interaction determination oligonucleotide, wherein the cellular component binding reagent of one of the second pair of interaction determination compositions is capable of specifically binding to a third cellular component target and the cellular component binding reagent of the other of the second pair of interaction determination compositions is capable of specifically binding to a fourth cellular component target. In some embodiments, the kit comprises: three or more pairs of interaction determination compositions.

In some embodiments, the kit comprises: a plurality of barcodes, wherein each of the plurality of barcodes comprises a barcode sequence and a capture sequence. The plurality of barcodes can comprise a plurality of stochastic barcodes, wherein the barcode sequence of each of the plurality of stochastic barcodes comprises a barcode sequence (e.g., a molecular label sequence), wherein the barcode sequences of at least two stochastic barcodes of the plurality of stochastic barcodes comprise different sequences. In some embodiments, the plurality of barcodes is associated with a particle. At least one barcode of the plurality of barcodes can be immobilized on the particle, partially immobilized on the particle, enclosed in the particle, partially enclosed in the particle, or any combination thereof. The particle can be disruptable. The particle can comprise a bead.

In some embodiments, the kit comprises: a DNA polymerase. The kit can comprise a reverse transcriptase. The kit can comprise: a Moloney Murine Leukemia Virus (M-MLV) reverse transcriptase or a Taq DNA polymerase. In some embodiments, the method comprises a fixation agent (e.g., formalin, paraformaldehyde, glutaraldehyde/osmium tetroxide, Alcoholic fixatives, Hepes-glutamic acid buffer-mediated organic solvent protection effect (HOPE), Bouin solution, or any combination thereof).

Systems for Use in Preparing a Labeled Biomolecule Reagent

Labeled biomolecule reagent compositions that are used in many analyte assays include a biomolecule that is conjugated to a detectable marker compound. The biomolecule is conjugated to the detectable marker by one or more covalent bonds to the backbone or a side chain of the biomolecule or may be coupled together by ionic or other non-covalent interactions. Often, the biomolecule is a probe compound having a specific binding region for an analyte of interest and the detectable marker is a compound that can visualized, for example under a microscope, with the unaided eye or by some form of optical spectroscopy (e.g., UV-vis, fluorescence spectroscopy, etc.). In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

Assays for determining the presence and concentration of analytes in a biological fluid often rely on the specific binding of a probe compound. Depending on the analyte of interest, the probe compound may be a polypeptide, such as an antibody or an oligonucleotide, each having a specific binding region. To detect the binding of the target analyte, a marker that can be visualized (e.g., detectable by spectroscopy) is conjugated to the probe compound. Currently, to prepare labeled biomolecule reagents, each biomolecule (e.g., CD4-RPA-T4) is separately conjugated to a detectable label (PE-Cy5) by individual synthetic protocols, followed by purification (e.g., column chromatography). Since each labeled biomolecule reagent is separately prepared and purified, the process of providing an assay-ready specific binding probe composition is expensive and labor intensive, in particular for small scale customer requests. In addition, on-demand preparation of a performance specific and high quality probe composition is not possible due to the amount of lead time necessary for synthesis of the labeled biomolecule and subsequent purification. Commercially, commonly used labeled biomolecule reagents are prepared and stored in advance and customers can only select from a limited database of pre-synthesized labeled biomolecule reagent compositions.

Figure 12:
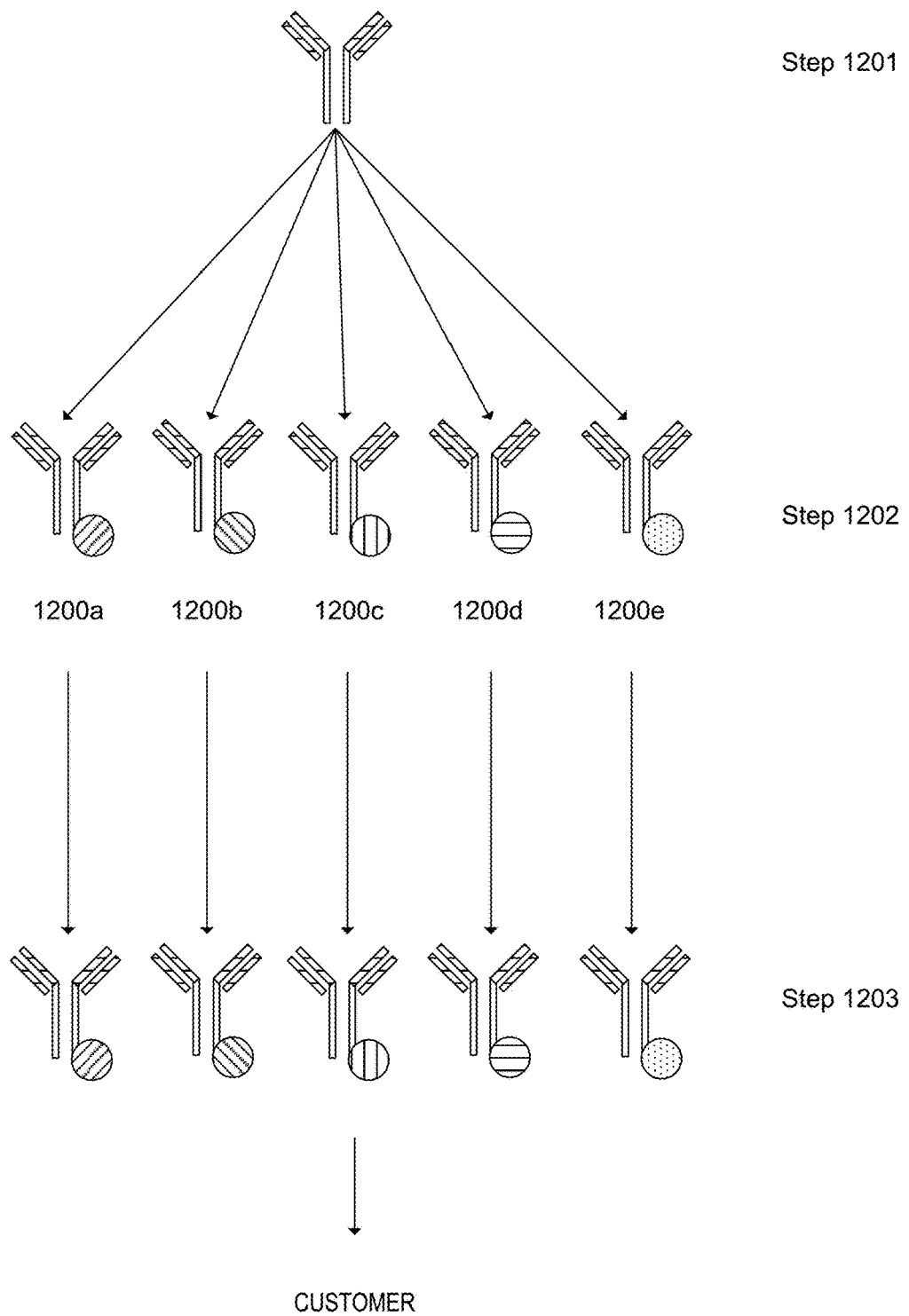
FIG. 12 illustrates the steps for the preparation of labeled biomolecule reagents used to provide labeled biomolecule reagent compositions for laboratory and clinical assays according to one embodiment.

FIG. 12 illustrates the steps for the preparation of labeled biomolecule reagents used to provide labeled biomolecule reagent compositions for laboratory and clinical assays according to one embodiment. A biomolecule (antibody probe) of interest is first purified (step 1201) and subjected to reaction conditions (step 1202) sufficient to conjugate the biomolecule with five different detectable markers producing labeled biomolecules 1200a, 1200b, 1200c, 1200d and 1200e. Labeled biomolecules 1200a, 1200b, 1200c, 1200d and 1200e are then each purified (step 1203) and stored. Upon request from a customer, the labeled biomolecules 1200a, 1200b, 1200c, 1200d and 1200e are formulated into labeled biomolecule reagent compositions and packaged for delivery to the customer.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

Figure 13:
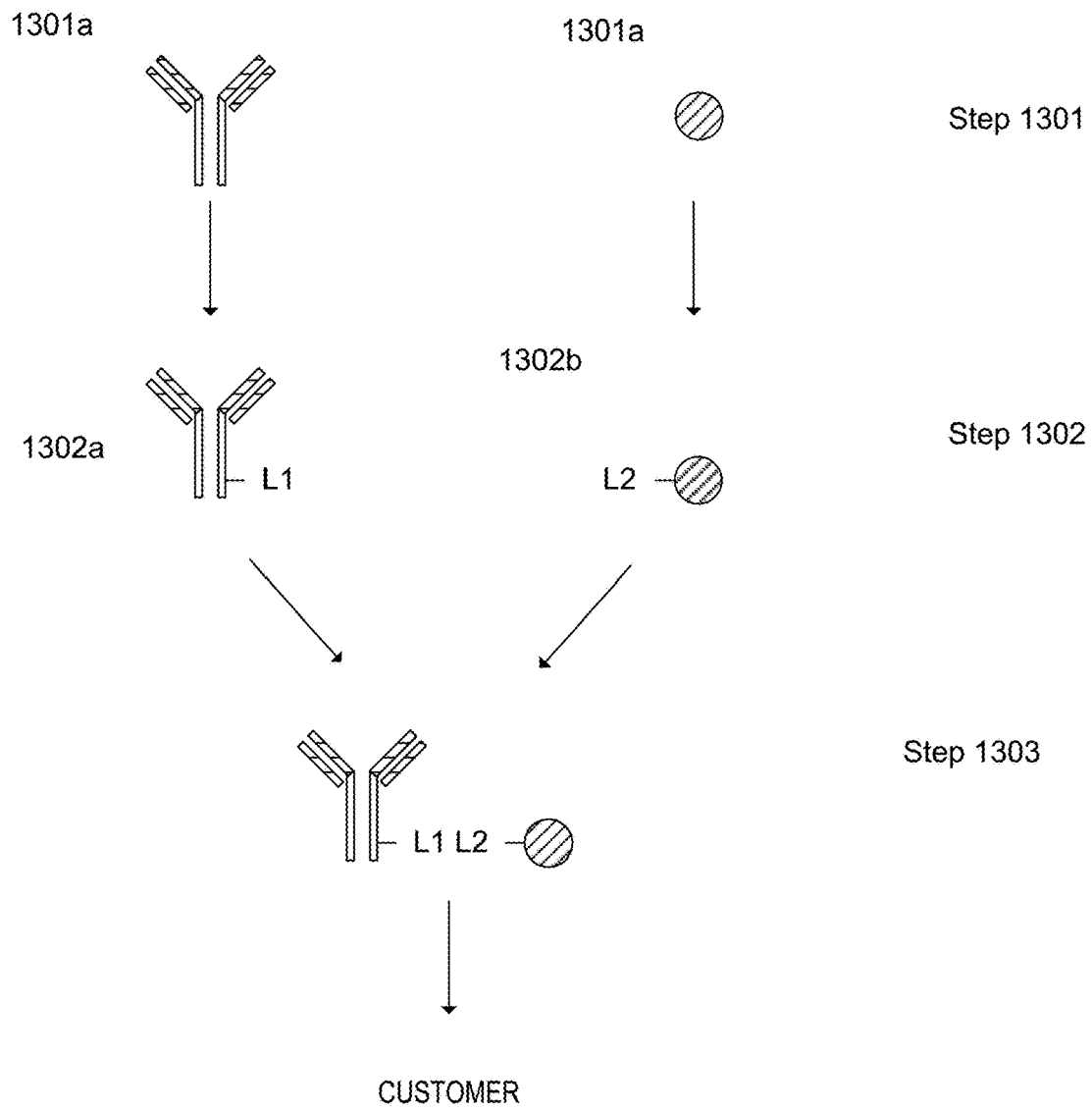
FIG. 13 provides an illustration of a method according to an embodiment of the invention.

Disclosed herein are systems and methods for delivering high quality and performance specific products across a wide range of biomolecule and detectable label portfolios in a fast, efficient and highly scalable manner. In embodiments of the invention, a request for a labeled biomolecule is made and in response to the request the labeled biomolecule is prepared from a pre-existing collection of activated biomolecules and activated labels. FIG. 13 provides an illustration of a method according to an embodiment of the invention. In FIG. 13, a collection of biomolecules (1301a) and collection of detectable labels or markers (1301b) are first purified (Step 1301). Each biomolecule is then conjugated to a reactive linker to functionalize the biomolecules with a reactive moiety (i.e., activate the biomolecules with reactive linker L1, 1302a). The collection of activated biomolecules is then purified and stored. Separately, a collection of detectable markers are also conjugated to reactive linkers to functionalize the collection of detectable markers with a reactive moiety (i.e., activate the labels with reactive linker L2, 1302*b*). The collection of activated labels is also purified and stored (Step 1302). Upon request of a labeled biomolecule reagent from a customer, a biomolecule is conjugated to a label by reacting an activated biomolecule (L1) with an activated label (L2) (Step 1303) to form labeled biomolecule (bonded through linkage L1-L2). In this way, any desired combination of biomolecule and detectable marker can be prepared on-demand by simply mixing an activated biomolecule with an activated label.

Figure 14:
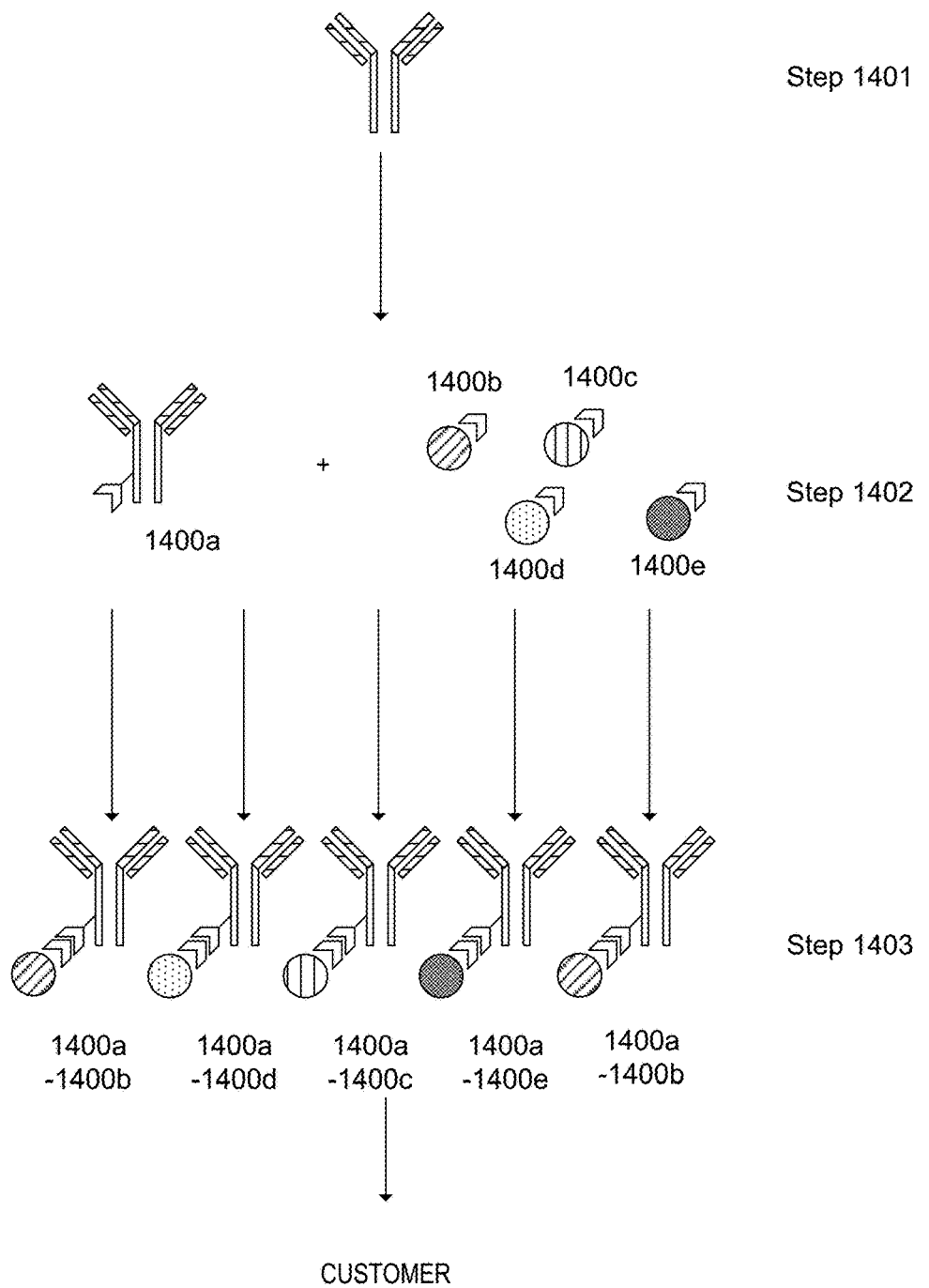
FIG. 14 illustrates a method of the present disclosure for providing customizable labeled biomolecule reagents on-demand.

FIG. 14 illustrates this unique and new method of the present disclosure for providing customizable labeled biomolecule reagents on-demand. A biomolecule of interest can be purified (step 1401) and then functionalized with a reactive linker (step 1402) to produce an activated biomolecule 1400*a*. Activated labels 1400*b*, 1400*c*, 1400*d*, and 1400*e* are separately prepared by functionalizing detectable markers with reactive linkers. Upon receipt of a request from a customer, any combination of activated biomolecule 1400*a* and activated labels 1400*b*, 1400*c*, 1400*d* and 1400*e* can be prepared on-demand by reaction of the reactive linker of activated biomolecule 500*a* with the reactive linkers of activated labels 1400*b*, 1400*c*, 1400*d* and 1400*e*. Once conjugated, the labeled biomolecules 1400*a*-1400*b*, 1400*a*-1400*c*, 1400*a*-1400*d* and 1400*a*-1400*e* are formulated into labeled biomolecule reagent compositions and packaged for delivery to the customer. In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

The present disclosure provides systems for use in preparing a labeled biomolecule reagent. In further describing embodiments of the disclosure, systems having an input manager for receiving a labeled biomolecule reagent request and an output manager for providing biomolecule and label storage identifiers are first described in greater detail. Next, a reagent preparatory apparatus for preparing the labeled biomolecule reagent from an activated biomolecule and an activated label are described. Methods for communicating and receiving a labeled biomolecule reagent request and preparing the subject labeled biomolecule reagents are also provided.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

Aspects of the present disclosure include systems for use in preparing a labeled biomolecule reagent. Systems according to some embodiments include an input manager for receiving a request for a labeled biomolecule reagent, a memory for storing a dataset having a plurality of storage identifiers that correspond to the one or more components of the labeled biomolecule reagent request (e.g., biomolecule, label, etc.), a processing module communicatively coupled to the memory and configured to identify a storage identifier from the dataset that corresponds to the components of the labeled biomolecule reagent request and an output manager for providing the identified storage identifiers. As described in greater detail below, the term "labeled biomolecule" reagent refers to a biological macromolecule coupled (e.g., through a covalent bond) to a detectable marker. The biological macromolecule may be a biopolymer. A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source. As such, biomolecules may include polysaccharides, nucleic acids and polypeptides. For example, the nucleic acid may be an oligonucleotide, truncated or full-length DNA or RNA. In embodiments, oligonucleotides, truncated and full-length DNA or RNA are comprised of 10 nucleotide monomers or more, such as 15 or more, such as 25 or more, such as 50 or more, such as 100 or more, such as 250 or more and including 500 nucleotide monomers or more. For example, oligonucleotides, truncated and full-length DNA or RNA of interest may range in length from 10 nucleotides to $10^8$ nucleotides, such as from $10^2$ nucleotides to $10^7$ nucleotides, including from $10^3$ nucleotides to $10^6$ nucleotides. In embodiments, biopolymers are not single nucleotides or short chain oligonucleotides (e.g., less than 10 nucleotides). By "full length" is meant that the DNA or RNA is a nucleic acid polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the DNA or RNA (such as found in nature).

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

Polypeptides may be, in some embodiments, truncated or full length proteins, enzyme or antibodies. In embodiments, polypeptides, truncated and full-length proteins, enzymes or antibodies are comprised of 10 amino acid monomers or more, such as 15 or more, such as 25 or more, such as 50 or more, such as 100 or more, such as 250 or more and including 500 amino acid monomers or more. For example, polypeptides, truncated and full-length proteins, enzymes or antibodies of interest may range in length from 10 amino acids to $10^8$ amino acids, such as from $10^2$ amino acids to $10^7$ amino acids, including from $10^3$ amino acids to $10^6$ amino acids. In embodiments, biopolymers are not single amino acids or short chain polypeptides (e.g., less than 10 amino acids). By "full length" is meant that the protein, enzyme or antibody is a polypeptide polymer having 70% or more of its complete sequence (such as found in nature), such as 75% or more, such as 80% or more, such as 85% or more, such as 90% or more, such as 95% or more, such as 97% or more, such as 99% or more and including 100% of the full length sequence of the protein, enzyme or antibody (such as found in nature) In embodiments of the present disclosure, labels are detectable moieties or markers that are detectible based on, for example, fluorescence emission, absorbance, fluorescence polarization, fluorescence lifetime, fluorescence wavelength, absorbance maxima, absorbance wavelength, Stokes shift, light scatter, mass, molecular mass, redox, acoustic, Raman, magnetism, radio frequency, enzymatic reactions (including chemiluminescence and electro-chemiluminescence) or combinations thereof. For example, the label may be a fluorophore, a chromophore, an enzyme, an enzyme substrate, a catalyst, a redox label, a radiolabel, an acoustic label, a Raman (SERS) tag, a mass tag, an isotope tag (e.g., isotopically pure rare earth element), a magnetic particle, a microparticle, a nanoparticle, an oligonucleotide, or any combination thereof.

Systems described herein can include an input manager for receiving a labeled biomolecule reagent request. The labeled biomolecule reagent request may include one or more components. In some instances, the labeled biomolecule reagent request includes a single component and is a labeled biomolecule request (i.e., a request for a biomolecule covalently bonded to a label through a reactive linker). In some embodiments, the labeled biomolecule reagent request includes two or more components. For example, the labeled biomolecule reagent request includes a biomolecule request and a label request. In some embodiments, the biomolecule request is an activated biomolecule request that includes a biomolecule and a reactive linker and the label request is an activated label request that includes a label and a reactive linker. In some embodiments, the label request comprises an enzyme request and a substrate request.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

The phrases "labeled biomolecule request", "biomolecule request" and "label request" are used herein to refer to information or data associated with a particular labeled biomolecule, biomolecule or label, respectively. The request may include a string of one or more characters (e.g., alphanumeric characters), symbols, images or other graphical representation(s) associated with a particular labeled biomolecule, biomolecule, label, activated biomolecule, activated label or reactive linker. In some instances, the request is a "shorthand" designation of the labeled biomolecule, biomolecule, label, activated biomolecule, activated label or reactive linker. For example, the request may include an accession number or an abbreviated probe sequence. The request may also include descriptive information, such as chemical structure or reactivity. Information or data, in some embodiments, may be any suitable identifier of the labeled biomolecule, biomolecule or label and may include, but is not limited to, the name, monomer sequence, sequence identification number, ascension number or biological source of the biomolecule as well as the name, chemical structure, Chemical Abstracts Service (CAS) registry number or marker class (e.g., fluorescence, magnetic) of the label.

In some embodiments, the biomolecule is a biological probe for an analyte of interest and the biomolecule request includes information or data pertaining to a specific binding domain that binds to the analyte of interest. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In some instances, the biomolecule is a polypeptide and the biomolecule request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number.

In some embodiments, the biomolecule is a nucleic acid and the biomolecule request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence.

In some embodiments, the label request comprises an enzyme request and a substrate request. The enzyme request can include, but is not limited to, an enzyme name, a polypeptide sequence, a class of enzymes, an EC number, a polypeptide consensus sequence, a conserved domain name and/or sequence or a plurality of related proteins (e.g., proteins belonging to the same protein family), or any combination thereof. The substrate request can include, but is not limited to, a substrate name, a function group of a substrate, a class of substrates, one or more substrates for one or more enzymes with a particular EC number, or any combination thereof.

As discussed above, labels may include detectable moieties or markers that are detectible based on, for example, fluorescence emission, absorbance, fluorescence polarization, fluorescence lifetime, fluorescence wavelength, absorbance wavelength, Stokes shift, light scatter, mass, molecular mass, redox, acoustic, Raman, magnetism, radio frequency, enzymatic reactions (including chemiluminescence and electro-chemiluminescence) or combinations thereof. For example, the label may be a fluorophore, a chromophore, an enzyme, an enzyme substrate, a catalyst, a redox label, a radio label, an acoustic label, a Raman (SERS) tag, a mass tag, an isotope tag (e.g., isotopically pure rare earth element), a magnetic particle, a microparticle, a nanoparticle, an oligonucleotide, or any combination thereof. In some embodiments, the label is a fluorophore (i.e., a fluorescent label, fluorescent dye, etc.). Fluorophores of interest may include but are not limited to dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more of the aforementioned dyes (e.g., in tandem), polymeric dyes having one or more monomeric dye units and mixtures of two or more of the aforementioned dyes thereof. A large number of dyes are commercially available from a variety of sources, such as, for example, Molecular Probes (Eugene, OR), Dyomics GmbH (Jena, Germany), Sigma-Aldrich (St. Louis, MO), Sirigen, Inc. (Santa Barbara, CA) and Exciton (Dayton, OH). For example, the fluorophore may include 4-acetamido-4'-isothiocyanatostilbene-2,2'disulfonic acid; acridine and derivatives such as acridine, acridine orange, acridine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more dyes (e.g., in tandem), polymeric dyes having one or more monomeric dye units and mixtures of two or more of the aforementioned dyes or combinations thereof.

In some instances, the fluorophore (i.e., dye) is a fluorescent polymeric dye. Fluorescent polymeric dyes that find use in the subject methods and systems can vary. In some instances of the method, the polymeric dye includes a conjugated polymer.

Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. As summarized above, the structural characteristics of the polymeric dyes can have an effect on the fluorescence properties of the molecules.

Any convenient polymeric dye may be utilized in the subject methods and systems. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some embodiments, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via energy transfer.

In some instances the polymer may be used as a direct fluorescent reporter, for example fluorescent polymers having high extinction coefficients, high brightness, etc. In some instances, the polymer may be used as a strong chromophore where the color or optical density is used as an indicator.

Polymeric dyes of interest include, but are not limited to, those dyes described by Gaylord el al. in US Publication Nos. 20040142344, 20080293164, 20080064042, 20100136702, 20110256549, 20120028828, 20120252986, 20130190193 and 20160025735 the disclosures of which are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina el al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some embodiments, the hydrophilic water soluble group is charged, e.g., positively or negatively charged or zwitterionic. In some embodiments, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —(CH$_2$—CH$_2$—O—)$_n$- or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{zz}$, and R$^{zz}$ and R$^{YY}$ are independently selected from H and C1-3 alkyl.

The polymeric dye may have any convenient length. In some embodiments, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In some embodiments, the number of monomeric repeat units or segments of the polymeric dye is within the range of 2 to 1000 units or segments, such as from 2 to 750 units or segments, such as from 2 to 500 units or segments, such as from 2 to 250 units or segment, such as from 2 to 150 units or segment, such as from 2 to 100 units or segments, such as from 2 to 75 units or segments, such as from 2 to 50 units or segments and including from 2 to 25 units or segments.

The polymeric dyes may be of any convenient molecular weight (MW). In some embodiments, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In some embodiments, the polymeric dye has an average molecular weight of 70,000.

In some embodiments, the polymeric dye includes the following structure:

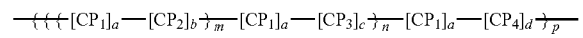

wherein CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-modifying n-conjugated repeat units.

In some embodiments, the conjugated polymer is a polyfluorene conjugated polymer, a polyphenylene vinylene conjugated polymer, a polyphenylene ether conjugated polymer, a polyphenylene polymer, among other types of conjugated polymers.

In some instances, the polymeric dye includes the following structure:

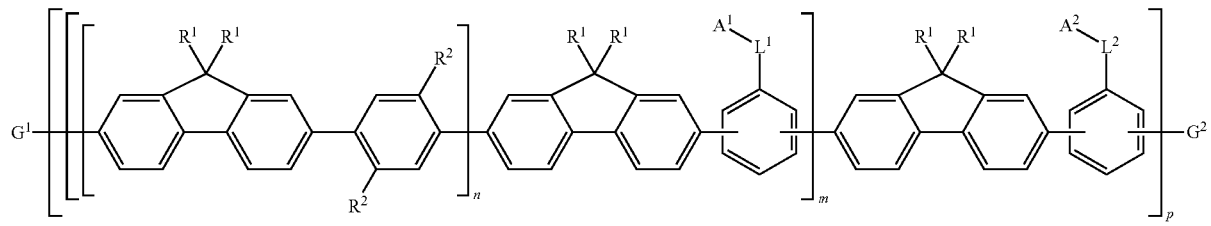

wherein each $R^1$ is independently a solubilizing group or a linker-dye; $L^1$ and $L^2$ are optional linkers; each $R^2$ is independently H or an aryl substituent; each $A^1$ and $A^2$ is independently H, an aryl substituent or a fluorophore; $G^1$ and $G^2$ are each independently selected from the group consisting of a terminal group, a πconjugated segment, a linker and a linked specific binding member; each n and each m are independently 0 or an integer from 1 to 10,000; and p is an integer from 1 to 100,000. Solubilizing groups of interest include, but is not limited to a water-soluble functional group such as a hydrophilic polymer (e.g., polyalkylene oxide, cellulose, chitosan, etc.), as well as alkyl, aryl and heterocycle groups further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group and the like.

In some embodiments, the polymeric dye includes, as part of the polymeric backbone, a conjugated segment having one of the following structures:

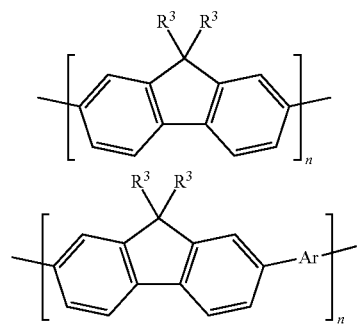

where each $R^3$ is independently an optionally substituted wat-soluble functional group such as a hydrophilic polymer (e.g., polyalkylene oxide, cellulose, chitosan, etc.) or an alkyl or aryl group further substituted with a hydrophilic group such as a polyalkylene oxide (e.g., polyethylglycol including a PEG of 2-20 units), an ammonium, a sulphonium, a phosphonium, as well has a charged (positively, negatively or zwitterionic) hydrophilic water soluble group; Ar is an optionally substituted aryl or heteroaryl group; and n is 1 to 10000. In some embodiments, R3 is an optionally substituted alkyl group. In some embodiments, $R^3$ is an optionally substituted aryl group. In some embodiments, $R^3$ is substituted with a polyethyleneglycol, a dye, a chemoselective functional group or a specific binding moiety. In some embodiments, Ar is substituted with a polyethyleneglycol, a dye, a chemoselective functional group or a specific binding moiety.

In some embodiments, the polymeric dye includes the following structure:

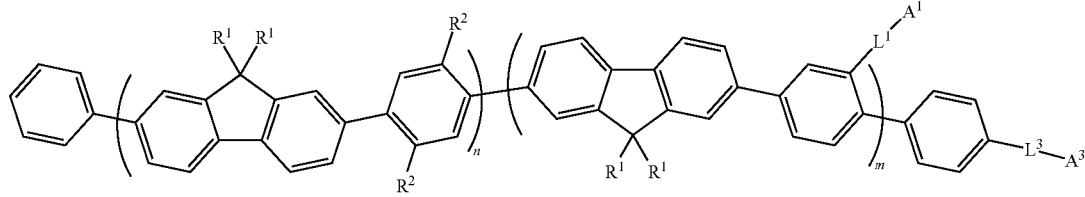

wherein each $R^1$ is a solubilizing group or a linker dye group; each $R^2$ is independently H or an aryl substituent; $L_1$ and $L_2$ are optional linkers; each A1 and A3 are independently H, a fluorophore, a functional group or a specific binding moiety (e.g., an antibody); and n and m are each independently 0 to 10000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." Cytometry Part A, 81A (6), 456-466, 2012).

In some embodiments, the polymeric dye has an absorption curve between 280 and 850 nm. In some embodiments, the polymeric dye has an absorption maximum in the range 280 and 850 nm. In some embodiments, the polymeric dye absorbs incident light having a wavelength in the range between 280 and 850 nm, where specific examples of absorption maxima of interest include, but are not limited to: 348 nm, 355 nm, 405 nm, 407 nm, 445 nm, 488 nm, 640 nm and 652 nm. In some embodiments, the polymeric dye has an absorption maximum wavelength in a range selected from the group consisting of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In some embodiments, the polymeric dye has an absorption maximum wavelength of 348 nm. In some embodiments, the polymeric dye has an absorption maximum wavelength of 355 nm. In some embodiments, the polymeric dye has an absorption maximum wavelength of 405 nm. In some embodiments, the polymeric dye has an absorption maximum wavelength of 407 nm. In some embodiments, the polymeric dye has an absorption maximum wavelength of 445 nm. In some embodiments, the polymeric dye has an absorption maximum wavelength of 488 nm. In some embodiments, the polymeric dye has an absorption maximum wavelength of 640 nm. In some embodiments, the polymeric dye has an absorption maximum wavelength of 652 nm.

In some embodiments, the polymeric dye has an emission maximum wavelength ranging from 400 to 850 nm, such as 415 to 800 nm, where specific examples of emission maxima of interest include, but are not limited to: 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm. In some embodiments, the polymeric dye has an emission maximum wavelength in a range selected from the group consisting of 380-400 nm, 410-430 nm, 470-490 nm, 490-510 nm, 500-520 nm, 560-580 nm, 570-595 nm, 590-610 nm, 610-650 nm, 640-660 nm, 650-700 nm, 700-720 nm, 710-750 nm, 740-780 nm and 775-795 nm. In some embodiments, the polymeric dye has an emission maximum of 395 nm. In some embodiments, the polymeric dye has an emission maximum wavelength of 421 nm. In some embodiments, the polymeric dye has an emission maximum wavelength of 478 nm. In some embodiments, the polymeric dye has an emission maximum wavelength of 480 nm. In some embodiments, the polymeric dye has an emission maximum wavelength of 485 nm. In some embodiments, the polymeric dye has an emission maximum wavelength of 496 nm. In some embodiments, the polymeric dye has an emission maximum wavelength of 510 nm. In some embodiments, the polymeric dye has an emission maximum wavelength of 570 nm. In some embodiments, the polymeric dye has an emission maximum wavelength of 602 nm. In some embodiments, the polymeric dye has an emission maximum wavelength of 650 nm. In some embodiments, the polymeric dye has an emission maximum wavelength of 711 nm. In some embodiments, the polymeric dye has an emission maximum wavelength of 737 nm. In some embodiments, the polymeric dye has an emission maximum wavelength of 750 nm. In some embodiments, the polymeric dye has an emission maximum wavelength of 786 nm. In some embodiments, the polymeric dye has an emission maximum wavelength of 421 nm±5 nm. In some embodiments, the polymeric dye has an emission maximum wavelength of 510 nm±5 nm. In some embodiments, the polymeric dye has an emission maximum wavelength of 570 nm±5 nm. In some embodiments, the polymeric dye has an emission maximum wavelength of 602 nm±5 nm. In some embodiments, the polymeric dye has an emission maximum wavelength of 650 nm±5 nm. In some embodiments, the polymeric dye has an emission maximum wavelength of 711 nm±5 nm. In some embodiments, the polymeric dye has an emission maximum wavelength of 786 nm±5 nm. In some embodiments, the polymeric dye has an emission maximum selected from the group consisting of 421 nm, 510 nm, 570 nm, 602 nm, 650 nm, 71 nm and 786 nm.

In some embodiments, the polymeric dye has an extinction coefficient of $1 \times 10^6$ cm-1M-1 or more, such as $2 \times 10^6$ $cm^{-1}M^{-1}$ or more, $2.5 \times 10^6$ $cm^{-1}M^{-1}$ or more, $3 \times 10^6$ $cm^{-1}M^{-1}$ or more, $4 \times 10^6$ $cm^{-1}M^{-1}$ or more, $5 \times 10^6$ $cm^{-1}M^{-1}$ or more, $6 \times 10^6$ $cm^{-1}M^{-1}$ or more, $7 \times 10^6$ $cm^{-1}M^{-1}$ or more, or $8 \times 10^6$ $cm^{-1}M^{-1}$ or more. In some embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, 0.6 or more, 0.7 or more, 0.8 or more, 0.9 or more, 0.95 or more, 0.99 or more and including 0.999 or more. For example, the quantum yield of polymeric dyes of interest may range from 0.05 to 1, such as from 0.1 to 0.95, such as from 0.15 to 0.9, such as from 0.2 to 0.85, such as from 0.25 to 0.75, such as from 0.3 to 0.7 and including a quantum yield of from 0.4 to 0.6. In some embodiments, the polymeric dye has a quantum yield of 0.1 or more. In some embodiments, the polymeric dye has a quantum yield of 0.3 or more. In some embodiments, the polymeric dye has a quantum yield of 0.5 or more. In some embodiments, the polymeric dye has a quantum yield of 0.6 or more. In some embodiments, the polymeric dye has a quantum yield of 0.7 or more. In some embodiments, the polymeric dye has a quantum yield of 0.8 or more. In some embodiments, the polymeric dye has a quantum yield of 0.9 or more. In some embodiments, the polymeric dye has a quantum yield of 0.95 or more. In some embodiments, the polymeric dye has an extinction coefficient of $1 \times 10^6$ or more and a quantum yield of 0.3 or more. In some embodiments, the polymeric dye has an extinction coefficient of $2 \times 106$ or more and a quantum yield of 0.5 or more.

In some embodiments, the label comprises an enzyme, an enzyme substrate, or a combination thereof. The enzyme can be capable of modifying the enzyme substrate into a corresponding modified enzyme substrate. In some embodiments, the enzymes can be, or can include, Enzyme Commission (EC) 1 oxidoreductases (e.g., a dehydrogenase or an oxidase); EC 2 transferases (e.g., a transaminase or a kinase); EC 3 Hydrolases (e.g., a lipase, an amylase, or a peptidase); EC 4 Lyases (e.g., a decarboxylase); EC 5 Isomerases (e.g., an isomerase or a mutase); or EC 6 Ligases (e.g., a synthetase).

In some embodiments, the enzymes can be, or can include, EC 1.1 oxidoreductases acting on the CH—OH group of donors; EC 1.2 oxidoreductases acting on the aldehyde or oxo group of donors; EC 1.3 oxidoreductases acting on the CH—CH group of donors; EC 1.4 oxidoreductases acting on the CH—NH(2) group of donors; EC 1.5 oxidoreductases acting on the CH—NH group of donors; EC 1.6 oxidoreductases acting on NADH or NADPH; EC 1.7 oxidoreductases acting on other nitrogenous compounds as donors; EC 1.8 oxidoreductases acting on a sulfur group of donors; EC 1.9 oxidoreductases acting on a heme group of donors; EC 1.10 oxidoreductases acting on diphenols and related substances as donors; EC 1.16 oxidoreductases oxidizing metal ions; EC 1.17 oxidoreductases acting on CH or CH(2) groups; EC 1.18 oxidoreductases acting on iron-sulfur proteins as donors; EC 1.19 oxidoreductases acting on reduced flavodoxin as donor; EC 1.20 oxidoreductases acting on phosphorus or arsenic in donors; EC 1.21 oxidoreductases catalyzing the reaction X—H+Y—H='X—Y'; EC 1.22 oxidoreductases acting on halogen in donors; EC 1.23 oxidoreductases reducing C—O—C group as acceptor, or EC 1.97 other oxidoreductases.

In some embodiments, the enzymes can be, or can include, EC 2.1 transferases transferring one-carbon groups with substrates: DNA, RNA, catechol; EC 2.2 transferases transferring aldehyde or ketonic groups; EC 2.3 acyltransferases; EC 2.4 glycosyltransferases; EC 2.5 transferases transferring alkyl or aryl groups, other than methyl groups; EC 2.6 transferases transferring nitrogenous groups; EC 2.7 transferases transferring phosphorus-containing groups; EC 2.8 transferases transferring sulfur-containing groups; EC 2.9 transferases transferring selenium-containing groups; or EC 2.10 transferases transferring molybdenum- or tungsten-containing groups.

In some embodiments, the enzymes can be, or can include, EC 3.1 hydrolases acting on ester bonds; EC 3.2 glycosylases; EC 3.3 hydrolases acting on ether bonds; EC 3.4 hydrolases acting on peptide bonds (peptidases); EC 3.5 hydrolases acting on carbon-nitrogen bonds, other than peptide bonds; EC 3.6 hydrolases acting on acid anhydrides; EC 3.7 hydrolases acting on carbon-carbon bonds; EC 3.8 hydrolases acting on halide bonds; EC 3.9 hydrolases acting on phosphorus-nitrogen bonds; EC 3.10 hydrolases acting on sulfur-nitrogen bonds; EC 3.11 hydrolases acting on carbon-phosphorus bonds; EC 3.12 hydrolases acting on sulfur-sulfur bonds; or EC 3.13 hydrolases acting on carbon-sulfur bonds.

In some embodiments, the enzymes can be, or can include, glycosyl hydrolases (enzymes that are useful for breaking down plant biomass for the production of biofuels), aminotransferases (proteins that are involved in binding and transport of small organic molecules or proteins that are important for biomanufacturing), solute binding proteins of ATP-binding cassette (ABC) transporter proteins (proteins involved in the metabolism of soil microbes with a potential impact in bioremediation), or any combination thereof.

In some embodiments, the enzymes can be, or can include, EC 4.1 carbon-carbon lyases; EC 4.2 carbon-oxygen lyases; EC 4.3 carbon-nitrogen lyases; EC 4.4 carbon-sulfur lyases; EC 4.5 carbon-halide lyases; EC 4.6 phosphorus-oxygen lyases; EC 4.7 carbon-phosphorus lyases; or EC 4.99 other lyases.

In some embodiments, the enzymes can be, or can include, EC 6.1 ligases forming carbon-oxygen bonds; EC 6.2 ligases forming carbon-sulfur bonds; EC 6.3 ligases forming carbon-nitrogen bonds; EC 6.4 ligases forming carbon-carbon bonds; EC 6.5 ligases forming phosphoric ester bonds; or EC 6.6 ligases forming nitrogen-metal bonds.

In some embodiments, the enzyme substrate can differ from the corresponding modified enzyme substrate by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate, or any combination thereof.

In some embodiments, the enzyme can comprise a methyltransferase, a glycoside hydrolase, a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, a xylosidase, or a combination thereof.

In some embodiment, the enzyme substrate can comprise 6-mercaptopurine, cellobiose, cellotetraose, xylotetraose, isoprimeverose, β-D-gentiobiose, xyloglucan and mannotriose, agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof. The label request can comprise an enzyme request and a substrate request.

The labeled biomolecule reagent is prepared by coupling an activated biomolecule to an activated label. The term "activated" is used herein to refer to a biomolecule or label having a reactive linker or a reactive moiety that, when carried out under appropriate conditions, reacts with a second reactive linker or second reactive moiety to form a chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated label to produce an ionic bond. In other embodiments, the reactive linker or moiety of the activated biomolecule reacts with the reactive linker or moiety of the activated label to produce a non-covalent bond. In yet other embodiments, the reactive linker or moiety of the activated biomolecule reacts with the reactive linker or moiety of the activated label to produce a covalent bond.

In some embodiments, the reactive linker or moiety of the activated biomolecule reacts with the reactive linker or moiety of the activated label to produce a covalent bond. Any convenient protocol for forming a covalent bond between the reactive linker of the activated biomolecule and the reactive linker of the activated label may be employed, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the activated biomolecule may be conjugated to the activated label through reactive linking chemistry such as where reactive linker pairs include, but is not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide·TFA)/thiol; azide/triarylphosphine; nitrone/cyclooctyne; azide/tetrazine and formylbenzamide/hydrazino-nicotinamide. In some embodiments, the reactive linker of the activated biomolecule and the reactive linker of the activated label undergo a cycloaddition reaction, such as a [1+2]-cycloaddition, a [2+2]-cycloaddition, a [3+2]-cycloaddition, a [2+4]-cycloaddition, a [4+6]-cycloaddition, or cheleotropic reactions, including linkers that undergo a 1,3-dipolar cycloaddition (e.g., azide-alkyne Huisgen cycloaddition), a Diels-Alder reaction, an inverse electron demand Diels Alder cycloaddition, an ene reaction or a [2+2] photochemical cycloaddition reaction.

In some embodiments, the biomolecule request and the label request include information or data pertaining to the reactive linker of the activated biomolecule and the activated label. For example, the biomolecule request and the label request may include information or data pertaining to the name of the reactive linker, a chemical structure, a structural description of the reactive linker or the reactive linker CAS number. In some embodiments, the biomolecule request and the label request includes the name of reactive linker pairs, such as where the reactive linker pairs is may be selected from maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/BMPH (N-[β-Maleimidopropionic acid]hydrazide·TFA)/thiol; azide/triarylphosphine; nitrone/cyclooctyne; azide/tetrazine and formylbenzamide/hydrazino-nicotinamide; a diene/a dienophile; and a 1,3-dipole/a dipolarophile.

In some embodiments, the label request comprises an enzyme request and a substrate request. The enzyme request can include, but is not limited to, an enzyme name, a polypeptide sequence, a class of enzymes, an EC number, a polypeptide consensus sequence, a conserved domain name and/or sequence or a plurality of related proteins (e.g., proteins belonging to the same protein family), or any combination thereof. The substrate request can include, but is not limited to, a substrate name, a function group of a substrate, a class of substrates, one or more substrates for one or more enzymes with a particular EC number, or any combination thereof.

The input manager is configured to receive the request for the labeled biomolecule. To receive the labeled biomolecule reagent request, the input manager is operatively coupled to a graphical user interface where one or more labeled biomolecule reagents requests are entered. In some embodiments, the labeled biomolecule reagent request is entered on an internet website menu interface (e.g., at a remote location) and communicated to the input manager, over the internet or a local area network. In some embodiments, the input manager is configured receive a plurality of labeled biomolecule reagent requests. For example, the input manager may be configured to receive 2 or more labeled biomolecule reagent requests, such as 5 or more, such as 10 or more and including 25 or more labeled biomolecule reagent requests.

Where the request for a labeled biomolecule reagent includes only a single component and is a labeled biomolecule request, the input manager may be configured to receive 2 or more labeled biomolecule requests, such as 5 or more, such as 10 or more and including 25 or more labeled biomolecule requests. Where the labeled biomolecule reagent request includes two components, such as a biomolecule request and a label request, the input manager may be configured to receive 2 or more biomolecule requests, such as 5 or more, such as 10 or more and including 25 or more biomolecule requests and configured to receive 2 or more label requests, such as 5 or more, such as 10 or more and including 25 or more label requests. In some embodiments, the input manager is configured to receive a labeled biomolecule reagent request that includes a single biomolecule request and single label request. In some embodiments, the input manager is configured to receive a labeled biomolecule reagent request that includes a single biomolecule request and a plurality of different label requests. In yet some embodiments, the input manager is configured to receive a labeled biomolecule reagent request that includes a plurality of different biomolecule requests and a single label request. In still some embodiments, the input manager is configured to receive a labeled biomolecule reagent request that includes a plurality of different biomolecule requests and a plurality of different label requests. The input manager is configured to receive labeled biomolecule requests from a single user or a plurality of different users, such as 2 or more different users, such as 5 or more different users, such as 10 or more different users, such as 25 or more different users and including 100 or more different users. In some embodiments, the label request comprises an enzyme request and a substrate request.

In embodiments, the input manager is also configured to receive a quantity request corresponding to the desired amount of requested labeled biomolecule reagent. The quantity request may be entered by typing a numerical and a unit (e.g., μg, μmoles, μM, etc.) value into a text box, selecting a check box corresponding to the appropriate numerical and unit values or selecting a numerical value from a first drop-down menu and a unit value from a second drop-down menu.

In some embodiments, the input manager is operatively coupled to one or more searchable databases (e.g., catalog) of labeled biomolecules, activated biomolecules, biomolecules, activated labels, labels and reactive linkers. In some embodiments, the input manager includes a database of labeled biomolecules. In some embodiments, the input manager includes a database of activated biomolecules and activated labels. In yet some embodiments, the input manager includes a database of biomolecules, labels and reactive linkers.

All or part of each database of labeled biomolecules, activated biomolecules, biomolecules, activated labels, labels and reactive linkers may be displayed on the graphical user interface, such as in a list, drop-down menu or other configuration (e.g., tiles). For example, the graphical user interface may display a list of each labeled biomolecule, activated biomolecule, biomolecule, activated label, label and reactive linkers simultaneously (i.e., on a single screen) or may contain drop-down menus for each component of the labeled biomolecule reagent request. In other embodiments, the labeled biomolecule reagent request is provided by inputting information into appropriate text fields, selecting check boxes, selecting one or more items from a drop-down menu, or by using a combination thereof.

In one example, the graphical user interface includes a drop-down menu to input a labeled biomolecule reagent request by selecting one or more labeled biomolecules from the drop-down menu. In another example, the graphical user interface includes a first drop-down menu to input a biomolecule request and a second drop-down menu to input a label request by selecting one or more biomolecules and one or more labels from the first and second drop-down menus. In yet another example, the graphical user interface includes a first drop-down menu to input a biomolecule request, a second drop-down menu to input a label request and a third drop-down menu to input a reactive linker request by selecting one or more biomolecules, one or more labels and one or more reactive linkers from the drop-down menus.

In still another example, the graphical user interface includes a first drop down menu to input an activated biomolecule request and a second drop-down menu to input an activated label request by selecting one or more activated biomolecules and one or more activated linkers from the first and second drop-down menus. In some embodiments, the label request comprises an enzyme request and a substrate request. The graphical user interface can include a first drop down menu to input an activated biomolecule request, a second drop-down menu to input an activated enzyme request, and a third drop-down menu to input an enzyme substrate. The graphical user interface can include a first drop down menu to input an activated biomolecule request, a second drop-down menu to input an activated substrate, and a third drop-down menu to input an enzyme.

In another example, the graphical user interface includes a list of labeled biomolecules, activated biomolecules, biomolecules, activated labels, labels and reactive linkers that are available in the database. For example, the graphical user interface may display a list of each labeled biomolecule, activated biomolecule, biomolecule, activated label, label and reactive linkers simultaneously on one or more screens or may contain drop-down menus for each component of the labeled biomolecule reagent request. In some embodiments, a list of all available labeled biomolecules, activated biomolecules, biomolecules, activated labels, labels and reactive linkers displayed on a single page. In some embodiments, the list of all available labeled biomolecules, activated biomolecules, biomolecules, activated labels, labels and reactive linkers displayed on a plurality of pages, such as 2 or more pages, such as 3 or more pages, such as 5 or more pages, such as 10 or more pages and including 25 or more pages. In yet some embodiments, the list of all available labeled biomolecules, activated biomolecules, biomolecules, activated labels, labels and reactive linkers are each displayed in separate drop-down menus on a single page.

FIG. 15 depicts a graphical user interface for communicating a request for a labeled biomolecule reagent according to some embodiments. To communicate the labeled biomolecule reagent request, a user inputs a biomolecule request and a label request onto Request form 1500. The label request is inputted by selecting a detectable marker (e.g., a fluorophore) from drop down menu 1501a and the biomolecule request is inputted by selecting a biomolecule (e.g., an antibody probe) from drop-down menu 1501b. Request form 1500 also includes a text box for entering the quantity request 1502 corresponding to the desired amount of labeled biomolecule reagent in micrograms. In some embodiments, the label request comprises an enzyme request and a substrate request.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

In some embodiments, the input manager includes a search engine for searching for, adding or modifying labeled biomolecule reagent requests and for responding to user queries (e.g., inputted into the graphical user interface locally or from a remote location over the internet or local area network). In some embodiments, each persistent object in the system memory has an associated table in a system database and object attributes are mapped to table columns. In a further aspect, each object has an object relational mapping file which binds that object to the table in the database.

Objects are also associated with each other and this association is mapped as the relation between the tables. Objects are also associated with each other by many different relationships, such as one-to-one, one-to-many, many-to-one and many-to-many. Search criteria provided in user queries may include descriptions of attributes or properties associated with an object or by values corresponding to those attributes.

Relationships may also be used as search criteria. Basic search criteria can depend upon an object's attributes and advanced search criteria can depend upon association of the object with other objects, e.g., by searching properties of related objects. In some embodiments, search engines of interest include a finder framework, which will construct a plurality of searchable conditions (e.g., all possible queryable conditions). When a user specifies an entity or object to search for, the framework generates all possible search conditions for that object and then gives the result as per the conditions selected by the user.

Using the search engine, a user of the system can search for available labeled biomolecules, biomolecules, activated biomolecules, labels, activated labels and reactive linkers. The search engine is also configured for searching for pending or completed labeled biomolecule reagent requests. In addition, a user can use the search engine to inquire and find labeled biomolecules, biomolecules, activated biomolecules, labels, activated labels and reactive linkers that may be of interest. For example, a user can search for a particular biomolecule that functions as a specific antigen probe or a label that is detectable by fluorescence of a predetermined wavelength of light. Search conditions may be different for different objects and in one instance, a generic finder framework gives a generic solution for such searching.

In some embodiments, the search engine can build queries, save queries, modify queries, and/or update queries used to identify labeled biomolecules, biomolecules, activated biomolecules, labels, activated labels or reactive linkers. In some embodiments, the search results can be shared, compared or modified. In some embodiments, systems are configured to set a maximum of search results that fit a search criteria to be displayed on the graphical user interface. In some embodiments, search results are displayed on a Webpage which includes capabilities for allowing possible actions. Such capabilities can include, but are not limited to, links, buttons, drop down menus, fields for receiving information from a user, and the like. In certain aspects, the system further includes a result formatter for formatting search results (e.g., to build appropriate user interfaces such as Web pages, to specify links, provide a way to associate actions (e.g., "delete," "edit," etc.) with images, text, hyperlinks and/or other displays.

The system may also display the search criteria for an object under search on the web page. In one aspect, the system takes input data from the finder framework and creates a web page dynamically showing the search criteria for that object. In another aspect, the finder framework creates all possible queryable conditions for the object under search. These conditions are displayed on search web page as different fields. A user can select or specify value(s) for these field(s) and execute a search. The fields that are to be displayed have their labels in localized form. Fields may be in the form of a "select" box, or a text box or other area for inputting text. For example, a user may desire to search for a biomolecule. Biomolecules in the searchable database include queryable conditions such as compound name or sequence number (e.g., accession number).

In one embodiment, the search engine supports searching for each of the labeled biomolecules, biomolecules, activated biomolecules, labels, activated labels and reactive linkers in the database. In some embodiments, the system provides a generic finder framework to create all queryable conditions for an object under search. Such conditions will generally depend upon the properties of the object and its relationship(s) with other objects. In other embodiments, the finder framework retrieves localized field names for these conditions and their order and stores these in the system memory (e.g., in an objectdefinition.xml file). In one example, fields are displayed on a search page in the order in which they are stored in a file as a set of search parameters for which a user can select or enter values. The search parameters may be in the form of a list of objects and the parameters may relate to attribute categories. For example, in response to a user searching for a labeled biomolecule, the system may display the queryable conditions: "name of labeled biomolecule," "keywords used for search," "created by," "modified by," "modification date," "annotation" and the like. The finder framework can return the queryable conditions in the form of a collection, which can be displayed on a search page, which lists or represents the various search fields corresponding to the attribute categories in a localized form. A user may enter values for these fields and perform, e.g., selecting one or more of a labeled biomolecule, biomolecule, activated biomolecule, label, activated label and reactive linker having a specific name, structure, registry number, etc., providing specific keywords, identifying a desired domain, creator, modification date, annotation, and the like. The system then displays a list of labeled biomolecules, biomolecules, activated biomolecules, labels, activated labels or reactive linkers that satisfy the search conditions. In some embodiments, the system displays information regarding the criteria used to perform the search.

In some embodiments, the input manager includes a labeled biomolecule design platform which is configured to provide a recommendation for choosing one or more biomolecules, activated biomolecules, labels, activated labels or reactive linkers. In some embodiments, the design platform is configured to provide a recommendation for choosing one or more biomolecules, activated biomolecules, labels, activated labels or reactive linkers based on user input of one or more parameters of the desired labeled biomolecule. For example, parameters of the desired labeled biomolecule which may be inputted by the user into the design platform may include, but are not limited to, desired physical properties of the labeled biomolecule (e.g., molecular mass, melting point, purity, etc.); desired chemical properties of the labeled biomolecule (e.g., chemical structure, structural similarity to a second labeled biomolecule, ionizability, solvation, hydrolysis, chemical reactivity, enzymatic reactivity, binding affinity, etc.); spectroscopic properties (e.g., absorbance wavelength range, absorbance maxima, emission wavelength range, emission maxima, Stokes shift, quantum yield, molar extinction coefficient, etc.) In some embodiments, the design platform is configured to provide a recommendation for choosing one or more biomolecules, activated biomolecules, labels, activated labels or reactive linkers based on the application of the labeled biomolecule. For example, the design platform may be configured to provide a recommendation for choosing each component of the labeled biomolecule based on instruments that will be used (e.g., flow cytometer, fluorescence spectrometer, etc.), instrument configuration, as well as experimental parameters (e.g., target abundance such as antigen density on a cell). The graphical user interface may include one or more text input fields or drop-down menus for inputting data used by the design platform to provide a recommendation for choosing one or more biomolecules, activated biomolecules, labels, activated labels or reactive linkers.

The labeled biomolecule design platform may be configured to provide a recommendation for a plurality of different biomolecules, activated biomolecules, labels, activated labels or reactive linkers based on information (e.g., properties of the labeled biomolecule or expected application of the labeled biomolecule) inputted by the user.

For example, the design platform may be configured to recommend 2 or more different biomolecules, activated biomolecules, labels, activated labels or reactive linkers based on information inputted by the user, such as 3 or more, such as 4 or more, such as 5 or more, such as 10 or more and including 25 or more biomolecules, activated biomolecules, labels, activated labels or reactive linkers.

In some embodiments, the labeled biomolecule design platform is configured to provide a recommendation as to the combination of biomolecule, label, activated label or reactive linker that is best suited for a particular application (e.g., configuration of a flow cytometer). For example, the design platform may be configured such that a user enters a list of one or more biomolecules and one or more labels as well as application information (e.g., instrument configuration, target abundance, etc.) and the design platform outputs combinations a recommendation of biomolecules, labels, activated labels and reactive linkers best suited for the stated application. In some embodiments, the recommendation for a labeled biomolecule, biomolecule, activated biomolecule, label, activated label or reactive linker is displayed on a display (e.g., an electronic display) or may be printed with a printer, such as onto a human (paper) readable medium or in a machine readable format (e.g., as a barcode). In other embodiments, the recommendation for a labeled biomolecule, biomolecule, activated biomolecule, label, activated label or reactive linker may be communicated to the input manager and the recommended labeled biomolecule may be prepared as described above.

Systems of the present disclosure also include a memory for storing a dataset having a plurality of storage identifiers that correspond with the components the of the label biomolecule reagent request. The term "memory" is used herein in its conventional sense to refer to a device that stores information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices). The memory may be a computer readable medium or permanent memory. In embodiments, the memory may include one or more datasets having a plurality of storage identifiers that correspond to each labeled biomolecule, biomolecule, label, activated biomolecule, activated label and reactive linker in the system database.

The datasets stored in the memory include storage identifiers that correspond with each labeled biomolecule, biomolecule, label, activated biomolecule, activated label or reactive linker. The storage identifiers may be presented in the dataset as a string of one or more characters (e.g., alphanumeric characters), symbols, images or other graphical representation(s) associated with a particular labeled biomolecule, biomolecule, label, activated biomolecule, activated label or linker. In some embodiments, the storage identifier is abbreviated designation of the labeled biomolecule, biomolecule, label, activated biomolecule, activated label or linker. For example, the storage identifier may include references to accession number, sequence identification number, identifiable probe sequence, CAS registry number or may be a custom identification code.

The number of storage identifiers in each dataset stored in memory may vary, depending on the type of storage identifiers. For example, the dataset stored in memory having a plurality of labeled biomolecule storage identifiers may include 10 or more labeled biomolecule storage identifiers, such as 25 or more, such as 50 or more, such as 100 or more identifiers, such 250 or more, such as 500 or more and including 1000 or more labeled biomolecule storage identifiers. The dataset stored in memory having a plurality of biomolecules or activated biomolecules may include 25 or more biomolecule or activated biomolecule storage identifiers, such as 50 or more, such as 100 or more, such as 250 or more, such as 500 or more and including 1000 or more biomolecule or activated biomolecule storage identifiers. The dataset stored in memory having a plurality of labels or activated labels may include 5 or more label or activated label storage identifiers, such as 10 or more, such as 15 or more, such as 25 or more and including 50 or more label or activated label storage identifiers. In some embodiments, the dataset stored in memory having a plurality of reactive linkers includes 2 or more reactive linker storage identifiers, such as 3 or more, such as 5 or more, such as 10 or more and including 15 or more reactive linker storage identifiers.

The memory is in operative communication with a processing module that identifies one or more storage identifiers from the dataset that corresponds to the request received by the input manager. In some embodiments, the request for a labeled biomolecule reagent is a labeled biomolecule request and the processing module identifies a labeled biomolecule storage identifier from a dataset in the memory having a plurality of labeled biomolecules storage identifiers. In other embodiments, the request for a labeled biomolecule reagent includes a biomolecule request and a label request and the processing module identifies: 1) a biomolecule storage identifier from a first dataset in the memory having a plurality of biomolecule storage identifiers; and 2) a label storage identifier from a second dataset in the memory having a plurality of label storage identifiers. In still other embodiments, the request for a labeled biomolecule reagent includes a biomolecule request, a label request and a reactive linker request and the processing module identifies: 1) a biomolecule storage identifier from a first dataset in the memory having a plurality of biomolecule storage identifiers; 2) a label storage identifier from a second dataset in the memory having a plurality of label storage identifiers; and 3) a reactive linker storage identifier from a third dataset in the memory having a plurality of reactive linker storage identifiers. In some embodiments, the label request comprises an enzyme request and a substrate request.

When a particular storage identifier that corresponds to a labeled biomolecule request, biomolecule request, label request, activated biomolecule request, activated label request or reactive linker request are not available (i.e., cannot be identified by the processing module from any dataset in the memory), the memory may include algorithm for providing a recommendation for an alternative labeled biomolecule, biomolecule, label, activated biomolecule, activated label or reactive linker. The recommendation may be based on similarities in chemical structure, reactivity, probe target, binding affinity, target abundance, target density, label cross-talk, size, price, etc. as the requested labeled biomolecule, biomolecule, label, activated biomolecule, activated label or reactive linker. The memory may be configured to provide a recommendation for one or more alternatives, such as 2 or more alternatives, such as 3 or more alternatives and including 5 or more alternatives, depending on the similarity between the requested component and available labeled biomolecule, biomolecule, label, activated biomolecule, activated label or reactive linkers.

The processing module may include a commercially available processor such as a processor made by Intel Corporation, a SPARC® processor made by Sun Microsystems, or it may be one of other processors that are or will become available.

The processor executes the operating system, which may be, for example, a WINDOWS®-type operating system from the Microsoft Corporation; a Unix® or Linux-type operating system or a future operating system; or some combination thereof. The operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Processing modules of the subject systems include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any type of known computer platform or a type to be developed in the future, although they typically will be of a class of computer commonly referred to as servers.

However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include WINDOWS NUCLEOTIDES®, Sun Solaris, Linux, OS/400, Compaq Tru64 Unix, SGI IRIX, Siemens Reliant Unix, and others. Other development products, such as the Java™2 platform from Sun Microsystems, Inc. may be employed in processors of the subject systems to provide suites of applications programming interfaces (API's) that, among other things, enhance the implementation of scalable and secure components. Various other software development approaches or architectures may be used to implement the functional elements of system and their interconnection, as will be appreciated by those of ordinary skill in the art.

Systems of the present disclosure also include an output manager that provides the identified storage identifiers from the processing module. In some embodiments, the output manager includes an electronic display and the identified storage identifiers are outputted onto the electronic display. One or more storage identifiers may be outputted onto the electronic display simultaneously, such as 2 or more, such as 3 or more, such as 5 or more, such as 10 or more, such as 25 or more, such as 100 or more and including 500 or more storage identifiers. The output manager may display the storage identifiers of the labeled biomolecule reagent requests from a single user or from a plurality of users, such as from 2 or more users, such as 5 or more users, such as 10 or more users, such as 25 or more users and including 100 or more users. The output manager may be configured to organize the displayed storage identifiers, as desired, such as grouping the storage identifiers according to each request for a labeled biomolecule, by user or by type of storage identifier (e.g., labeled biomolecule storage identifier, biomolecule storage identifier, label storage identifier, reactive linker storage identifier). In other embodiments, the output manager includes a printer and the identified storage identifiers are printed onto a human (paper) readable medium or as in a machine readable format (e.g., as a barcode).

In some embodiments, the output manager communicates the storage identifiers assembled by the processing module, e.g., one or more labeled biomolecule storage identifiers, biomolecule storage identifiers, label storage identifiers, reactive linker storage identifiers in an electronic format to a user, such as over a local area network or over the Internet. The electronic communication of data by the output manager may be implemented according to a convenient protocol, including but not limited to, SQL, HTML or XML documents, email or other files, or data in other forms.

The data may also include Internet URL addresses so that a user may retrieve additional SQL, HTML, XML, or other documents or data from remote sources.

Systems of the present disclosure for inputting a labeled biomolecule reagent request, storing a plurality of storage identifiers that correspond with the components the of the label biomolecule reagent request, identifying one or more storage identifiers and for outputting the identified storage identifiers include a computer. In some embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means.

The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in some embodiments, include a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent.

Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In some embodiments, the programming can contain a program, where the program can be composed of various modules, and a user interface module that permits a user to manually select or change the inputs to or the parameters used by the program. The data files can include various inputs for the program.

In some embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

In any embodiment, data can be forwarded to a "remote location," where "remote location," means a location other than the location at which the program is executed.

For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In some embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

Figure 16:
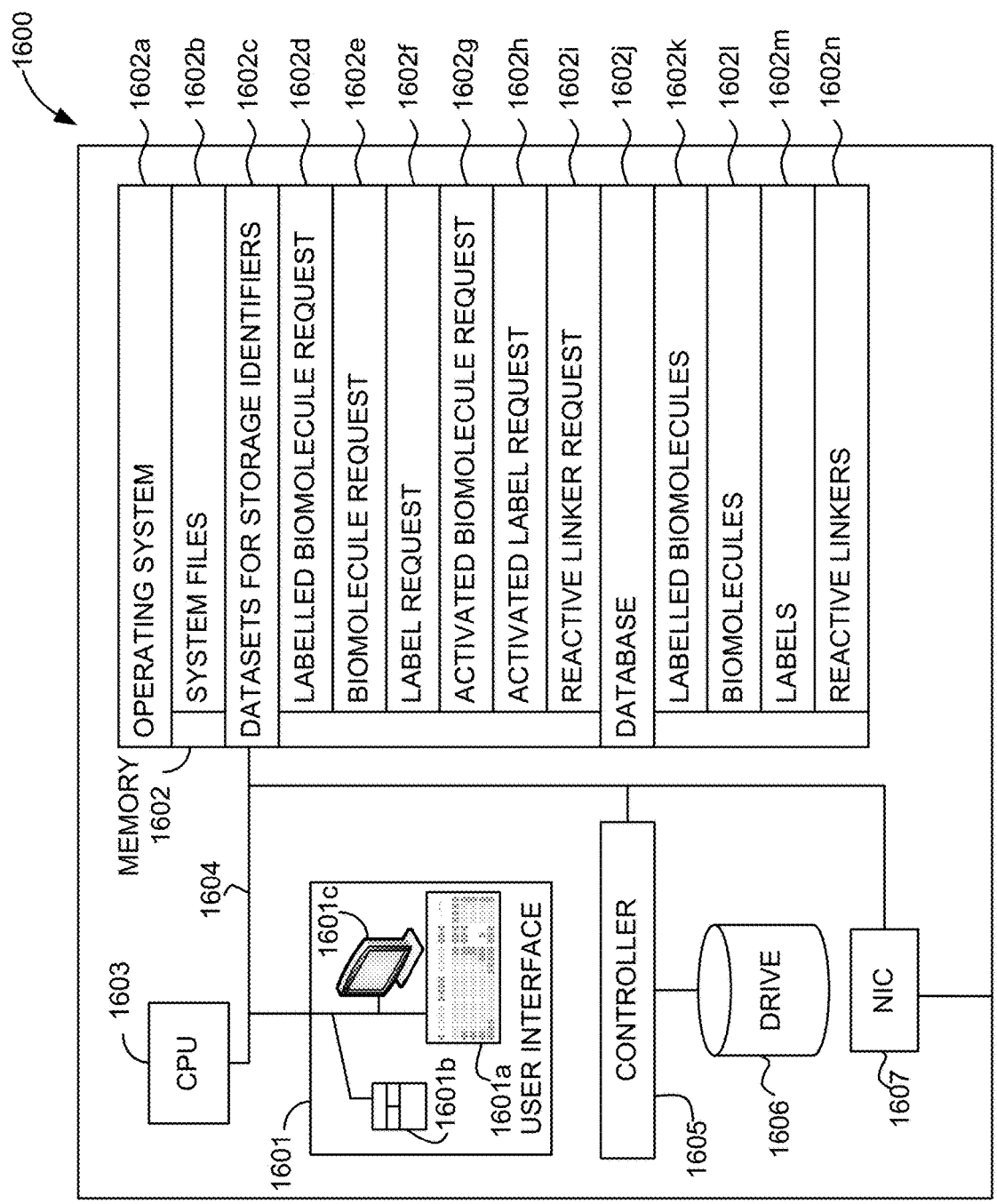
FIG. 16 depicts a computer system of the present disclosure according to some embodiments of the invention.

FIG. 16 depicts a computer system 1600 of the present disclosure according to some embodiments. The computer system includes user interface 1601 that includes a keyboard 1601*a*, a mouse 1601*b* and monitor 1601*c* for inputting a labeled biomolecule reagent request. User interface 1601 is operatively coupled to a memory 1602 that includes operating system 1602*a*, system files 1602*b* and datasets that include a plurality of storage identifiers that correspond to the components of the labeled biomolecule reagent request: 1) labeled biomolecule request 1602*d;* 2) biomolecule request 1602*e;* 3) label request 1602*f;* 4) activated biomolecule request 1602*g;* 5) activated label request 1602*h;* and 6) reactive linker request 1602*i*. Memory 1602 also includes a database 1602*j* that includes a searchable inventory listing of labeled biomolecules 1602*k*, biomolecules 1602*l*, labels 1602*m* and reactive linkers 1602*n*. In some embodiments, the label request comprises an enzyme request and a substrate request.

The memory and user interface are operatively coupled to a processor 1603 through connection 1604 that includes a storage drive 1606 that is controlled by disk controller 1605. As described above, the processor identifies one or more storage identifiers from the dataset that corresponds to the request received by the input manager.

To output the identified storage identifiers, systems of interest according to this embodiment include a network interface controller 1607 which outputs the storage identifiers. Network interface controller 1607 may be interfaced with an electronic display to visually display the identified storage identifiers or may be interfaced with a printer for presenting the identified storage identifiers onto a human (paper) readable medium or as in a machine readable format (e.g., as a barcode). In some embodiments, network interface controller 1607 communicates the storage identifiers in an electronic format, such as over a local area network or over the internet and may be implemented according to any electronic format, including but not limited to, SQL, HTML or XML documents, email or other files, or data in other forms.

Figure 17:
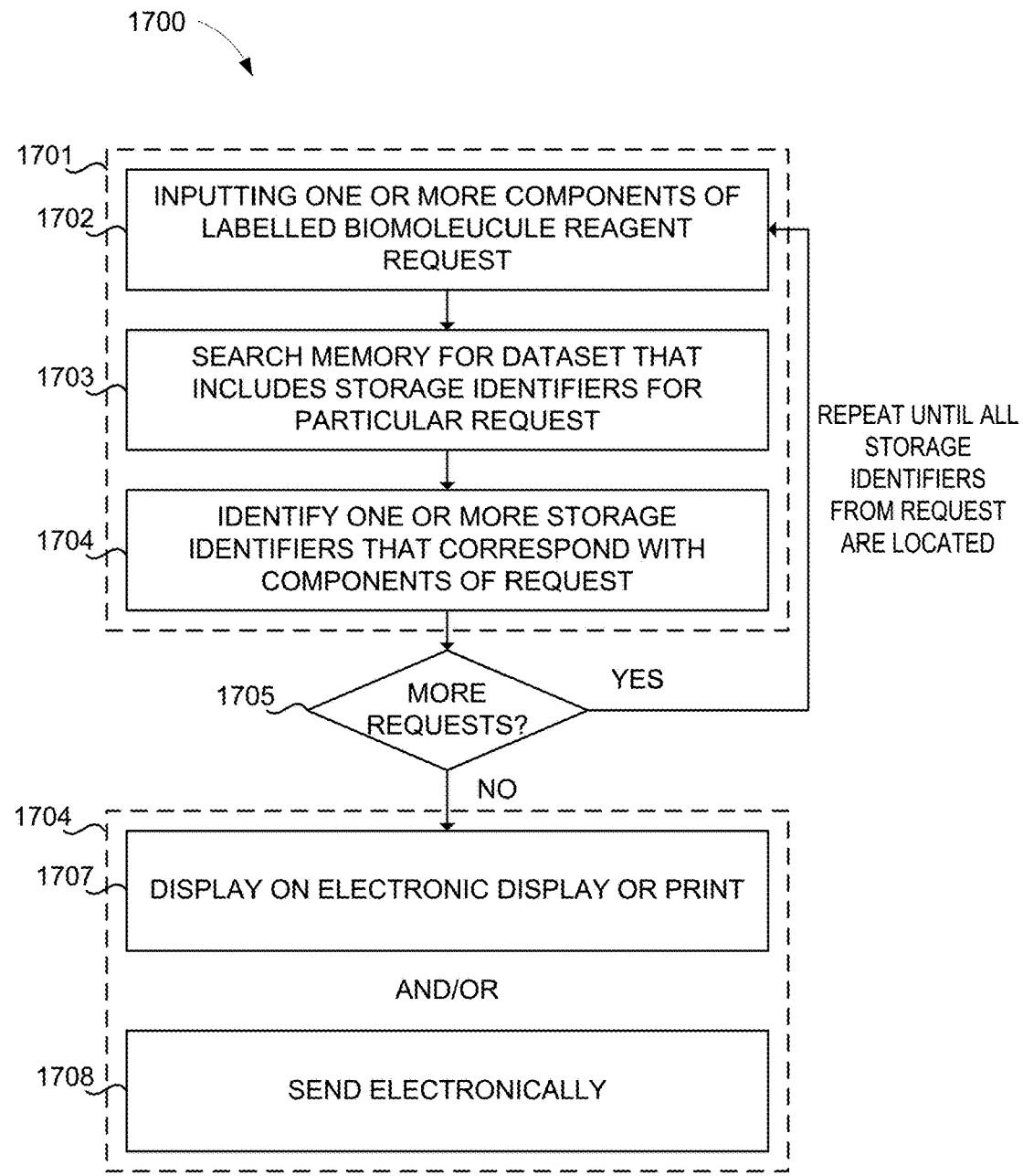
FIG. 17 illustrates a flow diagram for receiving, processing and outputting a request for a labeled biomolecule reagent according to some embodiments of the invention.

FIG. 17 illustrates a flow diagram 1700 for receiving, processing and outputting a request for a labeled biomolecule reagent according to some embodiments. Receiving and processing 1701 the request starts with inputting the one or more components of the labeled biomolecule reagent request (1702). As discussed above, the labeled biomolecule reagent request may include one or more of 1) a labeled biomolecule request; and 2) a biomolecule request and a label request. In some embodiments, the biomolecule request is an activated biomolecule request where biomolecule is coupled to a reactive linker. In some embodiments, the label request is an activated label request where the label is coupled to a reactive linker. In some embodiments, the label request comprises an enzyme request and a substrate request.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

After the systems has received the labeled biomolecule reagent request, a processor determines the components of the request (i.e., labeled biomolecule request; or biomolecule request and label request) and the system searches (1703) the memory for storage identifiers that correspond to that particular request. When the appropriate dataset is retrieved, the processing module identifies one or more storage identifiers that correspond with the components of the labeled biomolecule reagent request (1704). If more than one labeled biomolecule reagent request is inputted by a single user, the system may repeat the above until all storage identifiers from the user's requests are located and identified by the processor (1705).

Systems are configured to output (1706) the identified storage identifiers once the labeled biomolecule reagent request from the user has been processed. The output manager may display the storage identifiers on an electronic display or print the storage identifiers (1707). The storage identifiers may also be communicated electronically (1708), such as to a reagent preparatory apparatus or over the internet to a third party manufacturer.

In some embodiments, systems include a reagent preparatory apparatus for preparing the labeled biomolecule reagent that corresponds to the requested labeled biomolecule received by the input manager. The reagent preparatory apparatus is operatively coupled to the output manager and is configured to receive the identified storage identifiers (e.g., labeled biomolecule storage identifier, biomolecule storage identifier, label storage identifier, reactive linker storage identifier) and produce the labeled biomolecule reagent according to the received storage identifiers. In these embodiments, the reagent preparatory apparatus may be in communication with the output manager locally, such as through a cable or local area network or may be in a remote location and connected to the output manager through a wide-area network or through the internet. To facilitate connectivity between the reagent preparatory apparatus and the output manager, systems may include any suitable connectivity protocols, such as a cables, transmitters, relay stations, network servers, network interface cards, Ethernet modems, telephone network connections as well as satellite network connections. In some embodiments, the reagent preparatory apparatus includes a graphical user interface where the storage identifiers from the output manager are manually inputted into an input manager operatively coupled to the graphical user interface of the reagent preparatory apparatus.

In some embodiments, the reagent preparatory apparatus is fully automated.

By "fully automated" is meant that the reagent preparatory apparatus receives the identified storage identifiers from the output manager and prepares, formulates and packages the labeled biomolecule reagent with little to no human intervention or manual input into the subject systems. In some embodiments, the subject systems are configured to prepare, purify and package the labeled biomolecule reagent from an activated biomolecule and activated label without any human intervention.

The reagent preparatory apparatus includes a sampling device that provides an activated biomolecule and an activated label to a contacting apparatus. The sampling device may be any convenient device in fluid communication with each source of activated biomolecule and activated label, such as for example, a high throughput sample changer having a plurality of reagent vials containing activated biomolecules and activated labels. The sampling device may also include microfluidic channels, syringes, needles, pipets, aspirators, among other sampling devices. The contacting apparatus may be any suitable apparatus which allows for an activated biomolecule to be contacted with an activated label. For example, in some embodiments, the contacting apparatus is a sample chamber (e.g., enclosed, sealed, airtight, open, plate, etc.). In other embodiments, the contacting apparatus is a microtube. In other embodiments, the contacting apparatus is a test tube. In yet other embodiments, the contacting apparatus is a glass flask (e.g., beaker, volumetric flask, Erlenmeyer flask, etc.). In still other embodiments, the contacting apparatus is a 96-well plate. In some embodiments, the subject systems may further include a packaging unit configured to seal the produced labeled biomolecule reagent in the contacting apparatus (e.g., microtube, test tube, etc.). In other embodiments, the produced labeled biomolecule reagent is first characterized and further purified, diluted, concentrated or re-formulated before sealing in a container and packaged with the packaging unit.

The contacting apparatus may further include an agitator for mixing the combined activated biomolecule and activated label. The agitator may be any convenient agitator sufficient for mixing the subject compositions, including but not limited to vortexers, sonicators, shakers (e.g., manual, mechanical, or electrically powered shakers), rockers, oscillating plates, magnetic stirrers, static mixers, rotators, blenders, mixers, tumblers, orbital shakers, bubbles, microfluidic flow, among other agitating protocols.

In some embodiments, the reagent preparatory apparatus also includes a source of activated biomolecules and activated labels. The source may include a plurality of activated biomolecules and activated labels. In some embodiments, the reagent preparatory apparatus includes a source containing 5 or more different types of activated biomolecules, such as 10 or more, such as 100 or more, such as 250 or more, such as 500 or more and including 1000 or more different types of activated biomolecules. For example, the reagent preparatory apparatus may include a source containing 5 or more different types of activated antibody probes or activated oligonucleotide probes, such as 10 or more, such as 100 or more, such as 250 or more, such as 500 or more and including 1000 or more different types of activated antibody probes or activated oligonucleotide probes.

In some embodiments, the reagent preparatory apparatus includes a source containing 5 or more different types of activated labels, such as 10 or more, such as 15 or more, such as 25 or more, such as 50 or more and including 100 or more different types of activated labels. For example, the reagent preparatory apparatus may include a source containing 5 or more different types of activated fluorophores, such as 10 or more, such as 15 or more, such as 25 or more, such as 50 or more and including 100 or more different types of activated fluorophores.

The source of activated biomolecules and activated labels may be any suitable reservoir that is capable of storing and providing one or more type of activated biomolecule and activated label to the contacting apparatus. In one example, the source is a single high throughput reservoir that stores a plurality of different types of activated biomolecules and activated labels in separate, partitioned reagent chambers. In another example, the source of activated biomolecules and activated labels is a plurality of individual vials of each activated biomolecule and each activated label. In yet another example, the source of activated biomolecules and activated labels is a reservoir with pre-measured aliquots of each activated biomolecule and each activated label. For example, the reservoir may include pre-measured aliquots of each activated biomolecule and each activated label sufficient to prepare one or more labeled biomolecules, such as 2 or more, such as 5 or more, such as 10 or more, such as 25 or more, such as 100 or more, such as 500 or more and including 1000 or more labeled biomolecules.

Depending on the particular design of reservoir containing the activated biomolecules and activated labels, the reagent preparatory apparatus may further include one or more inlets for delivering the activated biomolecules and activated labels to the contacting apparatus.

The reagent preparatory apparatus may also include one or more reagent purifiers. Reagent purification protocols of interest may include, but is not limited to size exclusion chromatography, ion exchange chromatography, filtration (e.g., membrane filters, size cut-off filtration), liquid-liquid extraction, passive dialysis, active dialysis, centrifugation, precipitation, among other purification protocols.

The reagent preparatory apparatus may also include a reagent analyzer. In some embodiments, the sample analyzer may be mass cytometry, mass spectrometry (e.g., TOF mass spectrometry, inductively coupled plasma mass spectrometry), absorbance spectroscopy, fluorescence spectroscopy, volumetric analysis, conductivity analysis, nuclear magnetic resonance spectroscopy, infrared spectroscopy, UV-vis spectroscopy, colorimetry, elemental analysis, liquid chromatography-mass spectrometry or gas chromatography-mass spectrometry systems. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in some embodiments. Mass spectrometer systems may be any convenient mass spectrometry system, which in general contains an ion source for ionizing a sample, a mass analyzer for separating ions, and a detector that detects the ions. In some embodiments, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

The reagent preparatory apparatus may also be configured to formulate the labeled biomolecule reagent with one or more excipients, such as a buffer, preservative, drying agent, etc. In some embodiments, the reagent preparatory apparatus is configured to formulate the labeled biomolecule reagent with one or more buffers.

Example buffers may include but are not limited to PBS (phosphate) buffer, acetate buffer, N,N-bis(2-hydroxyethyl)glycine (Bicine) buffer, 3-([tris(hydroxymethyl)methyl]amino)propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-([tris(hydroxymethyl)methyl]amino)ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions.

The reagent preparatory apparatus may also include a packing unit for packaging the labeled biomolecule reagent. In some embodiments, the packaging unit may package the prepared labeled biomolecule reagent and prepare the labeled biomolecule reagent for shipping, such as by mail. In some embodiments, the prepared labeled biomolecule reagent is dispensed into a container and sealed. In some embodiments, the labeled biomolecule reagent is dispensed into a container, sealed and further packaged such as in a pouch, bag, tube, vial, microtube or bottle. Where desired, the packaging may be sterile.

In some embodiments, systems of interest include an on-demand standalone labeled biomolecule reagent dispensing station configured to: 1) receive one or more requests for a labeled biomolecule reagent; 2) prepare the requested labeled biomolecule reagent and 3) deliver the prepared labeled biomolecule reagent to the requestor (e.g., customer). For example, the standalone reagent dispensing station may be a self-vending machine that is configured to receive one or more labeled biomolecule reagent requests from a customer, prepare the requested labeled biomolecule and dispense the prepared labeled biomolecule to the customer on demand. Depending on the number of labeled biomolecule reagent requests and the amount of each labeled biomolecule reagents requested, standalone reagent dispensing stations of interest may prepare and dispense the labeled biomolecule to the requestor on demand in 10 seconds or more after input of the labeled biomolecule request, such as in 15 seconds or more, such as in 30 seconds or more, such as in 1 minute or more, such as in 5 minutes or more, such as in 10 minutes or more, such as in 15 minutes or more, such as in 30 minutes or more and including in 60 minutes or more, such as in 1.5 hours or more, such as in 2 hours or more, such as in 2.5 hours or more, such as in 3 hours or more, such as in 4 hours or more, such as in 5 hours or more, such as in 6 hours or more, such as in 8 hours or more, such as in 10 hours or more, such as in 12 hours or more, such as in 16 hours or more, such as in 18 hours or more and including in 24 hours or more. In some embodiments, the standalone reagent dispensing station is configured to prepare and dispense the labeled biomolecule to the requestor on demand in a duration that ranges from 5 seconds to 60 seconds, such as from 10 seconds to 50 seconds and including from 15 seconds to 45 seconds. In some embodiments, the standalone reagent dispensing station is configured to prepare and dispense the labeled biomolecule to the requestor on demand in a duration that ranges from 1 minute to 60 minutes, such as from 2 minutes to 55 minutes, such as from 5 minutes to 50 minutes, such as from 15 minutes to 45 minutes and including from 20 minutes to 40 minutes, for example preparing and dispensing the labeled biomolecule to the requestor in 30 minutes. In still some embodiments, the standalone reagent dispensing station is configured to prepare and dispense the labeled biomolecule to the requestor on demand in a duration that ranges from 0.5 hours to 24 hours, such as from 1 hour to 20 hours, such as from 1.5 hours to 18 hours, such as from 2 hours to 16 hours, such as from 2.5 hours to 12 hours, such as from 3 hours to 10 hours, such as from 3.5 hours to 8 hours and including from 4 hours to 6 hours.

In these embodiments, the subject standalone reagent dispensing stations may include the components for receiving a labeled biomolecule reagent request and preparing the requested labeled biomolecule reagent, as described above. For instance, the standalone labeled biomolecule reagent dispensing station may include an input module for receiving a request for a labeled biomolecule; a reagent preparatory apparatus; and a dispensing module for outputting a packaged labeled biomolecule. In these embodiments, the input module may include an input manager for receiving a request for a labeled biomolecule, a memory for storing a dataset having a plurality of storage identifiers that correspond to the one or more components of the labeled biomolecule reagent request (e.g., biomolecule, label, etc.), a processing module communicatively coupled to the memory and configured to identify a storage identifier from the dataset that corresponds to the components of the labeled biomolecule reagent request and an output manager for providing the identified storage identifiers. The standalone station also includes, as described above, a graphical user interface as well as user input devices for communicating the labeled biomolecule request to the input manager of the standalone dispensing station.

In embodiments, the output manager is communicatively coupled to the reagent preparatory apparatus in the standalone reagent dispensing station which is configured with one or more sources of biomolecules, labels, reactive linkers, activated biomolecules and activated labels and a contacting station for coupling an activated biomolecule and an activated label to produce the requested labeled biomolecule. In some embodiments, the standalone reagent dispensing station includes a plurality of pre-synthesized labeled biomolecules and the standalone reagent dispensing station is configured to aliquot an amount of the pre-synthesized labeled biomolecule reagent into a container and dispense the labeled biomolecule reagent to the requestor.

The standalone labeled biomolecule reagent dispensing station also includes a dispensing module that is configured to provide a packaged labeled biomolecule reagent. In embodiments, the dispensing module may include a packaging unit for packaging the prepared labeled biomolecule reagent. In some embodiments, the prepared labeled biomolecule reagent is dispensed into a container and sealed. In some embodiments, the labeled biomolecule reagent is dispensed into a container, sealed and further packaged such as in a pouch, bag, tube, vial, microtube or bottle. Where desired, the packaging may be sterile.

In some embodiments, the standalone reagent dispensing station is fully automated, where a labeled biomolecule request is received and the station prepares, purifies and packages the labeled biomolecule reagent with little to no human intervention or manual input into the subject systems apart from the labeled biomolecule request.

Methods for Preparing a Labeled Biomolecule Reagent

Aspects of the present disclosure also include methods for preparing a labeled biomolecule reagent. Methods according to some embodiments include receiving a request for a labeled biomolecule reagent and preparing a labeled biomolecule. In other embodiments, methods include receiving a request for a labeled biomolecule reagent with one or more input managers as described above, identifying a storage identifier that corresponds with the labeled biomolecule reagent request; outputting the one or more identified storage identifiers and preparing the labeled biomolecule from the identified storage identifiers.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

As discussed above, the labeled biomolecule reagent is a biological macromolecule that is coupled (e.g., covalently bonded) to a detectable marker. In some embodiments, methods include preparing a polypeptide coupled to a detectable marker, a nucleic acid coupled to a detectable marker, a polysaccharide coupled to a detectable marker, or a combination thereof. In one example, the biomolecule is an oligonucleotide, truncated or full-length DNA or RNA. In another example, the biomolecule is a polypeptide, protein, enzyme or antibody. In some embodiments, the biomolecule is a biological probe having a specific binding domain sufficient to bind an analyte of interest. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments, as well as molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

Labels of interest include detectable markers that are detectible based on, for example, fluorescence emission, fluorescence polarization, fluorescence lifetime, fluorescence wavelength, absorbance maxima, absorbance wavelength, Stokes shift, light scatter, mass, molecular mass, redox, acoustic, raman, magnetism, radio frequency, enzymatic reactions (including chemiluminescence and electrochemiluminescence) or combinations thereof. Labels of interest may include, but are not limited to fluorophores, chromophores, enzymes, enzyme substrates, catalysts, redox labels, radiolabels, acoustic labels, Raman (SERS) tag, mass tag, isotope tag (e.g., isotopically pure rare earth element), magnetic particles, microparticles, nanoparticles, oligonucleotides, or any combination thereof.

Methods include receiving a request for a labeled biomolecule reagent. In embodiments of the present disclosure, the labeled biomolecule reagent request includes one or more of: 1) a labeled biomolecule request; and 2) a biomolecule request and a label request. In some embodiments, the label request comprises an enzyme request and a substrate request. In some embodiments, the biomolecule request is an activated biomolecule request where biomolecule is coupled to a reactive linker. In some embodiments, the label request is an activated label request where the label is coupled to a reactive linker. The labeled biomolecule reagent request may be received by any convenient communication protocol including, but not limited to, receiving the labeled biomolecule reagent request over the telephone, by facsimile, electronic mail or postal mail. In some embodiments, the labeled biomolecule reagent request is communicated by inputting the labeled biomolecule reagent request into a graphical user interface on a computer, such as through an internet website.

One or more labeled biomolecule reagent requests may be received (simultaneously or sequentially), such as receiving 2 or more labeled biomolecule reagent requests, such as 5 or more, such as 10 or more and including receiving 25 or more labeled biomolecule reagent requests. Where the request for a labeled biomolecule reagent includes only a single component and is a labeled biomolecule request, methods may include receiving 2 or more labeled biomolecule requests, such as 5 or more, such as 10 or more and including 25 or more labeled biomolecule requests. Where the labeled biomolecule reagent request includes two components, such as a biomolecule request and a label request, methods may include receiving 2 or more biomolecule requests, such as 5 or more, such as 10 or more and including 25 or more biomolecule requests and configured to receive 2 or more label requests, such as 5 or more, such as 10 or more and including 25 or more label requests. In some embodiments, methods including receiving a labeled biomolecule reagent request that includes a single biomolecule request and single label request. In some embodiments, methods include receiving a labeled biomolecule reagent request that includes a single biomolecule request and a plurality of different label requests. In yet some embodiments, the methods include receiving a labeled biomolecule reagent request that includes a plurality of different biomolecule requests and a single label request. In still some embodiments, methods include receiving a labeled biomolecule reagent request that includes a plurality of different biomolecule requests and a plurality of different label requests.

The labeled biomolecule reagent requests may be received from a single user or a plurality of users, such as from 2 or more users, such as from 5 or more users, such as from 10 or more users, such as from 25 or more users and including receiving labeled biomolecule requests from 100 or more users.

In some embodiments, methods include receiving a request for a labeled biomolecule reagent and inputting the request into a graphical user interface of an input manager (as described above) entered through. In other embodiments, the user making the labeled biomolecule reagent request inputs the request directly into the graphical user interface. The labeled biomolecule request, in these embodiments, may be entered into the graphical user interface and communicated to the input manager as a string of one or more characters (e.g., alphanumeric characters), symbols, images or other graphical representation(s) of the labeled biomolecule. In some embodiments, the request is a "shorthand" designation or other suitable identifier of the labeled biomolecule, biomolecule, label, activated biomolecule, activated label or reactive linker. For example, the request may include biomolecule name, label name, ascension number, sequence identification number, abbreviated probe sequence, chemical structure or Chemical Abstracts Service (CAS) registry number.

As described above, after the labeled biomolecule request is received by the input manager, a processing module of the subject systems identifies one or more storage identifiers from a dataset stored in memory that corresponds to the components of the received labeled biomolecule reagent request (e.g., a labeled biomolecule storage identifier, a biomolecule storage identifier, a label storage identifier, a reactive linker storage identifier, etc.) The storage identifiers that correspond to each component of the received labeled biomolecule reagent request is outputted by an output manager. In some embodiments, each labeled biomolecule storage identifier is displayed on a monitor. In some embodiments, the storage identifiers is outputted by printing in a machine (e.g., as a barcode) or human readable format. Where the labeled biomolecule reagent is prepared by a computer controlled reagent preparatory apparatus (as described in greater detail below), the output manager is operatively coupled to the reagent preparatory apparatus and each storage identifier may electronically communicated to the reagent preparatory apparatus, such as through an internet protocol, including but not limited to SQL, HTML or XML documents, email or other files, or data in other forms.

Depending on the number of labeled biomolecule requests received, one or more storage identifiers may be simultaneously outputted by the output manager, such as 2 or more, such as 3 or more, such as 3 or more, such as 5 or more, such as 10 or more, such as 25 or more, such as 100 or more and including outputting 500 or more storage identifiers. Each set of outputted storage identifiers may correspond with the labeled biomolecule requests from a single user or from a plurality of users.

In some embodiments, the output manager organizes (e.g., groups together) storage identifiers based on a predetermined criteria before displaying or printing the storage identifiers. In one example, the output manager groups together all of the storage identifiers from a particular user. In another example, the output manager groups together all of the same labeled biomolecule storage identifiers. In yet another example, the output manager organizes the storage identifiers based on name or type of biomolecule (e.g., antibody, oligonucleotide). In still another example, the output manager organizes the storage identifiers based on the name or type of label (e.g., fluorescein, coumarin).

In some embodiments, methods include preparing a labeled biomolecule reagent according to the received request and/or the outputted storage identifiers. In some embodiments, preparing the labeled biomolecule reagent includes selecting an activated biomolecule and an activated label from a storage having a plurality of activated biomolecules and a plurality of activated labels. Each labeled biomolecule reagent may be prepared manually by one or more individuals, such as in a laboratory or may be prepared with a computer-controlled reagent preparatory apparatus (e.g., a high throughput preparatory system) as described above. In some embodiments, where the outputted storage identifier is a labeled biomolecule storage identifier, methods include retrieving the labeled biomolecule from a storage that corresponds to the outputted labeled biomolecule storage identifier. In these instances, methods may further include purifying the labeled biomolecule from the storage or adding one or more additional reagents (e.g., buffers, antioxidants, etc.) as desired. In some embodiments, the retrieved labeled biomolecule may be packaged and shipped to the user without further purification or additions to the composition.

In other embodiments, the labeled biomolecule is prepared by contacting an activated biomolecule that corresponds with the outputted biomolecule storage identifier with an activated label that corresponds with the outputted label storage identifier. Any convenient reaction protocol may be employed to mix the activated biomolecule with the activated label, so long as reaction is sufficient to form a covalent bond between the reactive linker of the activated biomolecule and the reactive linker of the activated label. Mixing, in some embodiments, may include stirring the mixture with a magnetic stir bar or manually stirring the mixture as well as vortexing of agitating the mixture either manually (i.e., by hand) or mechanically (i.e., by a mechanically or electrically powered shaking device). The activated biomolecule and activated label are contacted for a duration sufficient to couple the activated biomolecule to the activated label, such as for 1 minute or longer, such as for 5 minutes or longer, such as for 10 minutes or longer and including for 30 minutes or longer.

As discussed above, the activated biomolecule and activated label each include a reactive linker which when carried out under appropriate conditions, react together to form chemical linkage, such as for example, an ionic bond (charge-charge interaction), a non-covalent bond (e.g., dipole-dipole or charge-dipole) or a covalent bond. In some embodiments, the reactive linker or moiety of the activated biomolecule reacts with the reactive linker or moiety of the activated label to produce an ionic bond. In other embodiments, the reactive linker or moiety of the activated biomolecule reacts with the reactive linker or moiety of the activated label to produce a non-covalent bond. In yet other embodiments, the reactive linker or moiety of the activated biomolecule reacts with the reactive linker or moiety of the activated label to produce a covalent bond. In some embodiments, the reactive linker of the activated biomolecule and the reactive linker of the activated label react to produce a covalent bond. Any convenient protocol for forming a covalent bond between the reactive linker of the activated biomolecule and the reactive linker of the activated label may be employed, including but not limited to addition reactions, elimination reactions, substitution reactions, pericyclic reactions, photochemical reactions, redox reactions, radical reactions, reactions through a carbine intermediate, metathesis reaction, among other types of bond-forming reactions. In some embodiments, the activated biomolecule may be conjugated to the activated label through reactive linking chemistry such as where reactive linker pairs include, but is not limited to: maleimide/thiol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylate)/thiol and amine/ BMPH (N-[β-Maleimidopropionic acid]hydrazide·TFA)/ thiol; azide/triarylphosphine; nitrone/cyclooctyne; azide/ tetrazine and formylbenzamide/hydrazino-nicotinamide.

After contacting the activated biomolecule and activated label for a duration sufficient to form a chemical linkage (e.g., covalent bond) between each respective reactive linker, the labeled biomolecule may be further purified, such as by microextraction, gel electrophoresis, liquid-liquid extraction, centrifugation, precipitation, passive or active dialysis, or solid phase chromatography, including but not limited to ion exchange chromatography, liquid chromatography employing a reverse phase stationary column, size exclusion chromatography, high performance liquid chromatography and preparatory thin layer chromatography, ultrafiltration (membrane filters with size cut offs), among other purification protocols.

Methods may also include analysis of the prepared labeled biomolecule reagent.

By analyzed is meant characterizing the chemical composition of the labeled biomolecule reagent, including but not limited to the amount and types of compounds in the prepared reagent composition as well as any impurities present. Analysis of the prepared labeled biomolecule reagent may be conducted using any convenient protocol, such as for example by physical measurements (e.g., mass analysis, density analysis, volumetric analysis, etc.) mass spectrometry (e.g., TOF mass spectrometry, inductively coupled plasma mass spectrometry), mass cytometry, absorbance spectroscopy, fluorescence spectroscopy, conductivity analysis, infrared spectroscopy, UV-vis spectroscopy, colorimetry, elemental analysis and nuclear magnetic resonance spectroscopy. In some embodiments, analysis of the labeled biomolecule is conducted by mass spectrometry. In some embodiments, analysis of the labeled biomolecule is conducted by fluorescence spectroscopy. In some embodiments, analysis of the labeled biomolecule is conducted by gas chromatography. In some embodiments, analysis of the labeled biomolecule is conducted by liquid chromatography. In some embodiments, analysis of the labeled biomolecule is conducted by elemental analysis. In some embodiments, analysis of the labeled biomolecule reagent is conducted by gas chromatography-mass spectrometry. In other embodiments, analysis of the labeled biomolecule reagent is conducted by liquid chromatography-mass spectrometry. For example, the apparatus may include analytical separation device such as a liquid chromatograph (LC), including a high performance liquid chromatograph (HPLC), fast protein liquid chromatography (FPLC) a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, the subject sample may be applied to the LC-MS system by employing a nano- or micropump in some embodiments. Mass spectrometer systems may be any convenient mass spectrometry system, which in general contains an ion source for ionizing a sample, a mass analyzer for separating ions, and a detector that detects the ions. In some embodiments, the mass spectrometer may be a so-called "tandem" mass spectrometer that is capable of isolating precursor ions, fragmenting the precursor ions, and analyzing the fragmented precursor ions. The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

After preparation (as well as purification and analysis, where desired) of the labeled biomolecule reagent, each prepared labeled biomolecule reagent may be loaded into a container for packaging and delivery in accordance with the labeled biomolecule request (i.e., transported to the user originating the labeled biomolecule request). In some embodiments, the labeled biomolecule reagent is prepared and delivered to the user in the container used to contact the activated biomolecule with the activated label. For example, the labeled biomolecule reagent may be packaged and delivered in the microtube used to contact the activated biomolecule with the activated label. Methods may also include delivering the packaged labeled biomolecule reagent to the requestor, such as by mail.

The prepared labeled biomolecule reagent may be packaged with other components, such as for using or storing the labeled biomolecule reagent, including but not limited to buffers, syringes, needles, micropipets, glass slides, desiccants, etc. In addition, the packaged labeled biomolecule reagent may further include instructions for storing and using the labeled biomolecule reagent. The instructions may be recorded on a suitable recording medium, such as printed on paper or plastic, etc. The instructions may be present as a package insert, such as in the labeling of the container. In other embodiments, the instructions may be present as electronic storage data file present on a suitable computer readable storage medium, e.g. CD-ROM, SD card, USB drive etc. In yet other embodiments, the actual instructions are not present in the package, but means for obtaining the instructions from a remote source, e.g. via the internet, are provided. An example of this embodiment is a paper or plastic insert having a web address where the instructions can be viewed and/or from which the instructions can be downloaded.

Methods for Requesting and Receiving a Labeled Biomolecule Reagent

Aspects of the present disclosure also include methods for requesting and receiving a labeled biomolecule reagent. Methods according to some embodiments include communicating a request for a labeled biomolecule reagent, the labeled biomolecule request including one or more of: 1) a labeled biomolecule request; and 2) a biomolecule request and a label request and receiving a labeled biomolecule reagent that includes a biomolecule covalently bonded to a label. In some embodiments, the label request comprises an enzyme request and a substrate request. In practicing the subject methods, the labeled biomolecule request may be communicated by any convenient communication protocol including, but not limited to, communicating the labeled biomolecule request over the telephone, by facsimile, electronic mail or postal mail. In some embodiments, the labeled biomolecule request is communicated by inputting the labeled biomolecule reagent request into a graphical user interface on a computer, such as on an internet website.

In some embodiment, the biomolecule comprises a polypeptide, a nucleic acid, a polysaccharide, or any combination thereof. The nucleic acid can be an oligonucleotide, DNA or RNA. The polypeptide can be a protein, an enzyme or a protein binding reagent. The protein binding reagent can comprise an antibody, an aptamer, or a combination thereof. The protein binding reagent conjugated with the label can be capable of specifically binding to at least one of a plurality of protein targets.

In some embodiments, the plurality of protein targets comprises a cell-surface protein, a cell marker, a B-cell receptor, a T-cell receptor, an antibody, a major histocompatibility complex, a tumor antigen, a receptor, or any combination thereof. The plurality of protein targets can comprise, for example, 10-400 different protein targets. The biomolecule can be selected from at least 100, 1,000, or 10,000 different biomolecules.

In some embodiments, the oligonucleotide comprises a unique identifier for the biomolecule. The unique identifier can comprise a nucleotide sequence of 25-45 nucleotides in length. The unique identifier can be selected from a diverse set of unique identifiers. The diverse set of unique identifiers can comprise at least 100, 1,000, or 10,000 different unique identifiers. The oligonucleotide can have a sequence selected from at least 10, 100, or 1,000 different barcode sequences (e.g., molecular label sequences). In some embodiments, the oligonucleotide is conjugated to the biomolecule through a linker. The oligonucleotide can comprise the linker. The linker can comprise a chemical group. The chemical group can be reversibly attached to the biomolecule. The chemical group can be selected from the group consisting of a UV photocleavable group, a streptavidin, a biotin, an amine, and any combination thereof.

The unique identifier may not be homologous to genomic sequences of a sample. The sample can be a single cell, a plurality of cells, a tissue, a tumor sample, or any combination thereof. The sample can be a mammalian sample, a bacterial sample, a viral sample, a yeast sample, a fungal sample, or any combination thereof. The oligonucleotide can comprise a barcode sequence (e.g., a molecular label sequence), a poly(A) tail, or a combination thereof.

One or more labeled biomolecule reagent requests may be communicated, such as communicating 2 or more labeled biomolecule reagent requests, such as 5 or more, such as 10 or more and including communicating 25 or more labeled biomolecule reagent requests. In some embodiments, methods include communicating a labeled biomolecule reagent request that includes a single biomolecule request and a single label request. In other embodiments, the labeled biomolecule reagent request includes a single biomolecule request and a plurality of label requests. In yet other embodiments, the labeled biomolecule reagent request includes a plurality of biomolecule requests and a single label request. In still other embodiments, the labeled biomolecule request includes a plurality of biomolecule requests and a plurality of label requests. In some embodiments, the labeled biomolecule reagent request includes one or more labeled biomolecule requests. In some embodiments, the label request comprises an enzyme request and a substrate request.

In some embodiments, the labeled biomolecule reagent request is communicated by inputting the request on a graphical user interface, such as on an internet website. The graphical user interface may display all or part of a database (e.g., catalog) of labeled biomolecules, activated biomolecules, biomolecules, activated labels, labels and reactive linkers. Each category from the database may be displayed as a list, drop-down menu or other configuration. The labeled biomolecule reagent request may be entered by inputting information or data associated with the biomolecule and the label into appropriate text fields or by selecting check boxes or selecting one or more items from a drop-down menu, or by using a combination thereof.

In one example, a labeled biomolecule reagent request is inputted into the graphical user interface by selecting a labeled biomolecule from a drop-down menu. In another example, a labeled biomolecule reagent request is inputted into the graphical user interface by selecting one or more biomolecules from a first drop-down menu and one or more labels from a second drop-down menu. In yet another example, a labeled biomolecule reagent request is inputted into the graphical user interface by selecting one or more biomolecules from a first drop-down menu, one or more labels from a second drop-down menu and one or more reactive linkers from a third drop-down menu.

To input a labeled biomolecule reagent request, information or data associated with a particular labeled biomolecule, biomolecule or label is entered onto the graphical user interface. The information or data entered may be a string of one or more characters (e.g., alphanumeric characters), symbols, images or other graphical representation(s) of the labeled biomolecule. In some embodiments, a "shorthand" designation or other suitable identifier of the labeled biomolecule, biomolecule, label, activated biomolecule, activated label or reactive linker are entered. For example, biomolecule name, label name, ascension number, sequence identification number, abbreviated probe sequence, chemical structure or Chemical Abstracts Service (CAS) registry number may be entered.

In some embodiments, the labeled biomolecule reagent includes a polypeptide and the request may include information such as polypeptide name, protein name, enzyme name, antibody name or the name of protein, enzyme or antibody fragments thereof, polypeptides derived from specific biological fluids (e.g., blood, mucus, lymphatic fluid, synovial fluid, cerebrospinal fluid, saliva, bronchoalveolar lavage, amniotic fluid, amniotic cord blood, urine, vaginal fluid and semen), polypeptides derived from specific species (e.g., mouse monoclonal antibodies) as well as amino acid sequence identification number. In some embodiments, the labeled biomolecule reagent includes a biological probe and the request includes information or data associated with a specific binding domain.

In other embodiments, the labeled biomolecule reagent includes a nucleic acid and the request may include information such as oligonucleotide name, oligonucleotides identified by gene name, oligonucleotides identified by accession number, oligonucleotides of genes from specific species (e.g., mouse, human), oligonucleotides of genes associated with specific tissues (e.g., liver, brain, cardiac), oligonucleotides of genes associate with specific physiological functions (e.g., apoptosis, stress response), oligonucleotides of genes associated with specific disease states (e.g., cancer, cardiovascular disease) as well as nucleotide sequence identification number.

In some embodiments, methods for requesting a labeled biomolecule further include completing a questionnaire or survey related to the labeled biomolecule request. In these embodiments, the requestor of the labeled biomolecule is prompted with a series of questions, or in the form of a questionnaire or survey related to the labeled biomolecule request. For example, the questionnaire or survey may include one question related to the labeled biomolecule request, such as 2 or more questions, such as 3 or more questions, such as 4 or more questions and including 5 or more questions related to the labeled biomolecule request. The content of questionnaire or survey may vary depending on the information that is desired. For instance, questions in the questionnaire or survey may include, but are not limited to, requests to provide the contents of a requestor's reagent inventory, the types of experiments being conducted with the labeled biomolecule as well as the timing of the use of the labeled biomolecule reagent. The questionnaire may also include one or more open text fields for inputting. For example, the questionnaire may be an open text feedback form.

In some embodiments, methods include prompting the requestor to complete the series of questions or survey before the labeled biomolecule request is communicated (e.g., inputted into the graphical user interface). In other embodiments, methods include prompting the requestor to complete the series of questions or survey after the labeled biomolecule request is completed. In still other embodiments, the requestor may be prompted with questions related to the labeled biomolecule request concurrently with communicating the labeled biomolecule request. For instance, methods may include prompting the requestor with a question about the specific use (e.g., experiments being conducted) of the labeled biomolecule when communicating the labeled biomolecule request.

As described above, the completed series of questions or survey may be used by the design platform to provide a recommendation for one or more labeled biomolecule, biomolecule, activated biomolecule, label, activated label or reactive linker. For example, the answers to the questions or survey may be used by the design platform to recommend a labeled biomolecule, biomolecule, activated biomolecule, label, activated label or reactive linker that is best suited for use with a particular analytical instrument (e.g., flow cytometer, fluorescence spectrometer) or that is best suited for the intended application of the labeled biomolecule. The design platform, in some embodiments, is configured to use the answers to the completed series of questions or surveys to provide a recommendation for a labeled biomolecule, biomolecule, activated biomolecule, label, activated label or reactive linker based on the target density (e.g., antigen density on a cell)

The answers to the series of questions or survey may be communicated using the same or different protocol as used to communicate the labeled biomolecule request (e.g., telephone, facsimile, email, graphical user interface at a stand-alone station, graphical user interface through the internet). For example, where the labeled biomolecule is request is communicated through a graphical user interface through the internet, answers to the series of questions may also be inputted through the graphical user interface, such as with drop down menus or text fields.

Methods according to embodiments of the present disclosure also include receiving the labeled biomolecule reagent. The labeled biomolecule reagent may be received loaded in a container and may be packaged with one or more ancillary components, such as for using or storing the subject composition. In some embodiments, the labeled biomolecule reagent is received with buffers, syringes, needles, micropipets, glass slides, desiccants, etc. The packaged labeled biomolecule reagent may also be received with instructions for storing and using the labeled biomolecule reagent, such as instructions printed on paper, plastic or on a computer readable medium (e.g., CD-ROM, SD-card, USB drive) or as an insert providing instructions for retrieving instructions for storing and using the subject compositions from a remote source, such as on the internet.

Storage Containing a Plurality of Activated Biomolecules and a Plurality of Activated Labels Aspects of the disclosure also include a storage containing a plurality of activated biomolecules and a plurality of activated labels. As discussed in detail above, the subject labeled biomolecule reagents are prepared by contacting an activated biomolecule (e.g., an activated protein binding reagent, wherein the protein binding reagent is capable of specifically binding to a protein target) with an activated label (e.g., an activated oligonucleotide, wherein the oligonucleotide comprises a unique identifier for the protein binding reagent that it is conjugated therewith). In some embodiments, the activated biomolecules in the storage are polypeptides, nucleic acids, polypeptides or a combination thereof that are coupled to a reactive linker. In some embodiments, the activated biomolecules in the storage are biological probes coupled to a reactive linker where the probe includes a specific binding domain for an analyte of interest, such as antibody binding agents, proteins, peptides, haptens, nucleic acids, etc. Activated labels are marker compounds that may be detectible based on, for example, fluorescence emission, absorbance, fluorescence polarization, fluorescence lifetime, fluorescence wavelength, absorbance maxima, absorbance wavelength, Stokes shift, light scatter, mass, molecular mass, redox, acoustic, raman, magnetism, radio frequency, enzymatic reactions (including chemiluminescence and electro-chemiluminescence) or combinations thereof. For example, the label may be a fluorophore, a chromophore, an enzyme, an enzyme substrate, a catalyst, a redox label, a radiolabel, an acoustic label, a Raman (SERS) tag, a mass tag, an isotope tag (e.g., isotopically pure rare earth element), a magnetic particle, a microparticle, a nanoparticle, an oligonucleotide, or any combination thereof.

In some embodiments, activated labels in storage are fluorophores coupled to a reactive linker. Fluorophores of interest may include, but are not limited to, dyes suitable for use in analytical applications (e.g., flow cytometry, imaging, etc.), such as an acridine dye, anthraquinone dyes, arylmethane dyes, diarylmethane dyes (e.g., diphenyl methane dyes), chlorophyll containing dyes, triarylmethane dyes (e.g., triphenylmethane dyes), azo dyes, diazonium dyes, nitro dyes, nitroso dyes, phthalocyanine dyes, cyanine dyes, asymmetric cyanine dyes, quinon-imine dyes, azine dyes, eurhodin dyes, safranin dyes, indamins, indophenol dyes, fluorine dyes, oxazine dye, oxazone dyes, thiazine dyes, thiazole dyes, xanthene dyes, fluorene dyes, pyronin dyes, fluorine dyes, rhodamine dyes, phenanthridine dyes, as well as dyes combining two or more dyes (e.g., in tandem) as well as polymeric dyes having one or more monomeric dye units, as well as mixtures of two or more dyes thereof. For example, the fluorophore may be 4-acetamido-4'-isothiocyanatostilbene-2,2'disulfonic acid; acridine and derivatives such as acridine, acridine orange, acrindine yellow, acridine red, and acridine isothiocyanate; allophycocyanin, phycoerythrin, peridinin-chlorophyll protein, 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; dye-conjugated polymers (i.e., polymer-attached dyes) such as fluorescein isothiocyanate-dextran as well as dyes combining two or more of the aforementioned dyes (e.g., in tandem), polymeric dyes having one or more monomeric dye units and mixtures of two or more of the aforementioned dyes thereof.

In some embodiments, the fluorophore (i.e., dye) is a fluorescent polymeric dye. Fluorescent polymeric dyes that find use in the subject methods and systems are varied. In some embodiments of the method, the polymeric dye includes a conjugated polymer.

Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some embodiments, the polymeric dye includes a CP that has a rigid rod structure. As summarized above, the structural characteristics of the polymeric dyes can have an effect on the fluorescence properties of the molecules.

Any convenient polymeric dye may be utilized in the subject methods and systems. In some embodiments, a polymeric dye is a multichromophore that has a structure capable of harvesting light to amplify the fluorescent output of a fluorophore. In some embodiments, the polymeric dye is capable of harvesting light and efficiently converting it to emitted light at a longer wavelength. In some embodiments, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer) and the like. In some embodiments, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via energy transfer.

In some embodiments the polymer may be used as a direct fluorescent reporter, for example fluorescent polymers having high extinction coefficients, high brightness, etc. In some embodiments, the polymer may be used as an strong chromophore where the color or optical density is used as an indicator.

Polymeric dyes of interest include, but are not limited to, those dyes described by Gaylord et al. in US Publication Nos. 20040142344, 20080293164, 20080064042, 20100136702, 20110256549, 20120028828, 20120252986 and 20130190193 the disclosures of which are herein incorporated by reference in their entirety; and Gaylord el al., J. Am. Chem. Soc., 2001, 123 (26), pp 6417-6418; Feng el al., Chem. Soc. Rev., 2010, 39, 2411-2419; and Traina el al., J. Am. Chem. Soc., 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorbs light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some embodiments, the hydrophilic water soluble group is charged, e.g., positively or negatively charged or zwitterionic. In some embodiments, the hydrophilic water soluble group is a neutral hydrophilic group. In some embodiments, the WSG is a hydrophilic polymer, e.g., a polyethylene glycol, a cellulose, a chitosan, or a derivative thereof.

As used+herein, the terms "polyethylene oxide", "PEO", "polyethylene glycol" and "PEG" are used interchangeably and refer to a polymer including a chain described by the formula $—(CH_2—CH_2—O—)_n—$ or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, $—COOM'$, $—SO_3M'$, $—PO_3M'$, $—NR_3, Y'$, $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, $—(CH_2CH_2O)_{yy}CH_2CH_2XR^{yy}—$, $—(CH_2CH_2O)_{yy}CH_2CH_2X—$, $—X(CH_2CH_2O)_{yy}CH_2CH_2—$, glycol, and polyethylene glycol, wherein yy is selected from 1 to 1000, X is selected from O, S, and $NR^{ZZ}$, and $R^{ZZ}$ and $R^{YY}$ are independently selected from H and C1-3 alkyl.

The polymeric dye may have any convenient length. In some embodiments, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments. In some embodiments, the number of monomeric repeat units or segments of the polymeric dye is within the range of 2 to 1000 units or segments, such as from 2 to 750 units or segments, such as from 2 to 500 units or segments, such as from 2 to 250 units or segment, such as from 2 to 150 units or segment, such as from 2 to 100 units or segments, such as from 2 to 75 units or segments, such as from 2 to 50 units or segments and including from 2 to 25 units or segments.

The polymeric dyes may be of any convenient molecular weight (MW). In some embodiments, the MW of the polymeric dye may be expressed as an average molecular weight. In some embodiments, the polymeric dye has an average molecular weight of from 500 to 500,000, such as from 1,000 to 100,000, from 2,000 to 100,000, from 10,000 to 100,000 or even an average molecular weight of from 50,000 to 100,000. In some embodiments, the polymeric dye has an average molecular weight of 70,000.

The polymeric dye may have one or more desirable spectroscopic properties, such as a particular absorption maximum wavelength, a particular emission maximum wavelength, extinction coefficient, quantum yield, and the like.

In some embodiments, the polymeric dye has an absorption curve between 280 and 850 nm. In some embodiments, the polymeric dye has an absorption maximum in the range 280 and 850 nm. In some embodiments, the polymeric dye absorbs incident light having a wavelength in the range between 280 and 850 nm, where specific examples of absorption maxima of interest include, but are not limited to: 348 nm, 355 nm, 405 nm, 407 nm, 445 nm, 488 nm, 640 nm and 652 nm. In some embodiments, the polymeric dye has an absorption maximum wavelength in a range selected from the group consisting of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In some embodiments, the polymeric dye has an absorption maximum wavelength of 348 nm. In some embodiments, the polymeric dye has an absorption maximum wavelength of 355 nm. In some embodiments, the polymeric dye has an absorption maximum wavelength of 405 nm. In some embodiments, the polymeric dye has an absorption maximum wavelength of 407 nm. In some embodiments, the polymeric dye has an absorption maximum wavelength of 445 nm. In some embodiments, the polymeric dye has an absorption maximum wavelength of 488 nm. In some embodiments, the polymeric dye has an absorption maximum wavelength of 640 nm. In some embodiments, the polymeric dye has an absorption maximum wavelength of 652 nm.

In some embodiments, the polymeric dye has an emission maximum wavelength ranging from 400 to 850 nm, such as 415 to 800 nm, where specific examples of emission maxima of interest include, but are not limited to: 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, 805 nm. In some embodiments, the polymeric dye has an emission maximum wavelength in a range selected from the group consisting of 380-400 nm, 410-430 nm, 470-490 nm, 490-510 nm, 500-520 nm, 560-580 nm, 570-595 nm, 590-610 nm, 610-650 nm, 640-660 nm, 650-700 nm, 700-720 nm, 710-750 nm, 740-780 nm and 775-795 nm. In some embodiments, the polymeric dye has an emission maximum of 395 nm. In some embodiments, the polymeric dye has an emission maximum wavelength of 421 nm. In some embodiments, the polymeric dye has an emission maximum wavelength of 478 nm. In some embodiments, the polymeric dye has an emission maximum wavelength of 480 nm. In some embodiments, the polymeric dye has an emission maximum wavelength of 485 nm. In some embodiments, the polymeric dye has an emission maximum wavelength of 496 nm. In some embodiments, the polymeric dye has an emission maximum wavelength of 510 nm. In some embodiments, the polymeric dye has an emission maximum wavelength of 570 nm. In some embodiments, the polymeric dye has an emission maximum wavelength of 602 nm. In some embodiments, the polymeric dye has an emission maximum wavelength of 650 nm. In some embodiments, the polymeric dye has an emission maximum wavelength of 711 nm. In some embodiments, the polymeric dye has an emission maximum wavelength of 737 nm. In some embodiments, the polymeric dye has an emission maximum wavelength of 750 nm. In some embodiments, the polymeric dye has an emission maximum wavelength of 786 nm. In some embodiments, the polymeric dye has an emission maximum wavelength of 421 nm±5 nm. In some embodiments, the polymeric dye has an emission maximum wavelength of 510 nm±5 nm. In some embodiments, the polymeric dye has an emission maximum wavelength of 570 nm±5 nm. In some embodiments, the polymeric dye has an emission maximum wavelength of 602 nm±5 nm. In some embodiments, the polymeric dye has an emission maximum wavelength of 650 nm±5 nm. In some embodiments, the polymeric dye has an emission maximum wavelength of 71 nm±5 nm. In some embodiments, the polymeric dye has an emission maximum wavelength of 786 nm±5 nm. In some embodiments, the polymeric dye has an emission maximum selected from the group consisting of 421 nm, 510 nm, 570 nm, 602 nm, 650 nm, 711 nm and 786 nm.

In some embodiments, the polymeric dye has an extinction coefficient of $1\times10^6$ $cm^{-1}M^{-1}$ or more, such as $2\times10^6$ $cm^{-1}M^{-1}$ or more, $2.5\times10^6$ $cm^{-1}M^{-1}$ or more, $3\times10^6$ $cm^{-1}M^{-1}$ or more, $4\times10^6$ $c^{m-1}M^{-1}$ or more, $5\times10^6$ $cm^{-1}M^{-1}$ or more, $6\times10^6$ $cm^{-1}M^{-1}$ or more, $7\times10^6$ $cm^{-1}M^{-1}$ or more, or $8\times10^6$ $cm^{-1}M^{-1}$ or more. In some embodiments, the polymeric dye has a quantum yield of 0.05 or more, such as 0.1 or more, 0.15 or more, or more, 0.25 or more, 0.3 or more, 0.35 or more, 0.4 or more, 0.45 or more, 0.5 or more, 0.6 or more, 0.7 or more, 0.8 or more, 0.9 or more, 0.95 or more, 0.99 or more and including 0.999 or more. For example, the quantum yield of polymeric dyes of interest may range from 0.05 to 1, such as from 0.1 to 0.95, such as from 0.15 to 0.9, such as from 0.2 to 0.85, such as from 0.25 to 0.75, such as from 0.3 to 0.7 and including a quantum yield of from 0.4 to 0.6. In some embodiments, the polymeric dye has a quantum yield of 0.1 or more. In some embodiments, the polymeric dye has a quantum yield of or more. In some embodiments, the polymeric dye has a quantum yield of 0.5 or more. In some embodiments, the polymeric dye has a quantum yield of 0.6 or more. In some embodiments, the polymeric dye has a quantum yield of 0.7 or more. In some embodiments, the polymeric dye has a quantum yield of 0.8 or more. In some embodiments, the polymeric dye has a quantum yield of 0.9 or more. In some embodiments, the polymeric dye has a quantum yield of 0.95 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

In some embodiments, the label comprises a fluorophore, a chromophore, a polypeptide, a protein, an enzyme, an enzyme substrate, a catalyst, a redox label, a radiolabels, an acoustic label, a Raman (SERS) tag, a mass tag, an isotope tag, a magnetic particle, a microparticle, a nanoparticle, an oligonucleotide, or any combination thereof. In some embodiments, the label comprises an enzyme, an enzyme substrate, or a combination thereof, and wherein the enzyme is capable of modifying the enzyme substrate into a corresponding modified enzyme substrate.

In some embodiments, the enzyme substrate differs from the corresponding modified enzyme substrate by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, borinate, or any combination thereof.

In some embodiments, the enzyme comprises a methyltransferase, a glycoside hydrolase, a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, a xylosidase, or a combination thereof.

In some embodiments, the enzyme substrate comprises 6-mercaptopurine, cellobiose, cellotetraose, xylotetraose, isoprimeverose, β-D-gentiobiose, xyloglucan and mannotriose, agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

In embodiments, the activated biomolecules and activated labels for preparing the labeled biomolecule reagent in accordance with the labeled biomolecule reagent request are obtained from the storage. The storage may have 10 or more different activated biomolecules, such as 25 or more, such as 50 or more, such as 100 or more, such as 250 or more, such as 500 or more and including 1000 or more activated biomolecules. In one example, the storage includes 10 or more different activated oligonucleotides, such as 25 or more, such as 50 or more, such as 100 or more, such as 250 or more, such as 500 or more and including 1000 or more activated oligonucleotides. In another example the storage includes 10 or more different activated polypeptides, such as 25 or more, such as 50 or more, such as 100 or more, such as 250 or more, such as 500 or more and including 1000 or more activated polypeptides.

The storage may also include 10 or more different activated labels, such as 15 or more, such as 20 or more, such as 30 or more, such as 40 or more and including 50 or more different activated labels.

Each of the plurality of activated biomolecules and activated labels may be present in the storage in any suitable container capable of storing and providing the activated biomolecule or activated label when desired. In some embodiments, the plurality of different activated biomolecules and plurality of different activated labels are stored in a single reservoir partitioned into separate reagent chambers. In other embodiments, each of the plurality of different activated biomolecules and plurality of different activated labels are stored in individual containers (e.g., bottles, jugs, etc.) In yet other embodiments, each of the plurality of different activated biomolecules and plurality of different activated labels are stored in a plurality of vials, where each vial includes pre-measured aliquots of each activated biomolecule and each activated label. Each container in the storage may also include a label identifying the components of the activated biomolecule or activated label (e.g., name, structure, CAS registry number, ascension number, probe sequence, etc. of the biomolecule, label and reactive linker) The label may also include one or more machine readable components such as a Quick Response (QR) code or a bar code.

In some embodiments, the storage also includes a database of available activated biomolecules and activated labels. The database may be a printed catalog in paper or electronic form or may be a searchable electronic database, such as searchable by keyword, chemistry structure, ascension number, monomer sequence (e.g., amino acid or nucleotide sequence) or by CAS chemical registry number.

Utility

The subject systems and methods find use in preparing complex biological reagents (e.g., biological macromolecules coupled to detectable markers)—a process that is generally time consuming, financially inefficient and extraordinarily labor intensive when conducted on a large scale. The present disclosure provides a fast, efficient and highly scalable process for delivering high quality and performance specific products across a wide range of biomolecule and detectable label portfolios.

The systems and methods described herein also provide a unique and new way to request and provide customized biological reagents. In addition being able to choose pre-synthesized reagents from an extensive database (e.g., an online database), the subject systems and methods provide for user customization, where the user can create any desired labeled biomolecule on-demand. By simply choosing a biological macromolecule and a detectable marker on an easy-to-use graphical interface, a user can request any labeled biomolecule, which are used in a variety of different research applications and in medical diagnosis.

The present disclosure also provides access to large portfolios of complex biological reagents that are not possible when prepared by small scale synthesis. The subject systems and methods are scalable facilitating the preparation, on-demand, of thousands of different combinations of biomolecules and detectable markers. In some embodiments, the subject systems provide fully automated protocols so that the preparation of customized detectable biomolecule probes requires little, if any human input.

The present disclosure also finds use in applications where cell analysis from a biological sample may be desired for research, laboratory testing or for use in therapy. In some embodiments, the subject methods and systems may facilitate analysis of cells obtained from fluidic or tissue samples such as specimens for diseases such as cancer. Methods and systems of the present disclosure also allow for analyzing cells from a biological sample (e.g., organ, tissue, tissue fragment, fluid) with enhanced efficiency and low cost as compared to using probe compositions synthesized de novo.

EXAMPLES

Some aspects of the embodiments discussed above are disclosed in further detail in the following examples, which are not in any way intended to limit the scope of the present disclosure.

Example 1

Oligonucleotides for Conjugation with Protein Binding Reagents

This example demonstrates designing of oligonucleotides that can be conjugated with protein binding reagents. The oligonucleotides can be used to determine protein expression and gene expression simultaneously.

95mer Oligonucleotide Design

The following method was used to generate candidate oligonucleotide sequences and corresponding primer sequences for simultaneous determination of protein expression and gene expression.

1. Sequence Generation and Elimination

The following method was used to generate candidate oligonucleotide sequences for simultaneous determination of protein expression and gene expression.

1a. Randomly generate a number of candidate sequences (50,000 sequences) with the desired length (45 bps).

1b. Append the transcriptional regulator LSRR sequence to the 5' end of the sequences generated and a poly(A) sequence (25 bps) to the 3' end of the sequences generated.

1c. Remove sequences generated and appended that do not have GC contents in the range of 40% to 50%.

1d. Remove remaining sequences with one or more hairpin structures each.

The number of remaining candidate oligonucleotide sequences was 423.

2. Primer Design

The following method was used to design primers for the remaining 423 candidate oligonucleotide sequences.

2.1 N1 Primer: Use the universal N1 sequence: GTTGTCAAGATGCTACCGTTCAGAG (LSRR sequence; SEQ ID NO. 5) as the N1 primer.

2.2 N2 Primer (for amplifying specific antibody oligonucleotides: e.g., N2 primer in FIG. 18):

2.2a. Remove candidate N2 primers that do not start downstream of the N1 sequence.

2.2b. Remove candidate N2 primers that overlap in the last 35 bps of the candidate oligonucleotide sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT) to minimize or avoid primer-primer interactions.

Of the 423 candidate oligonucleotide sequences, N2 primers for 390 candidates were designed.

3. Filtering

The following method was used to filter the remaining 390 candidate primer sequences.

3a. Eliminate any candidate oligonucleotide sequence with a random sequence ending in As (i.e. the effective length of the poly(A) sequence is greater than 25 bps) to keep the poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 18 panel (a) shows a non-limiting exemplary candidate oligonucleotide sequence generated using the method above.

200mer Oligonucleotide Design

The following method was used to generate candidate oligonucleotide sequences and corresponding primer sequences for simultaneous determination of protein expression and gene expression.

1. Sequence Generation and Elimination

The following was used to generate candidate oligonucleotide sequences for simultaneous determination of protein expression and gene expression.

1a. Randomly generate a number of candidate sequences (100,000 sequences) with the desired length (128 bps).

1b. Append the transcriptional regulator LSRR sequence and an additional anchor sequence that is non-human, non-mouse to the 5' end of the sequences generated and a poly(A) sequence (25 bps) to the 3' end of the sequences generated.

1c. Remove sequences generated and appended that do not have GC contents in the range of 40% to 50%.

1d. Sort remaining candidate oligonucleotide sequences based on hairpin structure scores.

1e. Select 1,000 remaining candidate oligonucleotide sequences with the lowest hairpin scores.

2. Primer Design

The following method was used to design primers for 400 candidate oligonucleotide sequences with the lowest hairpin scores.

2.1 N1 Primer: Use the universal N1 sequence: GTTGT-CAAGATGCTACCGTTCAGAG (LSRR sequence; SEQ ID NO. 5) as the N1 primer.

2.2 N2 Primer (for amplifying specific antibody oligonucleotides: e.g., N2 primer in FIG. 18):

2.2a. Remove candidate N2 primers that do not start 23 nts downstream of the N1 sequence (The anchor sequence was universal across all candidate oligonucleotide sequences).

2.2b. Remove candidate N2 primers that overlap in the last 100 bps of the target sequence. The resulting primer candidates can be between the 48th nucleotide and 100th nucleotide of the target sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT) to minimize or avoid primer-primer interactions.

2.2e. Remove N2 primer candidates that overlap in the last 100 bps of the target sequence.

Of the 400 candidate oligonucleotide sequences, N2 primers for 392 candidates were designed.

3. Filtering

The following was used to filter the remaining 392 candidate primer sequences.

3a. Eliminate any candidate oligonucleotide sequence with a random sequence ending in As (i.e. the effective length of the poly(A) sequence is greater than 25 bps) to keep the poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 18 panel (b) shows a non-limiting exemplary candidate oligonucleotide sequence generated using the method above. The nested N2 primer shown in FIG. 18 panel (b) can bind to the antibody specific sequence for targeted amplification. FIG. 18 panel (c) shows the same non-limiting exemplary candidate oligonucleotide sequence with a nested universal N2 primer that corresponds to the anchor sequence for targeted amplification. FIG. 18 panel (d) shows the same non-limiting exemplary candidate oligonucleotide sequence with a N2 primer for one step targeted amplification.

Altogether, these data indicate that oligonucleotide sequences of different lengths can be designed for simultaneous determination of protein expression and gene expression. The oligonucleotide sequences can include a universal primer sequence, an antibody specific oligonucleotide sequence, and a poly(A) sequence.

Example 2

Comparison of Detection Sensitivity with Different Antibody:Oligonucleotide Ratios This example demonstrates detection sensitivity of CD4 protein using an anti-CD4 antibody conjugated with 1, 2, or 3 oligonucleotides.

Figure 19:
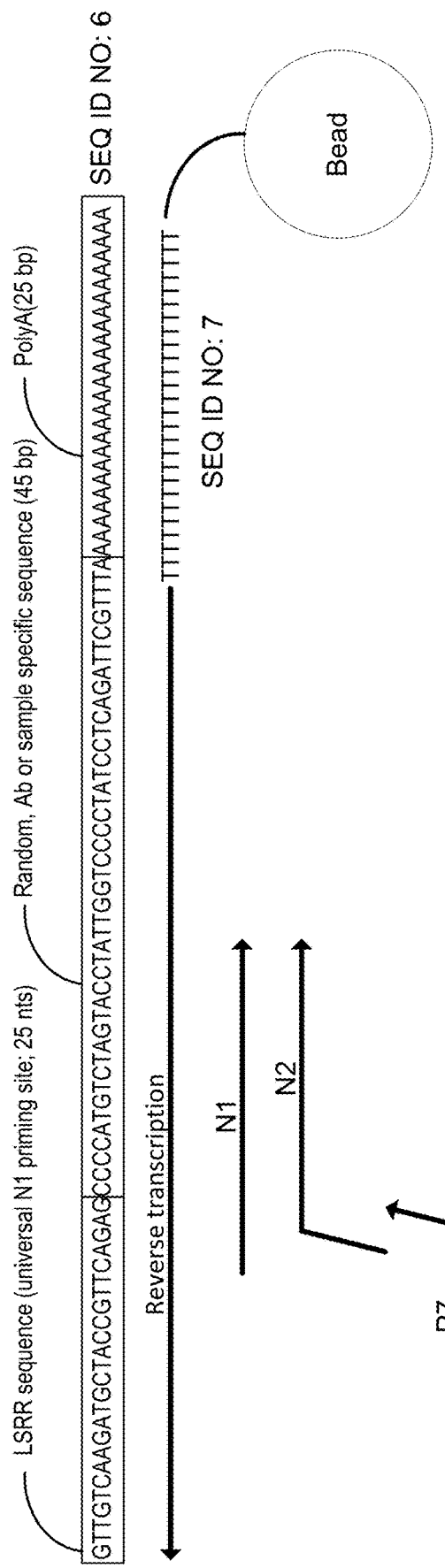
FIG. 19 shows a schematic illustration of a non-limiting exemplary oligonucleotide sequence for determining protein expression and gene expression simultaneously.

Frozen peripheral blood mononuclear cells (PBMCs) of a subject were thawed. The thawed PBMCs were stained with three types of anti-CD4 antibody at 0.06 µg/100 µl (1:333 dilution of oligonucleotide-conjugated antibody stocks) at room temperature for 20 minutes. Each type of the types of anti-CD4 antibody was conjugated with 1, 2, or 3 oligonucleotides ("antibody oligonucleotides"). The sequence of the antibody oligonucleotide is shown in FIG. 19. The cells were washed to remove unbound anti-CD4 antibodies. The cells were stained with Calcein AM (BD (Franklin Lake, New Jersey)) and Draq7™ (Abcam (Cambridge, United Kingdom)) for sorting with flow cytometry to obtain live cells. The cells were washed to remove excess Calcein AM and Draq7™. Single cells stained with Calcein AM (live cells) and not Draq7™ (cells that were not dead or permeabilized) were sorted, using flow cytometry, into a BD Resolve™ cartridge.

Of the wells containing a single cell and a bead, 3500 of the single cells in the wells were lysed in a lysis buffer with 5 mM DTT. The CD4 mRNA expression profile was determined using BD Resolve™ beads. The CD4 protein expression profile was determined using BD Resolve™ beads and the antibody oligonucleotides. Briefly, the mRNA molecules were released after cell lysis. The Resolve™ beads were associated with stochastic barcodes each containing a molecular label, a cell label, and a polyT region. The poly(A) regions of the mRNA molecules released from the lysed cells hybridized to the polyT regions of the stochastic barcodes. The poly(A) regions of the oligonucleotides hybridized to the polyT regions of the stochastic barcodes. The mRNA molecules were reverse transcribed using the stochastic barcodes. The antibody oligonucleotides were replicated using the stochastic barcodes. The reverse transcription and replication occurred in one sample aliquot at the same time.

The reverse transcribed products and replicated products were PCR amplified for 15 cycles at 60 degrees annealing temperature using primers for determining the mRNA expression profiles of 488 blood panel genes, using blood panel N1 primers, and the expression profile of CD4 protein, using the antibody oligonucleotide N1 primers ("PCR 1"). Excess stochastic barcodes were removed with Ampure cleanup. The products from PCR1 were divided into two aliquots, one aliquot for determining the mRNA expression profiles of the 488 blood panel genes, using the blood panel N2 primers, and one aliquot for determining the expression profile of CD4 protein, using the antibody oligonucleotide N2 primers ("PCR 2"). Both aliquots were PCR amplified for 15 cycles at 60 degrees annealing temperature. The expression of CD4 protein in the lysed cells was determined based on the antibody oligonucleotides as illustrated in FIG. 19 ("PCR 2"). Sequencing data was obtained and analyzed after sequencing adaptor ligation ("PCR 3"). Cell types were determined based on the expression profiles of the 488 blood panel genes.

Figure 20:
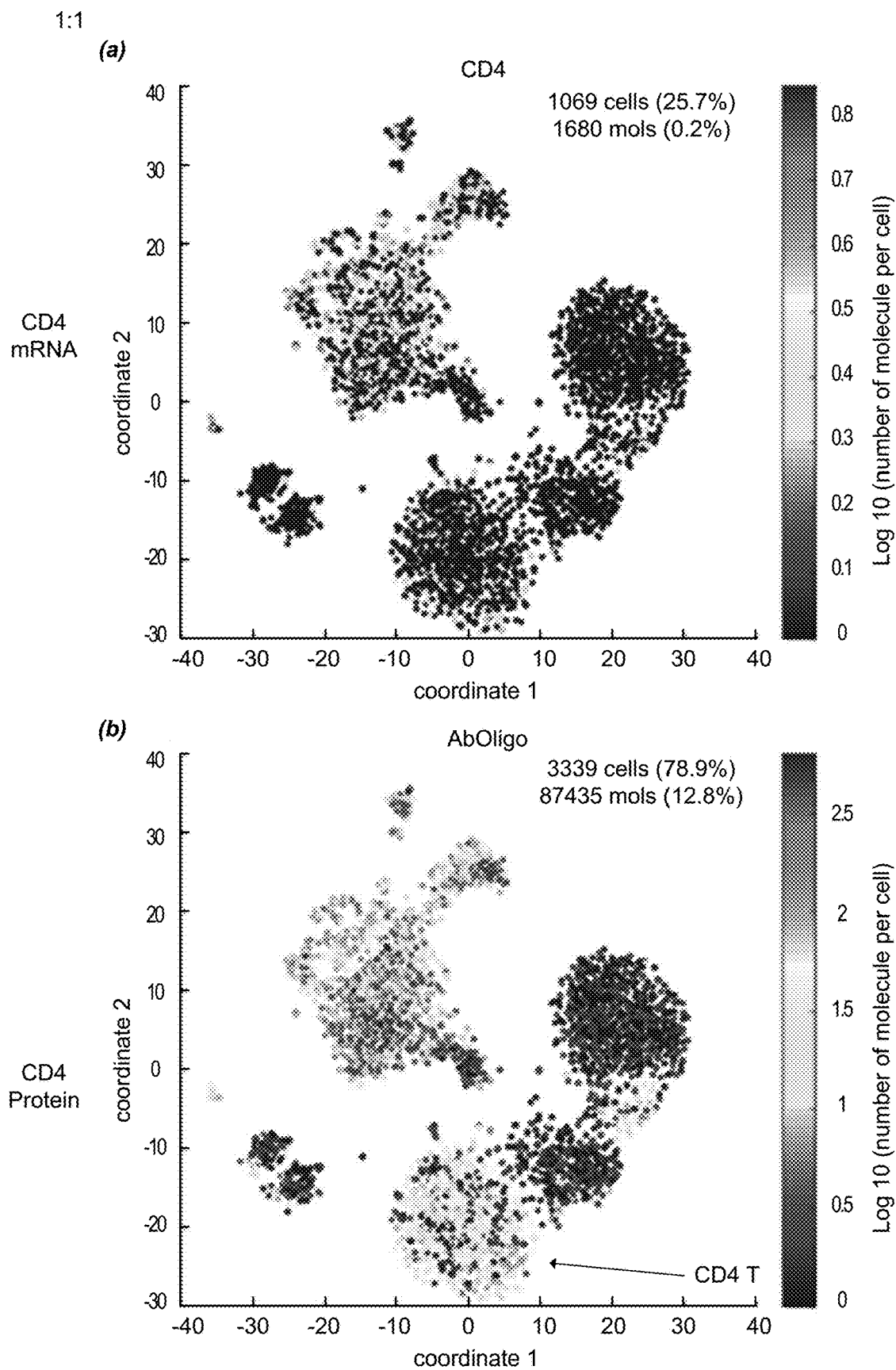
FIG. 20 panels (a)-(f) are non-limiting exemplary tSNE projection plots showing results of using oligonucleotide-conjugated antibodies to measure CD4 protein expression and gene expression simultaneously in a high throughput manner.
Figure 20:
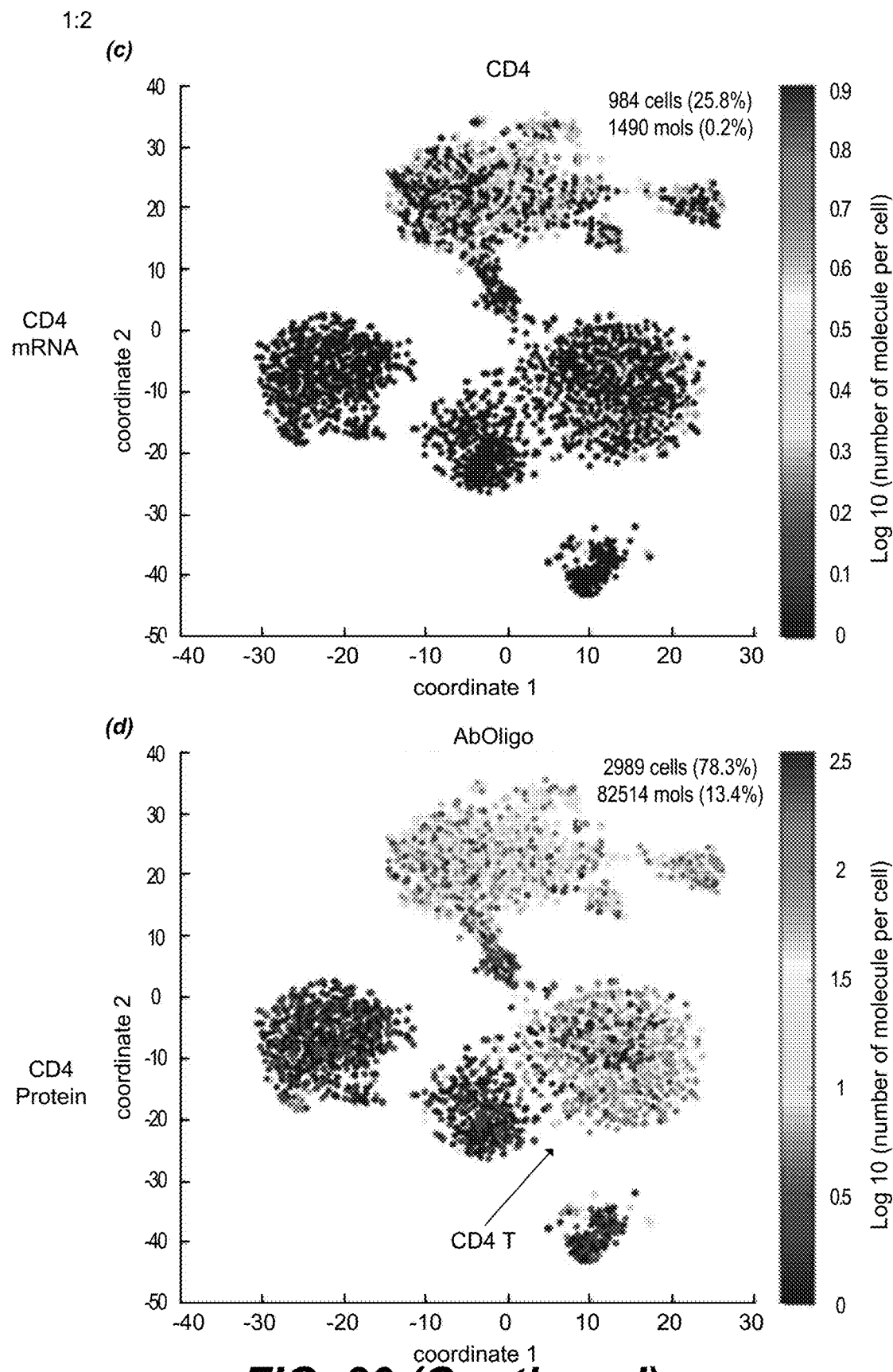
Figure 20:
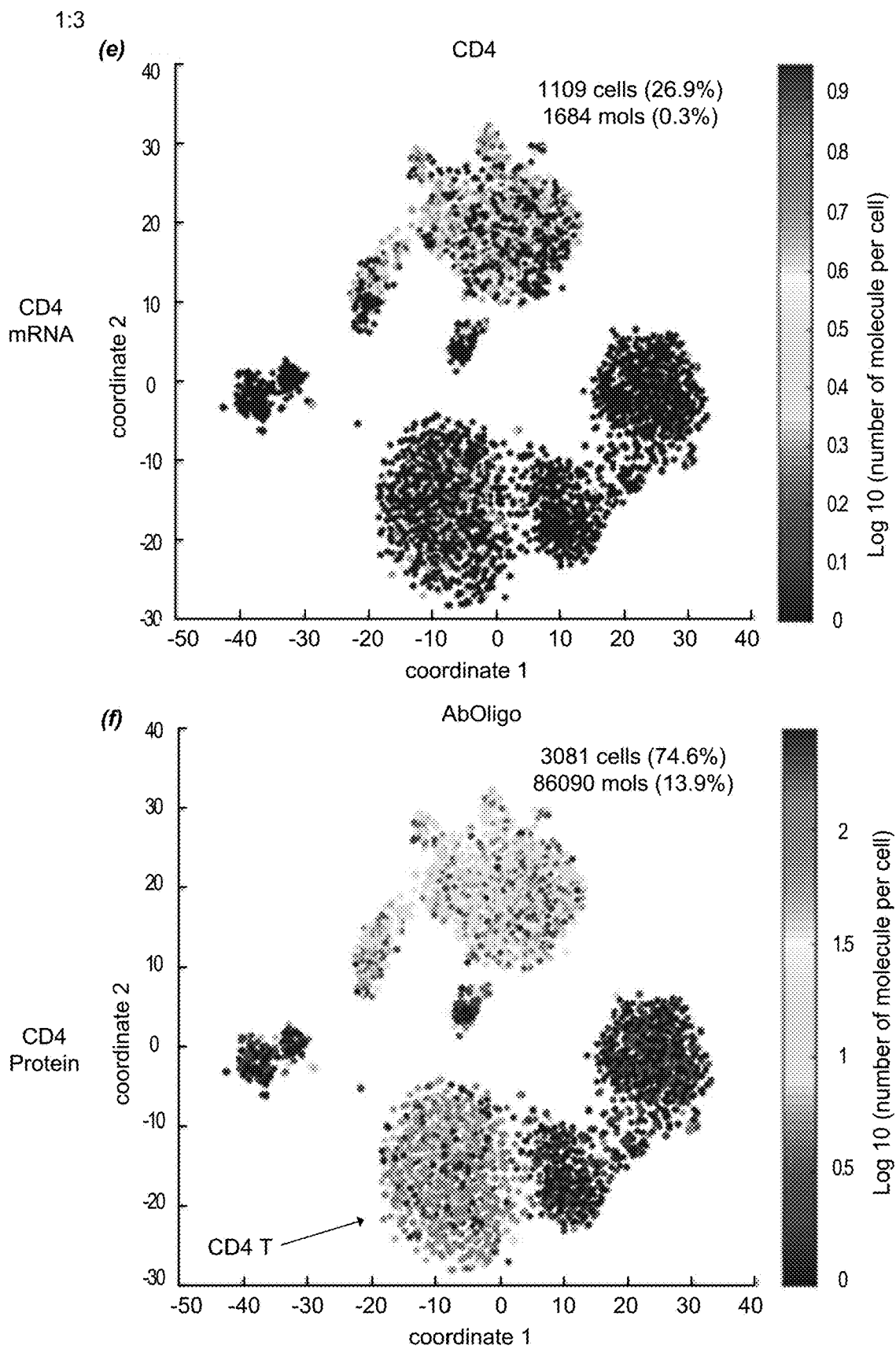
Figure 21:
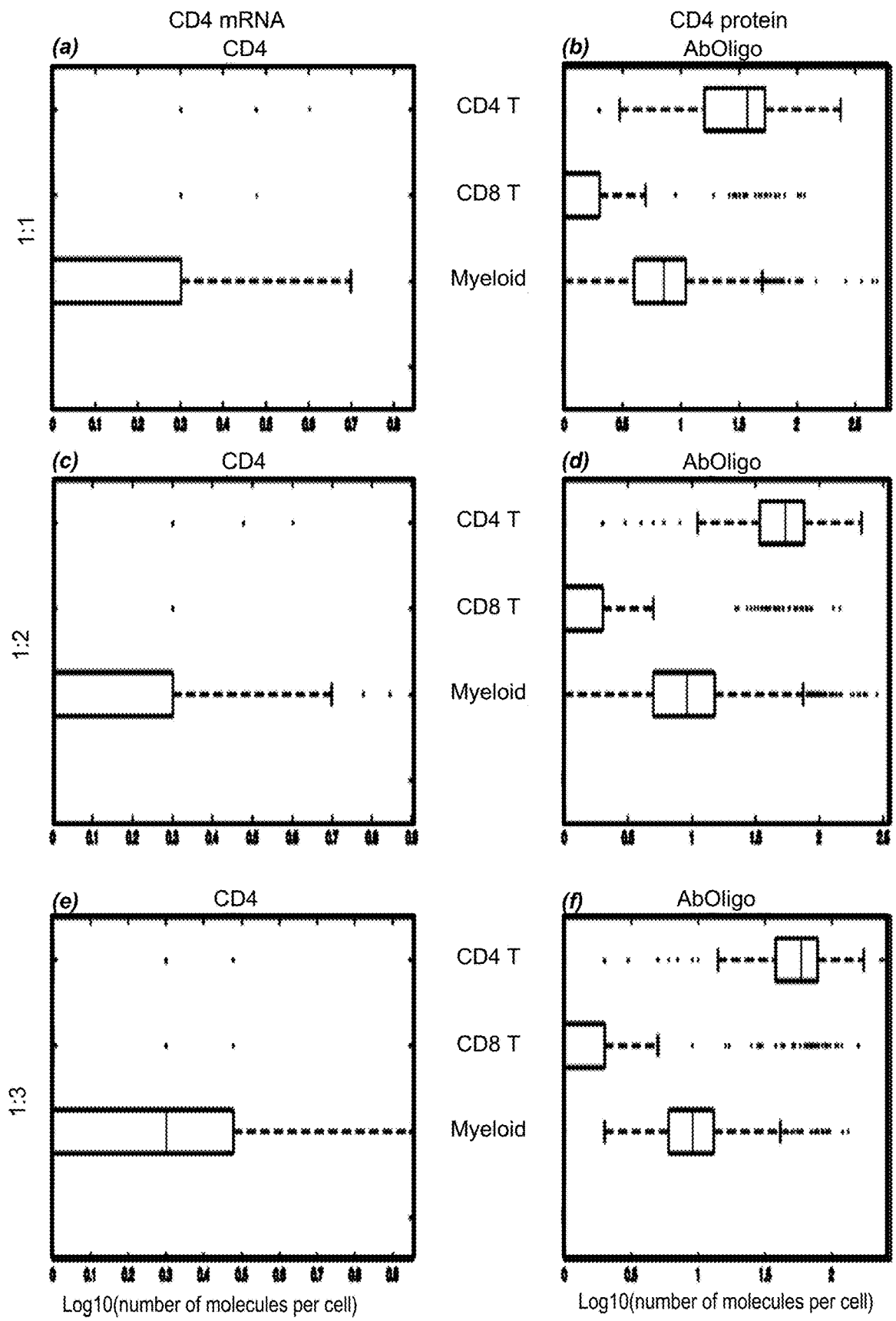
FIG. 21 panels (a)-(f) are non-limiting exemplary bar charts showing the expressions of CD4 mRNA and protein in CD4 T cells, CD8 T cells, and Myeloid cells.
Figure 22:
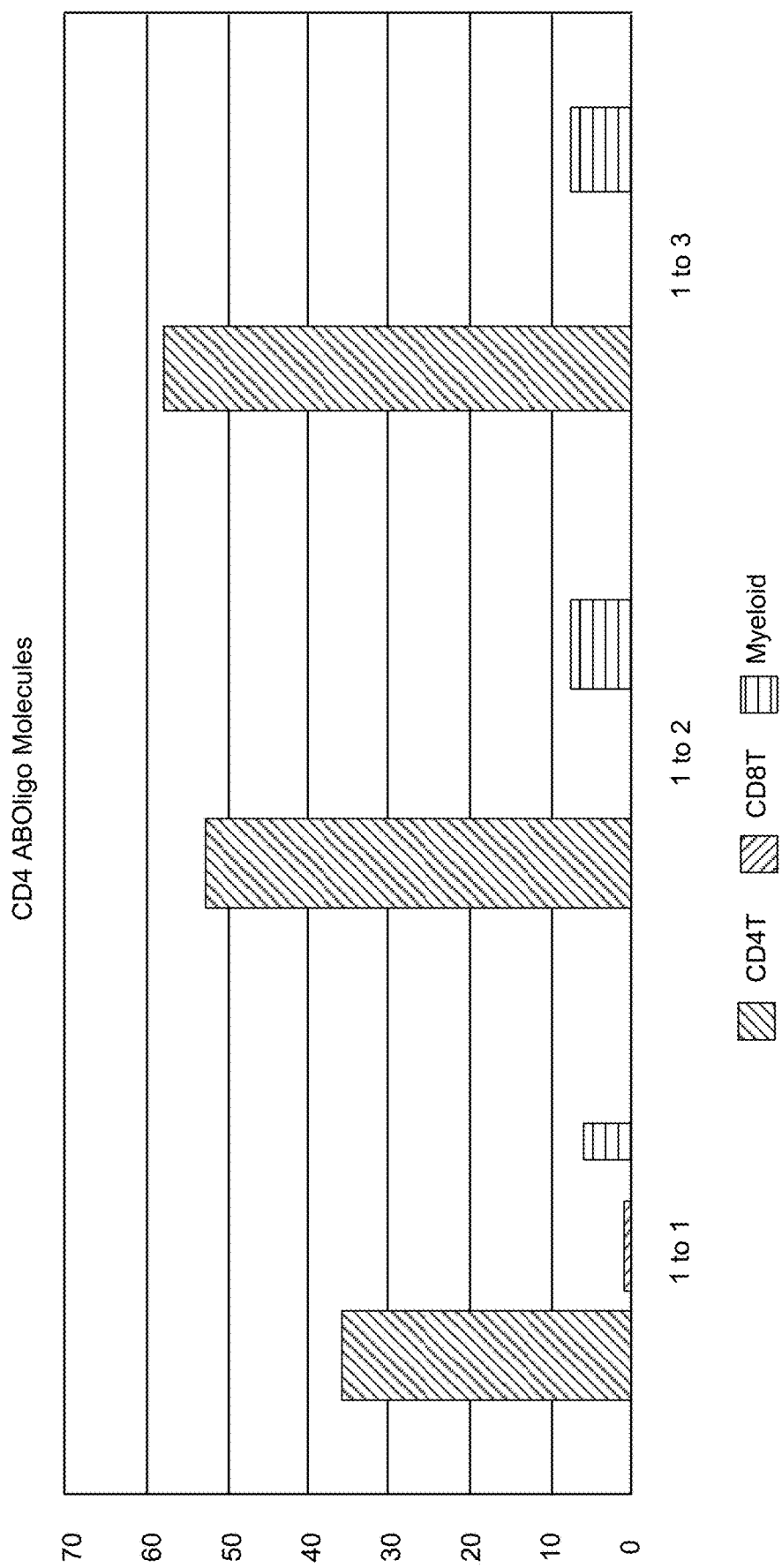
FIG. 22 is a non-limiting exemplary bar chart showing that, with similar sequencing depth, detection sensitivity for CD4 protein level increased with higher ratios of antibody:oligonucleotide, with the 1:3 ratio performing better than the 1:1 and 1:2 ratios.
Figure 23:
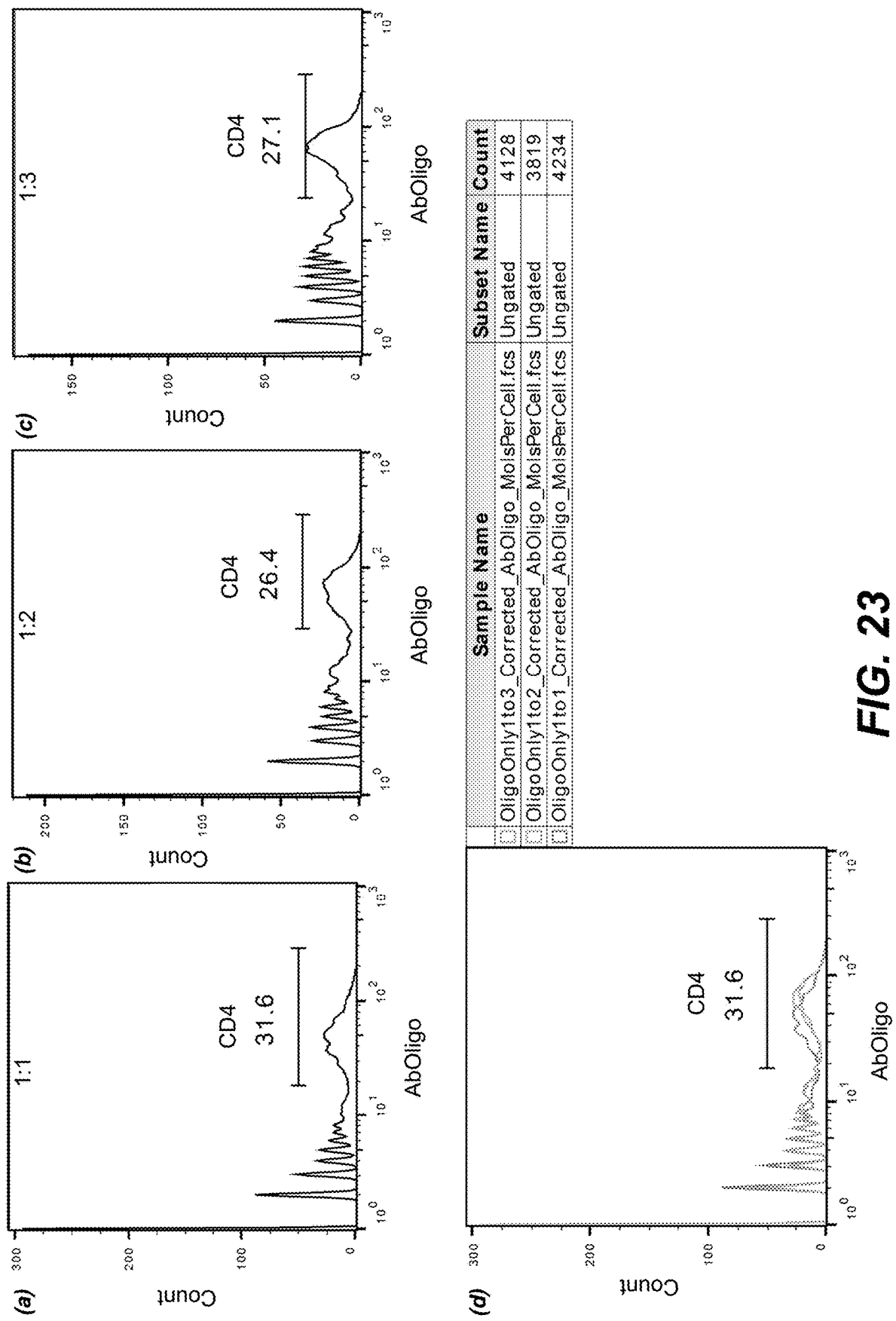
FIG. 23 panels (a)-(d) are plots showing the CD4 protein expression on cell surface of cells sorted using flow cytometry.
Figure 24:
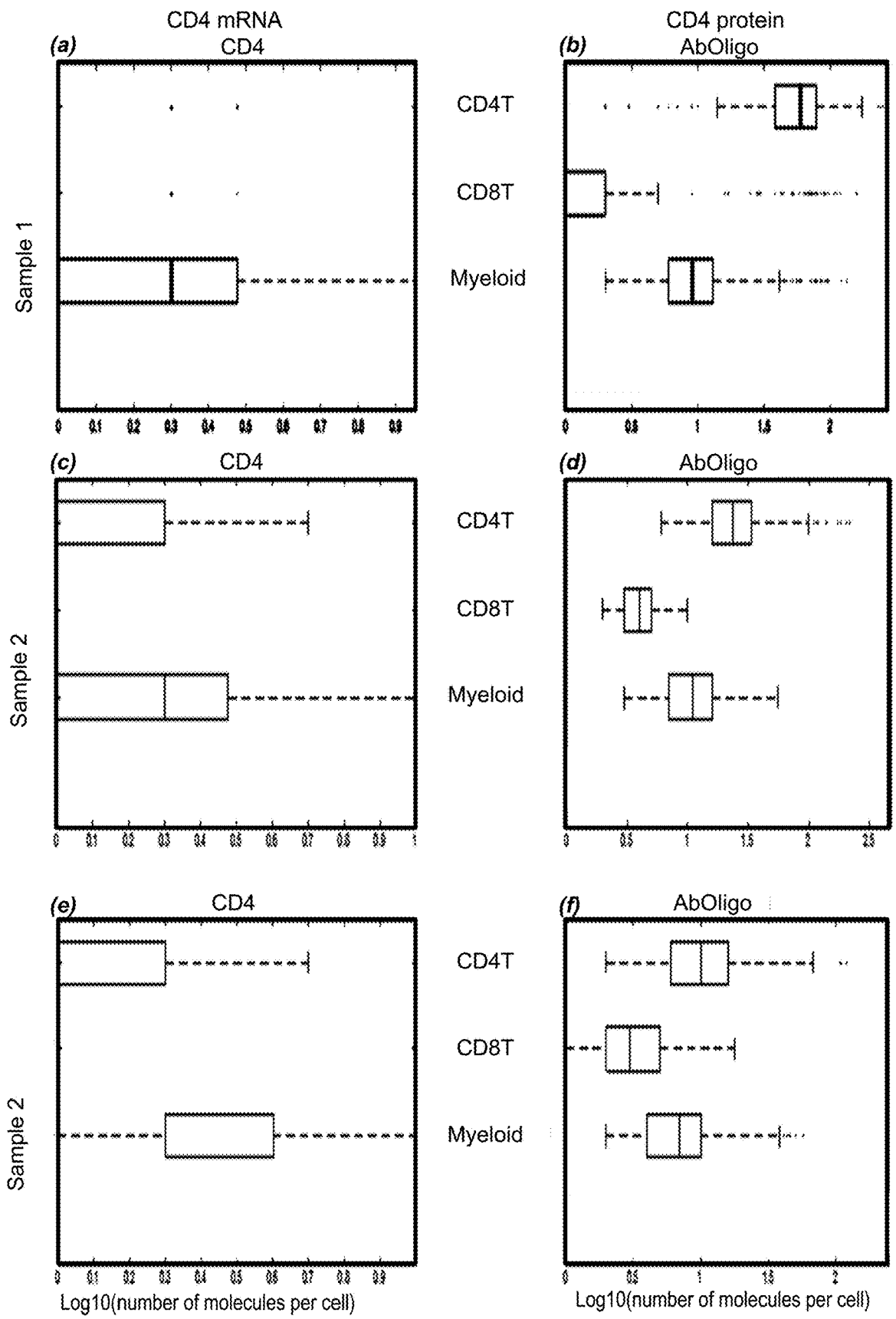
FIG. 24 panels (a)-(f) are non-limiting exemplary bar charts showing the expressions of CD4 mRNA and protein in CD4 T cells, CD8 T cells, and Myeloid cells of two samples.
Figure 25:
FIG. 25 is a non-limiting exemplary bar chart showing detection sensitivity for CD4 protein level determined using different sample preparation protocols with an antibody:oligonucleotide ratio of 1:3.

FIG. 20 panels (a)-(f) are non-limiting exemplary t-Distributed Stochastic Neighbor Embedding (tSNE) projection plots showing results of using oligonucleotide-conjugated antibodies to measure CD4 protein expression and gene expression simultaneously in a high throughput manner. CD4 protein expression was distinctly and robustly detected in CD4 expressing cell types (e.g., CD4 T cells) with anti-CD4 antibodies conjugated to 1, 2, or 3 antibody oligonucleotides (FIG. 20 panels (b), (d), and (f) respectively). FIG. 21, panels (a)-(f) are non-limiting exemplary bar charts showing the expressions of CD4 mRNA and protein in CD4 T cells (high CD4 expression), CD8 T cells (minimal CD4 expression), and Myeloid cells (some CD4 expression). With similar sequencing depth, detection sensitivity for CD4 protein level increased with higher ratios of antibody:oligonucleotide, with the 1:3 ratio performing better than the 1:1 and 1:2 ratios (FIG. 22). The expression of CD4 protein on cell surface of cells sorted using flow cytometry was confirmed using FlowJo (FlowJo (Ashland, OR)) as shown in FIG. 23 panels (a)-(d). FIG. 24 panels (a)-(f) are non-limiting exemplary bar charts showing the expressions of CD4 mRNA and CD4 protein in CD4 T cells, CD8 T cells, and Myeloid cells of two samples. The second sample was prepared using two different sample preparation protocols. FIG. 25 is a non-limiting exemplary bar chart showing detection sensitivity for CD4 protein level determined using different sample preparation protocols with an antibody:oligonucleotide ratio of 1:3.

Altogether, these data indicate that CD4 protein expression can be distinctly and robustly detected based on oligonucleotide-conjugated with anti-CD4 antibodies. Detection sensitivity for CD4 protein level can increase with higher antibody:oligonucleotide ratios.

Example 3

Hot:Cold Antibody Titration

This example demonstrates determining a ratio of oligonucleotide-conjugated antibodies ("hot antibodies") and antibodies not conjugated with oligonucleotides ("cold antibodies") such that the antibody oligonucleotides account for a desired percentage (e.g., 2%) of total reads in sequencing data.

Figure 26A:
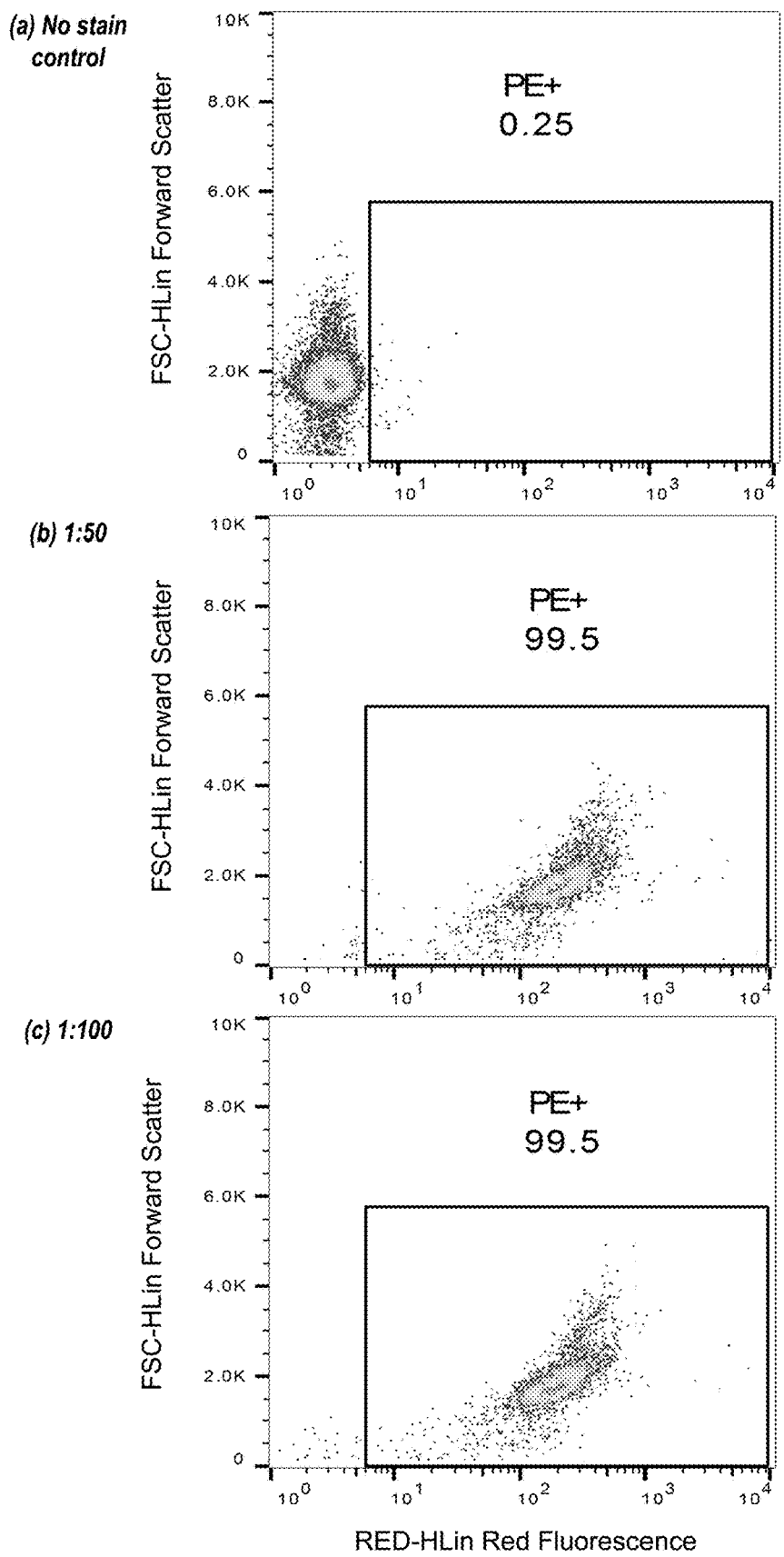
FIGS. 26A-26C are non-limiting exemplary plots showing determination of an optimal dilution of an antibody stock using dilution titration.
Figure 26A:
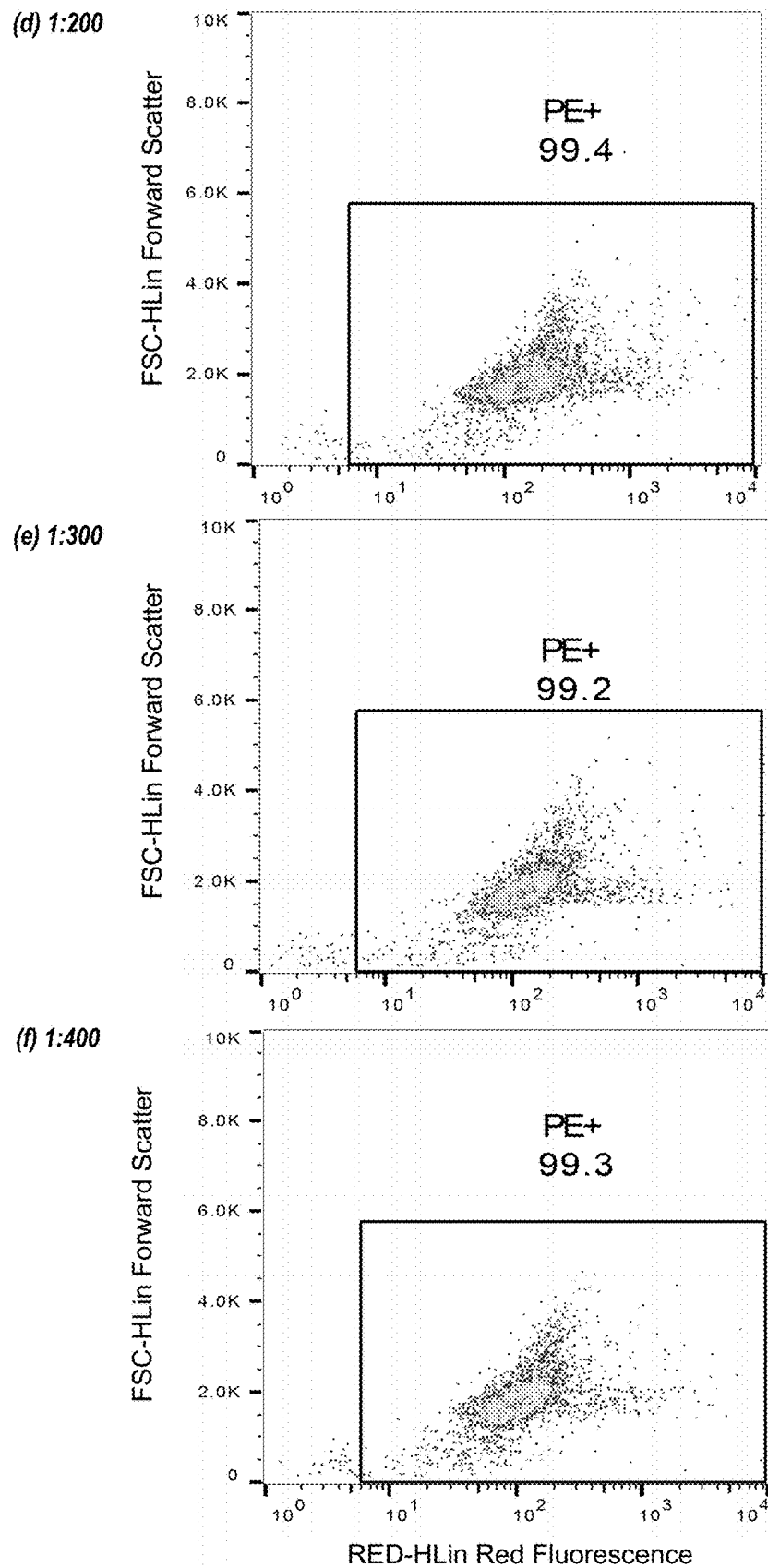
Figure 26A:
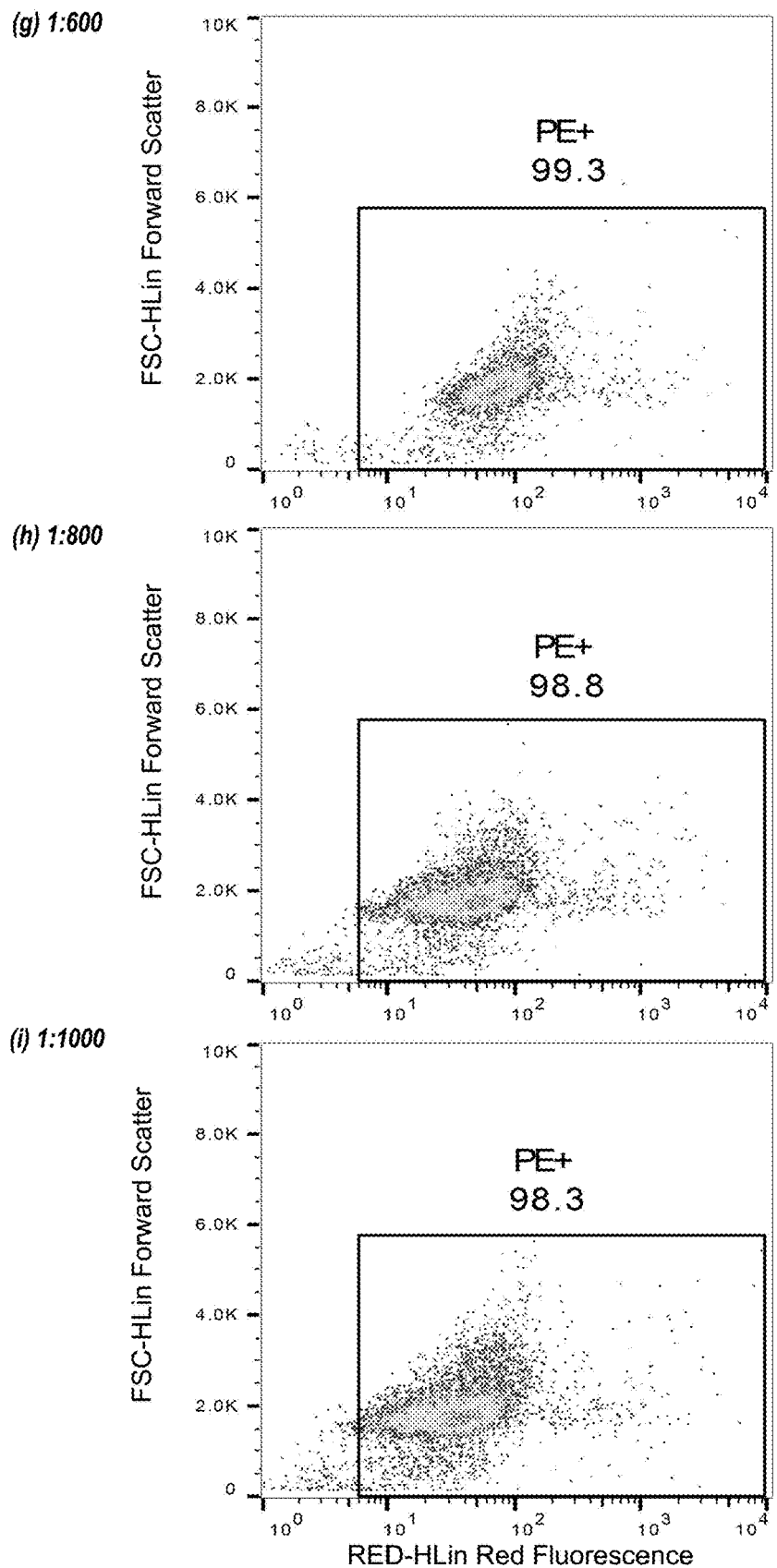
Figure 26B:
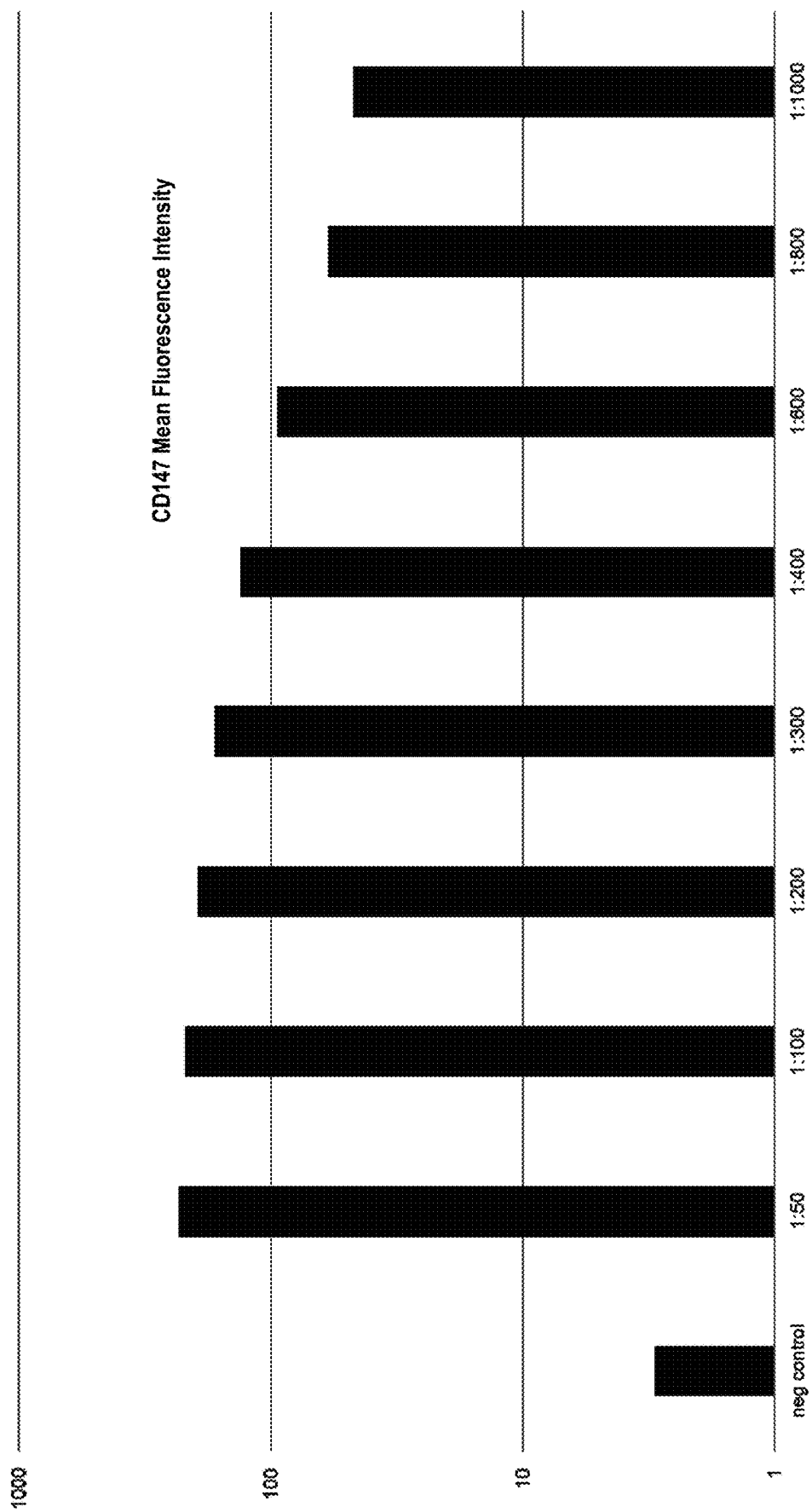
Figure 26C:
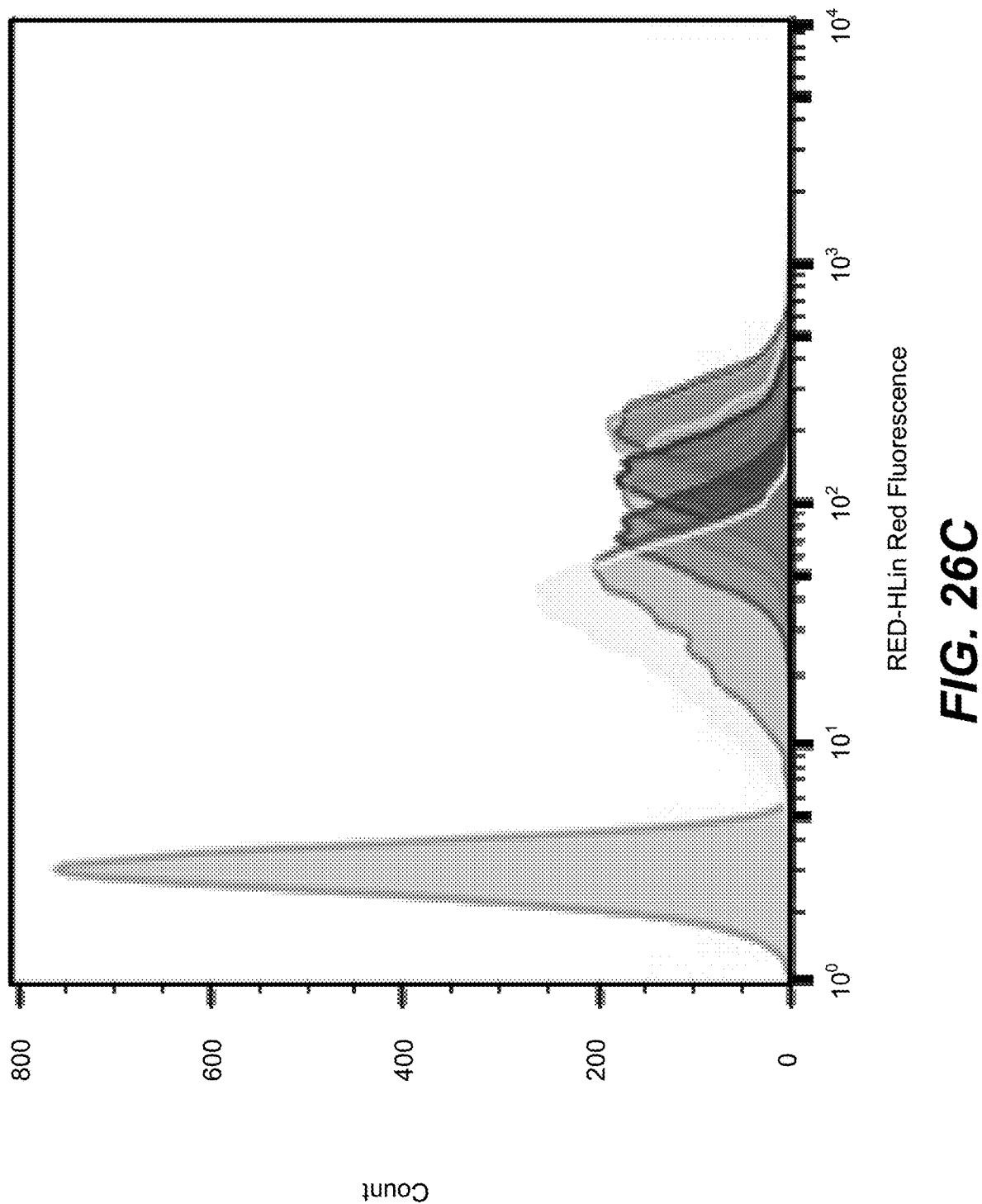

An anti-CD147 antibody stock was diluted at 1:20, 1:100, 1:200, 1:300, 1:400, 1:600, 1:800, and 1:1000 dilutions with PE buffer. Around 150,000 Jurkat cells in 100 µl of staining buffer (FBS) (BD (Franklin Lake, New Jersey)) were stained at various antibody dilutions for 20 minutes at room temperature. After staining, the cells were washed once with 500 µl of staining buffer and resuspended in 200 µl for measurement of fluorescence intensity. Muse™ Autophagy LC3-antibody (EMD Millipore (Billerica, MA)) was used to detect the anti-CD147 antibody bound to the Jurkat cells. The fluorescence intensities from cells stained at various anti-CD147 antibody dilutions or cells not stained were determined and compared to determine an optimal dilution for the antibody (FIGS. 26A-26C). Fluorescence intensity decreased with higher dilution. More than 99% of the cells were stained with a dilution ratio of 1:800. Fluorescence signals began to drop out at 1:800. Cells were stained to saturation up to a dilution ratio of 1:200. Cells were stained close to saturation up to a dilution ration of 1:400.

Figure 27:
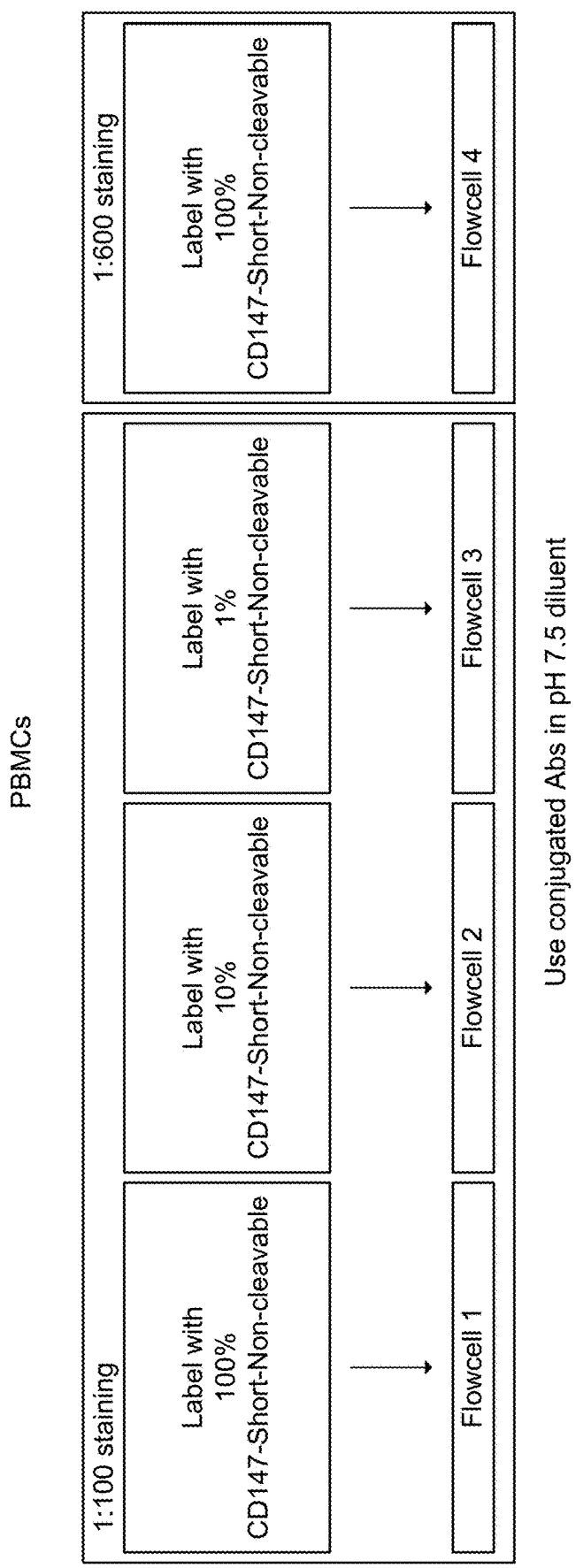
FIG. 27 shows a non-limiting exemplary experimental design for determining a staining concentration of oligonucleotide-conjugated antibodies such that the antibody oligonucleotides account for a desired percentage of total reads in sequencing data.

FIG. 27 shows a non-limiting exemplary experimental design for determining a staining concentration of oligonucleotide-conjugated antibodies such that the antibody oligonucleotides account for a desired percentage of total reads in sequencing data. An anti-CD147 antibody was conjugated with a cleavable 95mer antibody oligonucleotide at an antibody:oligonucleotide ratio of 1:3 ("hot antibody"). The hot antibody was diluted using a pH 7.5 diluent at a 1:100 ratio or a 1:800 ratio. A mixture of 10% hot antibody: 90° % cold antibody was prepared using 9 µl of cold anti-CD147 antibody and 1 µl of the hot antibody. A mixture of 1% hot antibody:90% cold antibody was prepared using 9 µl of the cold anti-CD147 antibody and 1 µl of the mixture of 10% hot antibody:90% cold antibody.

Thawed peripheral blood mononuclear cells (PBMCs) with around 0.5 million cells were stained in 100 µl of staining buffer (FBS) with the 1:100 diluted stock with 1000% hot antibody (1% of the stock hot antibody), the mixture of 10% hot antibody:90% cold antibody (0.1% of the stock hot antibody), the mixture of 1% hot antibody:99% cold antibody (0.01% of the stock hot antibody), and the 1:800 diluted stock with 100% hot antibody (0.0125% of the stock hot antibody). After staining, the cells were washed to remove unbound antibody molecules. The cells were stained with Calcein AM and Draq7™ for sorting with flow cytometry to obtain live cells. The cells were washed to remove excess Calcein AM and Draq7™. Single cells stained with Calcein AM (live cells) and not Draq7™ (cells that were not dead or permeabilized) were sorted, using flow cytometry, into a BD Resolve™ cartridge.

Of the wells containing a single cell and a bead, 1000 of the single cells in the wells were lysed in a lysis buffer. For each single cell, the mRNA molecules were reverse transcribed and the antibody oligonucleotides were replicated using stochastic barcodes conjugated with a bead for the cell. The samples after reverse transcription and replication were PCR amplified for 15 cycles at 60 degrees annealing temperature using primers for determining the mRNA expression profiles of 488 blood panel genes, using blood panel N1 primers, and the expression of CD147 protein, using the antibody oligonucleotide N1 primers ("PCR 1"). Excess primers were removed with Ampure cleanup. The products from PCR1 were further PCR amplified ("PCR 2") for 15 cycles at 60 degrees annealing temperature using blood panel N2 primers and antibody oligonucleotide N1 primers with a flanking sequence for adaptor ligation. Sequencing data was obtained and analyzed after sequencing adaptor ligation ("PCR 3").

Figure 28:
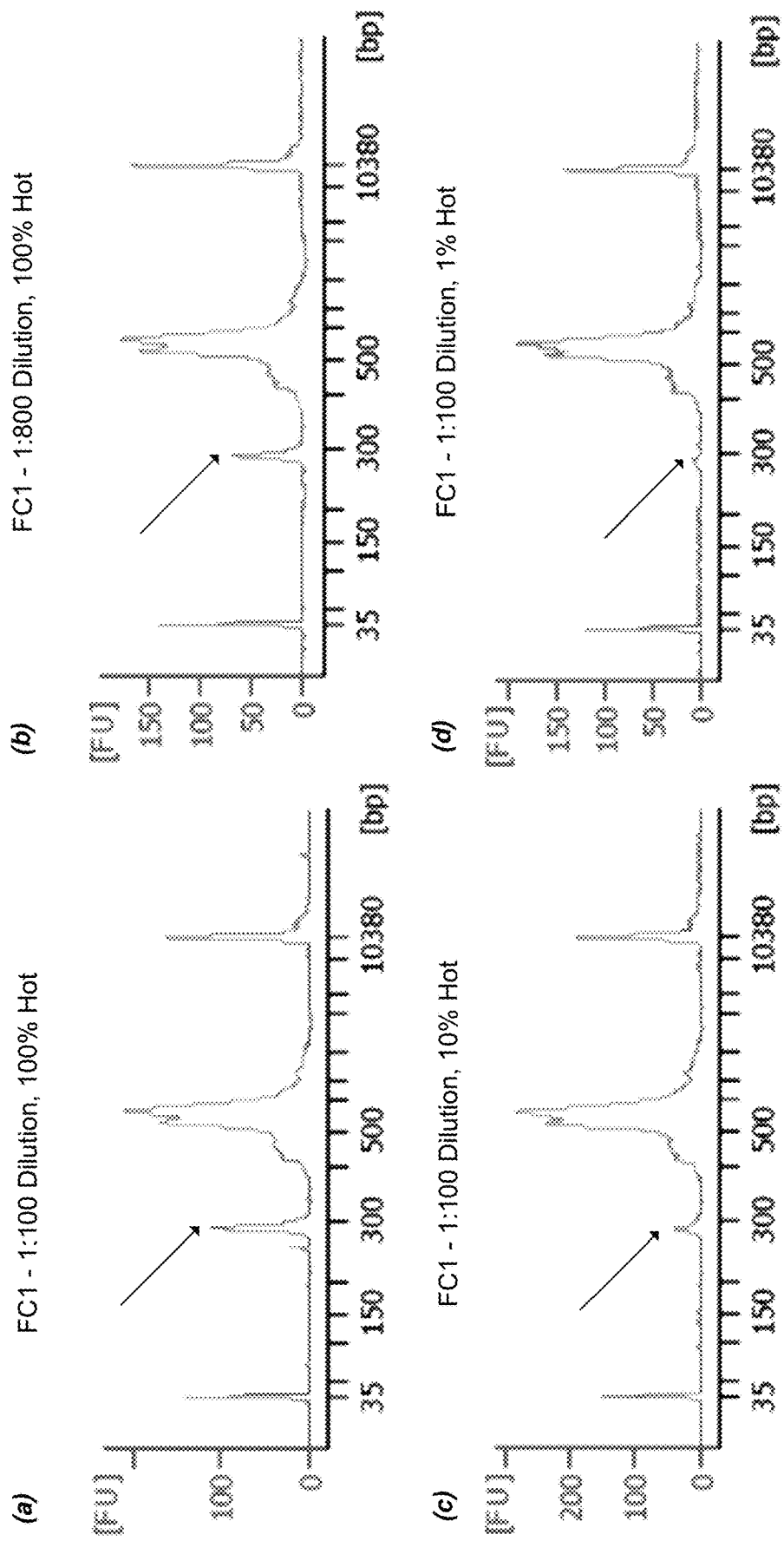
FIG. 28 panels (a)-(d) are non-limiting exemplary bioanalyzer traces showing peaks (indicated by arrows) consistent with the expected size of the antibody oligonucleotide.

FIG. 28 panels (a)-(d) are non-limiting exemplary bioanalyzer traces showing peaks (indicated by arrows) consistent with the expected size of the antibody oligonucleotide. The antibody oligonucleotide peaks decreased as the hot antibody was titrated with the cold antibody.

Figure 29:
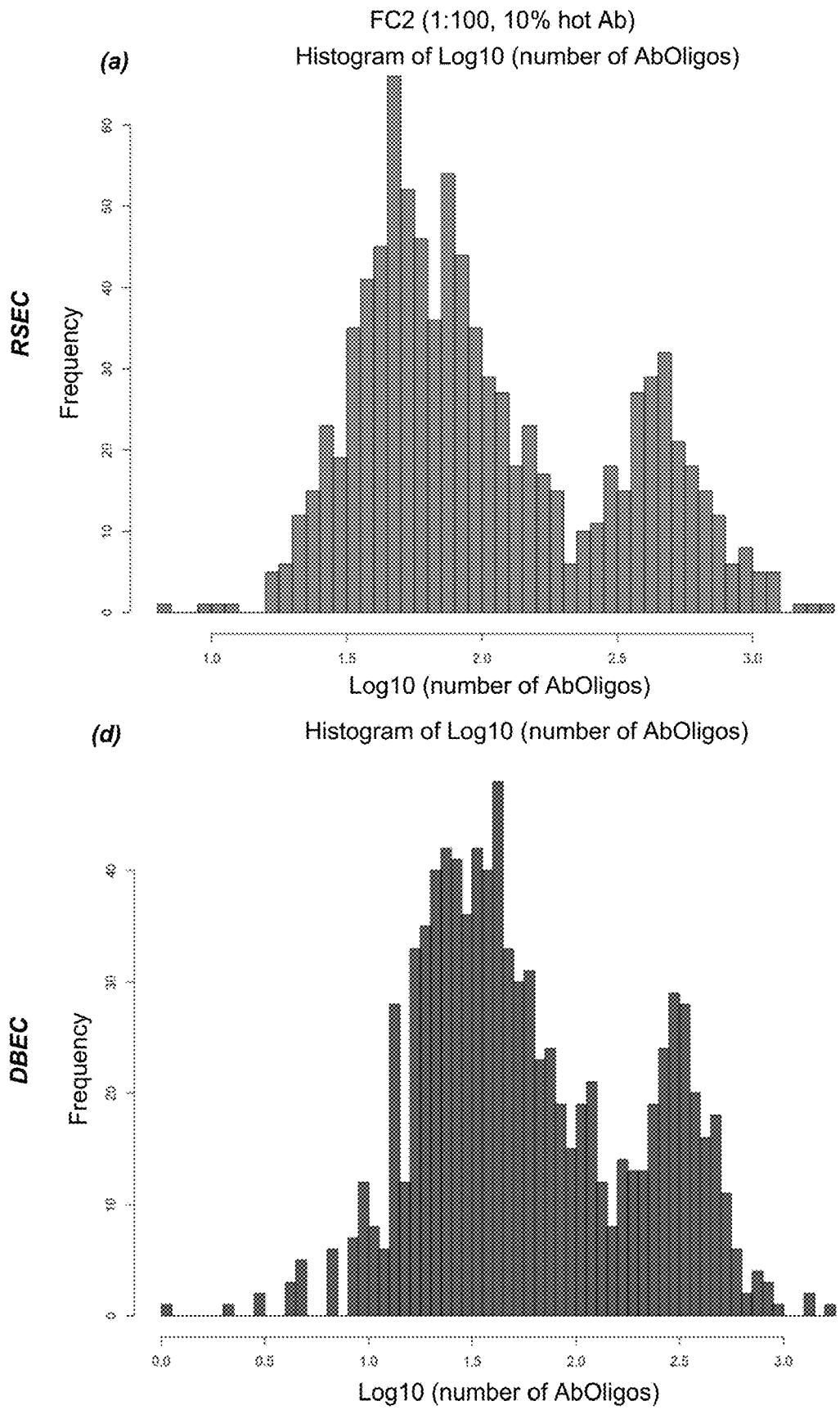
FIG. 29 panels (a)-(f) are non-limiting exemplary histograms showing the numbers of molecules of antibody oligonucleotides detected for samples stained with different antibody dilutions and different percentage of the antibody molecules conjugated with the antibody oligonucleotides ("hot antibody").
Figure 29:
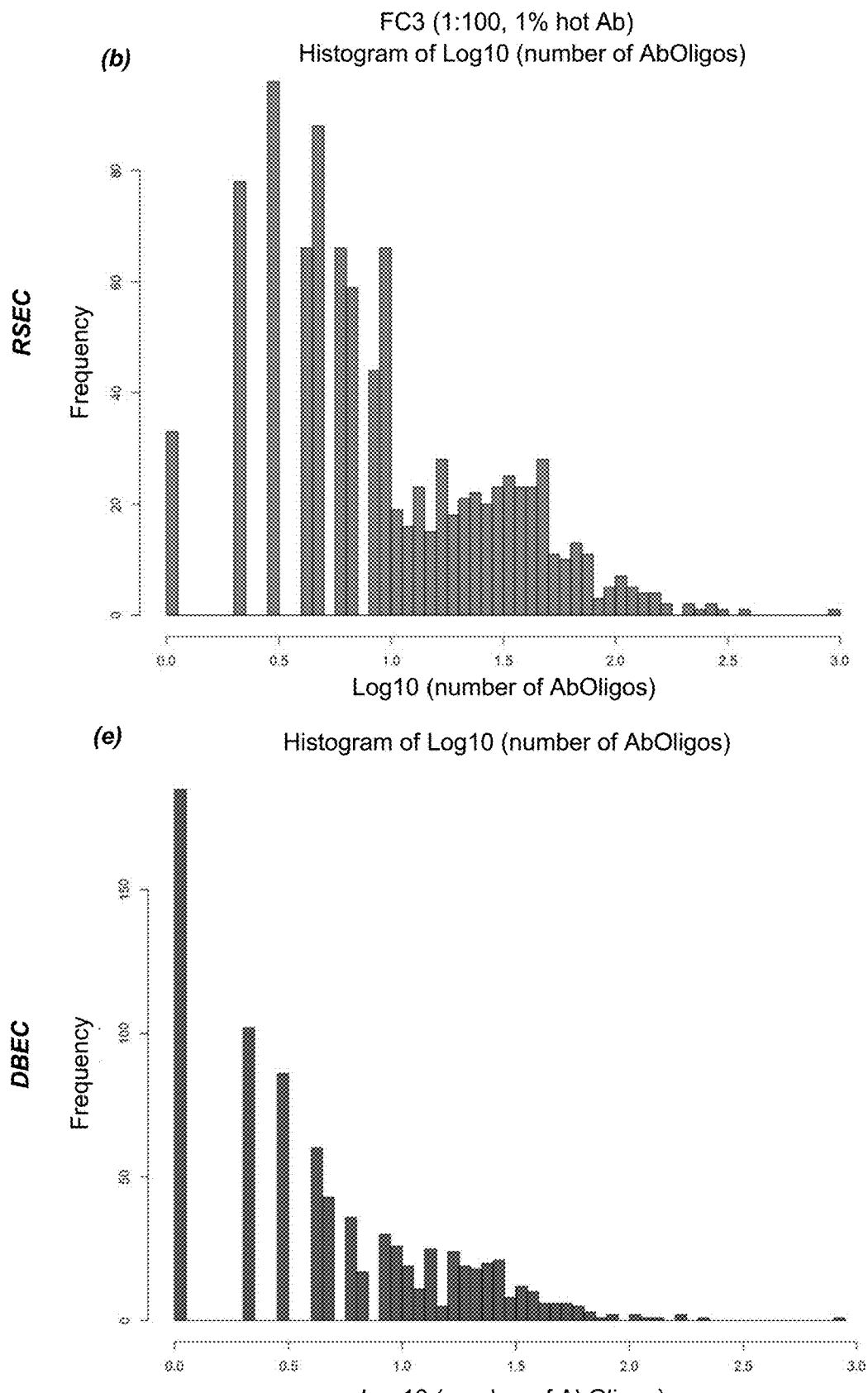
Figure 29:
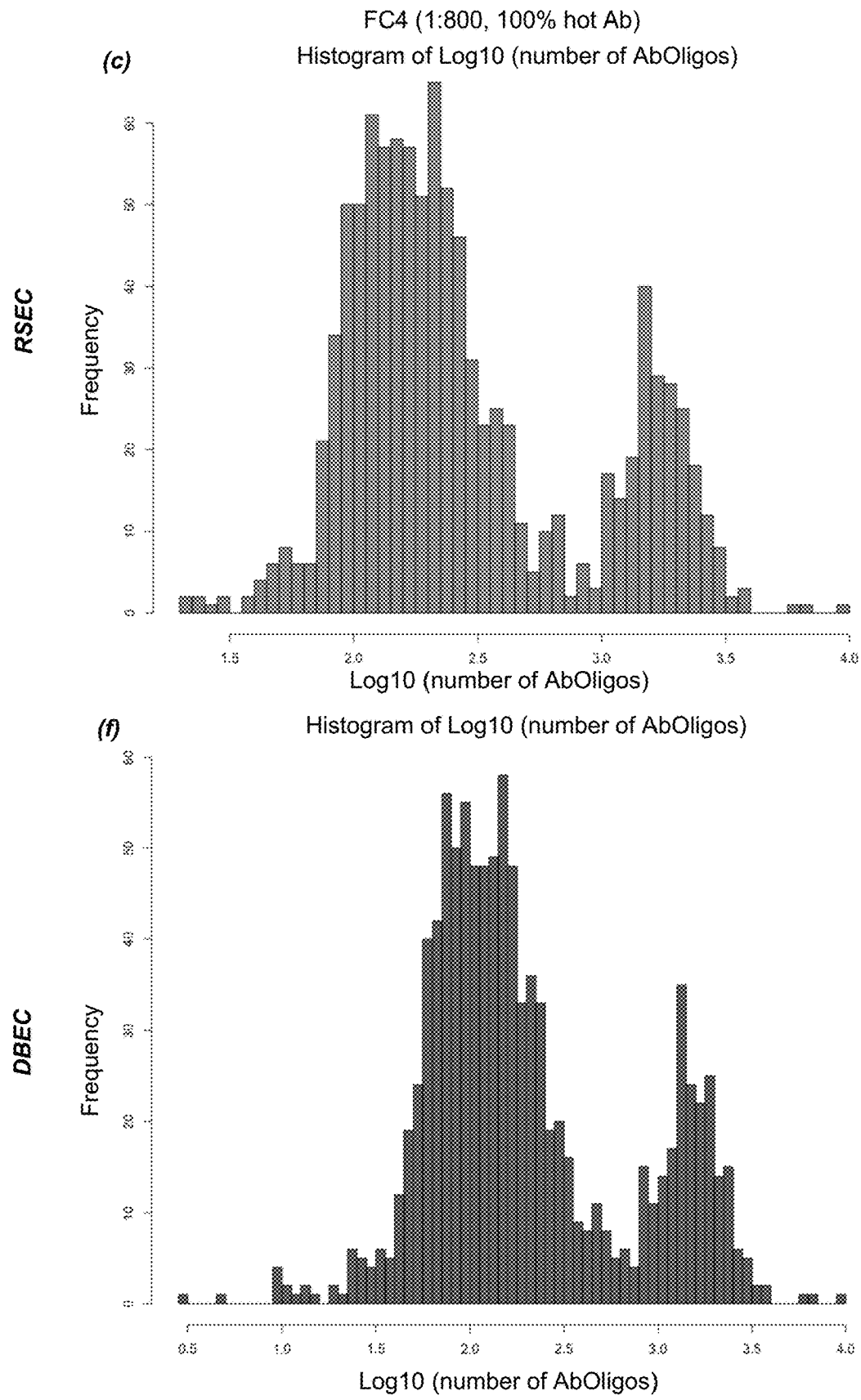

Table 1 is a summary of sequencing data metrics. By staining the cells with the mixture of 1% hot antibody:99% cold antibody prepared using the 1:100 diluted stock, the antibody oligonucleotides accounted for 2.4% of the total raw reads in the sequencing data. However, as shown in FIG. 29 panels (a)-(f) and FIGS. 30B, 31B, and 32B, a distribution histogram of the numbers of molecules of antibody oligonucleotides detected after recursive substitution error correction (RSEC) or distribution-based error correction (DBEC) did not include a clear signal peak if the cells were stained with the mixture of 1% hot antibody:99% cold antibody prepared using the 1:100 diluted stock. RSEC has been described in U.S. patent application Ser. No. 15/605,874, filed on May 25, 2017, the content of which is incorporated herein by reference in its entirety.

Figure 30A:
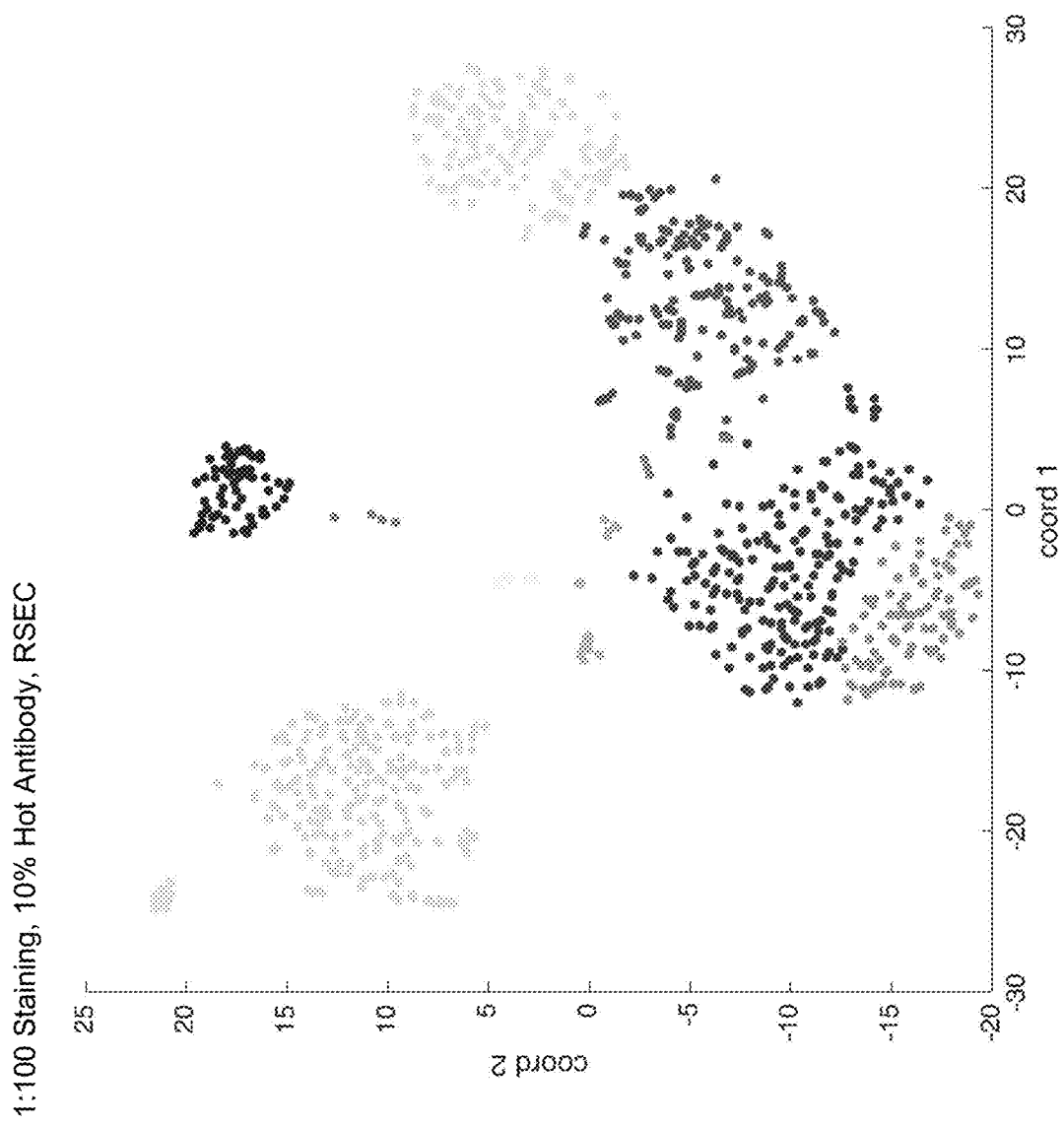
Figure 30B:
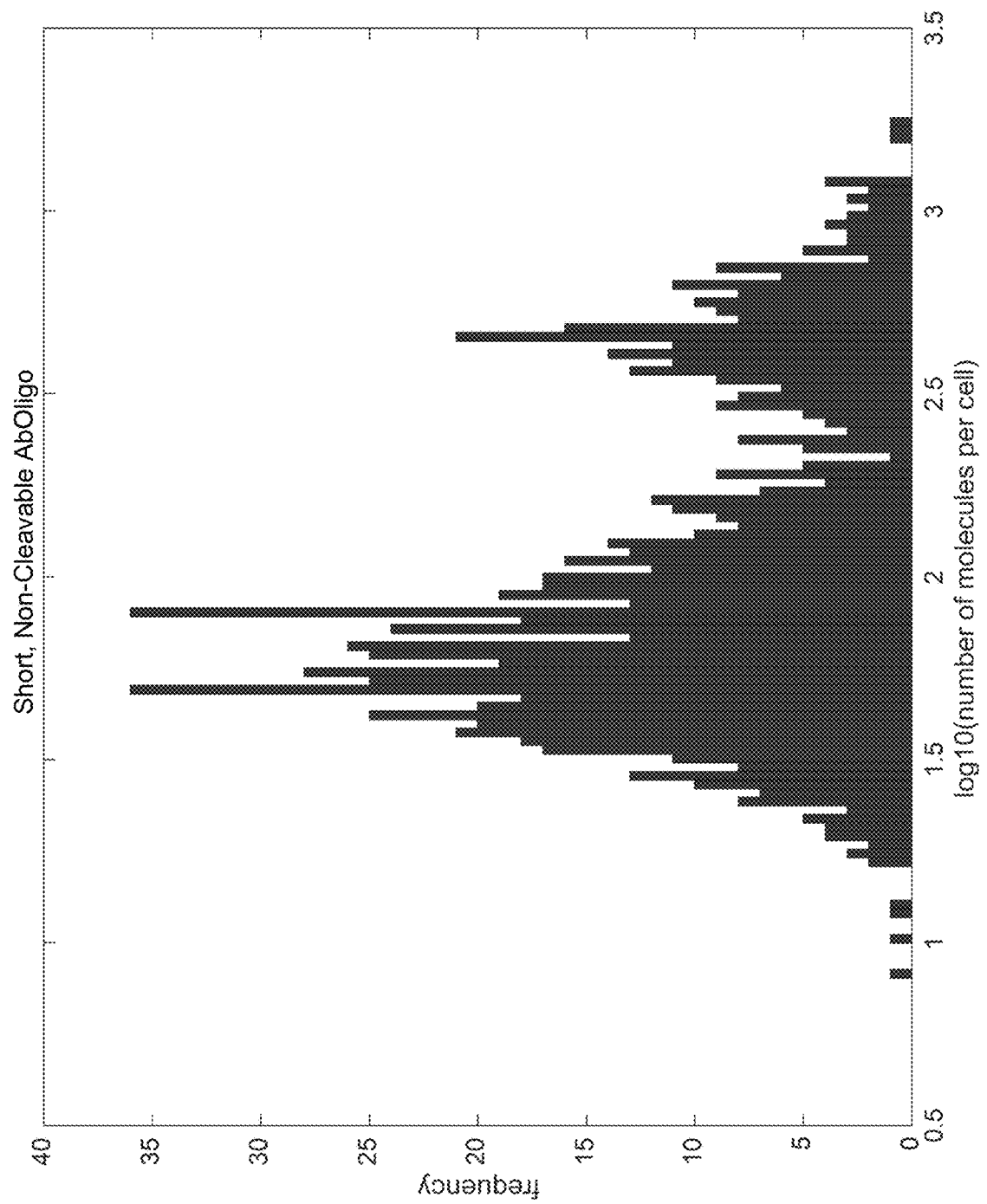

FIGS. 30A-30C are non-limiting exemplary plots showing that oligonucleotide-conjugated anti-CD147 antibody molecules can be used to label various cell types. The cell types were determined using the expression profiles of 488 genes in a blood panel (FIG. 30A). The cells were stained with a mixture of 10% hot antibody:90% cold antibody prepared using a 1:100 diluted stock, resulting in a clear signal in a histogram showing the numbers of molecules of antibody oligonucleotides detected (FIG. 30B). The labeling of the various cell types by the antibody oligonucleotide is shown in FIG. 30C.

Figure 31A:
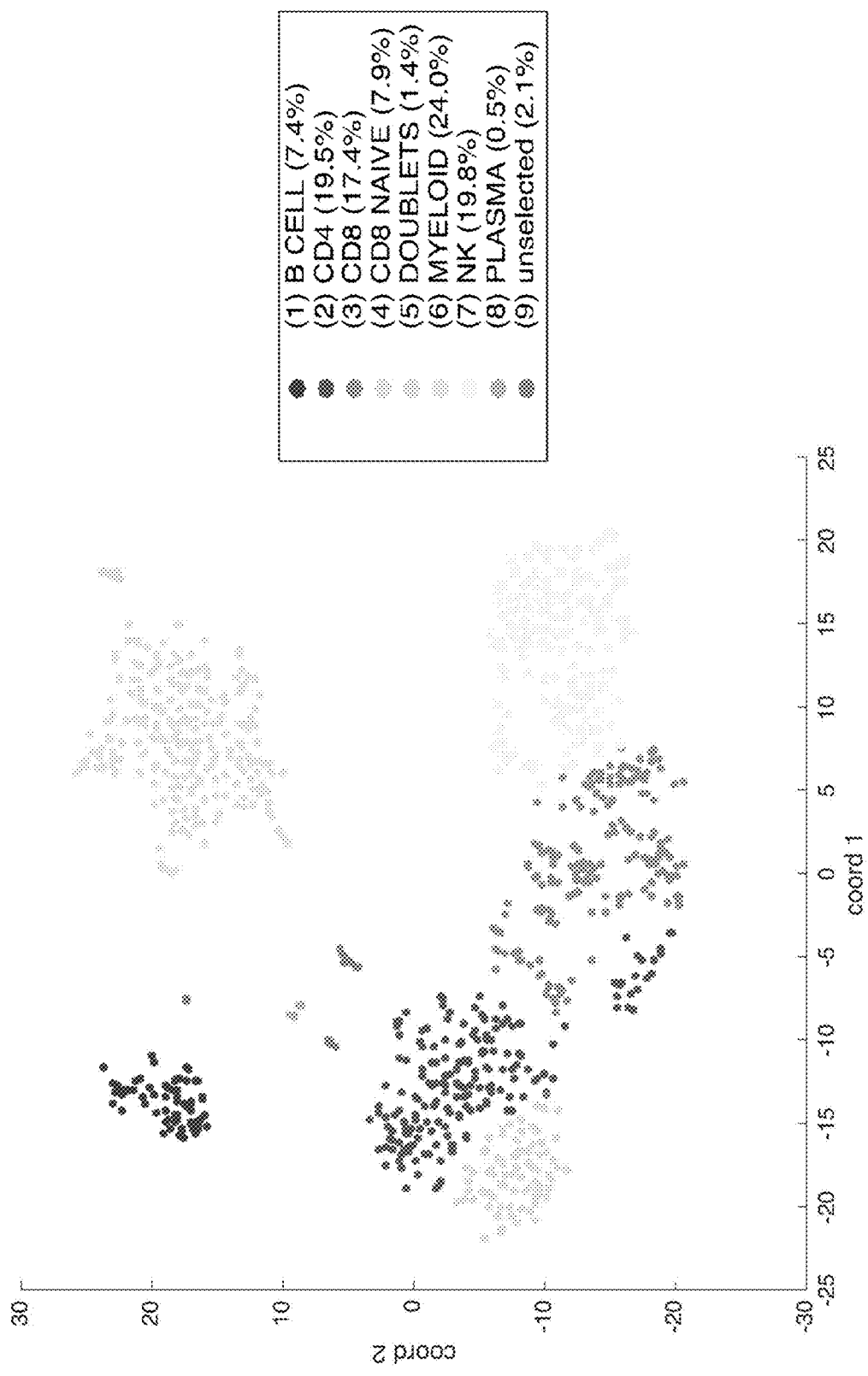
FIGS. 31A-31C are non-limiting exemplary plots showing that oligonucleotide-conjugated anti-CD147 antibodies can be used to label various cell types. The cell types were determined using the expression profiles of 488 genes in a blood panel (FIG. 31A). The cells were stained with a mixture of 1% hot antibody:99% cold antibody prepared using a 1:100 diluted stock, resulting in no clear signal in a histogram showing the numbers of molecules of antibody oligonucleotides detected (FIG. 31B). The labeling of the various cell types by the antibody oligonucleotide is shown in FIG. 31C.
Figure 31B:
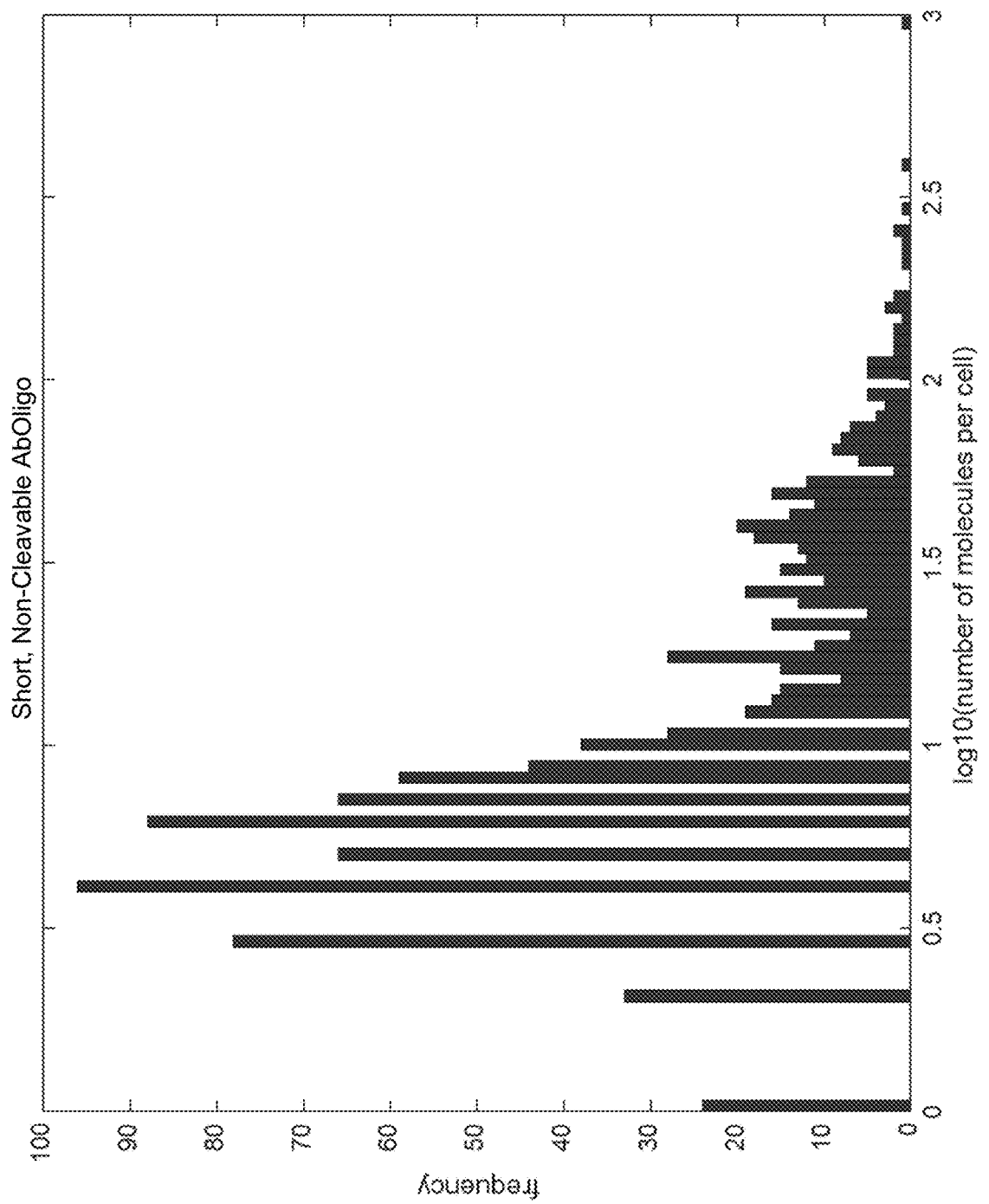
Figure 31C:
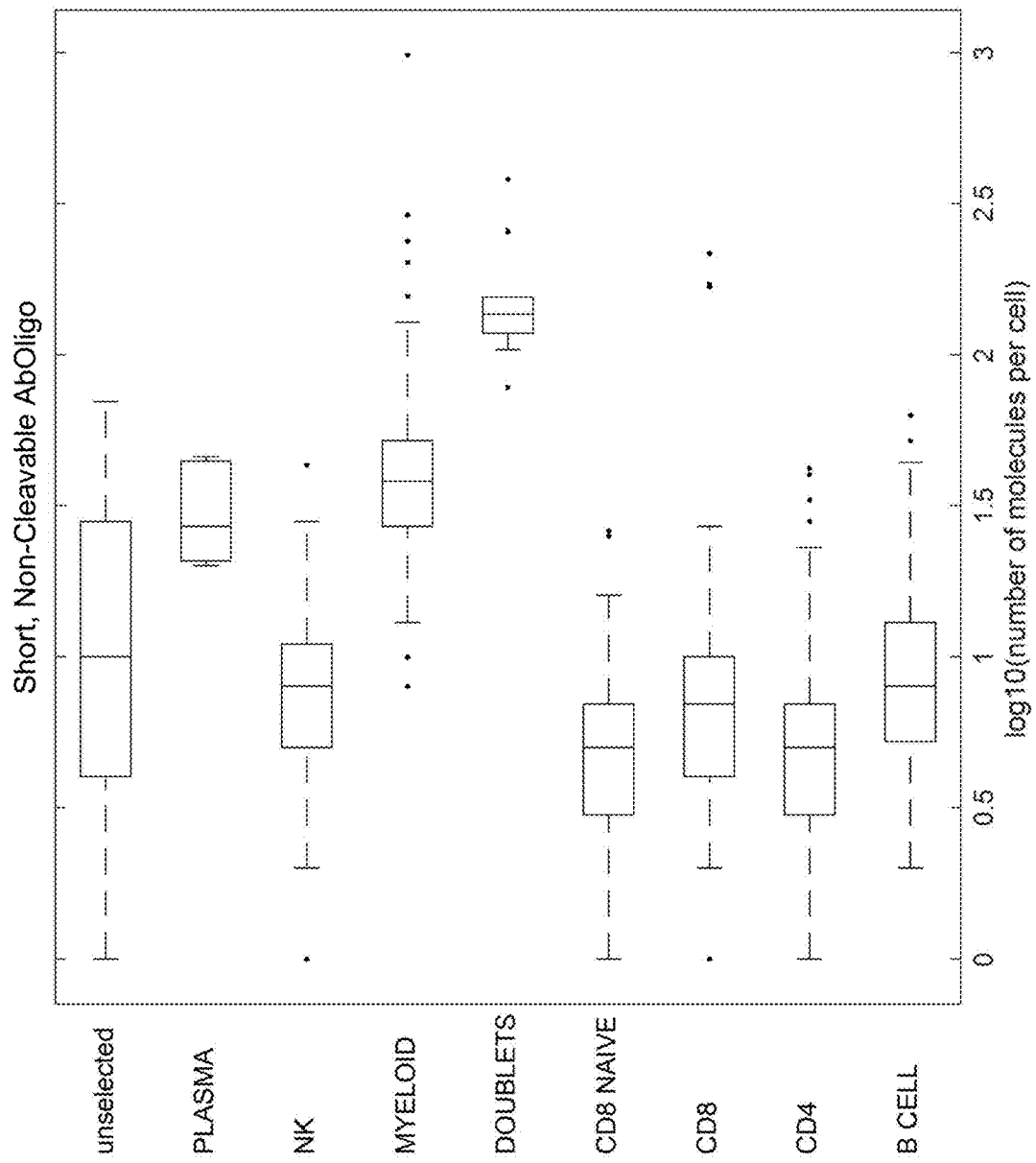

FIGS. 31A-31C are non-limiting exemplary plots showing that oligonucleotide-conjugated anti-CD147 antibodies can be used to label various cell types. The cell types were determined using the expression profiles of 488 genes in a blood panel (FIG. 31A). The cells were stained with a mixture of 1% hot antibody:99% cold antibody prepared using a 1:100 diluted stock, resulting in no clear signal in a histogram showing the numbers of molecules of antibody oligonucleotides detected (FIG. 31B). The labeling of the various cell types by the antibody oligonucleotide is shown in FIG. 31C.

Figure 32A:
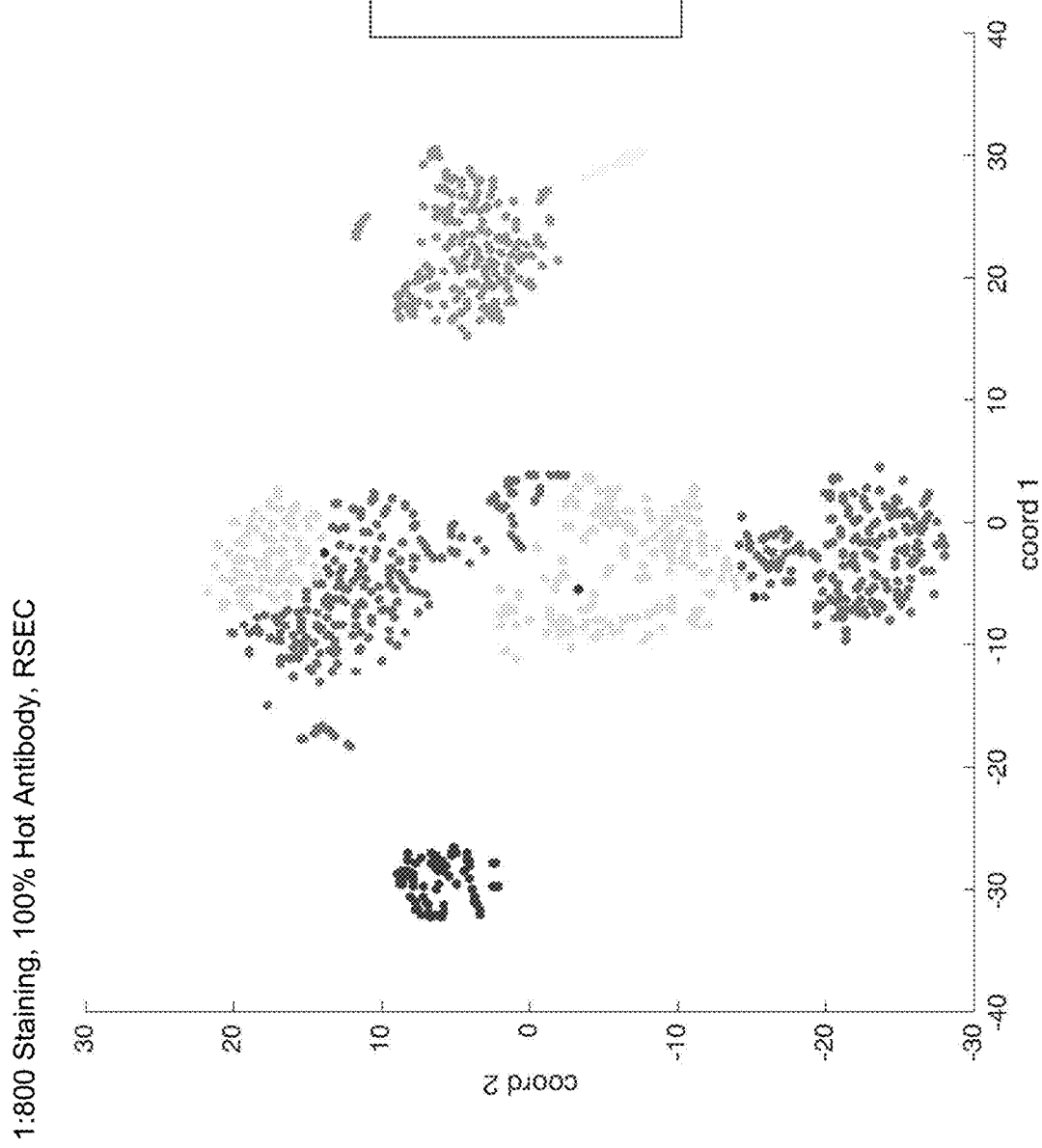
FIGS. 32A-32C are non-limiting exemplary plots showing that oligonucleotide-conjugated anti-CD147 antibody molecules can be used to label various cell types. The cell types were determined using the expression profiles of 488 genes in a blood panel (FIG. 32A). The cells were stained with a 1:800 diluted stock, resulting in a clear signal in a histogram showing the numbers of molecules of antibody oligonucleotides detected (FIG. 32B). The labeling of the various cell types by the antibody oligonucleotide is shown in FIG. 32C.
Figure 32B:
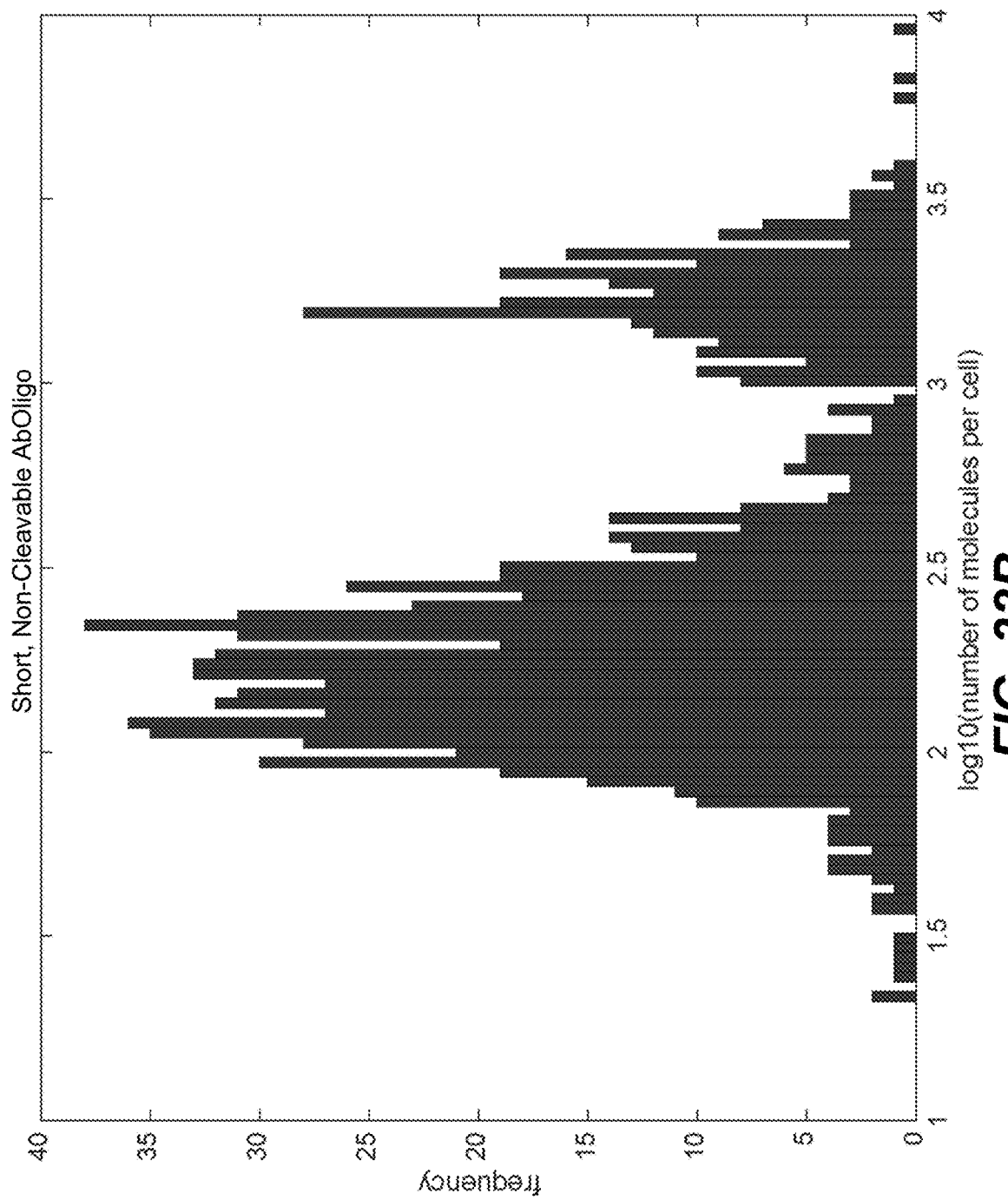
Figure 32C:
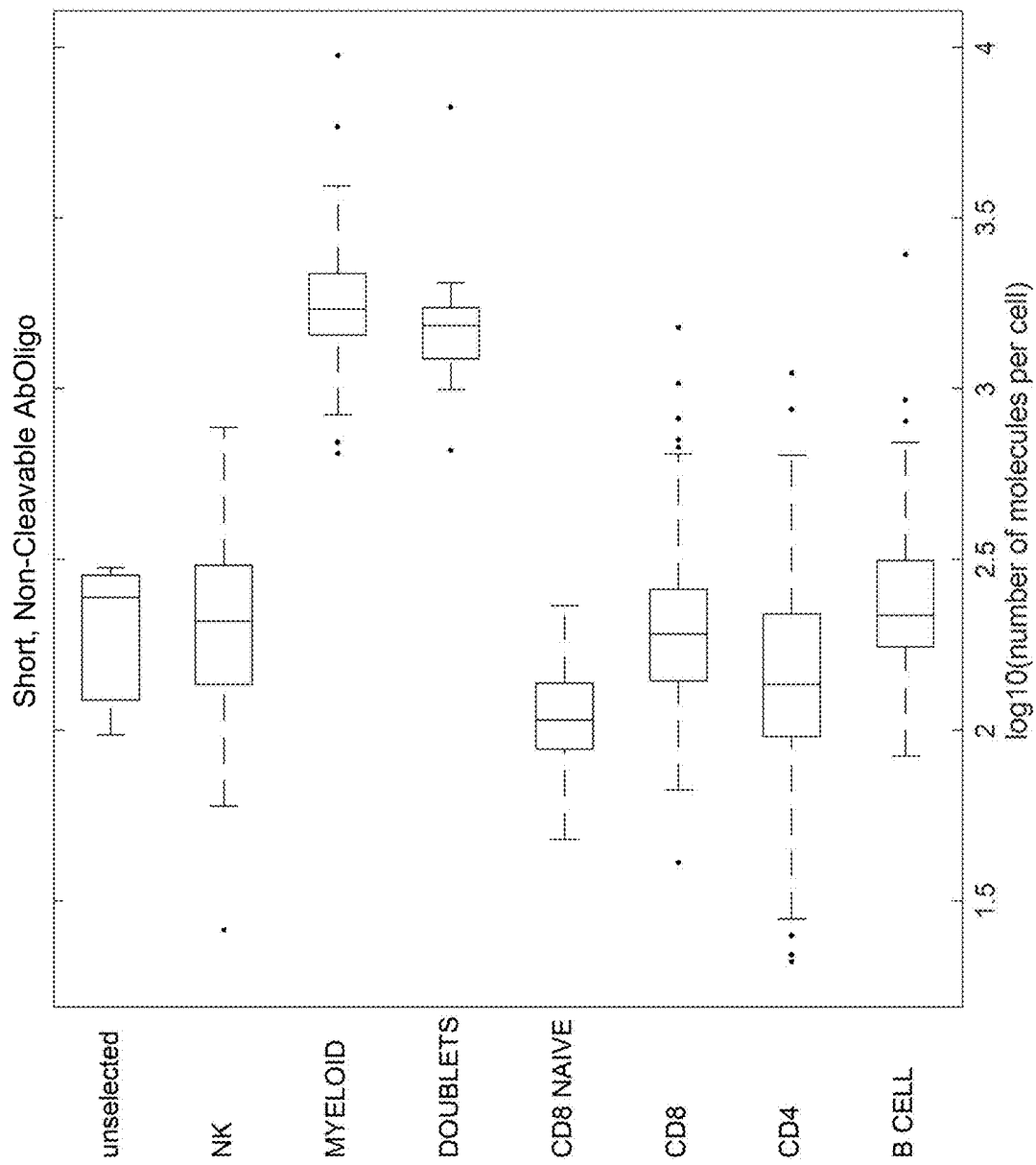

FIGS. 32A-32C are non-limiting exemplary plots showing that oligonucleotide-conjugated anti-CD147 antibody molecules can be used to label various cell types. The cell types were determined using the expression profiles of 488 genes in a blood panel (FIG. 32A). The cells were stained with a 1:800 diluted stock, resulting in a clear signal in a histogram showing the numbers of molecules of antibody oligonucleotides detected (FIG. 32B). The labeling of the various cell types by the antibody oligonucleotide is shown in FIG. 32C.

TABLE 1

Summary of sequencing data metrics

| Sample | FC4 - 1:800 Dilution, No Cold Antibody | FC3 - 1:100 Dilution, 1:100 Cold Antibody | FC2 - 1:100 Dilution, 1:10 Cold Antibody |
|---|---|---|---|
| Total Raw Reads | 31.3M | 27.3M | 29.2M |
| Total Raw Reads Assigned to Oligos | 9161642 (29.2%) | 660044 (2.4%) | 4013438 (13.7%) |
| Cell Detected | 1010 | 983 | 907 |
| RSEC Oligo MI | 577110 | 20054 | 170742 |
| DBEC Oligo MI | 477216 | 9319 | 110629 |
| % Q30 | 76.45 | 71.89 | 73.45 |
| % assigned to cell labels | 84.63 | 79.47 | 82.58 |
| % aligned uniquely to amplicons | 73.19 | 65.4 | 69.58 |
| Mean raw seq depth | 5.58 | 6.52 | 6.4 |
| Mean RSEC seq depth | 8.69 | 10.41 | 10.25 |
| Mean DBEC seq depth | 15.96 | 23.29 | 22.48 |
| AbOligo RSEC seq depth | 8.08 | 12.9 | 11.2 |
| AbOligo DBEC Seq depth | 12.4 | 30.9 | 21.2 |
| Mean reads per cell | 11257 | 14414 | 15150 |
| mean molecules per cell | 553.8 | 608.3 | 647.1 |
| Median mols per cell | 246.5 | 279 | 278 |
| No. of genes in panel | 489 | 489 | 489 |
| Total genes detected | 438 | 439 | 441 |
| Mean genes per cell | 68.39 | 73.6 | 73.12 |

Altogether, these data indicate that the ratio of oligonucleotide-conjugated antibodies ("hot antibodies") and antibodies not conjugated with oligonucleotides ("cold antibody") can be adjusted such that the antibody oligonucleotides account for a desired percentage of total reads in sequencing data and data representing signal antibody oligonucleotides is clearly separated from data representing noise antibody oligonucleotides.

Example 4

Normalization

This example demonstrates how normalization, using a mixture of oligonucleotide-conjugated antibodies ("hot antibodies") and antibodies not conjugated with oligonucleotides ("cold antibody"), can result in the antibody oligonucleotides accounting for a desired percentage of total reads in sequencing data with a desired coverage, irrespective of the abundance of the protein targets of the antibodies.

Table 2 shows a comparison of quantification of three cell surface markers of varying abundance in 10,000 B cells using hot antibodies. Total number of reads required to resolve relative expression levels of the three cell surface markers was 47.52 million reads.

TABLE 2

Example protein quantification using hot antibodies

| Antigen | Molecules per Cell | Relative abundance | Ratio of Hot: Cold Antibodies | Number of Molecules per Cell Detected by Sequencing | Number of reads given sequencing depth of 4 |
|---|---|---|---|---|---|
| CD21 | 210,000 | 105 | 1:0 | 840 | 33.6M |
| HLA-DR | 85,000 | 42.5 | 1:0 | 340 | 13.6M |
| CD40 | 2000 | 1 | 1:0 | 8 | 0.32M |

TABLE 3

Example protein quantification using hot and cold antibodies

| Antigen | Molecules per Cell | Relative abundance | Ratio of Hot: Cold Antibodies | Number of Molecules per Cell detected by sequencing | Number of reads given sequencing depth of 4 | Expected number of molecules based on Antibody ratio | Relative abundance by sequencing |
|---|---|---|---|---|---|---|---|
| CD21 | 210,000 | 105 | 1:100 | 8.3 | 0.33M | 8.3×10=830 | 103.75 |
| HLA-DR | 85,000 | 42.5 | 1:40 | 8.5 | 0.34M | 8.5×40=340 | 42.5 |
| CD40 | 2000 | 1 | 1:0 | 8 | 0.32M | 8×1=8 | 1 |

Table 3 shows that the total number of reads required to resolve relative expression levels of the three cell surface markers was 1 million reads using mixtures of hot antibodies:cold antibodies. Also, only 2% of the number of reads, compared to the quantification result shown in Table 2 (1 million reads vs. 47.52 million reads), is needed to achieve optimal coverage (e.g., sequencing depth of 4) of all three protein markers when mixtures of hot antibodies:cold antibodies were used to quantify expression levels of the three cell surface markers. Normalizing high expressing protein molecules, using a mixture with higher percentage of cold antibodies, decreased tradeoffs between detection of low abundance proteins, number of parameters, and sequencing cost, making the assay more attractive as a tool.

Altogether, these data indicate that a desired number of total reads in sequencing data with a desired coverage can be achieved for protein targets (e.g., antigens) of different abundance using mixtures of hot antibodies:cold antibodies.

Example 5

Identification of T Cell Subsets

This example demonstrates simultaneous digital measurements of protein and mRNA content by massively parallel single cell sequencing to better identify T cell subsets.

High throughput single cell RNA sequencing has been used to profile complex and heterogeneous cell populations and dynamics. However, the lack of information on protein expression can make identifying cell types that have conventionally been defined by cell surface markers challenging, as mRNA and protein expression may not tightly correlated. T cells in particular, contain relatively low abundance of transcripts, and different T cell subsets often exhibit highly similar transcriptional profiles. This example demonstrate a method of using oligonucleotide-conjugated antibodies to measure protein expression by sequencing, which enables simultaneous detection of protein and mRNA expression in a single cell.

The antibody specific oligos were captured, amplified and sequenced alongside mRNAs in a single workflow using BD™ Resolve, a massively parallel single cell analysis system. To demonstrate the power of the method, an oligonucleotide-conjugated antibody panel that included many common T cell markers was created. The panel was applied to human peripheral blood mononuclear cells (PBMCs). The detection of protein expression by oligonucleotide-conjugated antibodies was highly sensitive and specific. And the addition of protein marker measurement provided more distinct and robust clustering of single cell expression profile, especially in the T cell compartment, such as the separation of naïve CD4 vs CD8 T cells, and naïve vs memory T cells. In particular, a rare and recently described T cell subset, stem memory T cells, was identified. Stem memory T cells constitute a long-lasting memory T cell population with stem cell-like properties.

Altogether, the data show simultaneous digital measurements of protein and mRNA content by massively parallel single cell sequencing can transform both single cell transcriptional profiling and high parameter proteomics to further efforts in elucidating complex biological systems, understanding disease states and enabling more effective biomarker discovery.

Example 6

Control Particles

This example demonstrates generating control particles comprising control particle oligonucleotides with different sequences and use of the functionalized control particles to determine capture efficiency.

Materials

BD CompBead Plus Anti-Mouse Ig (7.5 um) Particles Set (51-9006274)

BD staining buffer (FBS)

Procedure

1. Vortex BD CompBead Plus thoroughly before use (1 minute at least).
2. Add 800 uL of staining buffer to tube (Table 7 shows the composition of the staining buffer with CD147 conjugated to oligonucleotides with five sequences at different abundance. FIG. 33A is a plot showing the composition of the staining buffer).
3. Add 5 full drops (approximately 300 uL) of CompBead Plus Anti-Mouse.
4. Add 20 uL of the staining cocktail below to the tube. Vortex.
5. Incubate 30 minutes at room temperature away from light.
6. Spin beads at 200 g for 10 minutes.
7. Remove supernatant carefully and resuspend with 1 mL staining buffer.
8. Spin beads at 200 g for 10 minutes.
9. Remove supernatant carefully and resuspend with 1 mL staining buffer to generate the functionalized CompBead stock solution.
10. Count beads.

TABLE 7

Staining Cocktail Composition

| Antibodies | Final % in Staining Buffer | Prior Dilution | Staining Solution (µl) |
|---|---|---|---|
| CD147-LZ15 | 1 | 1:1 | 1 |
| CD147-LZ16 | 0.2 | 1:5 | 1 |
| CD147-LZ17 | 0.1 | 1:10 | 1 |
| CD147-LZ18 | 0.02 | 1:50 | 1 |

TABLE 7-continued

Staining Cocktail Composition

| Antibodies | Final % in Staining Buffer | Prior Dilution | Staining Solution (μl) |
|---|---|---|---|
| CD147-LZ19 | 0.01 | 1:100 | 1 |
| Staining Buffer | | | 95 |

Results

Figure 34B:
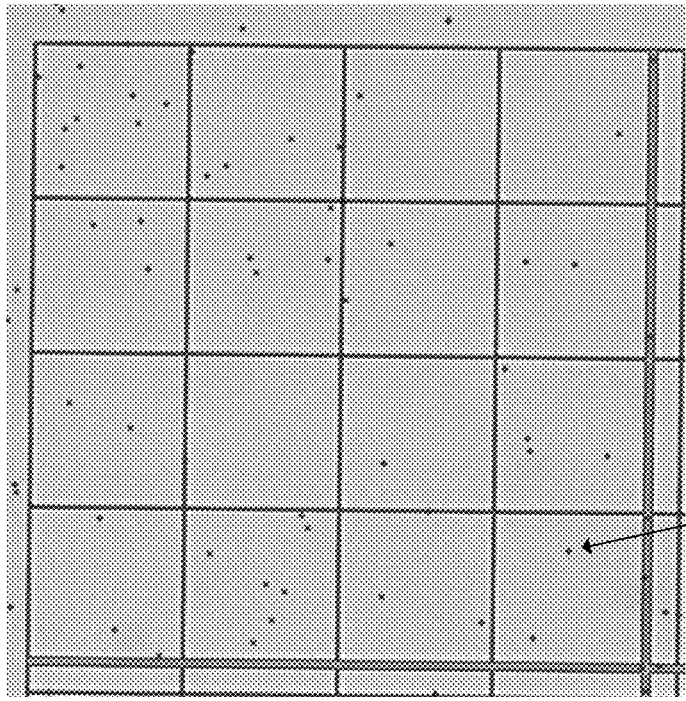
FIGS. 34A-34B are bright-field images of cells (FIG. 34A, white circles) and control particles (FIG. 34B, black circles) in a hemocytometer.
Figure 34A:
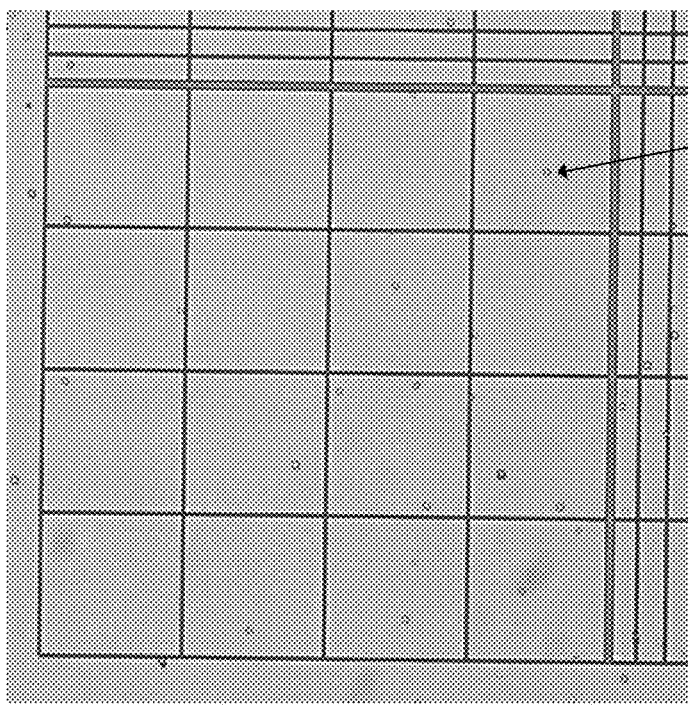
Figure 35B:
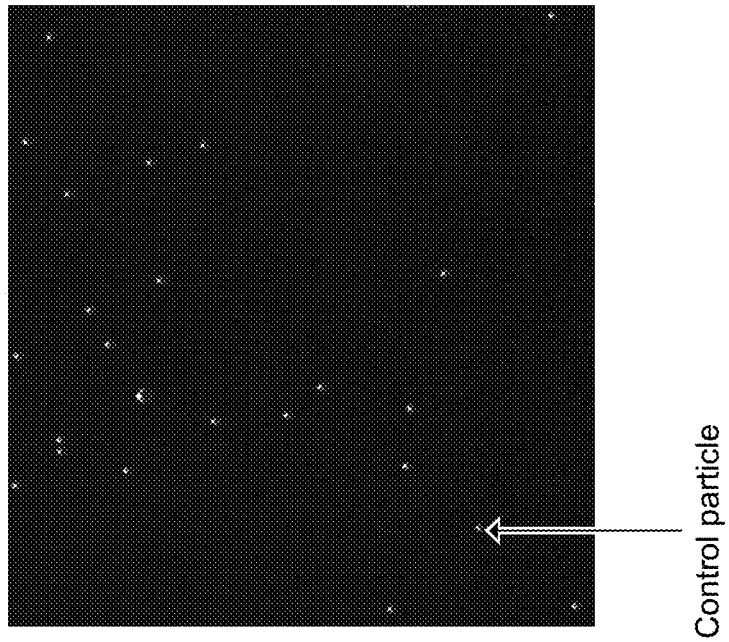
FIGS. 35A-35B are phase contrast (FIG. 35A, 10×) and fluorescent (FIG. 35B, 10×) images of control particles bound to oligonucleotide-conjugated antibodies associated with fluorophores.
Figure 35A:
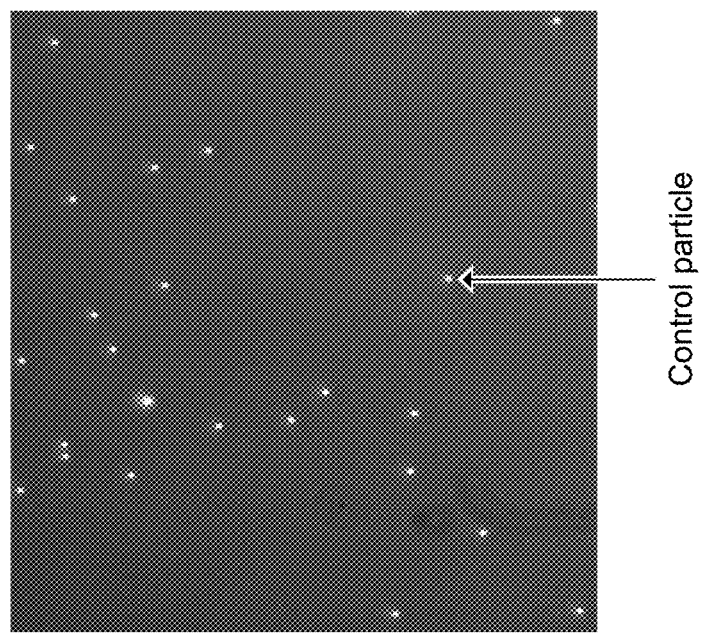

FIGS. 34A-34B are brightfield images of cells (FIG. 34A, white circles) and control particles (FIG. 34B, black circles) in a hemocytometer. FIGS. 35A-35B are phase contrast (FIG. 35A, 10×) and fluorescent (FIG. 35B, 10×) images of control particles bound to oligonucleotide-conjugated antibodies associated with fluorophores. Fluorescent microscope was used to determine that 5 ul of the functionalized CompBead stock solution contained ~2000 cells (4% of total input) with ~400000 functionalized CompBeads made.

Figure 36:
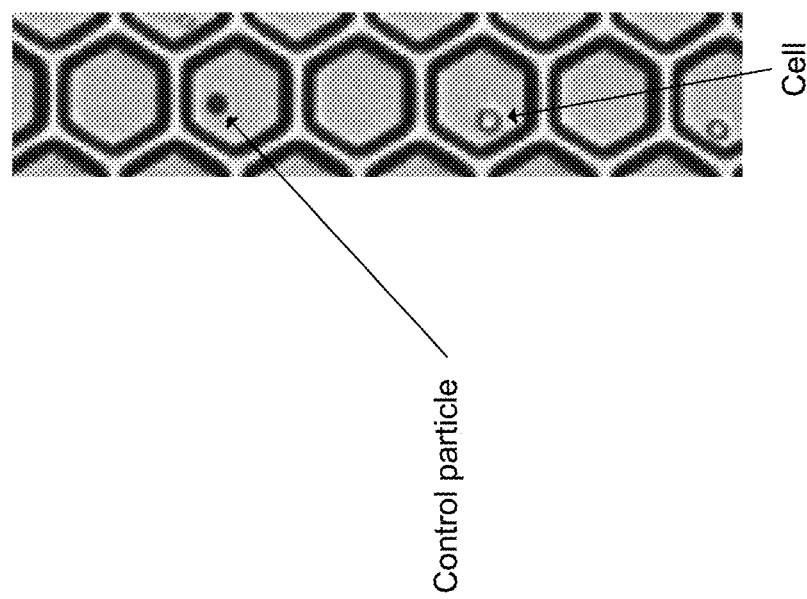
FIG. 36 is an image showing cells and a control particle being loaded into microwells of a cartridge.

FIG. 36 is an image of a control particle showing cells and a particle being loaded into microwells of a cartridge. CompBeads can be used with regular Resolve experiments. 522 functionalized CompBeads were added into a plurality of cells. Of the 20000 cells (including control particles) sequences, 156 had a sum of all control particle oligonucleotides greater than 20. Thus, 156 control particles were sequences. FIG. 33B is a plot showing the number of control particle oligonucleotides with the five different control barcode sequences (LZ15-LZ19) correlated with their abundance in the staining buffer.

Altogether, these data show that particles (e.g., CompBead Plus) can be functionalized with oligonucleotides (e.g., control particle oligonucleotides). Functionalized particles can be used with single cell sequencing workflow to determine the number of particles captured and sequenced.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A plurality of compositions each comprising a cellular component binding reagent associated with one or more oligonucleotides, wherein one of the at least one or more oligonucleotides comprises a target region and a unique identifier for the cellular component binding reagent that it is associated therewith, and the cellular component binding reagent is capable of specifically binding to a cellular component target, and the unique identifier is selected from a diverse set of unique identifiers comprising at least 100 different unique identifiers, and wherein the plurality of compositions further comprises one or more second cellular component binding reagents which are not associated with an oligonucleotide.

2. The plurality of compositions of claim 1, wherein the cellular component target is a carbohydrate, a lipid, a protein, an intracellular protein, an extracellular protein, a cell-surface protein, a cell marker, a B-cell receptor, a T-cell receptor, an antibody, a major histocompatibility complex, a tumor antigen, a receptor, or a combination thereof.

3. The plurality of compositions of claim 1, wherein the unique identifier sequence comprises a nucleotide sequence of 25-45 nucleotides in length.

4. The plurality of composition of claim 2, comprising at least 100 compositions each comprising the cellular component binding reagent associated with one or more oligonucleotides.

5. The plurality of composition of claim 4, wherein at least 10 of the at least 100 compositions comprise different unique identifier sequences.

6. The plurality of composition of claim 5, wherein at least 100 compositions comprise different unique identifier sequences.

7. The plurality of compositions of claim 1, wherein the oligonucleotide comprises a barcode sequence, a poly(A) sequence, or a combination thereof.

8. The plurality of compositions of claim 1, wherein the target region is at the 3' region of the oligonucleotide.

9. The plurality of composition of claim 1, wherein the target region comprises a poly(A) sequence.

10. The plurality of compositions of claim 1, wherein the oligonucleotide is associated to the cellular component binding reagent through a linker.

11. The plurality of compositions of claim 10, wherein the oligonucleotide comprises the linker.

12. The plurality of compositions of claim 1, wherein the oligonucleotide is reversibly associated to the cellular component binding reagent.

13. The plurality of compositions of claim 1, comprising at least 10 compositions each comprising a different cellular component binding reagent.

14. The plurality of compositions of claim 7, wherein the oligonucleotide associated with the cellular component binding reagent in each composition comprises at least one barcode sequence selected from a set of at least 10 different barcode sequences.

15. The plurality of compositions of claim 1, wherein the cellular component binding reagent and the one or more second cellular component binding reagents are the same.

16. The plurality of compositions of claim 1, wherein the cellular component binding reagent is capable of specifically binding to a plurality of cellular component targets.

17. The plurality of compositions of claim 16, wherein the plurality of cellular component targets comprises a carbohydrate, a lipid, a protein, an intracellular protein, an extracellular protein, a cell-surface protein, a cell marker, a B-cell receptor, a T-cell receptor, an antibody, a major histocompatibility complex, a tumor antigen, a receptor, or any combination thereof.

18. The plurality of compositions of claim 16, wherein the plurality of cellular component targets comprises 10 to 400 different cellular component targets.

19. A kit for simultaneous quantitative analysis of a plurality of cellular component targets and a plurality of nucleic acid target molecules in a sample, comprising
   a plurality of compositions each comprising a cellular component binding reagent associated with one or more oligonucleotides, wherein one of the at least one or more oligonucleotides comprises a target region and a unique identifier for the cellular component binding reagent that it is associated therewith, and the cellular component binding reagent is capable of specifically binding to a cellular component target, and the unique identifier is selected from a diverse set of unique identifiers comprising at least 100 different unique identifiers, and wherein the plurality of compositions further comprises one or more second cellular component binding reagents which are not associated with an oligonucleotide; and
   a plurality of oligonucleotide probes, wherein each of the plurality of oligonucleotide probes comprises a target binding region and a barcode sequence, wherein the barcode sequence is from a diverse set of unique barcode sequences.

20. The kit of claim 19, wherein the cellular component target is a carbohydrate, a lipid, a protein, an intracellular protein, an extracellular protein, a cell-surface protein, a cell marker, a B-cell receptor, a T-cell receptor, an antibody, a major histocompatibility complex, a tumor antigen, a receptor, or a combination thereof.

21. The kit of claim 19, comprising at least 10 compositions each comprising a different cellular component binding reagent.

22. The kit of claim 19, comprising at least 100 compositions each comprising the cellular component binding reagent associated with one or more oligonucleotides.

23. The kit of claim 22, wherein at least 100 compositions comprise different unique identifier sequences.

24. The kit of claim 19, wherein the oligonucleotide comprises a barcode sequence, a poly(A) sequence, or a combination thereof.

25. The kit of claim 19, wherein the target region comprises a poly(A) sequence.

26. The plurality of compositions of claim 1, wherein the cellular component binding reagent comprises an antibody, a tetramer, an aptamer, a protein scaffold, or a combination thereof.

27. The kit of claim 19, wherein the cellular component binding reagent comprises an antibody, a tetramer, an aptamer, a protein scaffold, or a combination thereof.

* * * * *

```
                               SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 1
aaaaaaaaaa aaaaaaaaaa                                                      20

<210> SEQ ID NO 2
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 2
tttttttttt tttttttttt                                                      20

<210> SEQ ID NO 3
<211> LENGTH: 95
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: 5AmMC6
<222> LOCATION: (1)..(1)
<223> OTHER INFORMATION: 5' Amino Modifier C6

<400> SEQUENCE: 3
gttgtcaaga tgctaccgtt cagagtacgt ggagttggtg gcccgacccc gagcgctacg          60 agcccccgg aaaaaaaaaa aaaaaaaaaa aaaaa                                      95

<210> SEQ ID NO 4
<211> LENGTH: 200
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: 5AmMC6
<222> LOCATION: (1)..(1)
<223> OTHER INFORMATION: 5' Amino Modifier C6

<400> SEQUENCE: 4
gttgtcaaga tgctaccgtt cagagctact gtccgaagtt accgtgtatc taccacgggt          60 ggttttcga atccggaaaa gatagtaata agtgttttag ttggaataag tcgcaacttt          120
tggagacggt tacctctcaa tttttctgat ccgtaggccc ccgatctcg gcctcaaaaa          180 aaaaaaaaaa aaaaaaaaaa                                                     200

<210> SEQ ID NO 5
<211> LENGTH: 25
<212> TYPE: DNA
```

```
<213> ORGANISM: Artificial Sequence
<220> FEATURE:
<223> OTHER INFORMATION: note="Description of Artificial Sequence:
      Synthetic Oligonucleotide"

<400> SEQUENCE: 5
gttgtcaaga tgctaccgtt cagag                                              25

<210> SEQ ID NO 6
<211> LENGTH: 95
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 6
gttgtcaaga tgctaccgtt cagagcccca tgtctagtac ctattggtcc cctatcctca        60
gattcgttta aaaaaaaaaa aaaaaaaaaa aaaaa                                   95

<210> SEQ ID NO 7
<211> LENGTH: 26
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 7
tttttttttt tttttttttt tttttt                                             26
```